(12) United States Patent
Horiuchi et al.

(10) Patent No.: US 8,623,577 B2
(45) Date of Patent: Jan. 7, 2014

(54) ACRYLIC ESTER COMPOUND AND MANUFACTURING INTERMEDIATE THEREOF, METHOD FOR MANUFACTURING ACRYLIC ESTER COMPOUND, AND LATENT ELECTROSTATIC IMAGE BEARING MEMBER, IMAGE FORMING METHOD, IMAGE FORMING APPARATUS AND PROCESS CARTRIDGE

(75) Inventors: Tamotsu Horiuchi, Shizuoka (JP); Kazukiyo Nagai, Numazu (JP); Hongguo Li, Numazu (JP); Tetsuro Suzuki, Fuji (JP); Hiroshi Tamura, Susono (JP)

(73) Assignee: Ricoh Company, Ltd., Tokyo (JP)

(*) Notice: Subject to any disclaimer, the term of this patent is extended or adjusted under 35 U.S.C. 154(b) by 1603 days.

(21) Appl. No.: 11/938,006

(22) Filed: Nov. 9, 2007

(65) Prior Publication Data

US 2011/0287353 A1   Nov. 24, 2011

Related U.S. Application Data

(63) Continuation of application No. PCT/JP2006/309769, filed on May 10, 2006.

(30) Foreign Application Priority Data

May 10, 2005 (JP) .................. 2005-137333
May 11, 2005 (JP) .................. 2005-139121
May 19, 2005 (JP) .................. 2005-147206
Jul. 27, 2005 (JP) .................. 2005-217873

(51) Int. Cl.
*G03G 5/047* (2006.01)

(52) U.S. Cl.
USPC ......... 430/58.35; 430/56; 430/58.3; 430/58.5

(58) Field of Classification Search
USPC ............................ 430/31–137.22
See application file for complete search history.

(56) References Cited

U.S. PATENT DOCUMENTS

5,929,194 A * 7/1999 Woo et al. ............... 528/229
2006/0160003 A1 * 7/2006 Nagai et al. ............. 430/58.7

FOREIGN PATENT DOCUMENTS

JP    56-048637    5/1981
JP    64-1728      1/1989

(Continued)

OTHER PUBLICATIONS

English translation of JP 2001166516 A, Jun. 2001, Ochi et al.*

(Continued)

*Primary Examiner* — Mark F Huff
*Assistant Examiner* — Rashid Alam
(74) *Attorney, Agent, or Firm* — Oblon, Spivak, McClelland, Maier & Neustadt, L.L.P.

(57) ABSTRACT

To provide: a latent electrostatic image bearing member including one of a cured material obtained through radical polymerization of a radically polymerizable compound of component (A1), and a cured material obtained through radical polymerization of a radically polymerizable compound of component (A2) in the outermost layer, wherein the component (A1) includes two radically polymerizable groups and a substituted amino group which does not include a radically polymerizable group in a molecule, and the radically polymerizable group and the nearest substituted amino group which does not include an unsaturated bond in between are connected with two or more aromatic hydrocarbon compounds, and, the radically polymerizable compound of component (A2) includes a condensed polycyclic aromatic hydrocarbon formed by bonding a radically polymerizable group and a non-radically polymerizable substituted amine group through a condensed polycyclic aromatic hydrocarbon group; and an image forming apparatus, image forming method and process cartridge which uses thereof.

9 Claims, 7 Drawing Sheets

IR Date No. 1

(56) References Cited

FOREIGN PATENT DOCUMENTS

| | | |
|---|---|---|
| JP | 3-174541 | 7/1991 |
| JP | 04-281461 | 10/1992 |
| JP | 2000-66424 | 3/2000 |
| JP | 2000-206716 | 7/2000 |
| JP | 3164426 | 3/2001 |
| JP | 2001-166516 | 6/2001 |
| JP | 3194392 | 6/2001 |
| JP | 2001166516 A * | 6/2001 |
| JP | 3262488 | 12/2001 |
| JP | 2004-212959 | 7/2004 |
| JP | 2005-53845 | 3/2005 |
| WO | WO 97/33193 | 9/1997 |

OTHER PUBLICATIONS

Lu et al, J. of Polymer Science: Part A: Polymer Chemistry, (2000), 38, pp. 2740-2478.

* cited by examiner

IR Date No. 1

IR Date No. 2

ACRYLIC ESTER COMPOUND AND MANUFACTURING INTERMEDIATE THEREOF, METHOD FOR MANUFACTURING ACRYLIC ESTER COMPOUND, AND LATENT ELECTROSTATIC IMAGE BEARING MEMBER, IMAGE FORMING METHOD, IMAGE FORMING APPARATUS AND PROCESS CARTRIDGE

CROSS-REFERENCE TO RELATED APPLICATION

This is a continuation of Application No. PCT/JP2006/309769, filed on May 10, 2006.

BACKGROUND OF THE INVENTION

1. Field of the Invention

The present invention relates to a novel acrylic ester compound which serves as an organic semiconductor material used for an organic electrophotographic photoconductor, an organic EL, an organic TFT and an organic solar cell; more specifically, it relates to an acrylic ester compound and a manufacturing intermediate, and a method for manufacturing an acrylic ester compound, wherein the acrylic ester compound includes a structural unit with a charge transport function, i.e. hole transport property, as well as an acrylic ester or methacrylic ester group in a molecule, and it can form a polymer with high crosslink density by means of a chain reaction.

The present invention relates to a highly abrasion-resistant and highly reliable electrophotographic photoconductor, which may also be hereinafter referred to as a photoconductor or a latent electrostatic image bearing member, as well as an image forming apparatus, an image forming method and a process cartridge, where the electrophotographic photoconductor has an extremely high abrasion resistance; moreover, it has superior electric properties such as charge property, sensitivity and rest potential accumulation property; and it can maintain high image quality with few image defects for a long period of time.

2. Description of the Related Art

An organic semiconductor material having a charge transport function is useful in various applications such as organic electrophotographic photoconductor, organic EL, organic TFT and organic solar cell. As a method for giving the charge transport property to an organic material used for such applications, i.e. resin used as a binder in forming a functional film, a method to mix and disperse a charge transport material in a resin is the most common, and this method is widely adopted for forming an electrophotographic photoconductor.

However, since it is difficult to ensure the mechanical strength and the heat resistance simply by mixing and dispersing a charge transport material in a resin, a material with sufficient properties cannot be achieved. Therefore, it is an effective method to attach and integrate a charge transport material and a resin used as a binder to improve these properties.

Consequently, the integration of a charge transport material with a resin has been recently addressed, and various charge transport monomers having a functional group for chain polymerization, e.g. radically polymerizable functional group, in their charge transport structure and polymers thereof have been proposed.

For example, various charge transport monomers having two or more functional groups for chain polymerization have been proposed, and an application of these to an electrophotographic photoconductor has been proposed. Among charge transport monomers proposals, an acrylic ester compound has a favorable cross-linking property, and many proposals thereof have been made including Japanese Patent Application Laid-Open (JP-A) Nos. 2000-66424 and 2000-206716. These proposals claim that the application of such charge transport monomers can improve the precipitation resistance, the abrasion resistance, the scratch resistance, the sensitivity and the rest potential.

Also, the applicants of the present invention have proposed before an acrylic ester having a triphenylamine moiety and a polymer thereof in Japanese Patent (JP-B) No. 3164426. The use of this acrylic ester can improve the sensitivity and the durability of an electrophotographic photoconductor.

With regard to the hole mobility which indicates the charge transport property, it has been known that an aminobiphenyl structure or amino-substituted stilbene structure with more expanded conjugated system than a simple triphenylamine structure shows high mobility; among the disclosed charge transport monomers, monomers having these structures are particularly useful. The formation of a three-dimensional cross-linking film with sufficiently high crosslink density by means of a chain reaction with such charge transport monomers provides a film with high degree of hardness and high heat resistance as well as scratch resistance. The durability may be improved by using such film for various organic semiconductor devices. However, the increase in the crosslink density reduces the essential charge transport property, and as a result, sufficient functions cannot be obtained.

In other words, many of the proposed charge transport monomers cannot simultaneously satisfy the formation of a structure with high crosslink density which can meet the various disabilities such as abrasion resistance and scratch resistance and the development of a favorable charge transport property. The development of a novel compound which can satisfy the both requirements has been desired.

Also, an organic photoconductor (OPC) has various advantages including: (1) optical properties such as wide light absorption wavelength range and large absorption quantity, (2) electric properties such as high sensitivity and stable charge property, (3) wide selection of materials, (4) the ease of manufacturing, (5) low cost, and (6) non-toxicity, and it has widely been used for a copier, facsimile, a laser printer and a complex machine thereof in place of an inorganic photoconductor.

Recently, the downsizing of an image forming apparatus has promoted the reduction in the diameter of the photoconductor. Combined with the moves towards the speeding-up and the maintenance free of apparatuses, the increased durability of a photoconductor has been highly craved. In this view, an organic photoconductor is generally soft since the charge conductor has a low-molecular charge transport material and an inert polymer, and it is disadvantageous since the mechanical load by a developing system and a cleaning system in an electrophotographic process can easily cause abrasion in a repeated use. Also, the demand for high image quality has reduced the size of toner particles, and the rubber hardness and the contact pressure of a cleaning blade have been increased to improve the cleaning ability. This is also one of the factors which promote the abrasion of a photoconductor. Such abrasion of a photoconductor degrades electric properties such as sensitivity and charge property, and it increases the occurrences of abnormal images such as decrease in image density and background fog. In addition, a scratch with local abrasion results in an image with streaks with insufficient cleaning.

Therefore, improvements in the abrasion resistance of a photoconductor have been examined. For example, JP-A No. 56-48637 discloses a photoconductor in which a crosslinking binder is used in the charge transport layer; JP-A No. 64-1728 discloses a photoconductor which a polymer charge transport material is used; JP-A No. 04-281461 discloses a photoconductor in which an inorganic filler is dispersed in the charge transport layer; JP-B No. 3262488 discloses a photoconductor which includes a polyfunctional acrylic ester monomer hardener; JP-B No. 3194392 discloses a photoconductor having a charge transport layer formed with a coating solution including a monomer with a carbon-carbon double bond, a charge transport agent with carbon-carbon double bond and a binder resin; and JP-A Nos. 2000-66425 and 2004-212959 disclose a photoconductor including a compound obtained by curing a hole transport compound having two or more functional groups for chain polymerization in a molecule.

These modifications improved the abrasion resistance compared to conventional equivalents. A conventional photoconductor had its surface refaced with abrasion even though an adhesion of a foreign substance or a scratch occurred on its surface, and image defect did not persist indefinitely. However, once an adhesion of a foreign substance or a scratch occurs on the surface of a photoconductor with improved abrasion resistance, the condition and image defect persist indefinitely.

Recent requirements for high image quality as well as energy saving has reduced the toner diameter, which has decreased the softening temperature. In order to secure the flowability of the toner, inorganic particles such as silica are added to the toner. There are occasions the silica particles stick in the OPC surface in the developing process. When this happens, the toner component such as wax accumulates around it and inhibits the development, and an image defect with white spot occurs.

The four hundred and several tens of radically polymerizable compounds disclosed in JP-A No. 2004-212959 could not simultaneously satisfy the high abrasion resistance and the electrical property with little occurrence of rest potential at a high level. The reason thereof is the presumably insufficient cross-linking. Various attempts have been made to improve this such as increasing the fraction of the radically polymerizable groups, polyfunctionalizing the radically polymerizable groups and reducing the molecular weight of the charge transport structure. However, there is a limitation in the reduction of the molecular weight of a structure which develops the favorable charge transport property. On the other hand, the polyfunctionalization is effective for increasing the fraction of the content but decreases the charge transport property after curing. The reason for this is not clear, but it is presumably because the heavy cross-linking constrains the molecular movement in the charge transport structure, reduces the space for free movement is reduced and decreases the hopping mobility of the charge.

Therefore, a latent electrostatic image bearing member with sufficiently satisfactory performance and a related technology thereof have not yet been obtained thus far even with the use of a specific radically polymerized compound.

BRIEF SUMMARY OF THE INVENTION

The present invention is aimed at providing a novel acrylic ester compound as well as a manufacturing method and a manufacturing intermediate thereof, where the acrylic ester compound includes a structural unit with a charge transport property, i.e. hole transport property, in a molecule and a functional group with a favorable chain polymerization property such as radical polymerization, and the acrylic ester compound can simultaneously satisfy the formation of a high-density crosslink structure by means of a chain reaction which can meet the requirements for mechanical durability to abrasion, for example, and heat resistance. In the present invention, an 'acrylic ester compound' is defined as a 'compound which includes an acrylic ester group and/or a methacrylic ester group.'

The present invention is also aimed at providing a latent electrostatic image bearing member which has an extremely high abrasion resistance, favorable electric properties such as charge property, sensitivity and rest potential accumulation property, is able to maintain high-quality image with reduced image defects, has high durability and high reliability, is resistant to image defects such as white spots and has a wide range of writing light source so that it is compatible with a blue-purple laser beam as a writing light source; a long-lasting and high-performance image forming method, an image forming apparatus and a process cartridge.

The means for solving the above problems are as follows.

<1> An acrylic ester compound having a structure represented by General Formula (1) below:

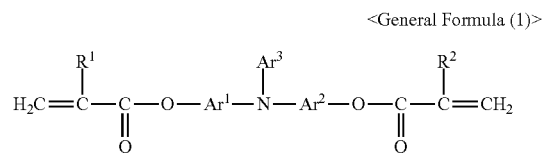

<General Formula (1)> wherein, in General Formula (1), $R^1$ and $R^2$ are the same or different and represent a hydrogen atom or a methyl group; $Ar^1$ and $Ar^2$ are the same or different and represent any one of two or more aromatic hydrocarbon groups which may have a bivalent substituent and a condensed polycyclic aromatic hydrocarbon group which may have a substituent and $Ar^3$ represents an alkyl group which may have a substituent, an aralkyl group which may have a substituent, an aryl group which may have a substituent, a condensed polycyclic hydrocarbon group which may have a substituent or a heterocyclic group which may have a substituent, and each substituent may be bonded with the alkyl group, the aralkyl group, the aryl group, the condensed polycyclic hydrocarbon group or the heterocyclic group through N, O, $CH_2$ or $C(CH_3)_2$.

<2> The acrylic ester compound according to <1>, wherein the compound represented by General Formula (1) is a compound represented by General Formula (1-1) below:

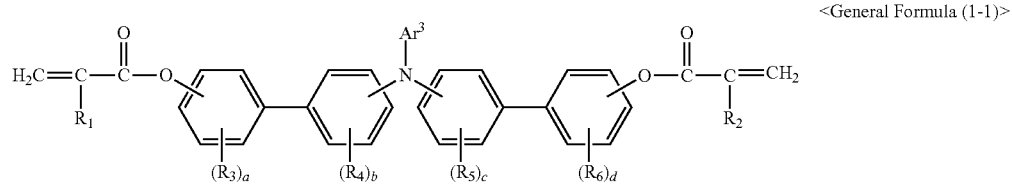

<General Formula (1-1)> wherein, in General Formula (1-1), $R_1$, $R_2$ and $Ar^3$ are equivalent to those in General Formula (1); $R_3$, $R_4$, $R_5$ and $R_6$ represent an alkyl group which may have a substituent, an alkoxy group which may have a substituent, an aryl group which may have a substituent, a heterocyclic group which may have a substituent or a halogen atom; and a, b, c and d are the same or different and represent an integer of zero to four.

<3> The acrylic ester compound according to <1>, wherein the compound represented by General Formula (1) is a compound represented by General Formula (1-2) below:

<General Formula (1-2)>

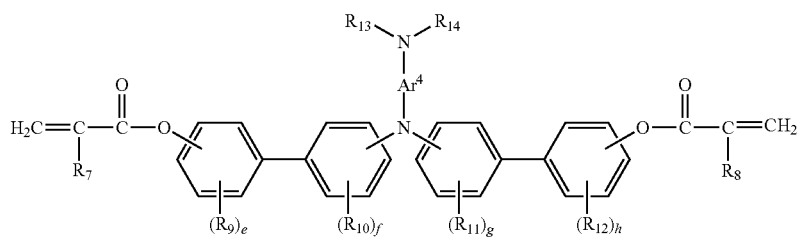

wherein, in General Formula (1-2), $R_7$ and $R_8$ are the same or different and represent a hydrogen atom or a methyl group; $R_9$, $R_{10}$, $R_{11}$ and $R_{12}$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $R_{13}$ and $R_{14}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{13}$ and $R_{14}$ may be bonded together to form a heterocycle; and e, f, g and h are the same or different and represent an integer of zero to four.

<4> The acrylic ester compound according to <1>, wherein the compound represented by General Formula (1) is a compound represented by General Formula (1-3) below:

wherein, in General Formula (1-3), $R_{15}$ and $R_{16}$ are the same or different and represent a hydrogen atom or a methyl group; $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; and i, j, k, l, m and n are the same or different and represent an integer of zero to four.

<5> An acrylic ester compound having a structure represented by General Formula (2) below:

<General Formula (2)>

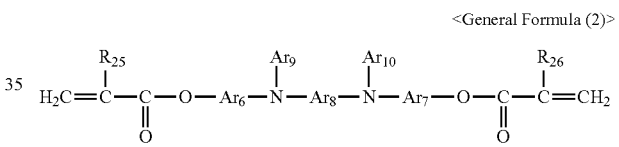

wherein, in General Formula (2), $R_{25}$ and $R_{26}$ represent a hydrogen atom or a methyl group, respectively; $Ar_6$ and $Ar_7$ represent any one of two or more aromatic hydrocarbon groups which may have a bivalent substituent and a condensed polycyclic aromatic hydrocarbon group which may have a substituent; $Ar_9$ and $Ar_{10}$ represents an alkyl group <General Formula (1-3)>

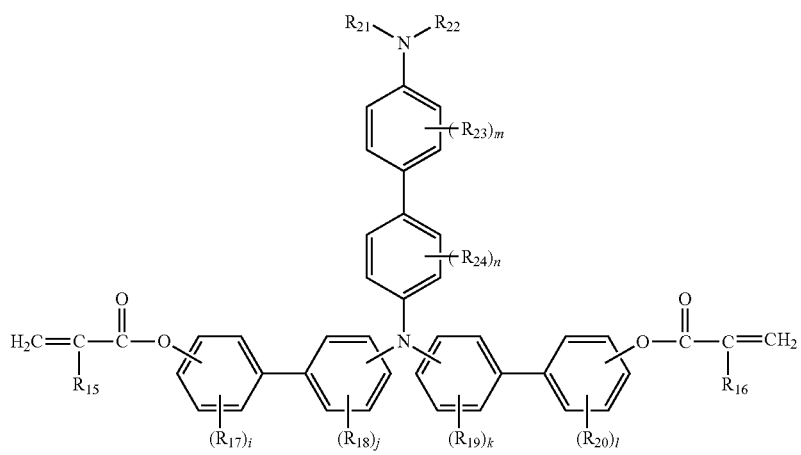

which may have a substituent, an aralkyl group which may have a substituent, an aryl group which may have a substituent or a heterocyclic group which may have a substituent; and $Ar_8$ represents an alkylene group which may have a bivalent substituent, an arylene group which may have a bivalent substituent or a heterocyclic group which may have a bivalent substituent;

<6> The acrylic ester compound according to <5> wherein the compound represented by General Formula (2) is a compound represented by General Formula (2-1) below:

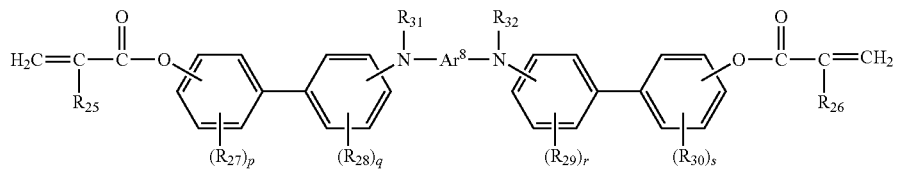

<General Formula (2-1)> wherein, in General Formula (2-1), $R_{27}$, $R_{28}$, $R_{29}$ and $R_{30}$ represent an alkyl group which may have a substituent, an alkoxy group which may have a substituent, an aryl group which may have a substituent, a heterocyclic group which may have a substituent or a halogen atom; $R_{31}$ and $R_{32}$ represent an alkyl group which may have a substituent, an aralkyl group which may have a substituent, an aryl group which may have a substituent, a heterocyclic group which may have a substituent or a heterocyclic group which may have a substituent; $R_{25}$, $R_{26}$ and $Ar^8$ are equivalent to those in General Formula (2); and p, q, r and s are the same or different and represent an integer of zero to four.

<7> A manufacturing intermediate of the acrylic ester compound represented by General Formula (1-1), wherein the manufacturing intermediate is a hydroxy compound represented by General Formula (1-1-1) below:

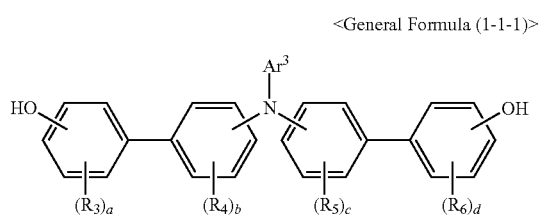

<General Formula (1-1-1)> wherein, in General Formula (1-1-1), $R_3$, $R_4$, $R_5$ and $R_6$ represent an alkyl group which may have a substituent, an alkoxy group which may have a substituent, an aryl group which may have a substituent, a heterocyclic group which may have a substituent or a halogen atom; $Ar^3$ represents an alkyl group which may have a substituent, an aralkyl group which may have a substituent, an aryl group which may have a substituent, a condensed polycyclic hydrocarbon group which may have a substituent or a heterocyclic group which may have a substituent, and each substituent may be bonded with the alkyl group, the aralkyl group, the aryl group, the condensed polycyclic hydrocarbon group or the heterocyclic group through N, O, $CH_2$ or $C(CH_3)_2$; and a, b, c and d are the same or different and represent an integer of zero to four.

<8> A manufacturing intermediate of the acrylic ester compound represented by General Formula (1-2), wherein the manufacturing intermediate is a hydroxy compound represented by General Formula (1-2-1) below:

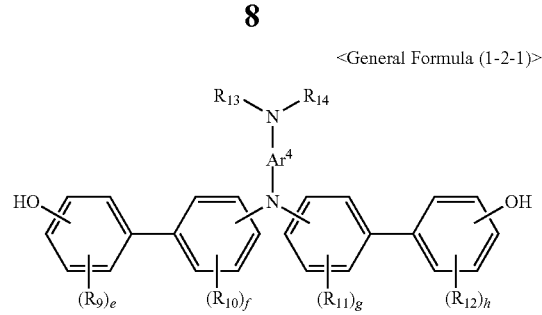

<General Formula (1-2-1)> wherein, in General Formula (1-2-1), $R_9$, $R_{10}$, $R_{11}$ and $R_{12}$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent heterocyclic group which may have a substituent or a bivalent condensed polycyclic hydrocarbon group which may have a substituent; $R_{13}$ and $R_{14}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{13}$ and $R_{14}$ may be bonded together to form a heterocycle; and e, f, g and h are the same or different and represent an integer of zero to four.

<9> A manufacturing intermediate of the acrylic ester compound represented by General Formula (1-3), wherein the manufacturing intermediate is a hydroxy compound represented by General Formula (1-3-1) below:

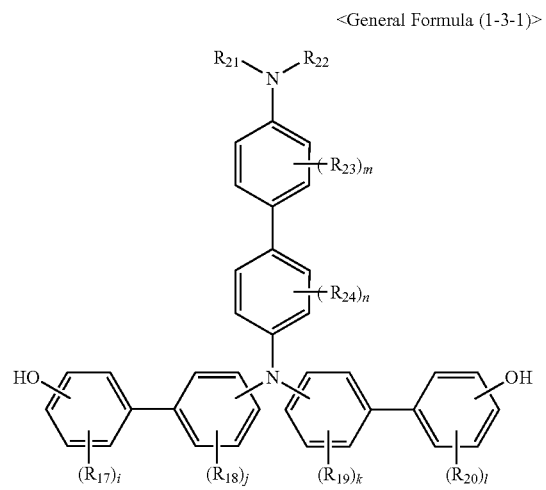

<General Formula (1-3-1)> wherein, in General Formula (1-3-1), $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; and i, j, k, l, m and m are the same or different and represent an integer of zero to four.

<10> A manufacturing intermediate of the acrylic ester compound represented by General Formula (2-1), wherein the manufacturing intermediate is a hydroxy compound represented by General Formula (2-1-1) below:

<General Formula (2-1-1)>

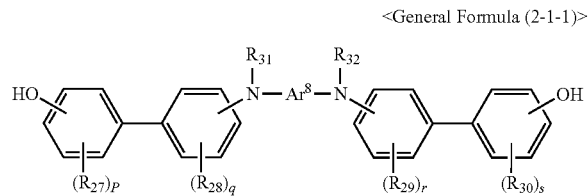

wherein, in General Formula (2-1-1), $R_{27}$, $R_{28}$, $R_{29}$ and $R_{30}$ represent an alkyl group which may have a substituent, an alkoxy group which may have a substituent, an aryl group which may have a substituent, a heterocyclic group which may have a substituent or a halogen atom; $R_{31}$ and $R_{32}$ represent an alkyl group which may have a substituent, an aralkyl group which may have a substituent, an aryl group which may have a substituent or a heterocyclic group which may have a substituent; $Ar^8$ represents an alkylene group which may have a substituent, an arylene group which may have a substituent, a bivalent heterocyclic group which may have a substituent or a bivalent condensed polycyclic hydrocarbon group which may have a substituent; and p, q, r and s are the same or different and represent an integer of zero to four.

<11> A method for manufacturing an acrylic ester compound, wherein the hydroxyl compound represented by General Formula (1-1-1) is reacted with acryloyl chloride or methacryloyl chloride.

<12> A method for manufacturing an acrylic ester compound, wherein the hydroxyl compound represented by General Formula (1-2-1) is reacted with acryloyl chloride or methacryloyl chloride.

<13> A method for manufacturing an acrylic ester compound, wherein the hydroxyl compound represented by General Formula (1-3-1) is reacted with acryloyl chloride or methacryloyl chloride.

<14> A method for manufacturing an acrylic ester compound, wherein the hydroxyl compound represented by General Formula (2-1-1) is reacted with acryloyl chloride or methacryloyl chloride.

<15> The acrylic ester compound according to <1>, wherein the compound represented by General Formula (1) is a compound represented by General Formula (1-4) below:

<General Formula (1-4)>

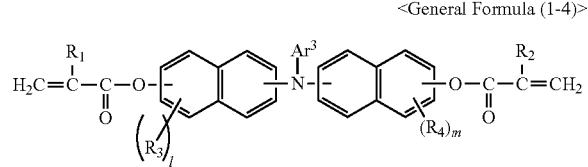

wherein, in General Formula (1-4), $R_1$, $R_2$ and $Ar^3$ are equivalent to those in General Formula (1); $R_3$ and $R_4$ represent an alkyl group which may have a substituent, an alkoxy group which may have a substituent, an aryl group which may have a substituent, a heterocyclic group which may have a substituent or a halogen atom; and l and m are the same or different and represent an integer of zero to six.

<16> The acrylic ester compound according to <1>, wherein the compound represented by General Formula (1) is a compound represented by General Formula (1-5) below.

<General Formula (1-5)>

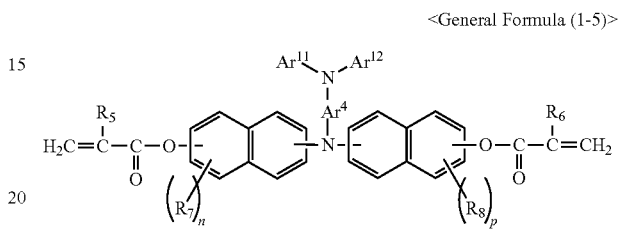

wherein, in General Formula (1-5), $R_5$ and $R_6$ are the same or different and represent a hydrogen atom or a methyl group; $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $Ar^{11}$ and $Ar^{12}$ represent an alkyl group which may have a substituent, an aryl group which may have a substituent or a condensed polycyclic hydrocarbon group which may have a substituent, and Aril and $Ar^{12}$ may be bonded together through adjacent carbon atoms to form a heterocycle; and n and p are the same or different and represent an integer of zero to six.

<17> The acrylic ester compound according to <1>, wherein the compound represented by General Formula (1) is a compound represented by General Formula (1-6) below:

<General Formula (1-6)>

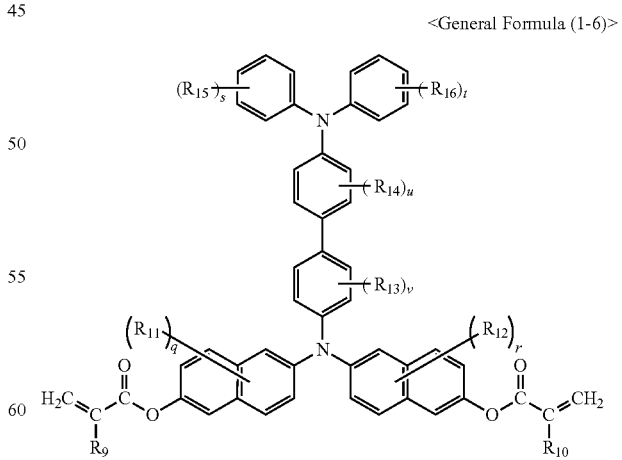

wherein, in General Formula (1-6), $R_9$ and $R_{10}$ are the same or different and represent a hydrogen atom or a methyl group; $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{19}$ represent an alkyl group which may have a substituent, an alkoxy group which may have a substituent, an aryl group which may have a substituent or a halogen atom; and q and r are the same or different and represent an integer of zero to six, s and t are the same or different and represent an integer of zero to five, and u and v are the same or different and represent an integer of zero to four.

<20> The acrylic ester compound according to <5>, wherein the compound represented by General Formula (2) is a compound represented by General Formula (2-2) below:

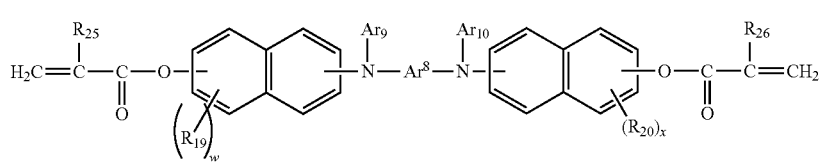

<General Formula (2-2)> wherein, in General Formula (2-2), $R_{19}$ and $R_{20}$ represent an alkyl group which may have a substituent, an alkoxy group which may have a substituent, an aryl group which may have a substituent, a heterocyclic group which may have a substituent or a halogen atom; $Ar_9$ and $Ar_{10}$ represents an alkyl group which may have a substituent, an aryl group which may have a substituent or a heterocyclic group which may have a substituent; $R^{25}$, $R^{26}$ and $Ar^8$ are equivalent to those in General Formula (2); and w and x are the same or different and represent an integer of zero to six.

<19> A manufacturing intermediate of the acrylic ester compound represented by General Formula (1-4), wherein the manufacturing intermediate is a hydroxy compound represented by General Formula (1-4-1) below:

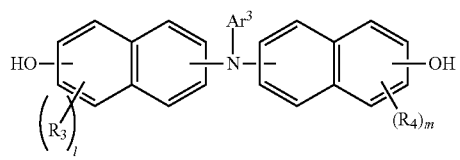

<General Formula (1-4-1)> wherein, in General Formula (1-6), $R_3$ and $R_4$, represent an alkyl group which may have a substituent, an alkoxy group which may have a substituent, an aryl group which may have a substituent, a heterocyclic group which may have a substituent or a halogen atom; $Ar^3$ represents an alkyl group which may have a substituent, an aryl group which may have a substituent, a condensed polycyclic hydrocarbon group or a heterocyclic group which may have a substituent, and each substituent may be bonded with the alkyl group, the aryl group, the condensed polycyclic hydrocarbon group or the heterocyclic group through a nitrogen atom; and l and m are the same or different and represent an integer of zero to six.

<20> A manufacturing intermediate of the acrylic ester compound represented by General Formula (1-5), wherein the manufacturing intermediate is a hydroxy compound represented by General Formula (1-5-1) below:

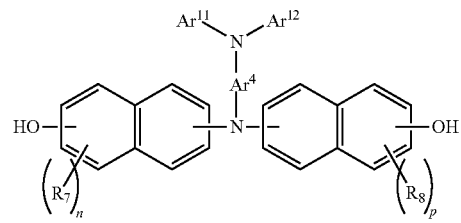

<General Formula (1-5-1)> wherein, in General Formula (1-5-1), $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $Ar^{11}$ and $Ar^{12}$ represent an alkyl group which may have a substituent, an aryl group which may have a substituent or a condensed polycyclic hydrocarbon group which may have a substituent, and $Ar^{11}$ and $Ar^{12}$ may be bonded together through adjacent carbon atoms to form a heterocycle; and n and p are the same or different and represent an integer of zero to six.

<21> A manufacturing intermediate of the acrylic ester compound represented by General Formula (1-6), wherein the manufacturing intermediate is a hydroxy compound represented by General Formula (1-6-1) below:

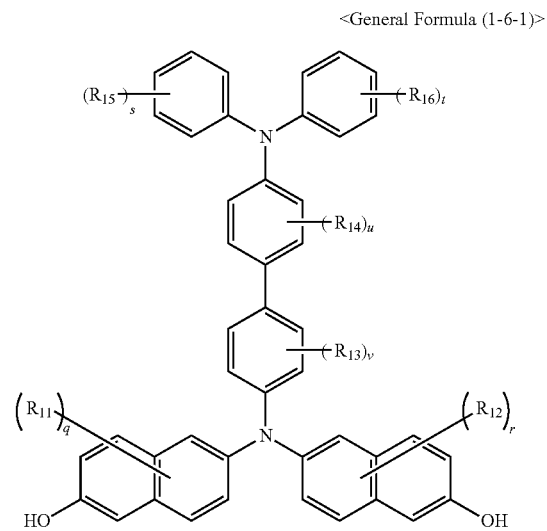

<General Formula (1-6-1)> wherein, in General Formula (1-6-1), $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{16}$ represent an alkyl group which may have a substituent, an alkoxy group which may have a substituent, an aryl group which may have a substituent or a halogen atom; and q and r are the same or different and represent an integer of zero to six, s and t are the same or different and represent an integer of zero to five, and u and v are the same or different and represent an integer of zero to four.

<22> A manufacturing intermediate of the acrylic ester compound represented by General Formula (2-2), wherein the manufacturing intermediate is a hydroxy compound represented by General Formula (2-2-1) below:

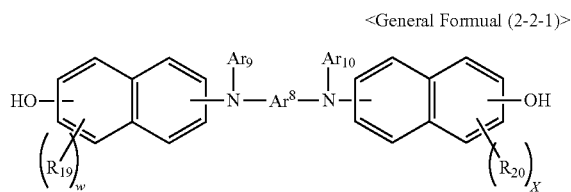

<General Formual (2-2-1)> wherein, in General Formula (2-2-1), $R_{19}$ and $R_{20}$ represent an alkyl group which may have a substituent, an alkoxy group which may have a substituent, an aryl group which may have a substituent, a heterocyclic group which may have a substituent or a halogen atom; $Ar^9$ and $Ar^{10}$ represent an alkyl group which may have a substituent, an aryl group which may have a substituent or a heterocyclic group which may have a substituent; $Ar^8$ represents an alkylene group which may have a substituent, an arylene group which may have a substituent or a bivalent condensed polycyclic hydrocarbon group which may have a substituent; and w and x are the same or different and represent an integer of zero to six.

<23> A method for manufacturing an acrylic ester compound, wherein the hydroxyl compound represented by General Formula (1-4-1) is reacted with acryloyl chloride or methacryloyl chloride.

<24> A method for manufacturing an acrylic ester compound, wherein the hydroxyl compound represented by General Formula (1-5-1) is reacted with acryloyl chloride or methacryloyl chloride.

<25> A method for manufacturing an acrylic ester compound, wherein the hydroxyl compound represented by General Formula (1-6-1) is reacted with acryloyl chloride or methacryloyl chloride.

<26> A method for manufacturing an acrylic ester compound, wherein the hydroxyl compound represented by General Formula (2-2-1) is reacted with acryloyl chloride or a methacryloyl chloride.

<27> A latent electrostatic image bearing member including a cured material obtained through a radical polymerization of a radically polymerizable compound of component (A1) and a cured material obtained through a radical polymerization of a radically polymerizable compound of component (A2) in the outermost layer, wherein the radically polymerizable compound of component (A1) includes two radically polymerizable groups and a substituted amino group in a molecule; the radically polymerizable group and the nearest substituted amino group which do not include an unsaturated bond in between are connected with two or more aromatic hydrocarbon compounds; and the radically polymerizable compound of component (A2) includes a condensed polycyclic aromatic hydrocarbon group formed by bonding a radically polymerizable group and a non-radically polymerizable substituted amine group through a condensed polycyclic aromatic hydrocarbon group.

<28> The latent electrostatic image bearing member according to <27>, wherein the outermost layer includes a radically polymerizable compound having three or more radically polymerizable groups in a molecule.

<29> The latent electrostatic image bearing member according to any one of <27> to <28>, wherein the outermost layer includes a photo-polymerization initiator.

<30> The latent electrostatic image bearing member according to any one of <27> to <29>, wherein the radically polymerizable group is any one of an acryloyloxy group and an methacryloyloxy group.

<31> The latent electrostatic image bearing member according to any one of <27> to <30>, wherein the radically polymerizable compound of component (A1) which is bonded with two or more aromatic hydrocarbon group is the acrylic ester compound according to any one of <1> to <6>.

<32> The latent electrostatic image bearing member according to any one of <27> to <30>, wherein the radically polymerizable compound in component (A2) which includes a condensed polycyclic aromatic hydrocarbon group is the acrylic ester compound according to any one of <1> and <15> to <18>.

<33> The latent electrostatic image bearing member according to any one of <27> to <32>, wherein the latent electrostatic image bearing member includes a substrate, and it also includes at least a charge generation layer, a charge transport layer and a cross-linked charge transport layer in this order on the substrate, and the cross-linked charge transport layer is the outermost layer.

<34> The latent electrostatic image bearing member according to <33>, wherein the cross-linked charge transport layer has a thickness of 1.0 μm to 11.5 μm.

<35> The latent electrostatic image bearing member according to any one of <33> to <34>, wherein the cross-linked charge transport layer is insoluble with an organic solvent.

<36> The latent electrostatic image bearing member according to any one of <33> to <35>, wherein in the cross-linked charge transport layer the ratio of the number of functional groups in the radically polymerizable compound which includes three or more radically polymerizable group in a molecule to the molecular weight of the radically polymerizable compound, i.e. molecular weight/the number of functional groups, is 250 or less.

<37> An image forming method including at least a latent electrostatic image forming process to form a latent electrostatic image on a latent electrostatic image bearing member, a developing process to form a toner image by developing the latent electrostatic image with a toner and a transferring process to transfer the toner image to a recording medium, wherein the latent electrostatic image bearing member is the latent electrostatic image bearing member according to any one of <27> to <36>.

<38> An image forming apparatus including at least a latent electrostatic image bearing member, a latent electrostatic image forming means to form a latent electrostatic image on the latent electrostatic image bearing member, a developing means to form a toner image by developing the latent electrostatic image with a toner and a transferring means to transfer the toner image to a recording medium, wherein the latent electrostatic image bearing member is the latent electrostatic image bearing member according to any one of <27> to <36>.

<39> A process cartridge including the latent electrostatic image bearing member according to any one of <27> to <36> and at least any one means selected from a charging means, a developing means, a transferring means, a cleaning means and a discharging means, wherein the process cartridge is detachably attached to an image forming apparatus body.

<40> The latent electrostatic image bearing member according to <31>, wherein the radically polymerizable compound of component (A1) which is bonded with two or more aromatic hydrocarbon group is a acrylic ester compound having a structure represented by General Formula (2) below:

<General Formula (2)>

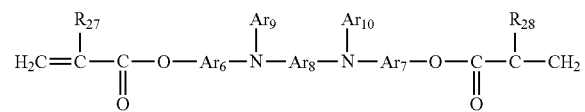

wherein, in General Formula (2), $R_{27}$ and $R_{28}$ represent a hydrogen atom or a methyl group, respectively;

$Ar_6$ and $Ar_7$ represent any one of two or more aromatic hydrocarbon groups which may have a bivalent substituent and a condensed polycyclic aromatic hydrocarbon group which may have a substituent;

$Ar_9$ and $Ar_{10}$ represents an alkyl group which may have a substituent, an aralkyl group which may have a substituent, an aryl group which may have a substituent or a heterocyclic group which may have a substituent; and $Ar_8$ represents an alkylene group which may have a bivalent substituent, an arylene group which may have a bivalent substituent or a heterocyclic group which may have a bivalent substituent.

The latent electrostatic image bearing member of the present invention includes one of a cured material obtained through a radical polymerization of a radically polymerizable compound of component (A1), and a cured material obtained through a radical polymerization of a radically polymerizable compound of component (A2) in the outermost layer, wherein the radically polymerizable compound of component (A1) includes two radically polymerizable groups and a substituted amino group in a molecule, and the radically polymerizable group and the nearest substituted amino group which do not include an unsaturated bond in between are connected with two or more aromatic hydrocarbon compounds, and, the radically polymerizable compound of component (A2) includes a condensed polycyclic aromatic hydrocarbon formed by bonding a radically polymerizable group and a non-radically polymerizable substituted amine group through a condensed polycyclic aromatic hydrocarbon group.

Regarding the latent electrostatic image bearing member, there were problems with conventional polyfunctional charge transport compounds such as occurrences of cracks and insufficient hardness despite the polyfunctionality due to the growing deformation in curing, but the cured material of the specific radically polymerizable compound of the present invention enables the formation of a uniform and smooth film with sufficient cross-linking and curing without occurrences of cracks, and it functions as a favorable surface layer of a photoconductor. Also, since it becomes possible to form a high-density charge transport cured film, the film strength is high enough to prevent external additives in a toner with extremely high hardness such as silica particles from sticking in the latent electrostatic image bearing member, and image defects such as white spots may be reduced.

In addition, the high-density cross-linked cured film may be obtained by employing one of a cured material obtained through a radical polymerization of a radically polymerizable compound of component (A1) and a cured material obtained through a radical polymerization of a radically polymerizable compound of component (A2) in the outermost layer, wherein the radically polymerizable compound of component (A1) includes two radically polymerizable groups and a substituted amino group in a molecule, and the radically polymerizable group and the nearest substituted amino group which do not include an unsaturated bond in between are connected with two or more aromatic hydrocarbon compounds, and, the radically polymerizable compound of component (A2) includes a condensed polycyclic aromatic hydrocarbon formed by bonding a radically polymerizable group and a non-radically polymerizable substituted amine group through a condensed polycyclic aromatic hydrocarbon group. More preferably, a radically polymerizable compound having three or more radically polymerizable group in the molecule is preferably mixed in the component (A1) or (A2). Also, various heretofore known methods may be applied to the initiation of radical polymerization, and a latent electrostatic image bearing member with high crosslink density and superior mechanical strength may be obtained by adding a photo-polymerization initiator and irradiating a light for curing in a short period of time.

Also, it is possible to provide a long-lasting latent electrostatic image bearing member with few image defects by white spots because the both abrasion resistance properties and electric properties of the latent electrostatic image bearing member of the present invention become favorable by installing in the outermost layer any one of a radically polymerizable compound of component (A1) and a cured material obtained through a radical polymerization of a radically polymerizable compound of component (A2) in the outermost layer, wherein the radically polymerizable compound of component (A1) includes two radically polymerizable groups and a substituted amino group in a molecule, and the radically polymerizable group and the nearest substituted amino group which do not include an unsaturated bond in between are connected with two or more aromatic hydrocarbon compounds, and, the radically polymerizable compound of component (A2) includes a condensed polycyclic aromatic hydrocarbon formed by bonding a radically polymerizable group and a non-radically polymerizable substituted amine group through a condensed polycyclic aromatic hydrocarbon group. This is presumably because the condensed polycyclic aromatic hydrocarbon or two or more aromatic hydrocarbon compounds in the component (A1) or (A2) have expanded conjugation of pi electrons compared to benzene ring in a conventional component; therefore, favorable electrophotographic properties may be obtained because of the superior charge transfer. It is also because the addition of the components (A1) or (A2) provides a stronger polymerized film than a benzene ring alone, providing the superior abrasion resistance. Furthermore, the surface having the cured material obtained through radical polymerization of the (A1) or (A2) with the radically polymerizable compound having three or more radically polymerizable groups in a molecule enables to provide a totally non-conventional latent electrostatic image bearing member which has extremely superior abrasion resistance as well as superior charge transfer property with small rest potential. Especially regarding a latent electrostatic image bearing member having on its surface a cured material obtained through radical polymerization of the component (A1) or (A2), the radically polymerizable compound having three or more radically polymerizable group in a molecule and a photo-polymerization initiator, a latent electrostatic image bearing member having superior properties described above may be easily manufactured in a short period of time and thus provided in the market at a low cost.

The image forming apparatus of the present invention includes at least a latent electrostatic image bearing member, a latent electrostatic image forming means to form a latent electrostatic image on the latent electrostatic image bearing member, a developing means to form a visible image by developing the latent electrostatic image with a toner, a transferring means to transfer the visible age to a recording medium, a fixing means to fix a transfer image transferred to the recording medium and a cleaning means to clean the latent electrostatic image bearing member, and the latent electrostatic image bearing member is the latent electrostatic image bearing member of the present invention. Since the image forming apparatus of the present invention employs the latent electrostatic image bearing member of the present invention as the latent electrostatic image bearing member, an image with high durability and high quality may be obtained for a long period of time.

The image forming method of the present invention includes at least a latent electrostatic image forming process to form a latent electrostatic image on a latent electrostatic image bearing member, a developing process to form a visible image by developing the latent electrostatic image with a toner, a transferring process to transfer the visible image to a recording medium, a fixing process to fix a transferred image transferred on the recording medium and a cleaning process to clean the latent electrostatic image bearing member, and the latent electrostatic image bearing member is the latent electrostatic image bearing member of the present invention. Since the image forming method of the present invention employs the latent electrostatic image bearing member of the present invention as the latent electrostatic image bearing member, an image with high durability and high quality may be obtained for a long period of time.

The process cartridge of the present invention includes at least a latent electrostatic image bearing member and a developing means to form a visible image by developing a latent electrostatic image formed on the latent electrostatic image bearing member with a toner. Since the latent electrostatic image bearing member of the present invention is used as the latent electrostatic image bearing member, the process cartridge has high scratch resistance and abrasion resistance; the surface resistance does not decrease in a high-humidity environment; an image with high durability and high quality may be obtained for a long period of time even under a high-temperature environment, which is seen in high-speed processing; the abrasion of the latent electrostatic image bearing member is suppressed to a minimal even though a blade cleaning is performed; and the cleaning performance is favorable.

Figure 1:
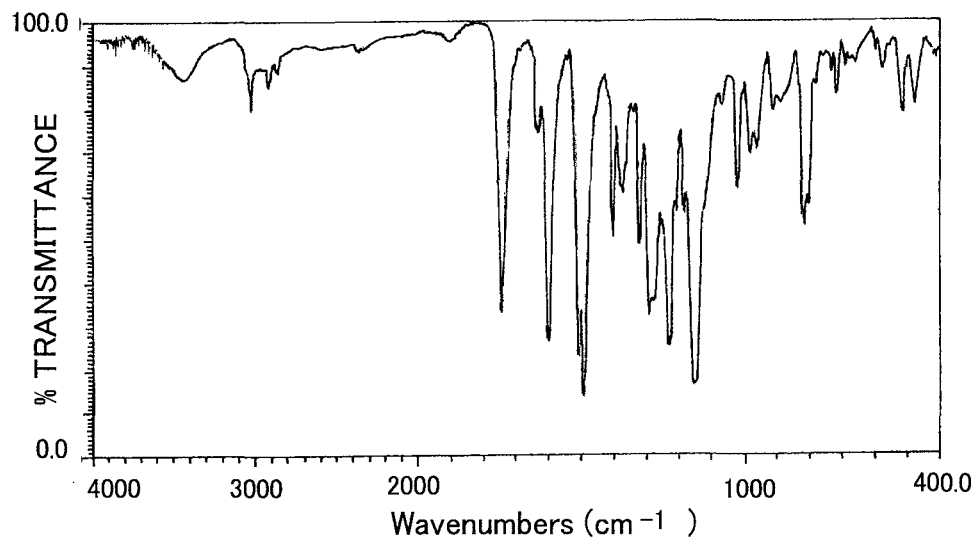
FIG. 1 is an infrared absorption spectral diagram of an Illustrative Compound B-35 obtained in Synthetic Example A-2 (IR data No. 1).

DETAILED DESCRIPTION OF THE INVENTION (Acrylic Ester Compound)

An acrylic ester compound of the present invention in the first aspect is represented by General Formula (1) below:

<General Formula (1)>

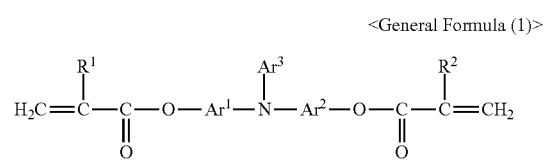

where, in General Formula (1), $R^1$ and $R^2$ are the same or different and represent a hydrogen atom or a methyl group; $Ar^1$ and $Ar^2$ are the same or different and represent any one of two or more aromatic hydrocarbon groups which may have a bivalent substituent and a condensed polycyclic aromatic hydrocarbon group which may have a substituent; $Ar^3$ represents an alkyl group which may have a substituent, an aralkyl group which may have a substituent, an aryl group which may have a substituent, a condensed polycyclic hydrocarbon group which may have a substituent or a heterocyclic group which may have a substituent, and each substituent may be bonded with the alkyl group, the aralkyl group, the aryl group, the condensed polycyclic hydrocarbon group or the heterocyclic group through N, O, $CH_2$ or $C(CH_3)_2$.

In General Formula (1) above, $R^1$ and $R^2$ are the same or different, and they may be a hydrogen atom or a methyl group. Since the hydrogen atom and the methyl group cause the difference in radical polymerization, they are appropriately selected and used according to the use environment.

In General Formula (1) above, $Ar^1$ and $Ar^2$ are the same or different and represent any one of two or more aromatic hydrocarbon groups which may have a bivalent substituent and a condensed polycyclic aromatic hydrocarbon group which may have a substituent.

As the two or more aromatic hydrocarbon groups which may have a bivalent substituent, those represented by the following formulae A-1 to A-13 may be given.

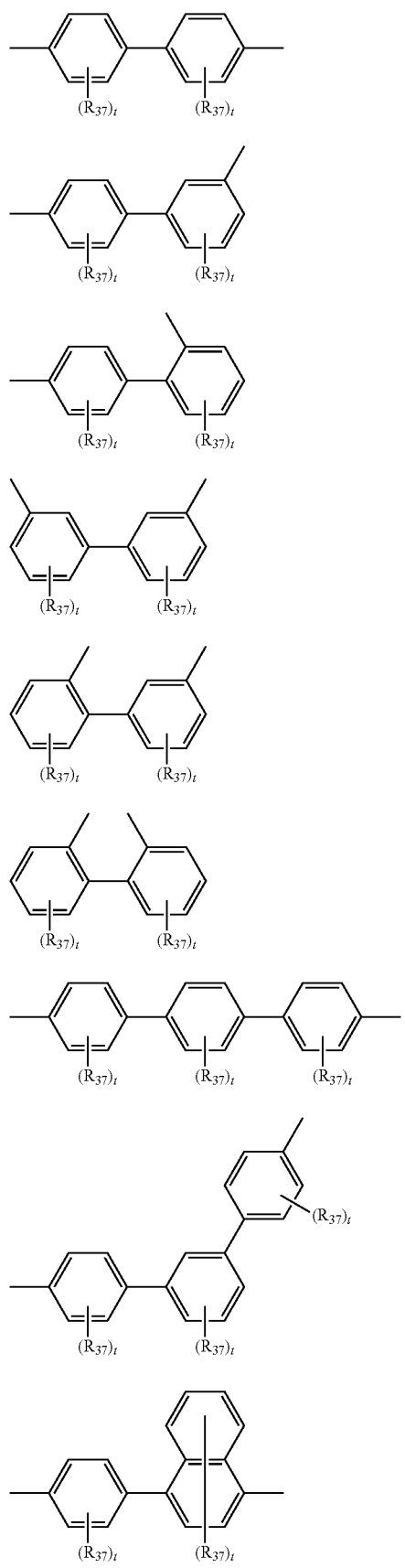
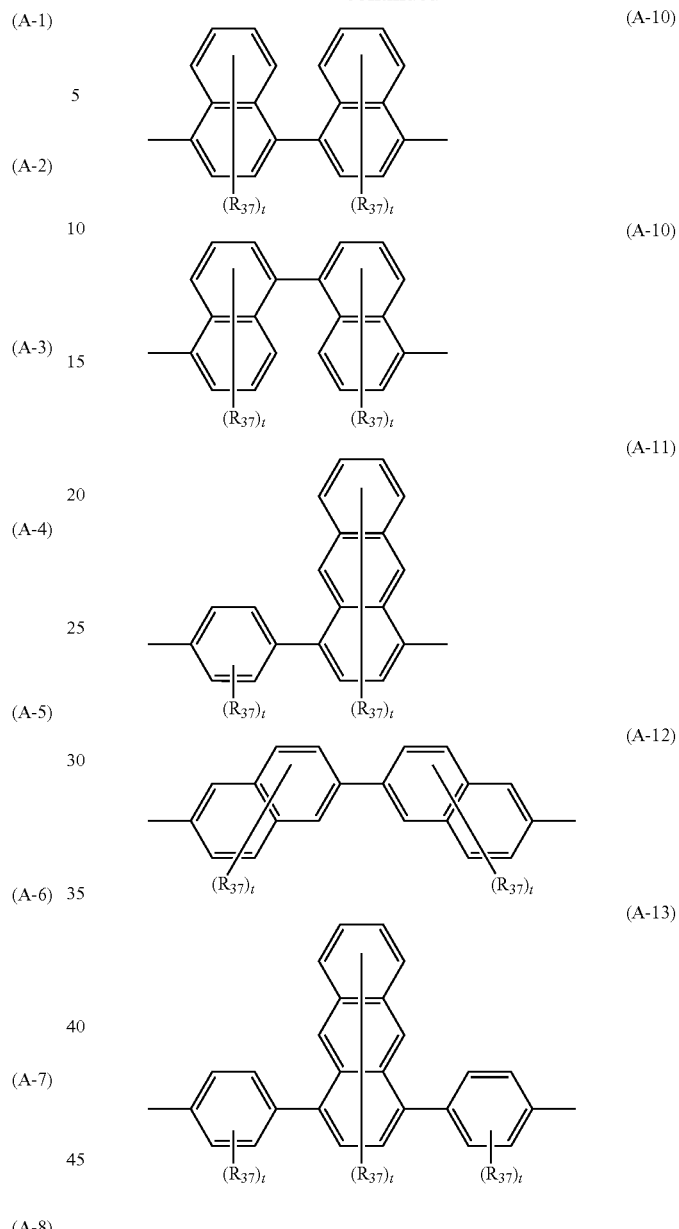

Here, $R_{37}$ represents an alkyl group which may have a substituent, an alkoxy group which may have a substituent, an aryl group which may have a substituent, a heterocyclic group which may have a substituent or a halogen atom, and t represent an integer of zero to four.

Specific examples of the alkyl group of $R_{37}$ which may have a substituent include a methyl group, an ethyl group, an isopropyl group and a 2-ethylhexyl group. Specific examples of the alkoxy group which may have a substituent include a methoxy group, an ethoxy group, an isopropoxy group and a 2-ethylhexyloxy group. Specific examples of the aryl group which may have a substituent include a phenyl group, an o-tolyl group, a p-tolyl group, an α-naphthyl group, a β-naphthyl group, a 4-biphenyl group, a pyrenyl group, a 2-fluorenyl group, a 9,9-dimethyl-2-fluorenyl group, an azulenyl group, an anthryl group, a triphenylenyl group and a chrysenyl group. Specific examples of the heterocyclic group which may have a substituent include a heterocyclic group of a 2-furyl group, a 2-thienyl group, a 5-methyl-2-thienyl group, a 2-pyridyl group and a 4-phenyl-2-pyridyl group. Specific examples of the halogen atom include a fluorine atom, a chlorine atom, a bromine atom and an iodine atom. Specific examples of the alkyl group of Ar₃ which may have a substituent include those alkyl groups given above. Specific examples of the aralkyl group which may have a substituent include a benzyl group, a 1-naphtylmethyl group and a phenethyl group. Specific examples of the aryl group which may have a substituent include those aryl groups given above. Specific examples of the heterocyclic group which may have a substituent include those heterocyclic groups given above.

As the condensed polycyclic aromatic hydrocarbon group which may have a substituent, the structures represented by the following formulae (B-1) to (B-12) may be given.

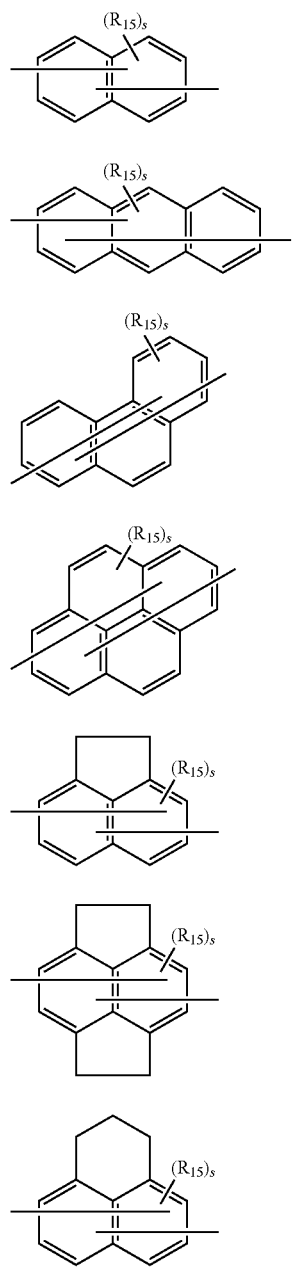

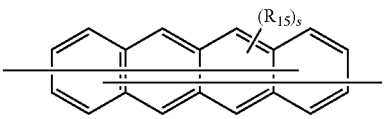

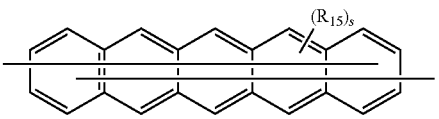

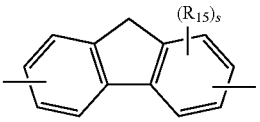

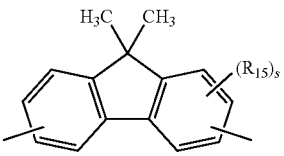

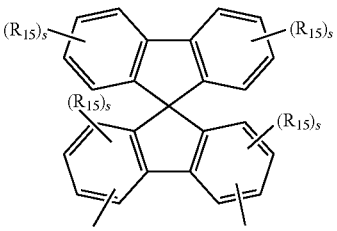

Here, $R_{15}$ represents a hydrogen atom, an alkyl group which may have a substituent, an alkoxy group which may have a substituent, an aryl group which may have a substituent, a heterocyclic group which may have a substituent or a halogen atom, and s represent an integer of zero to six Specific examples of the alkyl group of $R_{15}$ which may have a substituent include a methyl group, an ethyl group, an isopropyl group and a 2-ethylhexyl group. Specific examples of the alkoxy group which may have a substituent include a methoxy group, an ethoxy group, an isopropoxy group and a 2-ethylhexyloxy group. Specific examples of the aryl group which may have a substituent include a phenyl group, an o-tolyl group, a p-tolyl group, an α-naphthyl group, a β-naphthyl group, a 4-biphenyl group, a pyrenyl group, a 2-fluorenyl group, a 9,9-dimethyl-2-fluorenyl group, an azulenyl group, an anthryl group, a triphenylenyl group and a chrysenyl group. Specific examples of the heterocyclic group which may have a substituent include a heterocyclic group of a 2-furyl group, a 2-thienyl group, a 5-methyl-2-thienyl group, a 2-pyridyl group and a 4-phenyl-2-pyridyl group. Specific examples of the halogen atom include a fluorine atom, a chlorine atom, a bromine atom and an iodine atom.

In General Formula (1) above, Ar₃ represents an alkyl group which may have a substituent, an aryl group which may have a substituent or a heterocyclic group which may have a substituent.

Examples of the alkyl group which may have a substituent include a methyl group, an ethyl group, an isopropyl group and a 2-ethylhexyl group. Examples of the aryl group which may have a substituent include a phenyl group, an o-tolyl group, a p-tolyl group, an α-naphthyl group, a β-naphthyl group, a 4-biphenyl group, a pyrenyl group, a 2-fluorenyl group, a 9,9-dimethyl-2-fluorenyl group, an azulenyl group, an anthryl group, a triphenylenyl group and a chrysenyl group. Examples of the heterocyclic group which may have a substituent include a heterocyclic group of a 2-furyl group, a 2-thienyl group, a 5-methyl-2-thienyl group, a 2-pyridyl group and a 4-phenyl-2-pyridyl group.

An acrylic ester compound of the present invention in the second aspect is represented by General Formula (2) below:

<General Formula (2)>

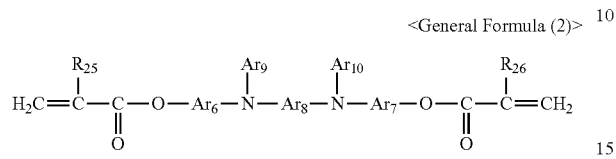

where, in General Formula (2), $R_{25}$ and $R_{26}$ represent a hydrogen atom or a methyl group; $Ar_6$ and $Ar_7$ represent any one of two or more aromatic hydrocarbon groups which may have a bivalent substituent and a condensed polycyclic aromatic hydrocarbon group which may have a substituent; $Ar_9$ and $Ar_{10}$ represent an alkyl group which may have a substituent, an aralkyl group which may have a substituent, an aryl group which may have a substituent or a heterocyclic group which may have a substituent; $Ar_8$ represents an alkylene group which may have a bivalent substituent, an arylene group which may have a bivalent substituent or a heterocyclic group which may have a bivalent substituent;

$Ar_6$ and $Ar_7$ are the same or different, and they represent any one of two or more aromatic hydrocarbon groups which may have a bivalent substituent and a condensed polycyclic aromatic hydrocarbon group which may have a substituent. Examples thereof include any one represented by General Formulae (A-1) to (A-13) above and General Formulae (B-1) to (B-12) above.

$Ar^9$ and $Ar^{10}$ are the same or different, and they represent an alkyl group which may have a substituent, an aryl group which may have a substituent or a heterocyclic group which may have a substituent. Compounds equivalent to those given for General Formula (1) above may be used.

$Ar^8$ represents an alkylene group which may have a substituent or an arylene group which may have a substituent. As the alkylene group which may have a substituent, those represented by the following formulae (C-1) to (C-6) may be given.

Also, as the arylene group which may have a substituent, those represented by the following formulae (C-7) to (C-17) may be given.

(C-1)

—CH$_2$—

(C-2)

—CH$_2$—CH$_2$—

(C-3)

—CH=CH—

(C-4)

—CH=CH—CH=CH—

(C-5)

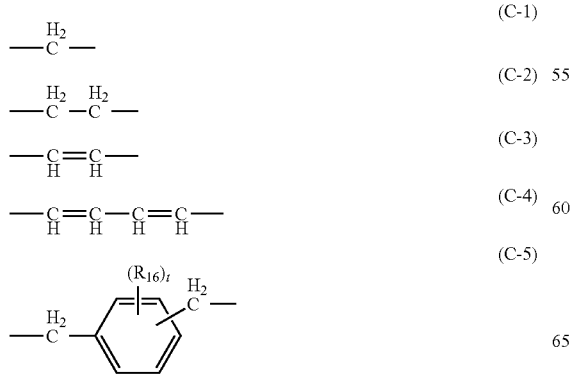

(C-6)

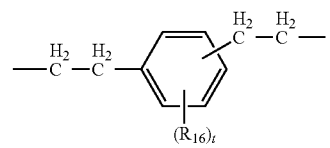

(C-7)

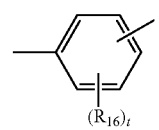

(C-8)

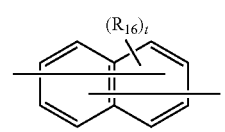

(C-9)

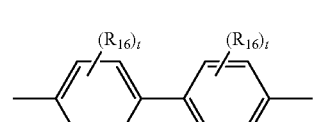

(C-10)

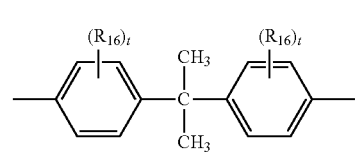

(C-11)

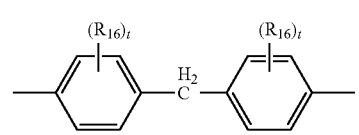

(C-12)

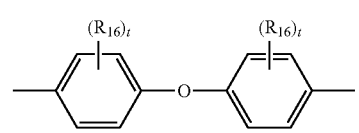

(C-13)

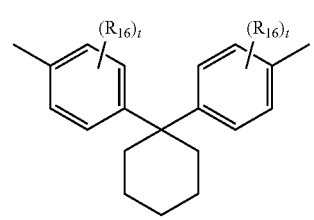

(C-14)

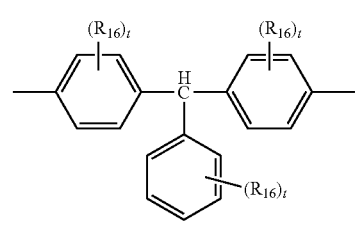

(C-15)

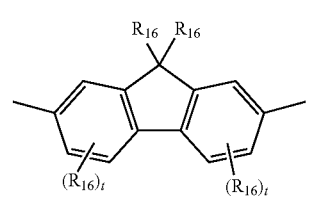

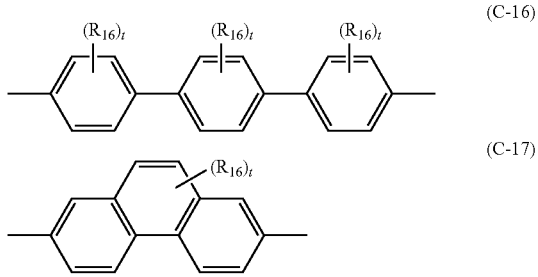

Here, $R_{16}$ represents a hydrogen atom, an alkyl group which may have a substituent, an alkoxy group which may have a substituent, an aryl group which may have a substituent, a heterocyclic group which may have a substituent or a halogen atom, and examples thereof are equivalent to those given for General Formula (1). Also, t represents an integer of zero to four.

<Acrylic Ester Compound Related to Aspect (1-1)>

An acrylic ester compound related to an aspect 1-1 is preferably a compound represented by General Formula (1-1) below. Regarding the acrylic ester compound related to the aspect 1-1, an acrylic ester compound which resolves the above-mentioned problems by introducing an acrylic ester or a methacrylic ester group to a hydroxy compound which has a ternary amine structure including a biphenyl structural unit in the molecule as a main moiety and has a charge transport function.

cause the difference in radical polymerization, they are appropriately selected and used according to the use environment.

Specific examples of $R_3$, $R_4$, $R_5$ and $R_6$ include an alkyl group such as methyl group, ethyl group, n-octyl group and 2-ethylhexyl group; an alkoxy group such as methoxy group, ethoxy group and 2-propoxy group; an aryl group such as phenyl group, p-tolyl group, 1-naphthyl group and 2-naphthyl group; a heterocyclic group such as 2-furyl group, 2-thienyl group, 3-thienyl group, benzothiophene-2-yl group and 2-benzothiazolyl group; and a halogen atom such as fluorine atom, chlorine atom and bromine atom. Among these, the alkyl group, the alkoxy group, the aryl group or the heterocyclic group may respectively have a substituent, and specific examples of the substituent includes those alkyl groups, alkoxy groups, aryl groups and halogen atoms listed above, respectively.

Specific examples of $Ar_3$ include an alkyl group such as methyl group, ethyl group, n-octyl group and a 2-ethylhexyl group; an aralkyl group such as benzyl group and phenethyl group; an aryl group such as phenyl group, p-tolyl group, 1-naphthyl group and 2-naphthyl group; a heterocyclic group such as 2-furyl group, 2-thienyl group, 3-thienyl group, benzothiophene-2-yl group and 2-benzothiazolyl group. These may have a substituent, and the examples of the substituent are those alkyl groups, alkoxy groups, aryl groups and halogen groups listed above.

<General Formula (1-1)>

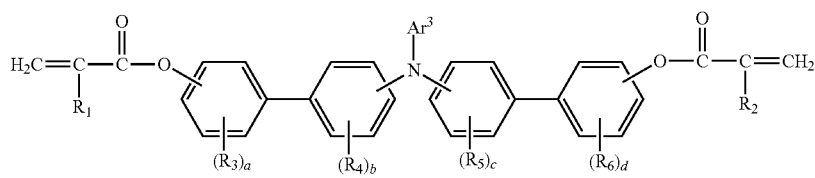

where in General Formula (1-1), $R_1$, $R_2$ and $Ar^3$ are equivalent to those in General Formula (1); $R_3$, $R_4$, $R_5$ and $R_6$ represent an alkyl group which may have a substituent, an alkoxy group which may have a substituent, an aryl group which may have a substituent, a heterocyclic group which may have a substituent or a halogen atom; a, b, c and d are the same or different and represent an integer of zero to four.

$R_1$ and $R_2$ in General Formula (1-1) above represents a hydrogen atom or a methyl group, and they are the same or different. Since the hydrogen atom and the methyl group These substituents of $Ar_3$ may be bonded with the alkyl group, aralkyl group, aryl group, condensed polycyclic hydrocarbon group or heterocyclic group through N, O, $CH_2$ or $C(CH_3)_2$. The substituent itself may have a substituent including the alkyl groups, alkoxy groups, aryl groups and halogen atoms mentioned above.

Also, the acrylic ester compound related to the aspect 1-1 is a compound preferably represented by General Formula (1-2) below.

<General Formula (1-2)>

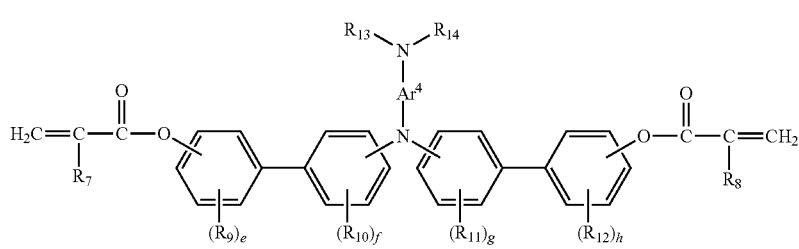

where, in General Formula (1-2), $R_7$ and $R_8$ are the same or different and represent a hydrogen atom or a methyl group; $R_9$, $R_{10}$, $R_{11}$ and $R_{12}$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $R_{13}$ and $R_{14}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{13}$ and $R_{14}$ may be bonded together to form a heterocycle; e, f, g and h are the same or different and represent an integer of zero to four.

In General Formula (1-2), $R_7$ and $R_8$ represent a hydrogen atom or a methyl group, and they are the same or different. Since the hydrogen atom and the methyl group cause the difference in radical polymerization, they are appropriately selected and used according to the use environment.

Specific examples of $R_9$, $R_{10}$, $R_{11}$ and $R_{12}$ are synonymous to the alkyl groups, the alkoxy groups, the aryl groups, the heterocyclic groups or the halogen atoms described for General Formula (1-1) above, respectively. Among these, the alkyl groups, the alkoxy groups, the aryl groups or the heterocyclic groups may have a substituent. Specific examples of the substituent include those alkyl groups, alkoxy groups, aryl groups and halogen atoms mentioned above.

Specific examples of $Ar_4$ include an alkylene group such as methylene group and 1,2-ethylene group; an arylene group such as 1,2-phenylene group, 1,4-phenylene group, 4,4'-biphenylene group and 2,6-naphthylene group; a bivalent condensed polycyclic hydrocarbon group such as fluorenylidene; and a bivalent heterocyclic group such as 2,5-thienylene and 2,5'-dithienylene. These may have a substituent, and the specific examples of the substituent include those alkyl groups, alkoxy groups, aryl groups or halogen atoms, respectively. Regarding the arylene group, the phenyl group may be a bivalent group which is bonded with a bivalent group such as oxygen atom, $CH_2$ and $C(CH_3)$.

Specific examples of $R_{13}$ and $R_{14}$ include the above-mentioned alkyl groups; aralkyl groups such as benzyl group and 1-naphtylmethyl group; the above-mentioned aryl groups; the above-mentioned heterocyclic groups; the above-mentioned condensed polycyclic hydrocarbon groups; and heterocyclic groups such as carbazole group which is formed by bonding $R_{13}$ and $R_{14}$, and each of these may have a substituent. Specific examples of the substituent include the above-mentioned alkyl groups, alkoxy groups, aryl groups and halogen atoms, respectively.

Also, the acrylic ester compound related to the aspect 1-1 is a compound preferably represented by General Formula (1-3) below.

<General Formula (1-3)>

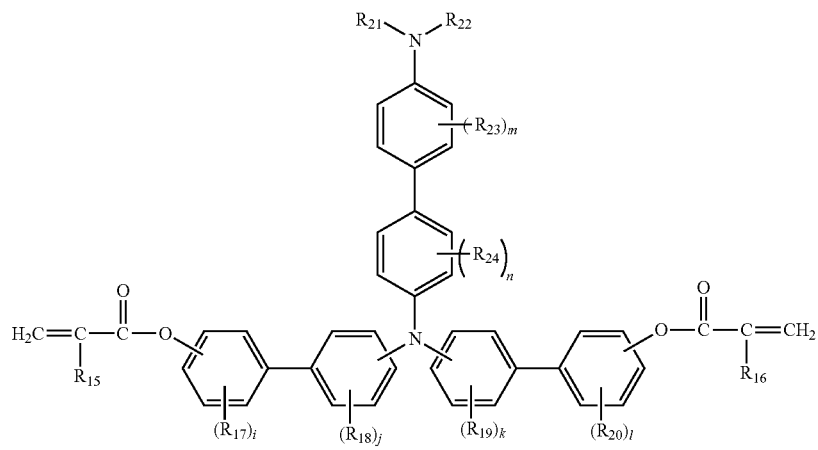

where, in General Formula (1-3), $R_{15}$ and $R_{16}$ are the same or different and represent a hydrogen atom or a methyl group; $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; i, j, k, l, m and n are the same or different and represent an integer of zero to four.

In General Formula (1-3), $R_{15}$ and $R_{16}$ represent a hydrogen atom or a methyl group, and they are the same or different. Since the hydrogen atom and the methyl group cause the difference in radical polymerization, they are appropriately selected and used according to the use environment.

Specific examples of $R_{17}$, $R_{18}$, $R_{19}$, $R_{20}$, $R_{23}$ and $R_{24}$ include the above-mentioned alkyl groups, alkoxy groups, aryl groups, heterocyclic groups or halogen atoms. Among these, the alkyl groups, the alkoxy groups, the aryl groups or the heterocyclic groups may have a substituent. Specific examples of the substituent include those alkyl groups, alkoxy groups, aryl groups and halogen atoms mentioned above.

Specific examples of $R_{21}$ and $R_{22}$ include the above-mentioned alkyl groups, aralkyl groups, aryl groups, heterocyclic groups and the condensed polycyclic hydrocarbon groups, and each of these may have a substituent. Specific examples of the substituent include those alkyl groups, alkoxy groups, aryl groups and halogen atoms mentioned above.

<Acrylic Ester Compound Related to Aspect 2-1>

An acrylic ester compound related to an aspect 2-1 of the present invention preferably is a compound represented by General Formula (2-1) below.

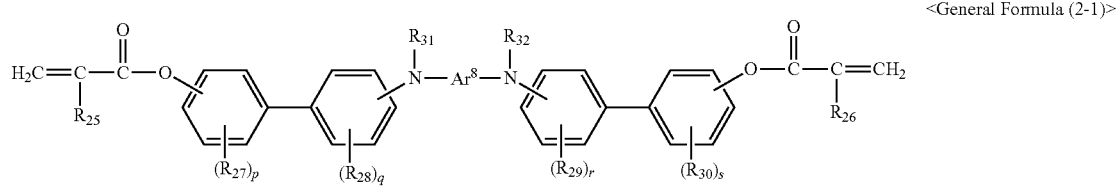

<General Formula (2-1)> where, in General Formula (2-1), $R_{27}$, $R_{28}$, $R_{29}$ and $R_{30}$ represent an alkyl group which may have a substituent, an alkoxy group which may have a substituent, an aryl group which may have a substituent, a heterocyclic group which may have a substituent or a halogen atom; $R_{31}$ and $R_{32}$ represent an alkyl group which may have a substituent, an aralkyl group which may have a substituent, an aryl group which may have a substituent, a heterocyclic group which may have a substituent or a heterocyclic group which may have a substituent; $R_{25}$, $R_{26}$ and $Ar^8$ are equivalent to those in General Formula (2); p, q, r and s are the same or different and represent an integer of zero to four.

In General Formula (2-1) above, $R_{25}$ and $R_{26}$ may be a hydrogen atom or a methyl group, and they are the same or different. As mentioned above, since the hydrogen atom and the methyl group cause the difference in chain polymerization such as radical polymerization, they are appropriately selected and used according to the use environment.

Specific examples of $R_{27}$, $R_{28}$, $R_{29}$ and $R_{30}$ include the above-mentioned alkyl groups, alkoxy groups, aryl groups, heterocyclic groups and halogen atoms, respectively. Among these, the alkyl groups, the alkoxy groups, the aryl groups or the heterocyclic groups may have a substituent. Specific examples of the substituent include those alkyl groups, alkoxy groups, aryl groups and halogen atoms mentioned above.

Specific examples of $R_{31}$ and $R_{32}$ include the above-mentioned alkyl groups, aralkyl groups, aryl groups or heterocyclic groups, and each of these may have a substituent. Specific examples of the substituent include those alkyl groups, alkoxy groups, aryl groups and halogen atoms mentioned above.

Specific examples of $Ar^8$ include those represented by the formulae (C-1) to (C-6) above, and specific examples of the arylene group which may have a substituent and the bivalent condensed polycyclic hydrocarbon group which may have a substituent include those represented by the formulae (C-7) to (C-17) above.

Specific examples of the acrylic ester compound of the present invention represented by General Formulae (1-1) to (1-3) and (2-1) above is given as follows, but these illustrative compounds are not to be construed as limiting the present invention.

First, acrylic ester compounds of the present invention represented by General Formulae (1-1) to (1-3) above are shown below as formulae (D-1) to (D-57).

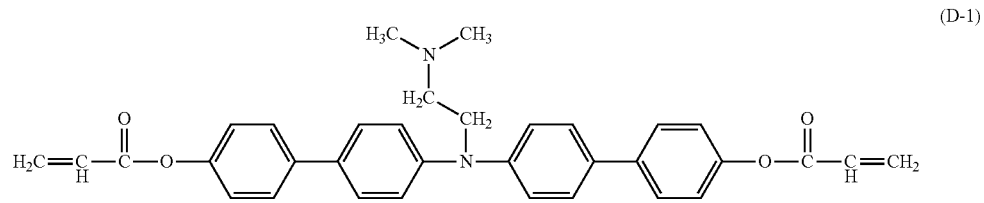

(D-1)

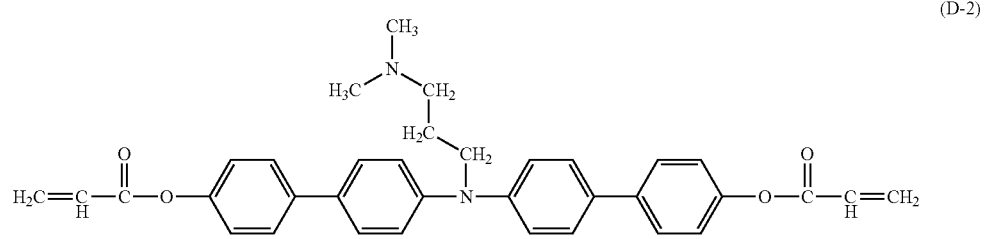

(D-2)

-continued
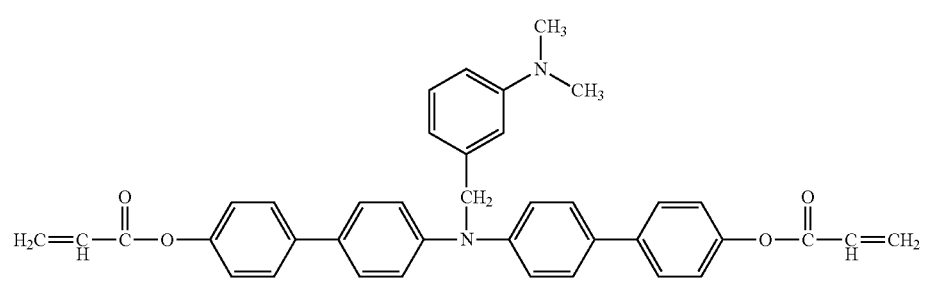
(D-3)
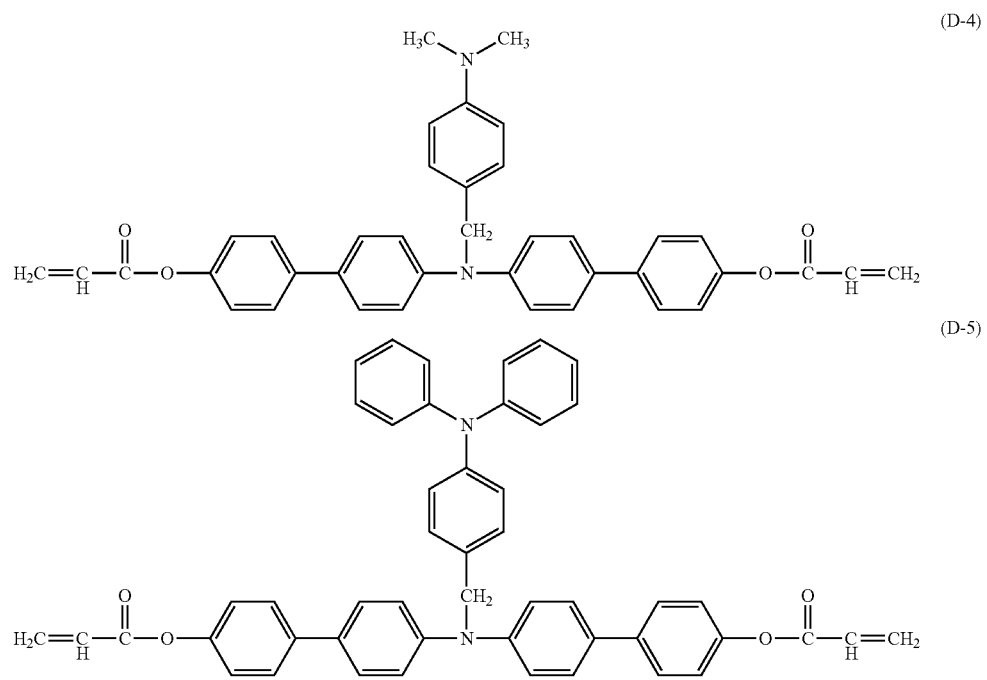
(D-4)
(D-5)
(D-6)
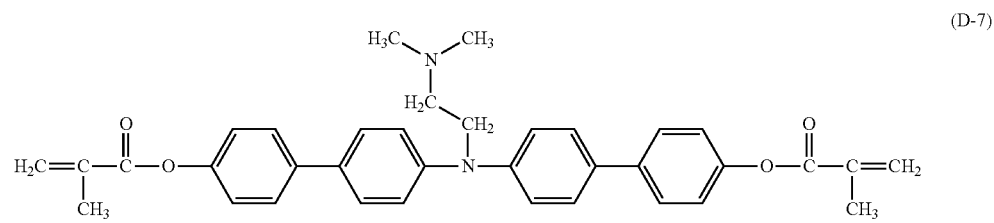
(D-7)

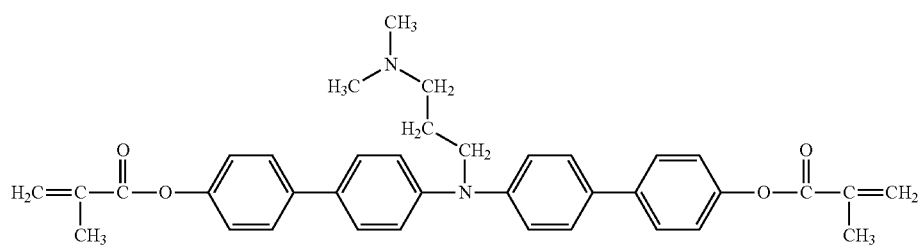
(D-8)
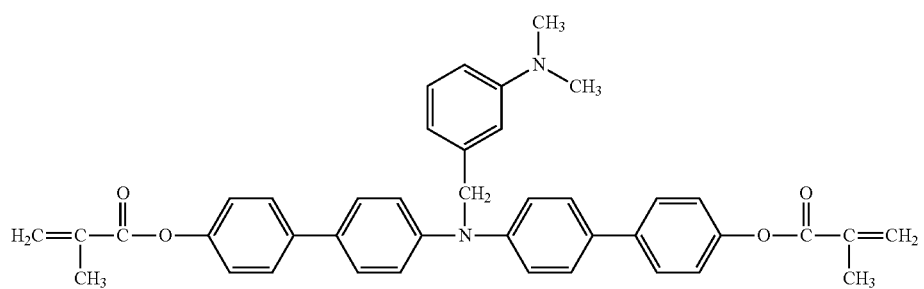
(D-9)
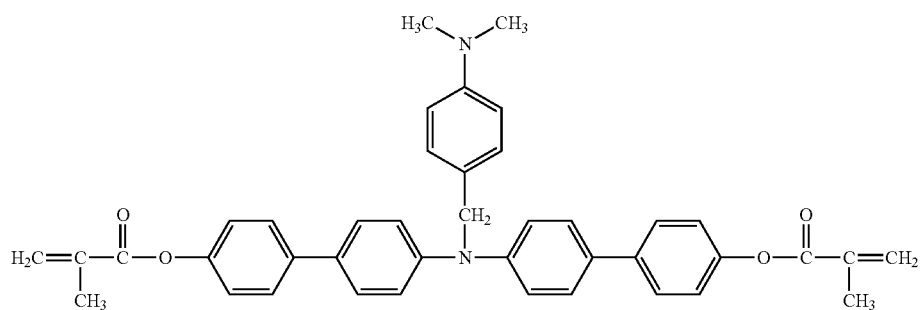
(D-10)
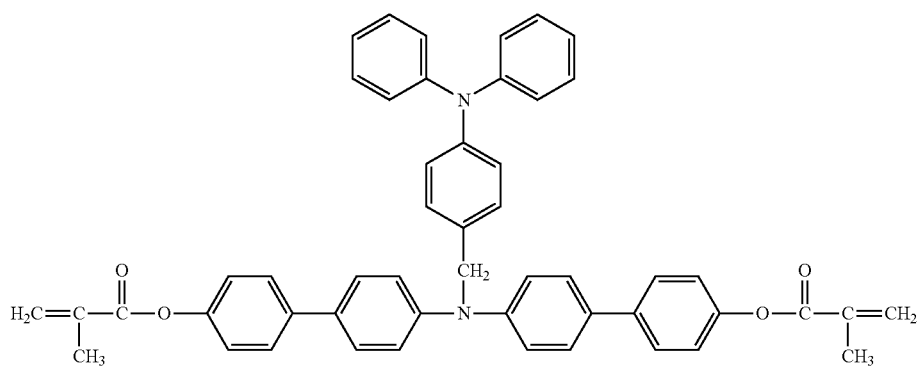
(D-11)
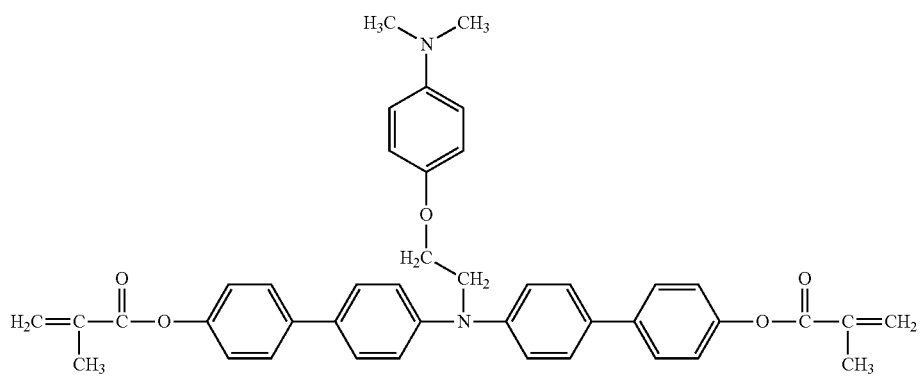
(D-12)

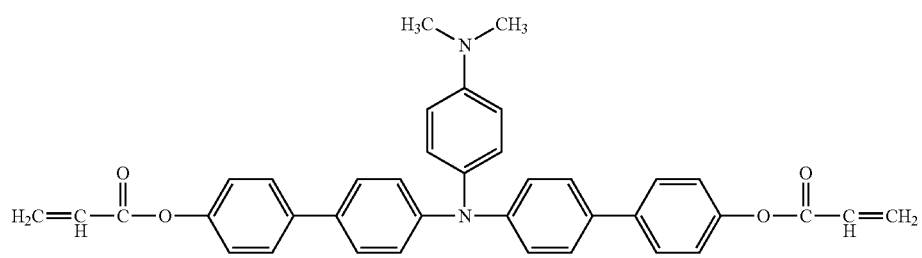
(D-13)
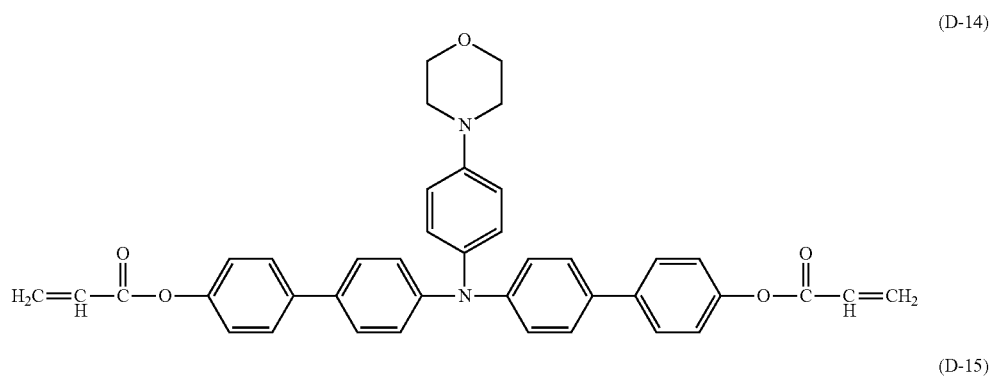
(D-14)
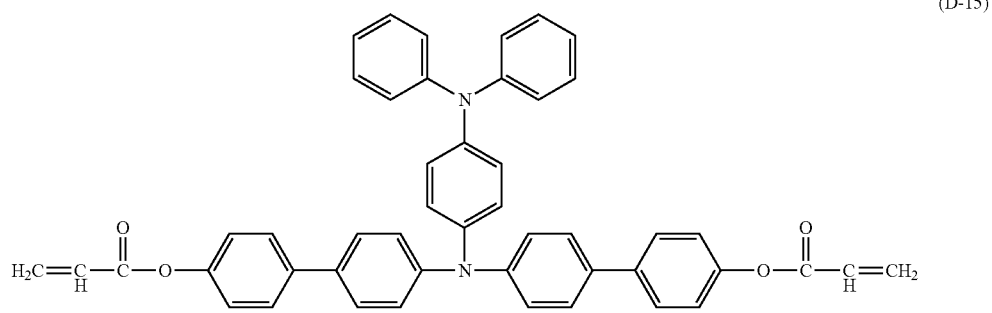
(D-15)
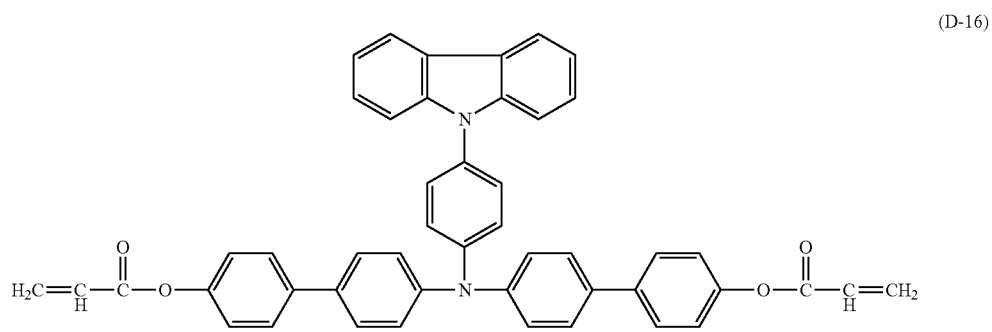
(D-16)
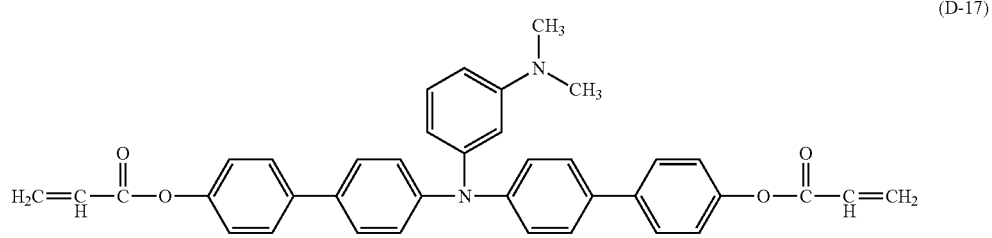
(D-17)

-continued
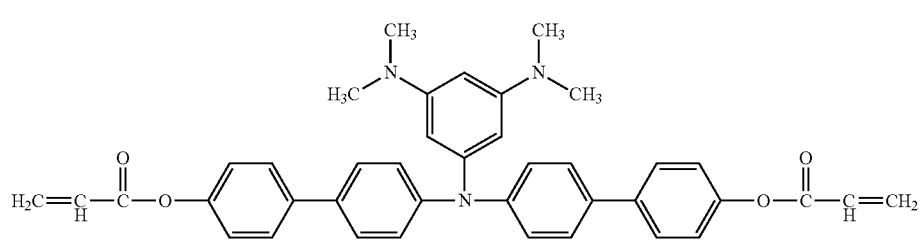
(D-18)
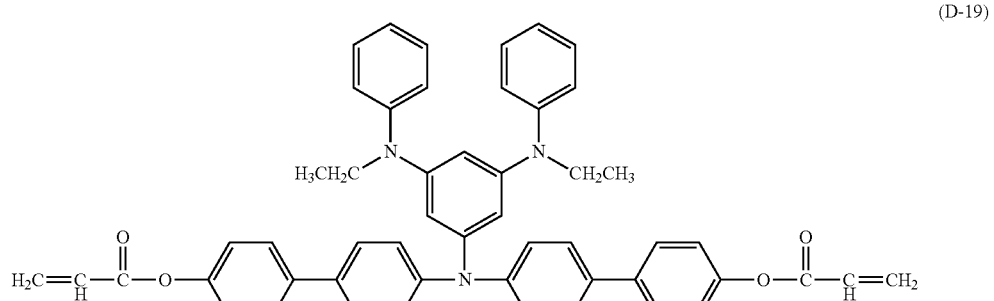
(D-19)
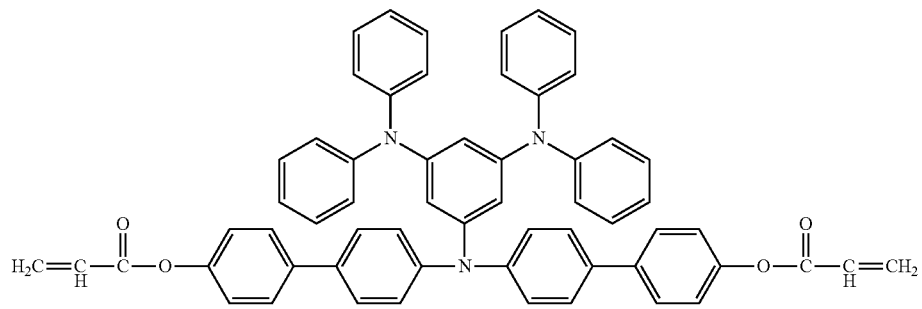
(D-20)
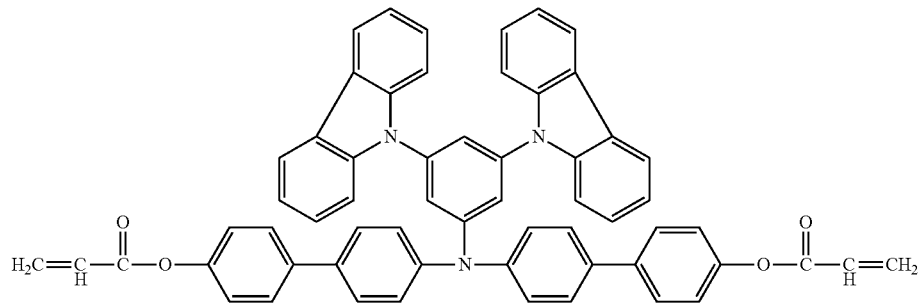
(D-21)
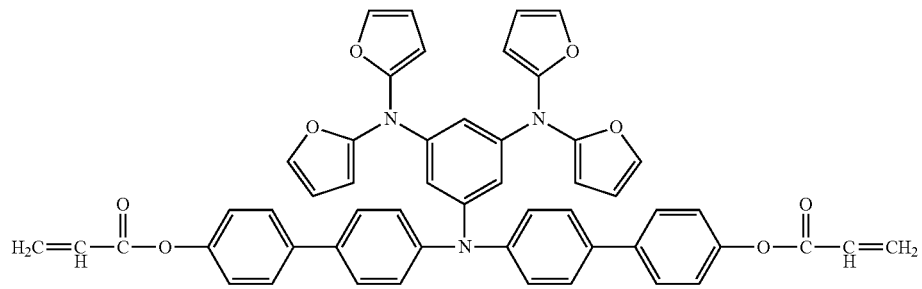
(D-22)

-continued
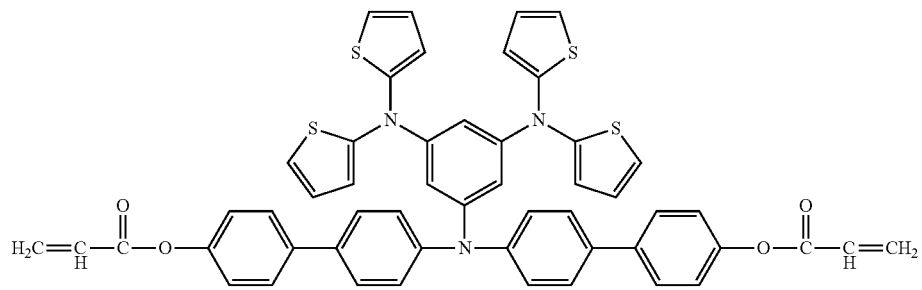
(D-23)
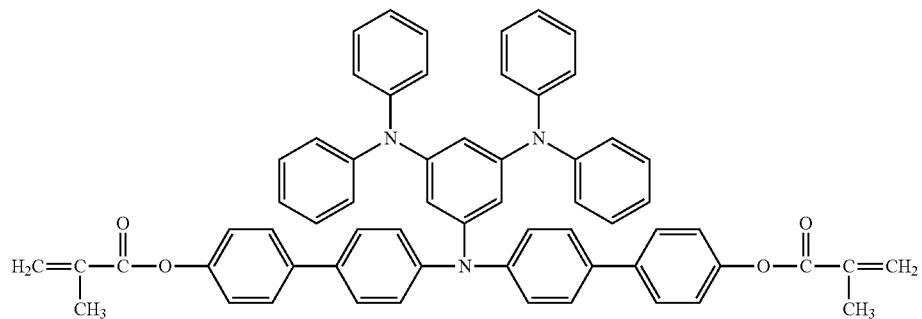
(D-24)
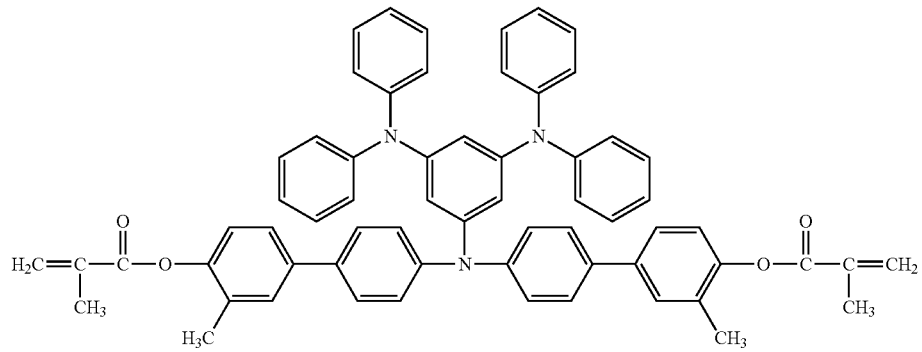
(D-25)
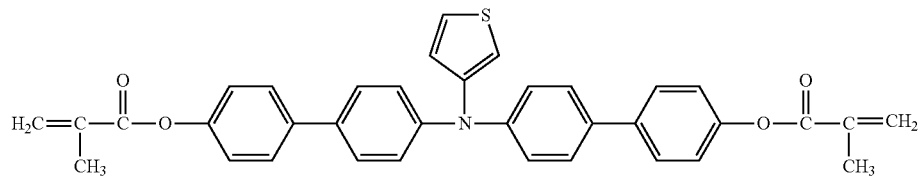
(D-26)
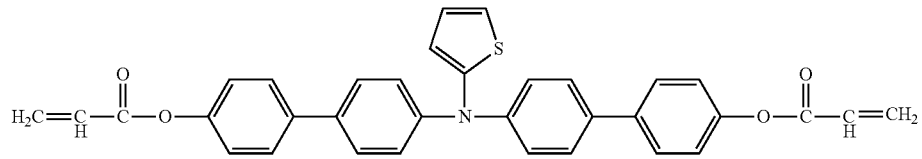
(D-27)
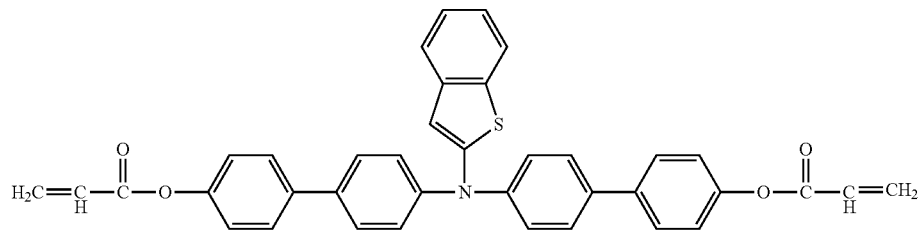
(D-28)

-continued
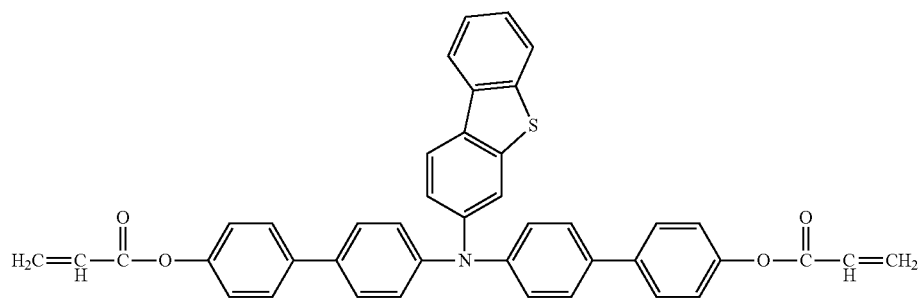
(D-29)
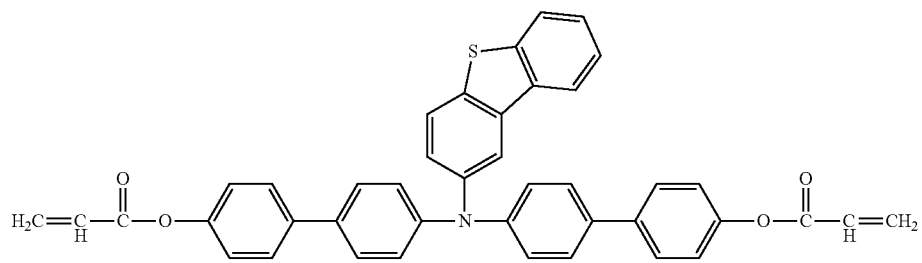
(D-30)
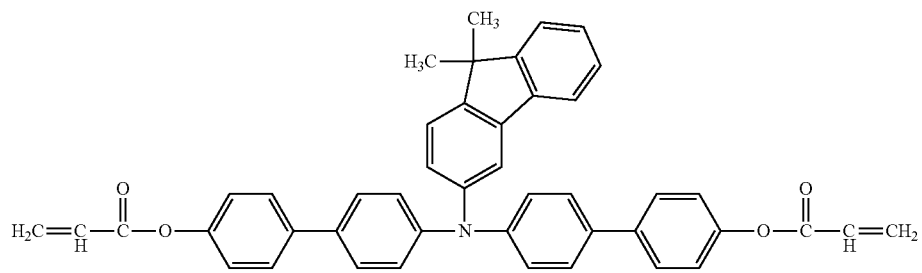
(D-31)
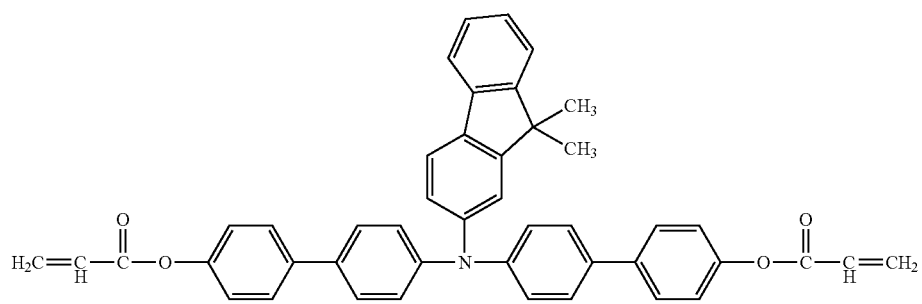
(D-32)
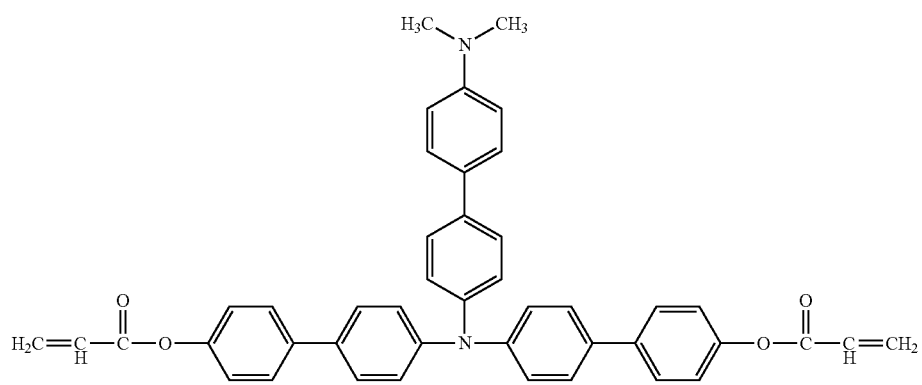
(D-33)

-continued
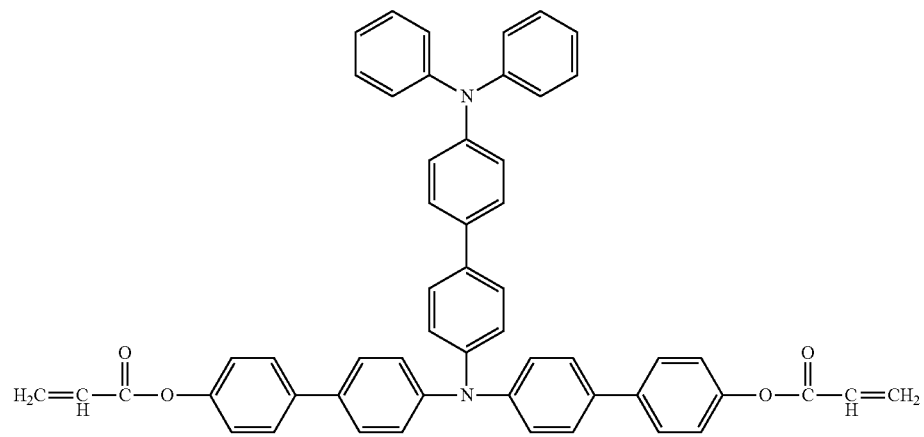
(D-34)
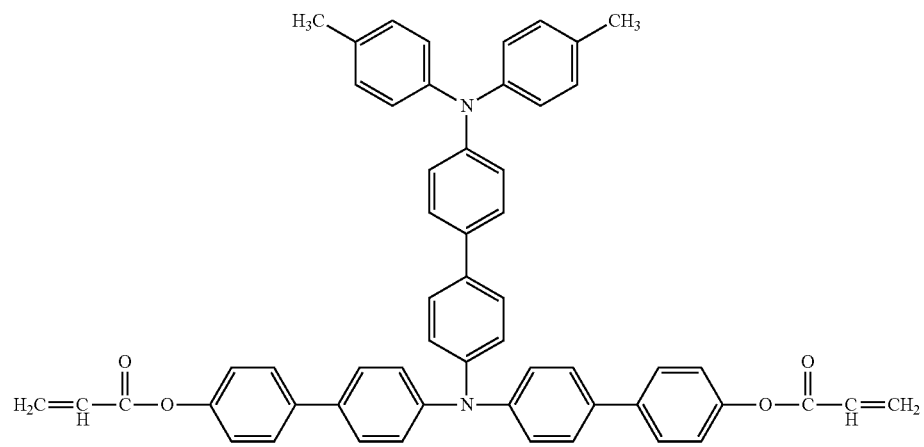
(D-35)
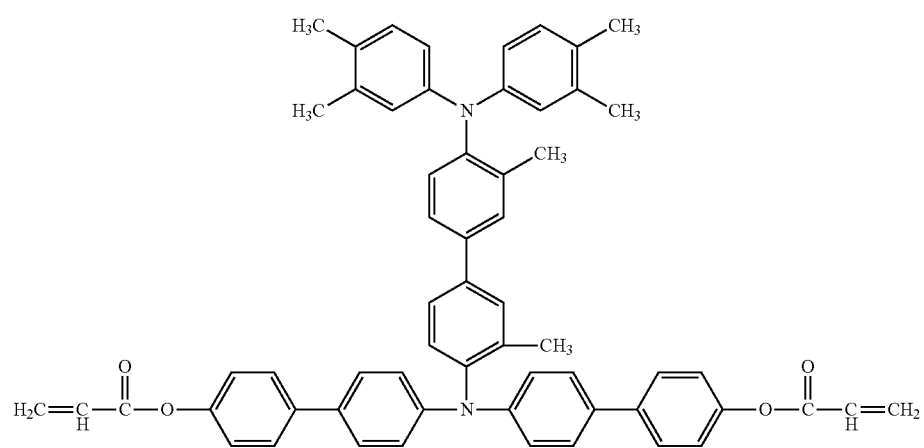
(D-36)

-continued
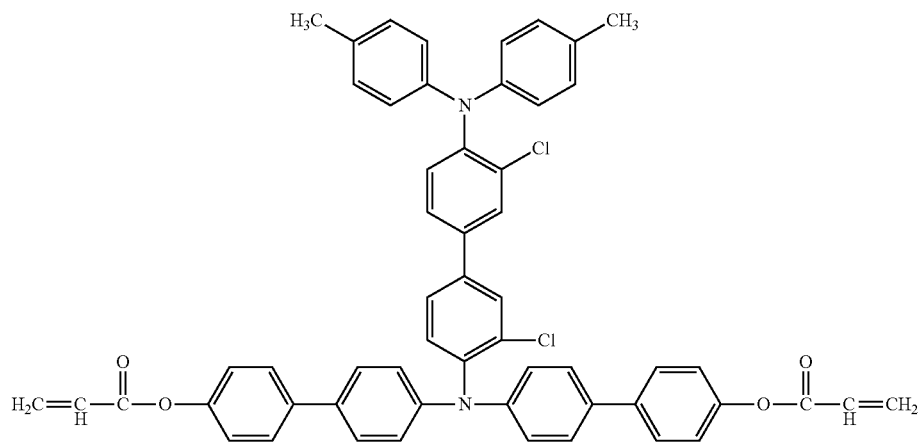
(D-37)
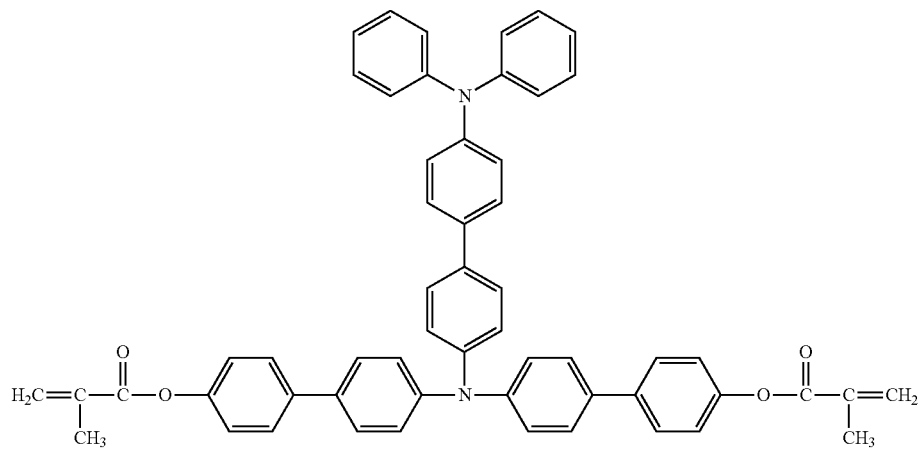
(D-38)
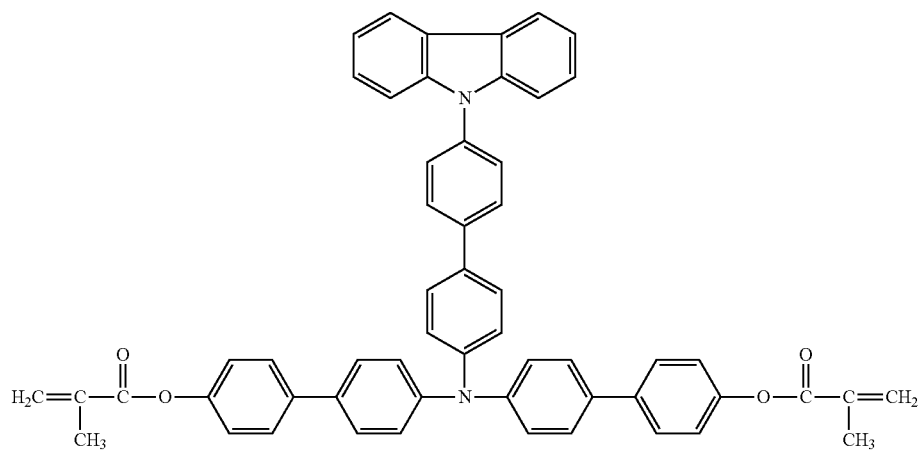
(D-39)

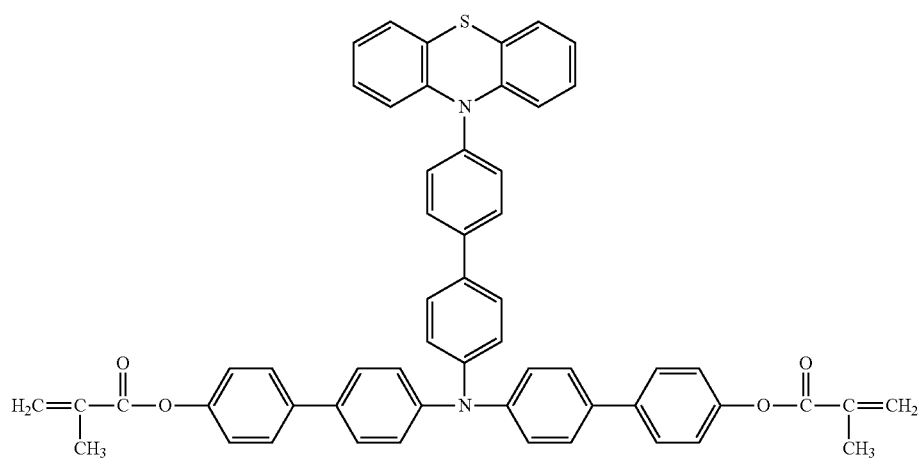
(D-40)
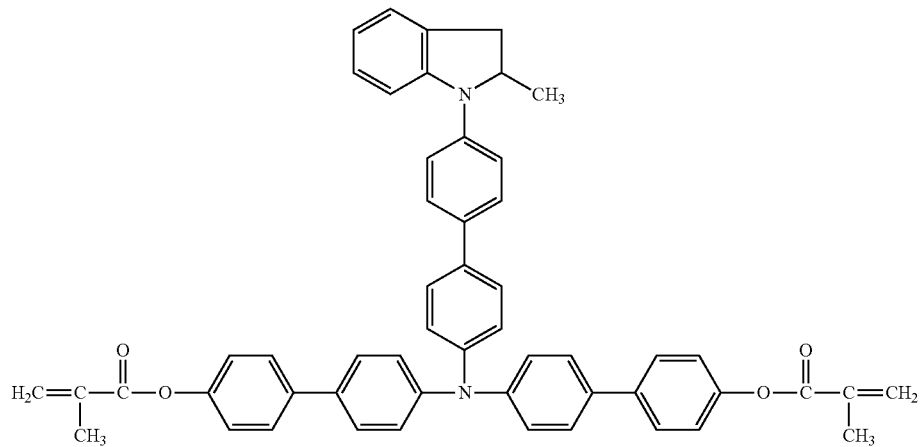
(D-41)
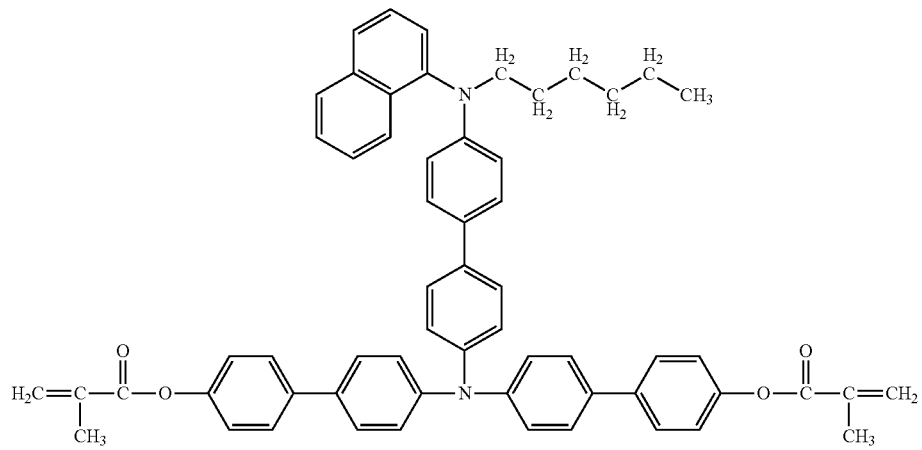
(D-42)

-continued
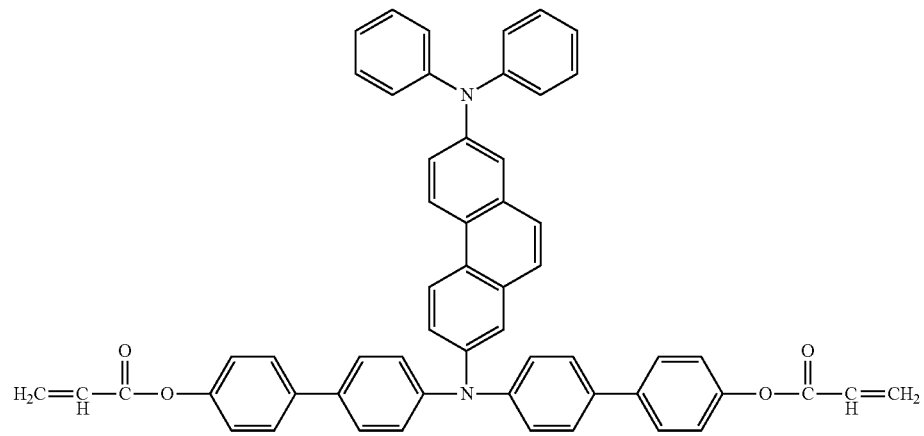
(D-43)
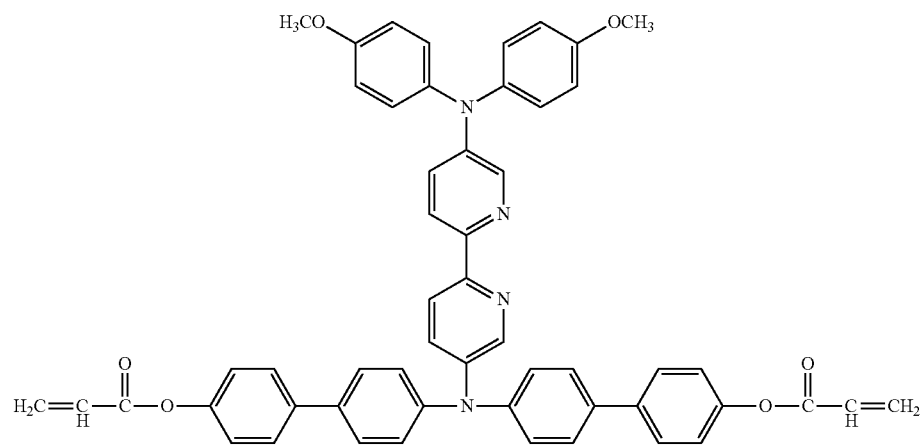
(D-44)
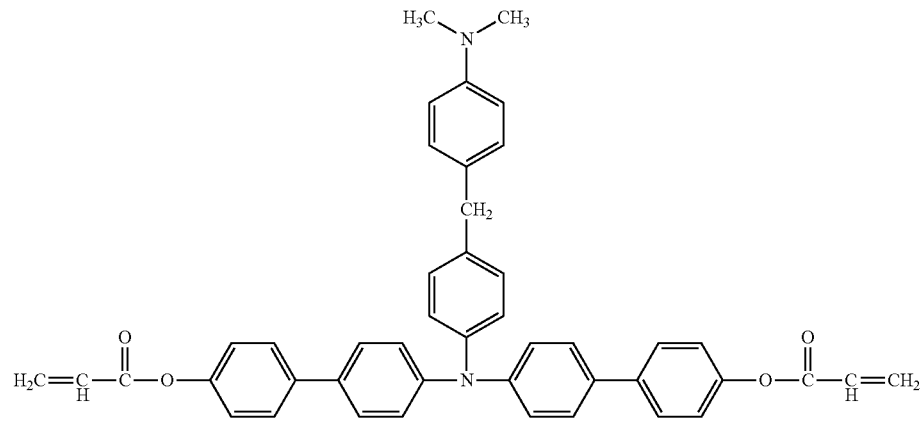
(D-45)

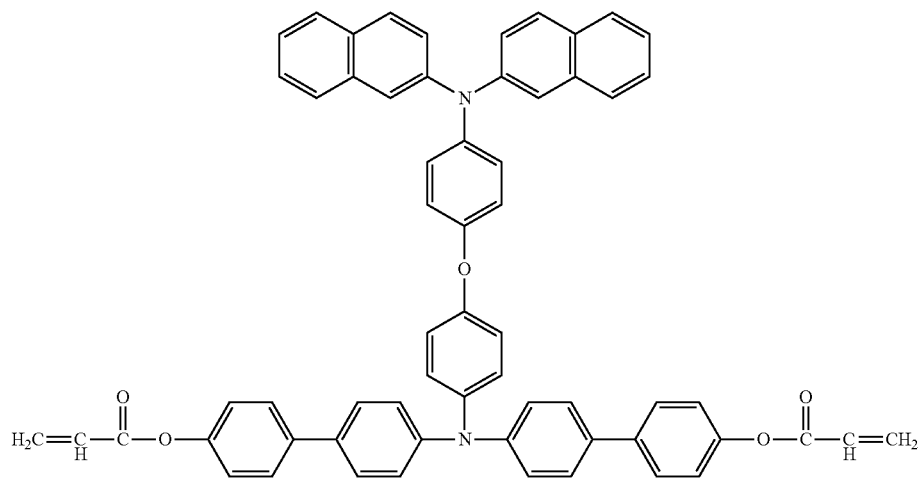
(D-46)
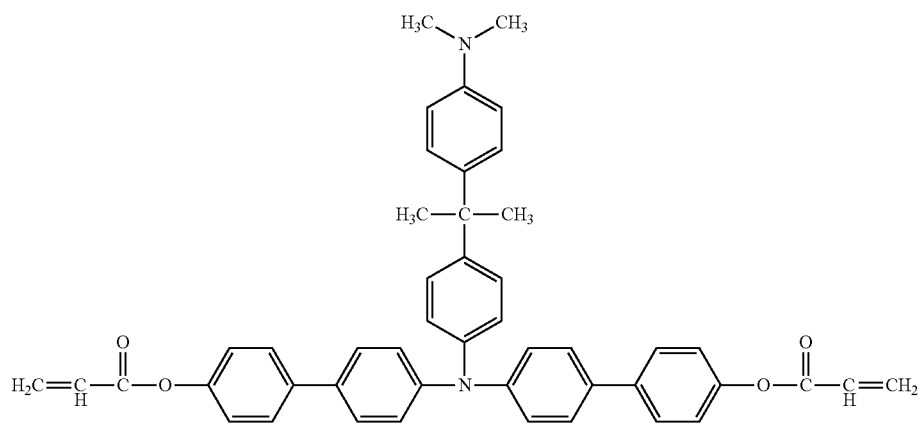
(D-47)
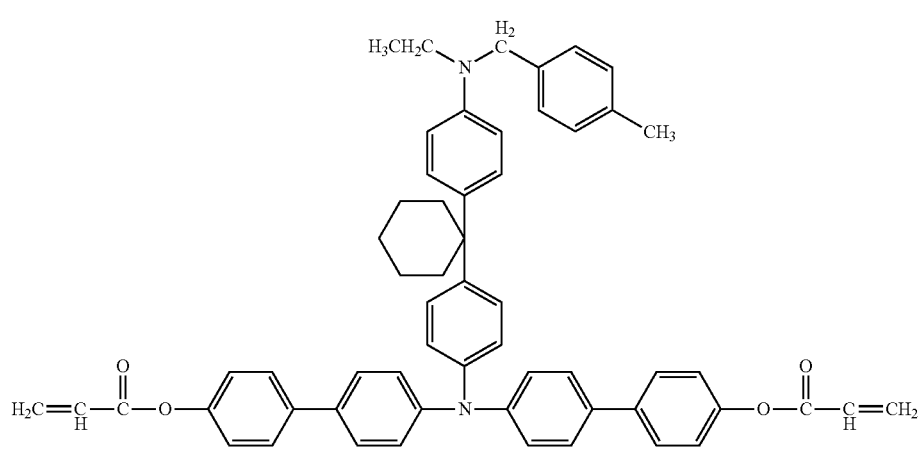
(D-48)

(D-49)
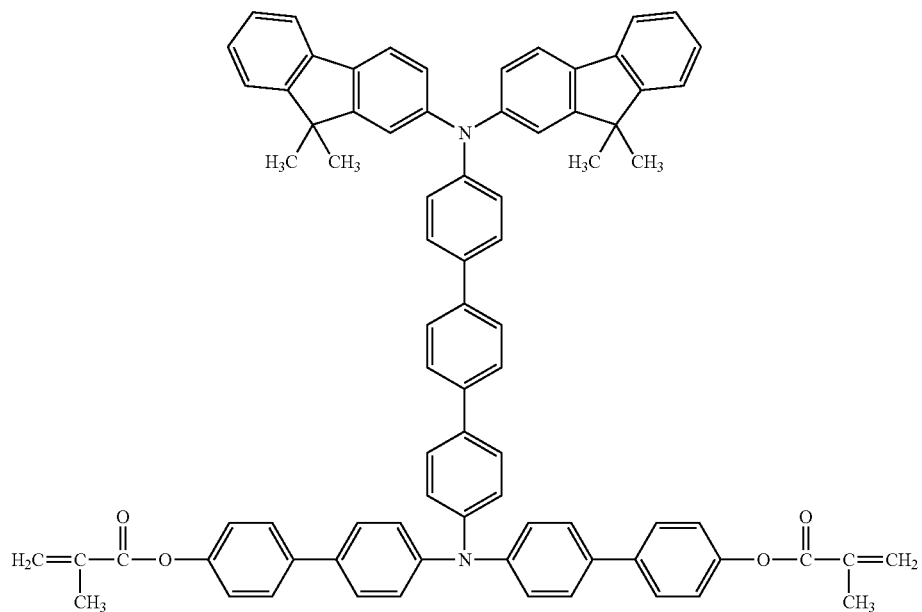
(D-50)
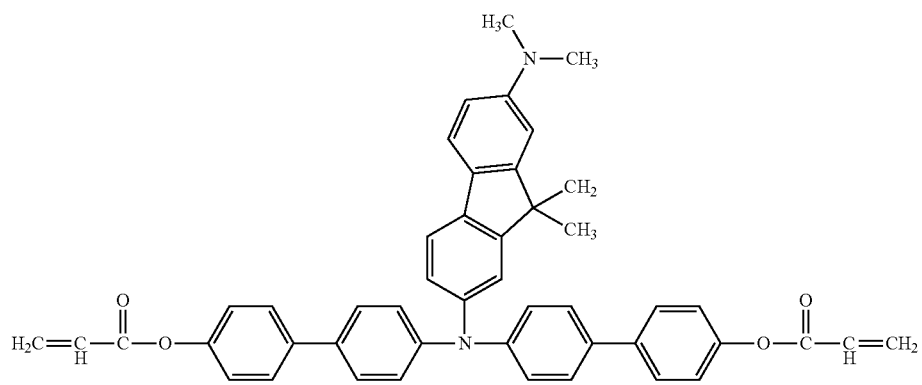
(D-51)
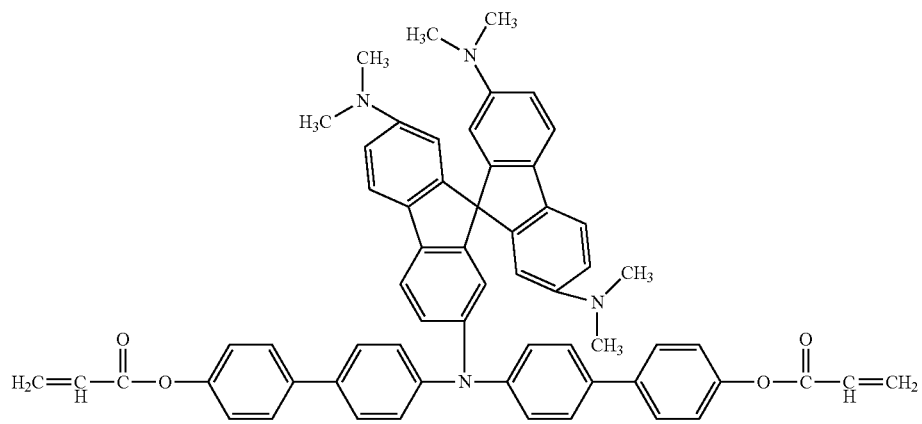

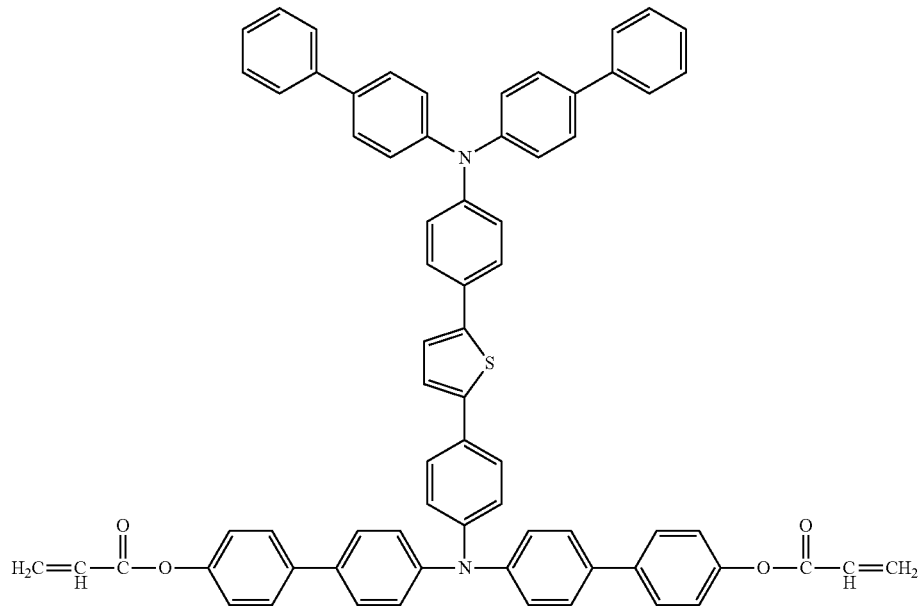
(D-52)
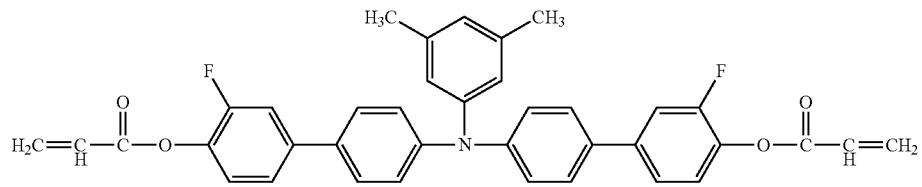
(D-53)
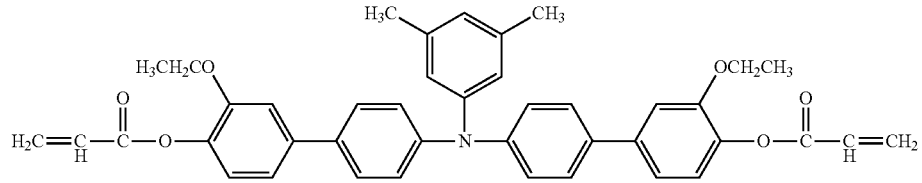
(D-54)
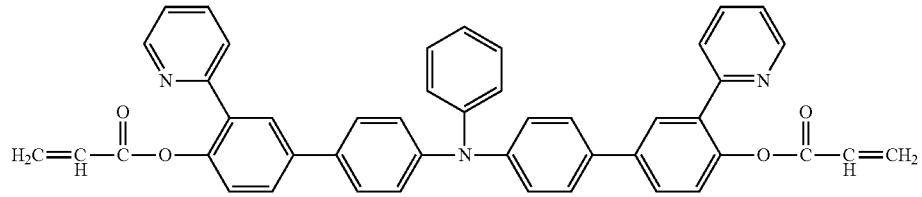
(D-55)
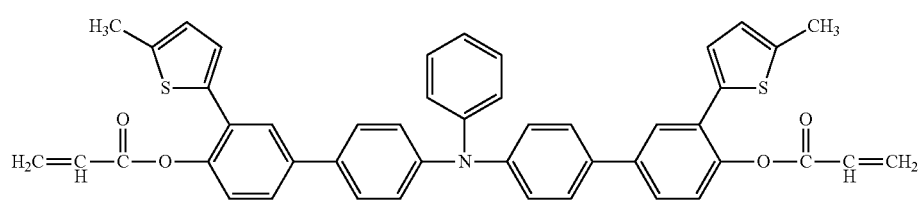
(D-56)

(D-57)
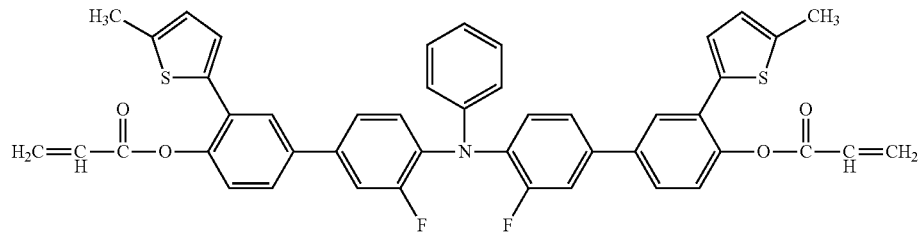
Next, acrylic ester compounds of the present invention represented by General Formulae (2-1) above are shown below as formulae (E-1) to (E-33).
(E1)
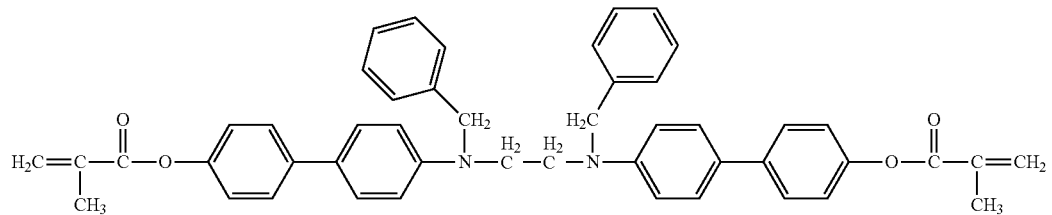
(E-2)
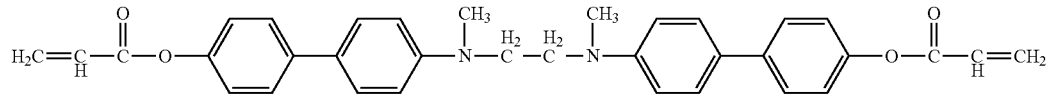
(E-3)
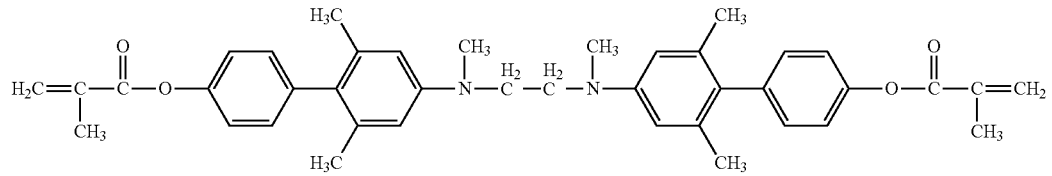
(E-4)
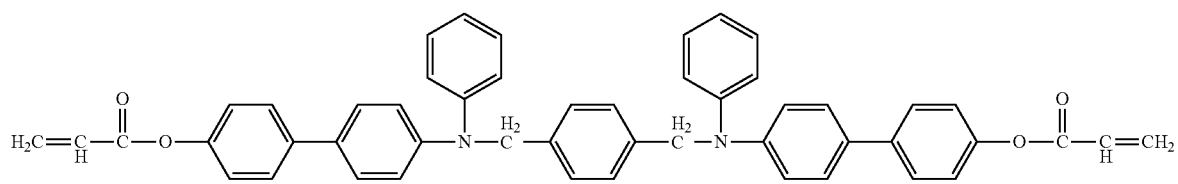
(E-5)
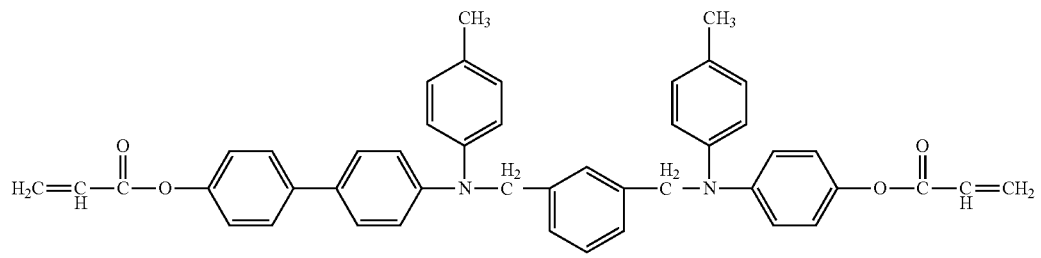
(E6)
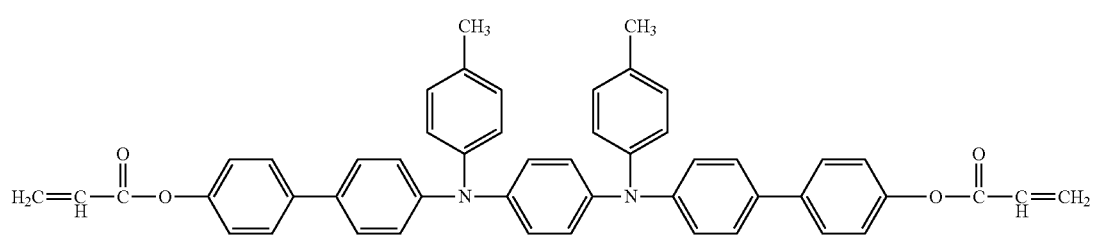

-continued
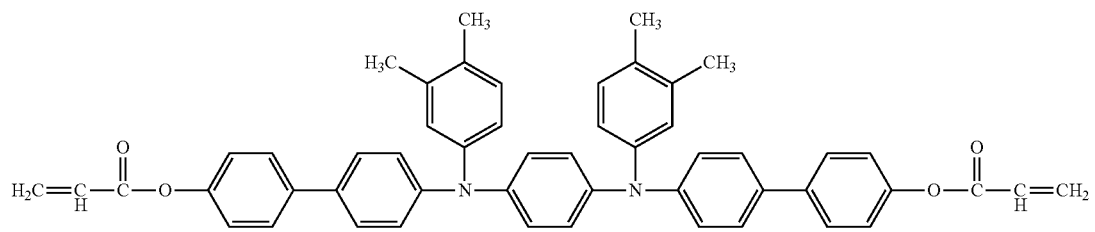
(E7)
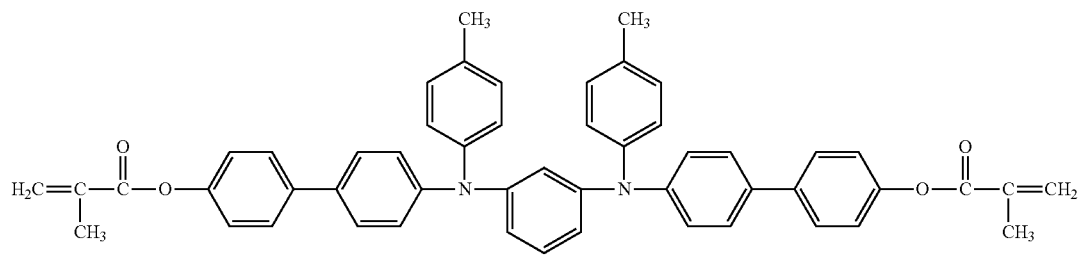
(E-8)
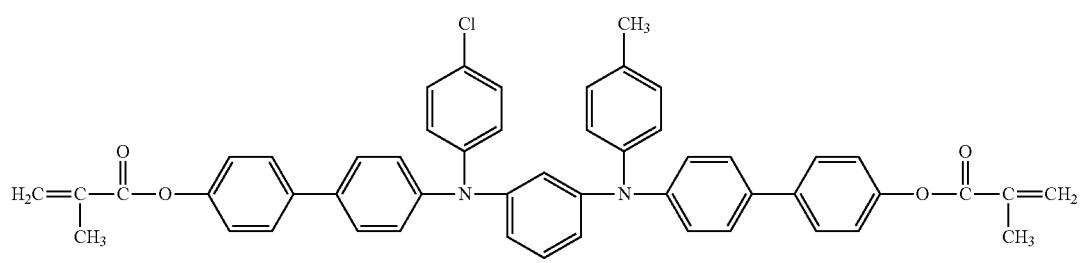
(E-9)
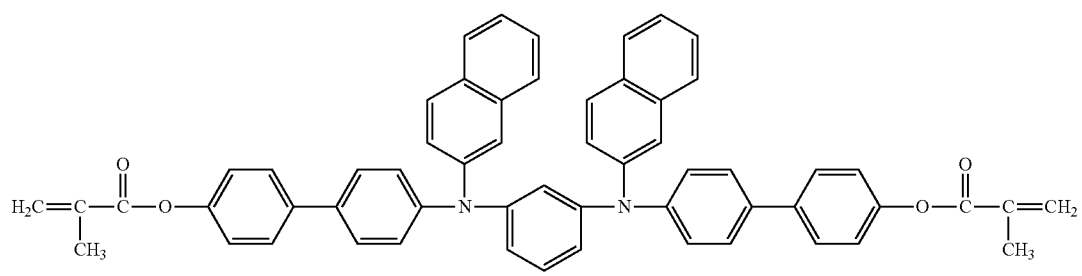
(E-10)
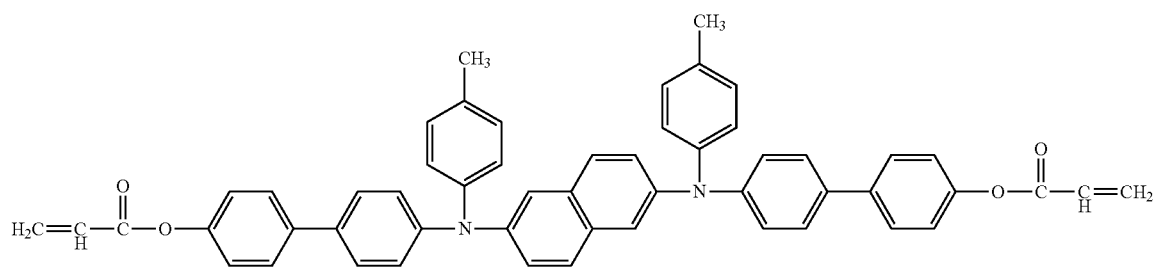
(E-11)
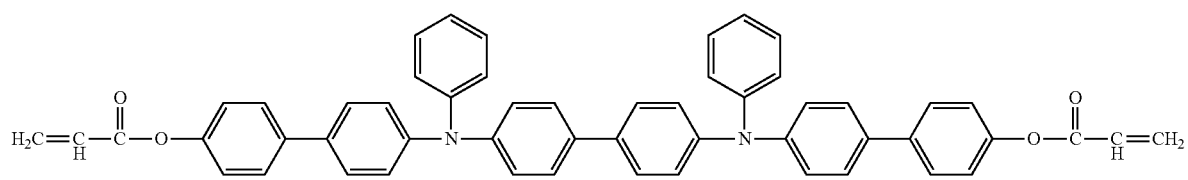
(E-12)

-continued
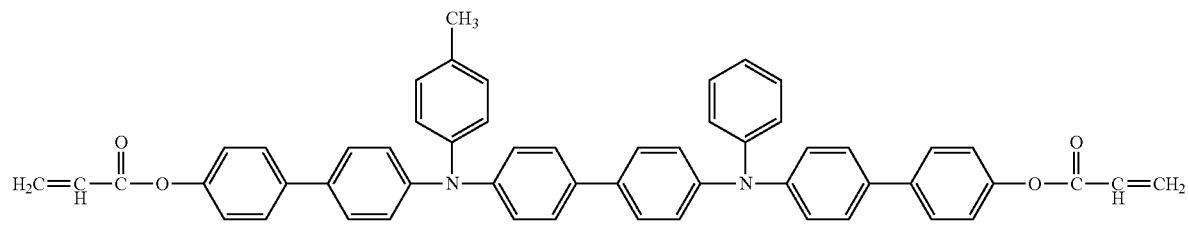
(E-13)
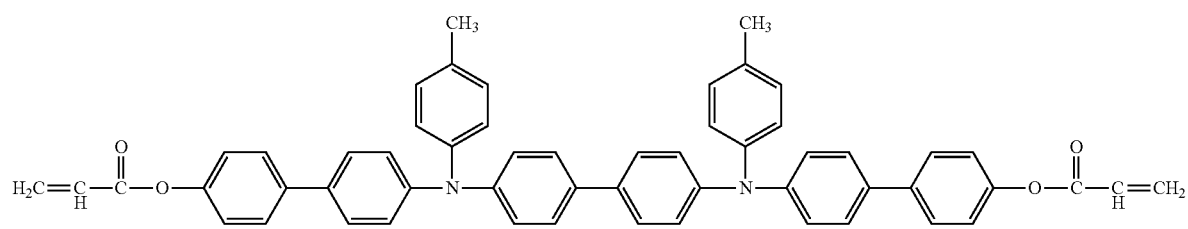
(E-14)
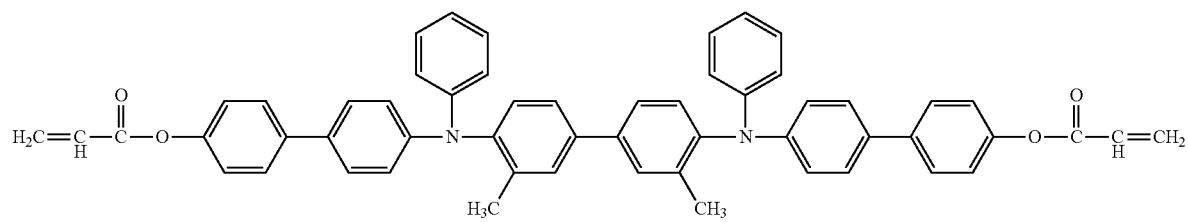
(E-15)
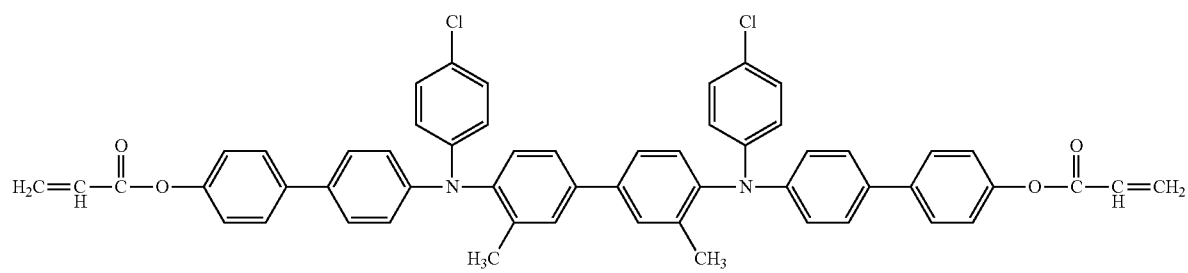
(E-16)
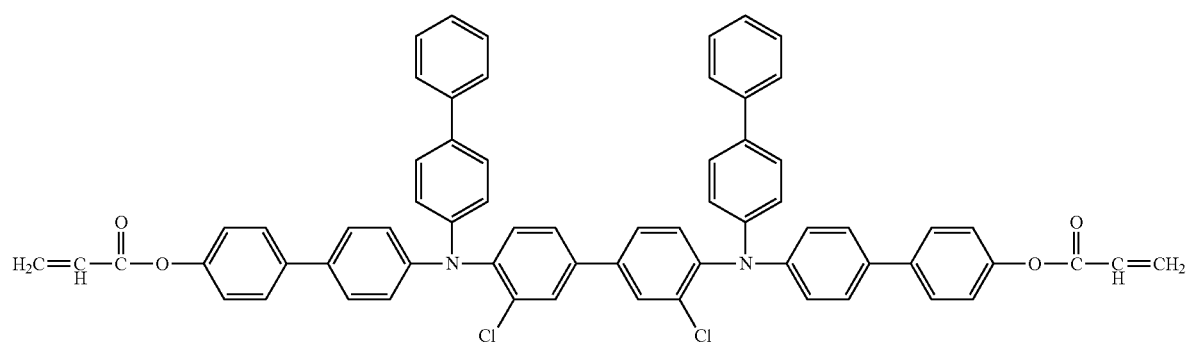
(E-17)

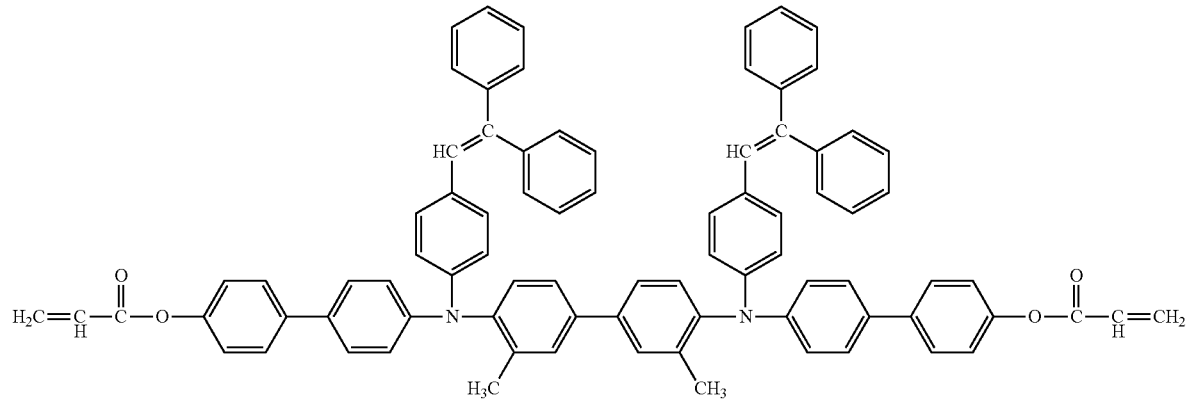
(E-18)
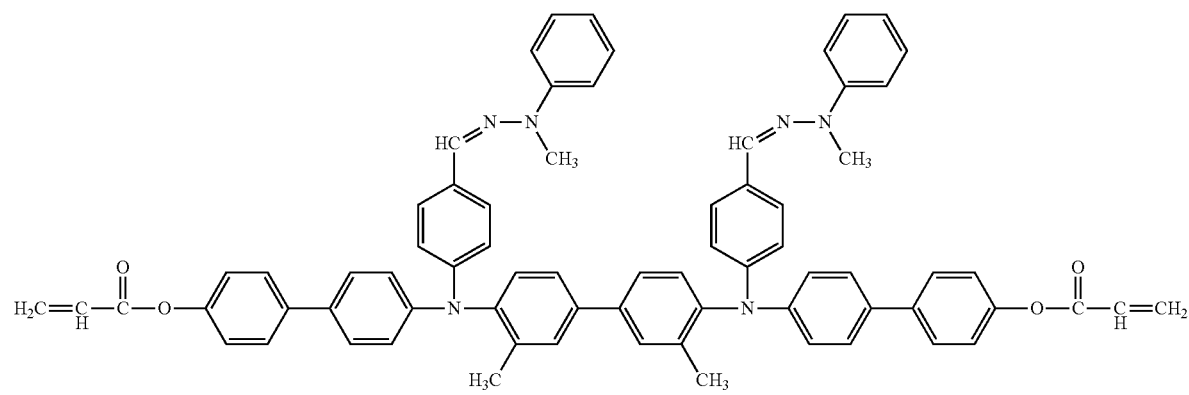
(E-19)
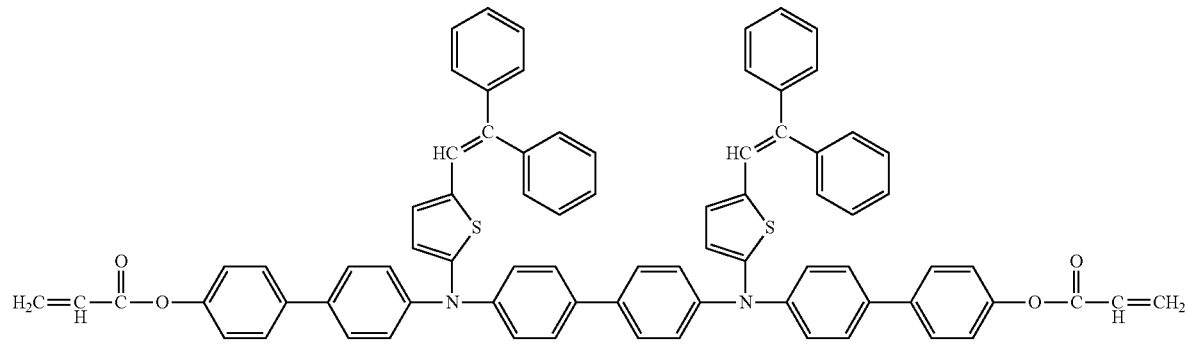
(E-20)
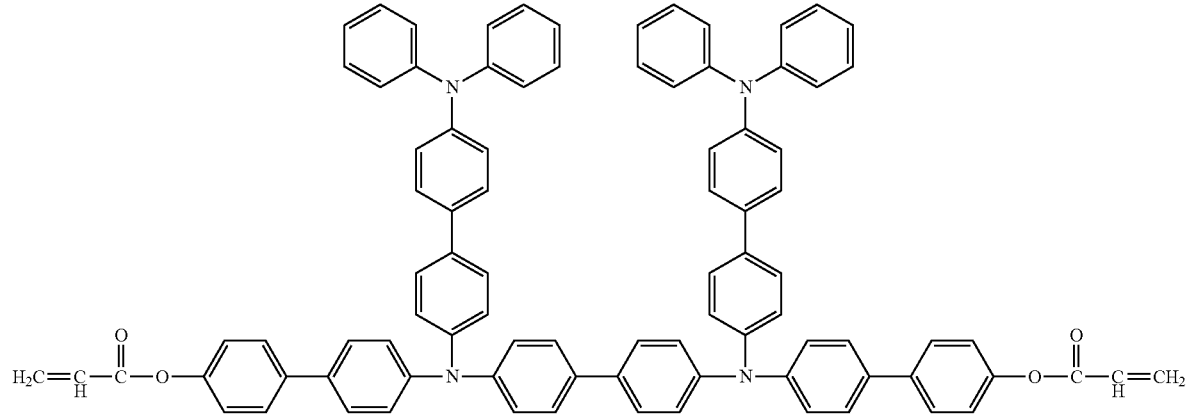
(E-21)

-continued
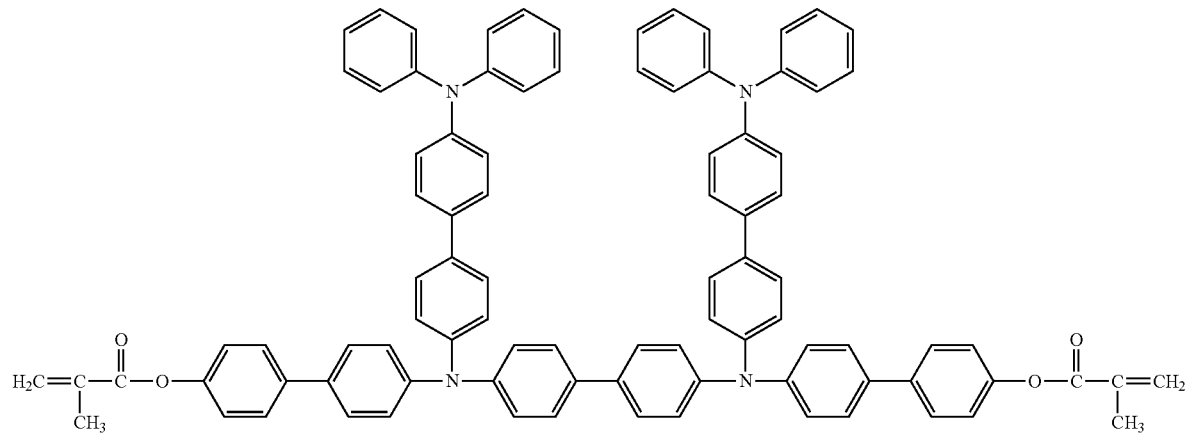
(E-22)
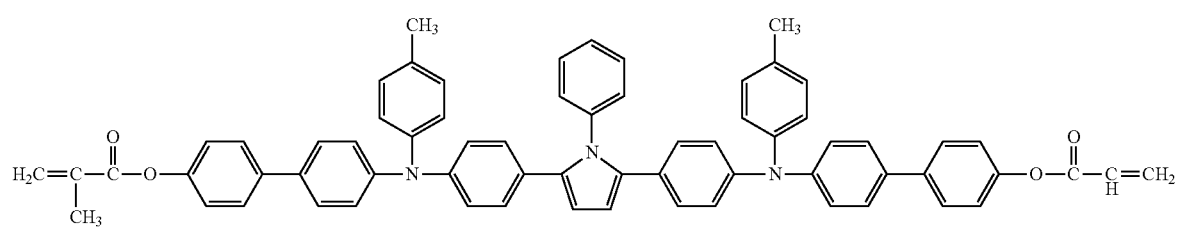
(E-23)
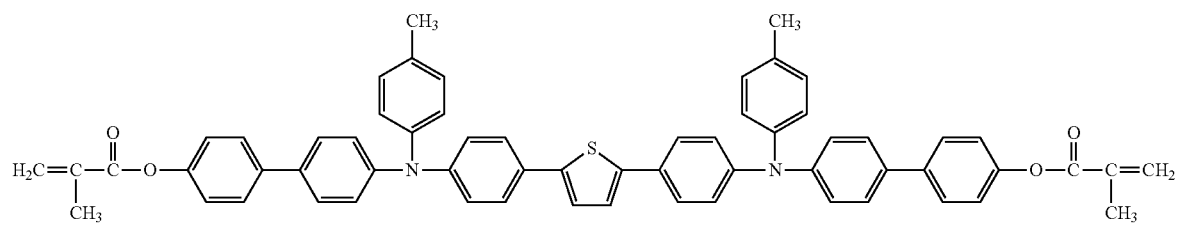
(E24)
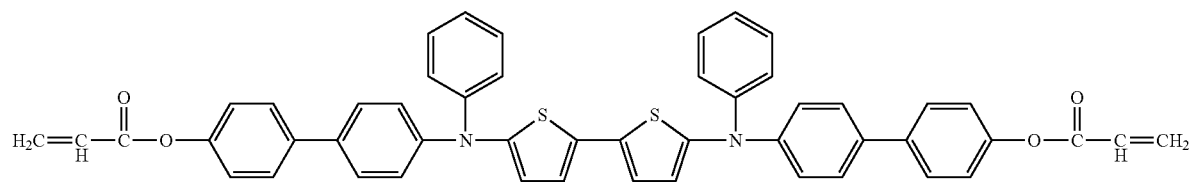
(E25)
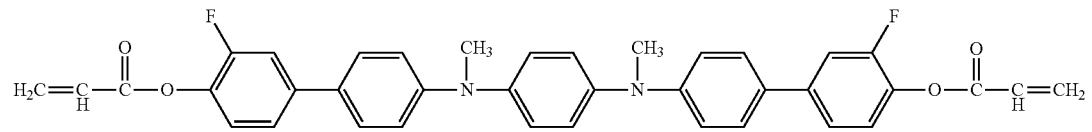
(E26)
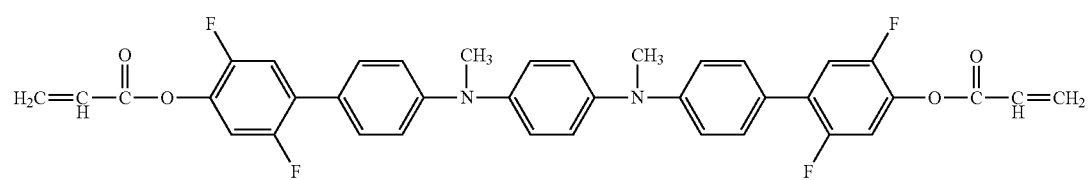
(E-27)

-continued
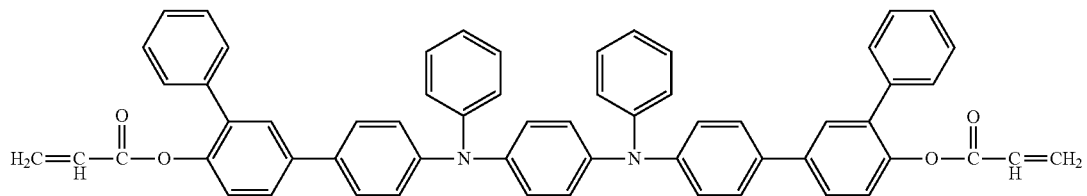
(E-28)
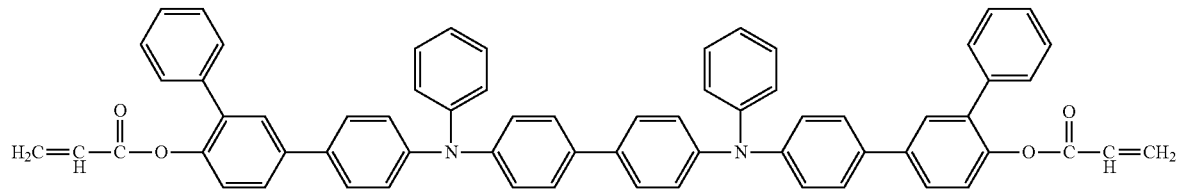
(E-29)
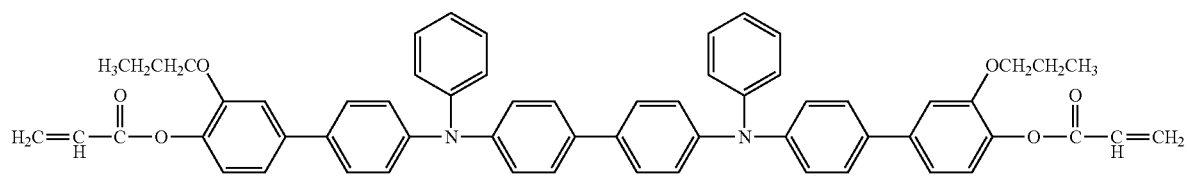
(E-30)
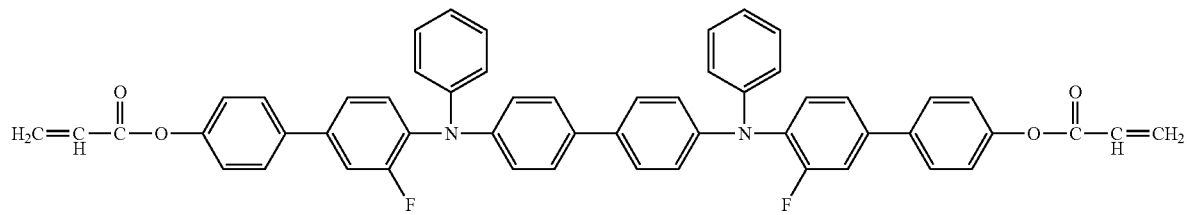
(E-31)
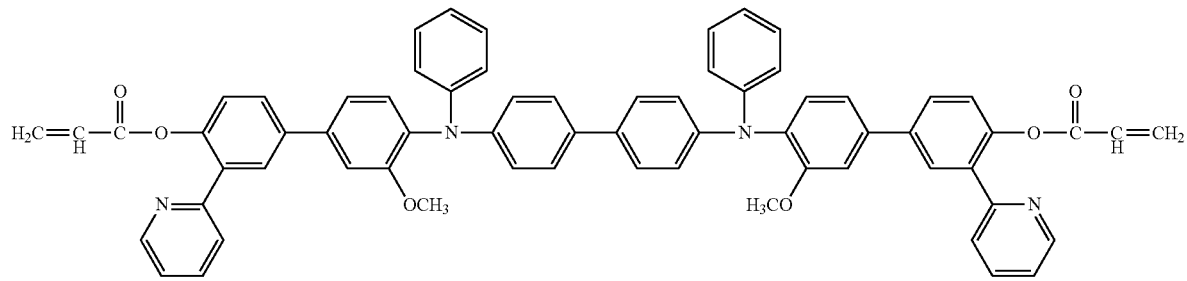
(E-32)
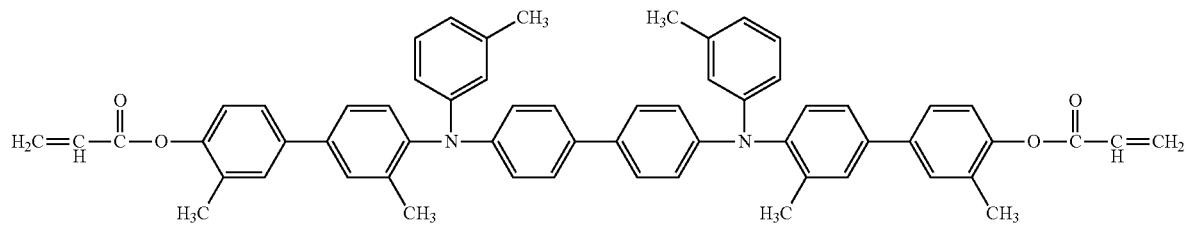
(E-33)

The acrylic ester compounds of the present invention represented by General Formulae (1-1) to (1-3) and (2-1) are novel substances, and they may be synthesized by using the hydroxy compound represented by General Formulae (1-1-1) to (1-3-1) and (2-1-1) as manufacturing intermediates, respectively, and by reacting these intermediates with acryloyl chloride or methacryloyl chloride.

For example, a hydroxy compound is synthesized with the following procedure, and the obtained hydroxy compound is reacted with acryloyl chloride or methacryloyl chloride. Thus, an acrylic compound or a methacrylic compound of the present invention may be easily synthesized.

<General Formula (1-1-1)>

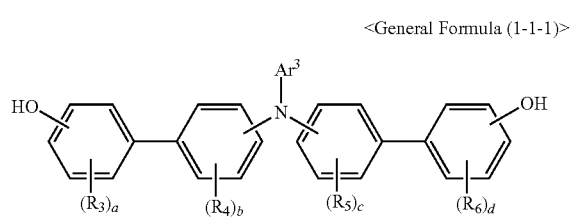

where, in General Formula (1-1-1), $R_3$, $R_4$, $R_5$ and $R_6$ represent an alkyl group which may have a substituent, an alkoxy group which may have a substituent, an aryl group which may have a substituent, a heterocyclic group which may have a substituent or a halogen atom; $Ar^3$ represents an alkyl group which may have a substituent, an aralkyl group which may have a substituent, an aryl group which may have a substituent, a condensed polycyclic hydrocarbon group which may have a substituent or a heterocyclic group which may have a substituent, and each substituent may be bonded with the alkyl group, the aralkyl group, the aryl group, the condensed polycyclic hydrocarbon group or the heterocyclic group through N, O, $CH_2$ or $C(CH_3)_2$; a, b, c and d are the same or different and represent an integer of zero to four.

<General Formula (1-2-1)>

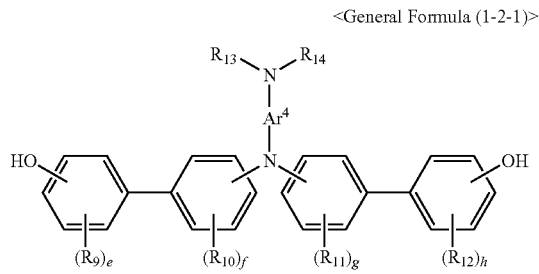

where, in General Formula (1-2-1), $R_9$, $R_{10}$, $R_{11}$ and $R_{12}$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent heterocyclic group which may have a substituent or a bivalent condensed polycyclic hydrocarbon group which may have a substituent, and $R_{13}$ and $R_{14}$ may be bonded together to form a heterocycle; e, f, g and h are the same or different and represent an integer of zero to four.

<General Formula (1-3-1)>

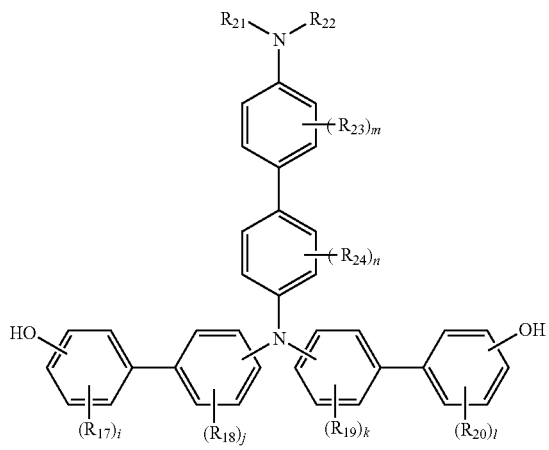

where, in General Formula (1-3-1), $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; i, j, k, l, m and m are the same or different and represent an integer of zero to four.

<General Formula (2-1-1)>

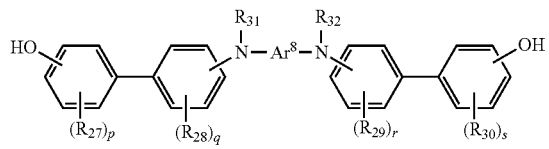

where, in General Formula (2-1-1), $R_{27}$, $R_{28}$, $R_{29}$ and $R_{30}$ represent an alkyl group which may have a substituent, an alkoxy group which may have a substituent, an aryl group which may have a substituent, a heterocyclic group which may have a substituent or a halogen atom; $R_{31}$ and $R_{32}$ represent an alkyl group which may have a substituent, an aralkyl group which may have a substituent, an aryl group which may have a substituent, a heterocyclic group which may have a substituent or a heterocyclic group which may have a substituent; $Ar^8$ represents an alkylene group which may have a substituent, an arylene group which may have a substituent, a bivalent heterocyclic group which may have a substituent or a bivalent condensed polycyclic hydrocarbon group which may have a substituent; p, q, r and s are the same or different and represent an integer of zero to four.

<Synthesis of Hydroxy Compound>

As shown in Reaction Formula (a), a methoxy compound (E1) as a raw material is demethylated by means of a heretofore known method to synthesize a hydroxy compound (E2) ('synthetic process of a hydroxy compound by demethylation').

Here, the structural formula of each compound in Reaction Formula (a) is abbreviated. The compound (E2) represents a compound whose structural formula corresponds to that of the hydroxy compounds represented by General Formulae (5) to (8), and the compound (E1) represents a methoxy compound with the corresponding structural formula.

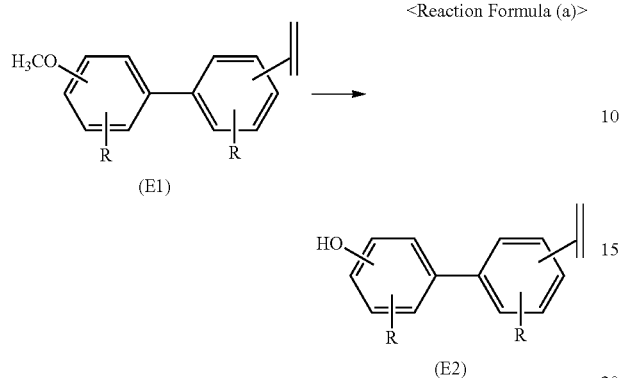

(E1)

(E2)

where, in Reaction Formula (a), R is synonymous to $R_3$ to $R_6$, $R_9$ to $R_{12}$, $R_{17}$ to $R_{20}$ and $R_{27}$ to $R_{30}$ in General Formulae (1-1-1) to (1-3-1) and (2-1-1).

Examples of the demethylation includes a method using acids such as concentrated hydrochloric acid, hydrobromic acid, hydriodic acid, trifluoroacetic acid, pyridine hydrochloride, magnesium iodide etherate, aluminum chloride, aluminum bromide, boron tribromide and boron tetrabromide; and a method using base or an organometallic reagents such as potassium hydroxide, Grignard reagent, sodium-butanol, lithium-biphenyl, lithium iodide-collidine, lithium diphenylphosphide-THF and sodium thiolate-DMF.

Among these, methods using boron tribromide and sodium thiolate-DMF are particularly effective, but the synthetic method for obtaining the intermediate of the present invention is not restricted to these. Specific synthetic examples are described hereinafter in Examples.

The hydroxy compound of the present invention obtained by the synthesis above is characterized by the expression of General Formulae (1-1-1) to (1-3-1) and (2-1-1). Examples of $R_3$ to $R_6$, $R_9$ to $R_{12}$, $R_{17}$ to $R_{20}$ and $R_{27}$ to $R_{30}$ are equivalent to those described for General Formulae (1-1) to (1-3) and (2-1).

<Synthesis of Acrylic Compound or Methacrylic Compound>

As shown in Reaction Formula (b), a hydroxy compound (E2) is used as a manufacturing intermediate, and an acrylic ester compound (E3) is synthesized similarly by means of a heretofore known esterification method ('acrylation or methacrylation process'). Here, the structural formula of each compound in Reaction Formula (b) is abbreviated. (E2) represents a compound whose structural formula corresponds to that of the hydroxy compounds represented by General Formulae (1-1-1) to (1-3-1) and (2-1-1), and E-3 represents a compound whose structural formula corresponds to that of the acrylic ester compound represented by General Formulae (1-1) to (1-3) and (2-1).

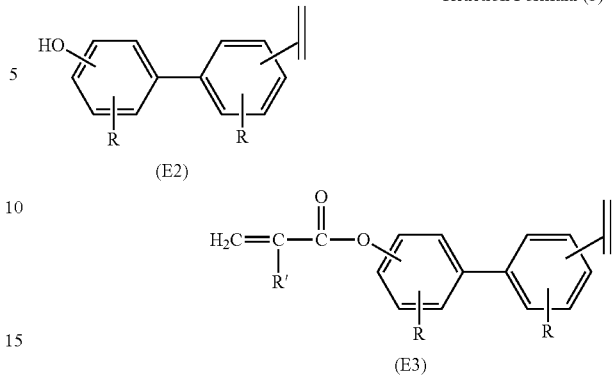

(E2)

(E3)

where, in Reaction Formula (b), R is synonymous to $R_3$ to $R_6$, $R_9$ to $R_{12}$, $R_{17}$ to $R_{20}$ and $R_{27}$ to $R_{30}$ in General Formulae (1-1-1) to (1-3-1) and (2-1-1), and R' is synonymous to $R_1$, $R_2$, $R_7$, $R_8$, $R_{15}$, $R_{16}$, $R_{25}$ and $R_{26}$ in General Formulae (1-1) to (1-3) and (2-1).

Examples of the methods for acrylation or methacrylation include a reaction of a hydroxy compound (E2) with acrylic acid or methacrylic acid, or an ester compound, acid halide or acid anhydride of these carboxylic acids.

For example, an acrylic ester compound may be synthesized by heating and stirring with dehydration a hydroxy compound (E2) and acrylic acid with an esterification catalyst in an organic solvent. It may also be synthesized simply by reacting a hydroxy compound and acryloyl chloride in an organic solvent under the presence of an alkali. Examples of the alkali used for this reaction includes alkalis such as sodium hydroxide and potassium hydroxide, aqueous solutions thereof, amine bases such as triethylamine and pyridine. Examples of the organic solvent used for the reaction includes a hydrocarbon solvent such as toluene; an ether solvent such as tetrahydrofuran; an ester solvent such as ethyl acetate; a ketone solvent such as methyl ethyl ketone; and a halogen solvent such as chloroform. Specific synthetic examples are shown in Examples hereinafter.

The acrylic ester compounds represented by General Formulae (1-1), (1-2), (1-3) and (2-1) above of the present invention have a triarylamine moiety with an expanded conjugated system having two naphthylene groups bonded in a molecule; therefore, a favorable charge transport function with high hole mobility is provided. Favorable chain polymerizability such as radical polymerizability may be provided as well since an acrylic ester or a methacrylic ester group is introduced. Therefore, a cured resin film with high crosslink density may be easily formed with the irradiation of ultraviolet (UV) rays, electron rays and radioactive rays and with the use of radical initiator. The acrylic ester compounds have superior film formation properties, and they can meet the demand for mechanical resistance such as abrasion and heat resistance; moreover, they can provide favorable charge transport properties as well. Because of such superior properties, they are extremely useful as an organic functional material for various organic semiconductor devices such as organic electrophotographic photoconductor, organic EL, organic TFT and organic solar cell.

In addition, the acrylic ester compound of the present invention has a favorable compatibility with other monomers. Examples of the other monomers include trimethylolpropane triacrylate, trimethylolpropane trimethacrylate, trimethylolpropane alkylene-modified triacrylate, trimethylolpropane ethylene oxide-modified triacrylate (ethylene oxide-modified is hereinafter abbreviated as 'EO-modified'), trimethylolpropane propylene oxide-modified triacrylate ('propylene oxide-modified' is hereinafter abbreviated as 'PO-modified'), trimethylolpropane caprolactone-modified triacrylate, trimethylolpropane alkylene -modified trimethacrylate, pentaerythritol triacrylate, pentaerythritol tetraacrylate, glycerol triacrylate, glycerol epichlorohydrin-modified triacrylate, glycerol EO-modified triacrylate, glycerol PO-modified triacrylate, tris(acryloxyethyl)isocyanurate, dipentaerythritol hexaacrylate, dipentaerythritol caprolactone-modified hexaacrylate, dipentaerythritol hydroxypentaacrylate, alkylated dipentaerythritol pentaacrylate, alkylated dipentaerythritol tetraacrylate, alkylated dipentaerythritol triacrylate, dimethylolpropane tetraacrylate, pentaerythritol ethoxytetraacrylate, EO-modified triacrylate phosphate and 2,2,5,5-tetrahydroxymethylcyclopentanone tetraacrylate.

These monomers may be used alone, or they may be used in combination and mixed in an acrylic ester compound of the present invention, which may be selected according to the demand characteristics to be achieved. The mixed quantities of these monomers vary according to applications; for an application to the charge transport layer of an electrophotographic photoconductor, the mixing ratio of the monomer to an acrylic ester compound on a mass basis is usually around 0.01% to 1,500%, and preferably around 1% to 500%.

<Acrylic Ester Compound Related to Aspect 1-2>

An acrylic ester compound related to an aspect 1-2 is preferably a compound represented by General Formula (1-4) below.

<General Formula (1-4)>

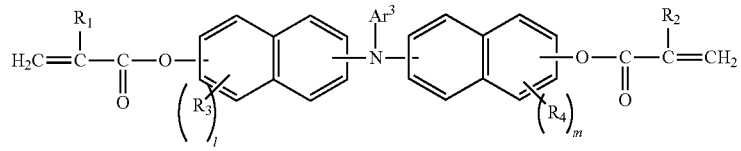

where, in General Formula (1-4), $R_1$, $R_2$ and $Ar^3$ are equivalent to those in General Formula (1); $R_3$ and $R_4$ represent an alkyl group which may have a substituent, an alkoxy group which may have a substituent, an aryl group which may have a substituent, a heterocyclic group which may have a substituent or a halogen atom; l and m are the same or different and represent an integer of zero to six.

$R_1$ and $R_2$ in General Formula (1-4) above represents a hydrogen atom or a methyl group, and they are the same or different. Since the hydrogen atom and the methyl group cause the difference in radical polymerization, they are appropriately selected and used according to the use environment.

Specific examples of $R_3$ and $R_4$ include an alkyl group such as methyl group, ethyl group, n-octyl group and 2-ethylhexyl group; an alkoxy group such as methoxy group, ethoxy group and 2-propoxy group; an aryl group such as phenyl group, p-tolyl group, 1-naphthyl group and 2-naphthyl group; a heterocyclic group such as 2-furyl group, 2-thienyl group, 3-thienyl group, benzothiophene-2-yl group and 2-benzothiazolyl group; and a halogen atom such as fluorine atom, chlorine atom and bromine atom. Among these, the alkyl group, the alkoxy group, the aryl group or the heterocyclic group may respectively have a substituent, and specific examples of the substituent are those alkyl groups, alkoxy groups, aryl groups or halogen atoms listed above, respectively.

Specific examples of $Ar_3$ include an alkyl group such as methyl group, ethyl group, n-octyl group and a 2-ethylhexyl group; an aryl group such as phenyl group, p-tolyl group, 1-naphthyl group and 2-naphthyl group; and a heterocyclic group such as 2-furyl group, 2-thienyl group, 3-thienyl group, benzothiophene-2-yl group and 2-benzothiazolyl group. These may have a substituent, and the examples of the substituent are those alkyl groups, alkoxy groups or halogen groups listed above.

These substituents of $Ar_3$ may be bonded with the alkyl group, aryl group, condensed polycyclic hydrocarbon group or heterocyclic group through a nitrogen atom. Examples of the alkyl group which may have a substituent include an aralkyl group such as benzyl group. Examples of the substituent include a 8-phenyl-substituted styryl group. Also, the aryl group includes aromatic hydrocarbon groups which are bonded through a bivalent group such as oxygen atom, $CH_2$ and $C(CH_3)$.

An acrylic ester compound related to the aspect 1-2 is preferably a compound represented by General Formula (1-5) below.

<General Formula (1-5)>

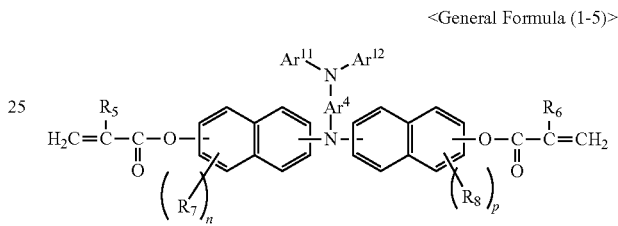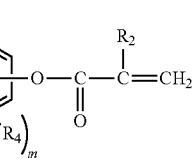

where, in General Formula (1-5), $R_5$ and $R_6$ are the same or different and represent a hydrogen atom or a methyl group; $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $Ar^{11}$ and $Ar^{12}$ represent an alkyl group which may have a substituent, an aryl group which may have a substituent or a condensed polycyclic hydrocarbon group which may have a substituent, and $Ar^{11}$ and $Ar^{12}$ may be bonded together through adjacent carbon atoms to form a heterocycle; n and p are the same or different and represent an integer of zero to six.

In General Formula (1-5) above, $R^5$ and $R^6$ may be a hydrogen atom or a methyl group, and they are the same or different. Examples of $R^7$ and $R^8$ are synonymous to the alkyl groups, alkoxy groups, aryl groups or halogen atoms, respectively, which are described for General Formula (1-4). Among these, the alkyl groups, alkoxy groups or the aryl groups may have a substituent.

Examples of $R^7$ and $R^8$ are synonymous to the alkyl groups, alkoxy groups, aryl groups or halogen atoms, respectively, and among these, the alkyl groups, alkoxy groups or the aryl groups may have a substituent. Examples of the substituents are synonymous to the above-mentioned alkyl groups, alkoxy groups, aryl groups or halogen atoms, respectively.

Specific examples of $Ar^4$ include an alkylene group such as methylene group and 1,2-ethylene group; an arylene group such as 1,2-phenylene group, 1,4-phenylene group, 4,4'-biphenylene group and 2,6-naphthylene group; a bivalent condensed polycyclic hydrocarbon group such as fluorenylidene; and a bivalent heterocyclic group such as 2,5-thienylene and 2,5'-dithienylene. Regarding the arylene group, the phenyl group may be a bivalent group which is bonded with a bivalent group such as oxygen atom, $CH_2$ and $C(CH_3)$. These may have a substituent, and the specific examples of the substituent include those alkyl groups, alkoxy groups, aryl groups and halogen atoms, respectively.

Examples of $Ar_{11}$ and $Ar_{12}$ include an alkyl group such as methyl group; an aryl groups such as phenyl group, p-tolyl group and biphenyl group; a condensed polycyclic hydrocarbon group such as fluorenyl group; a heterocyclic group such as carbazole group which is formed by bonding the adjacent carbon atoms of $Ar_{11}$ and $Ar_{12}$, and these may have a substituent. Examples of the substituent include the above-mentioned alkyl groups, alkoxy groups and halogen atoms, respectively.

Also, the acrylic ester compound related to the aspect 1-2 is a compound preferably represented by General Formula (1-6) below.

<General Formula (1-6)>

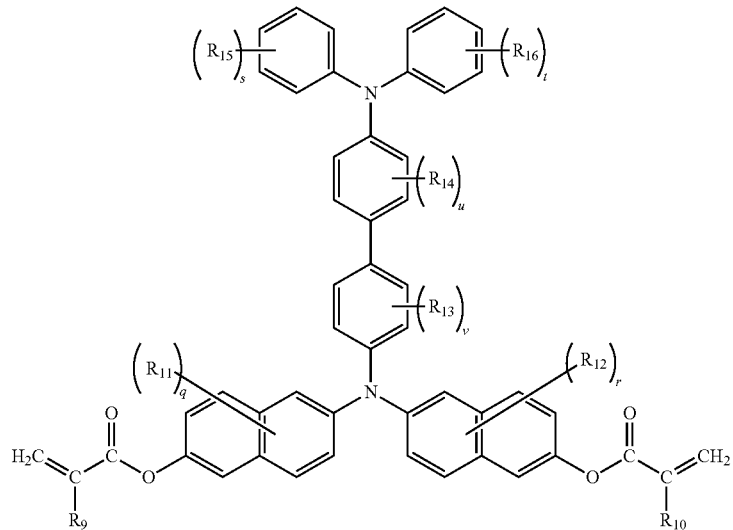

where, in General Formula (1-6), $R_9$ and $R_{10}$ are the same or different and represent a hydrogen atom or a methyl group; $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{16}$ represent an alkyl group which may have a substituent, an alkoxy group which may have a substituent, an aryl group which may have a substituent or a halogen atom; q and r are the same or different and represent an integer of zero to six, s and t are the same or different and represent an integer of zero to five, and u and v are the same or different and represent an integer of zero to four.

In General Formula (1-6) above, $R_9$ and $R_{10}$ may be a hydrogen atom or a methyl group, and they are the same or different. Examples of $R_{11}$ and $R_{12}$ are synonymous to the above-mentioned alkyl groups, alkoxy groups, aryl groups, heterocyclic groups or halogen atoms, respectively. Among these, the alkyl groups, alkoxy groups, the aryl groups or the heterocyclic groups may have a substituent. Examples of the substituents are synonymous to the above-mentioned alkyl groups, alkoxy groups, aryl groups or halogen atoms, respectively.

Examples of $R^{13}$, $R^{14}$, $R^{15}$ and $R^{16}$ are synonymous to the alkyl groups, alkoxy groups, aryl groups or halogen atoms, respectively, and these alkyl groups, alkoxy groups or the aryl groups may have a substituent. Examples of the substituents are synonymous to the above-mentioned alkyl groups, alkoxy groups, aryl groups or halogen atoms, respectively.

<Acrylic Ester Compound Related to Aspect (2-2)>

An acrylic ester compound related to an aspect 2-2 is preferably a compound represented by General Formula (2-2) below.

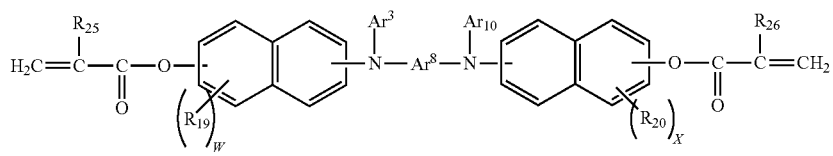

<General Formula (2-2)> where, in General Formula (2-2), $R^{19}$ and $R^{20}$ represent an alkyl group which may have a substituent, an alkoxy group which may have a substituent, an aryl group which may have a substituent, a heterocyclic group which may have a substituent or a halogen atom; $Ar_9$ and $Ar_{10}$ represent an alkyl group which may have a substituent, an aryl group which may have a substituent or a heterocyclic group which may have a substituent; $R^{25}$, $R^{26}$ and $Ar^8$ are equivalent to those in General Formula (2); w and x are the same or different and represent an integer of zero to six.

In General Formula (2-2) above, $R^{25}$ and $R^{26}$ may be a hydrogen atom or a methyl group, and they are the same or different.

Examples of $R_{19}$ and $R_{20}$ are synonymous to the alkyl groups, alkoxy groups, halogen atoms, aryl groups or heterocyclic groups, respectively, and these alkyl groups, alkoxy groups, the aryl groups or the heterocyclic groups may have a substituent. Examples of the substituents are synonymous to the above-mentioned alkyl groups, alkoxy groups, aryl groups or halogen atoms, respectively.

Examples of $Ar_9$ and $Ar_{10}$ are synonymous to the alkyl groups, aryl groups or heterocyclic groups, respectively, and these may have a substituent. Examples of the substituents are synonymous to the above-mentioned alkyl groups, alkoxy groups, aryl groups or halogen atoms, respectively.

Specific examples of $Ar_8$ include those represented by the formulae (C-1) to (C-6) below, and specific examples of the arylene group which may have a substituent and the bivalent condensed polycyclic hydrocarbon group which may have a substituent include those represented by the formulae (C-7) to (C-17) below.

Specific examples of the acrylic ester compound of the present invention represented by General Formulae (1-4) to (1-6) and (2-2) above is given as follows, but these illustrative compounds are not to be construed as limiting the present invention.

First, acrylic ester compounds of the present invention represented by General Formulae (1-4) to (1-6) above are shown below as formulae (F-1) to (F-48).

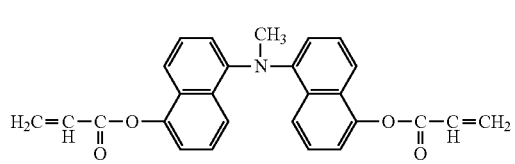

(F-1)

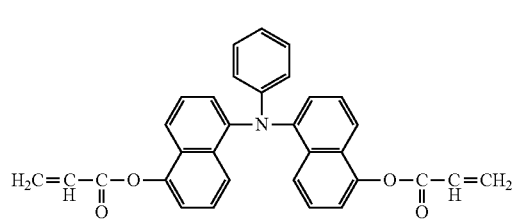

(F-2)

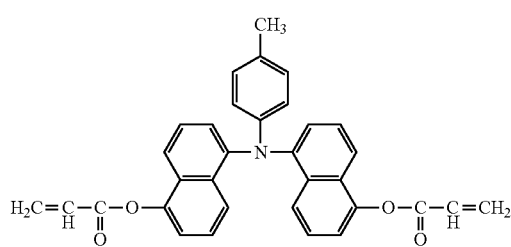

(F-3)

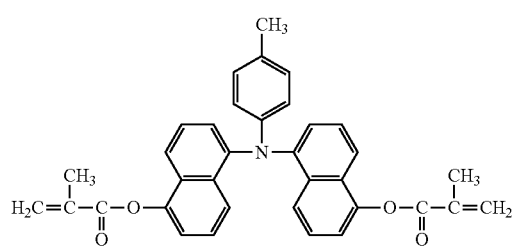

(F-4)

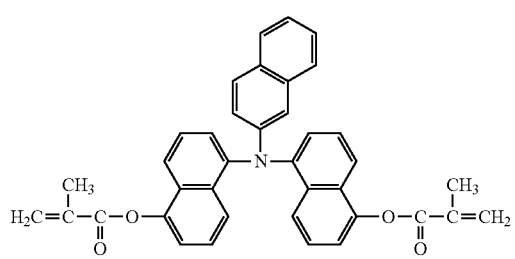

(F-5)

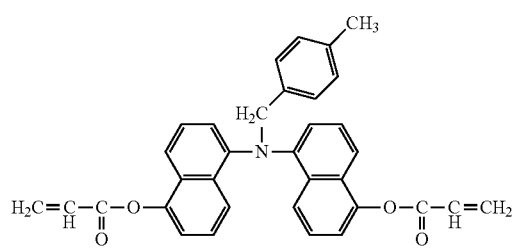

(F-6)

-continued
(F-7)
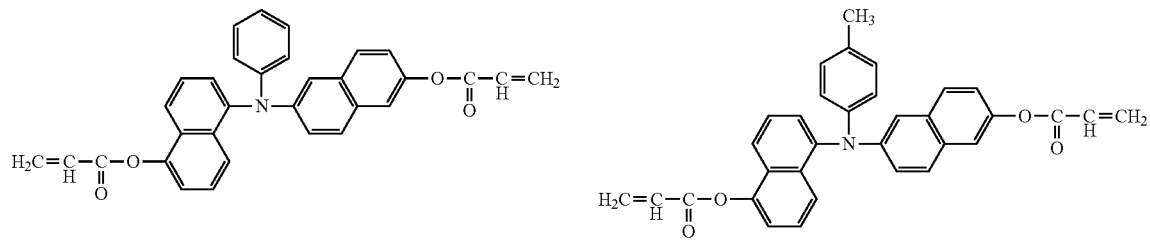
(F-8)
(F-9)
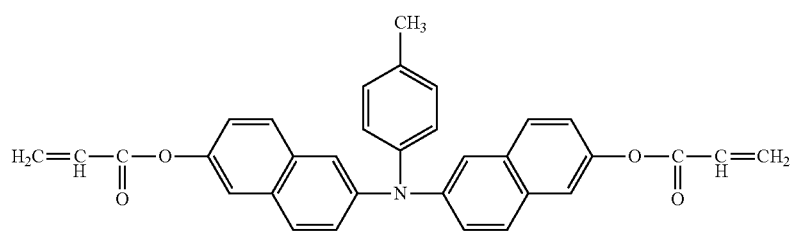
(F-10)
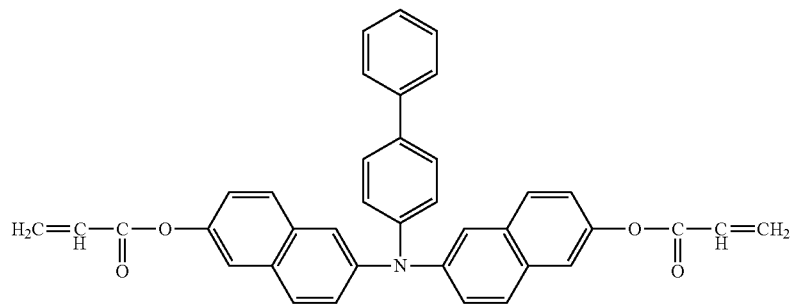
(F-11)
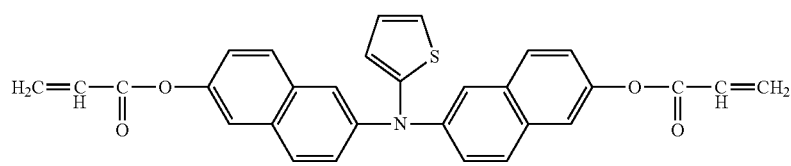
(F-11)
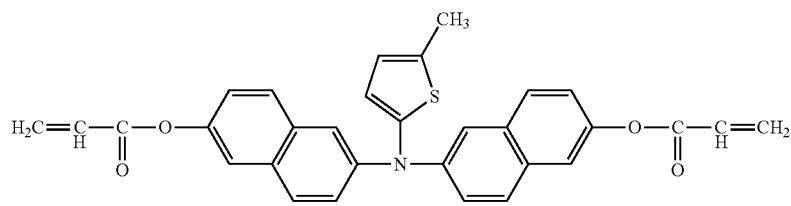
(F-12)
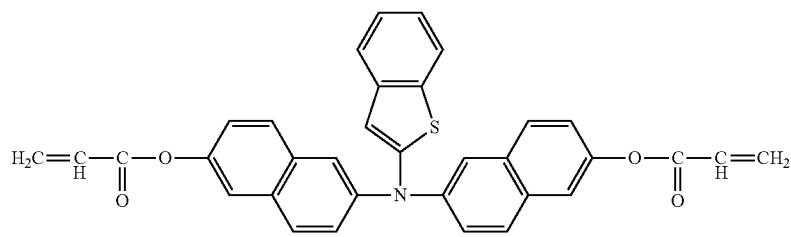

-continued
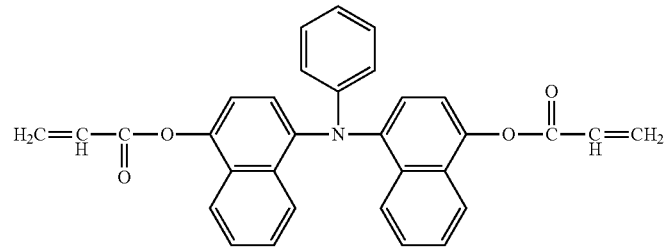
(F-13)
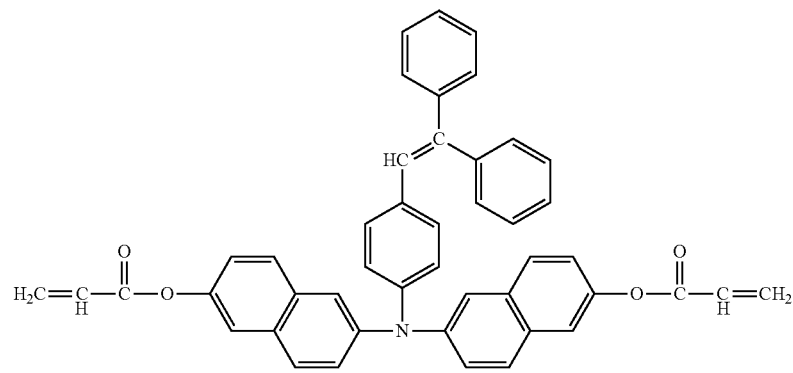
(F-14)
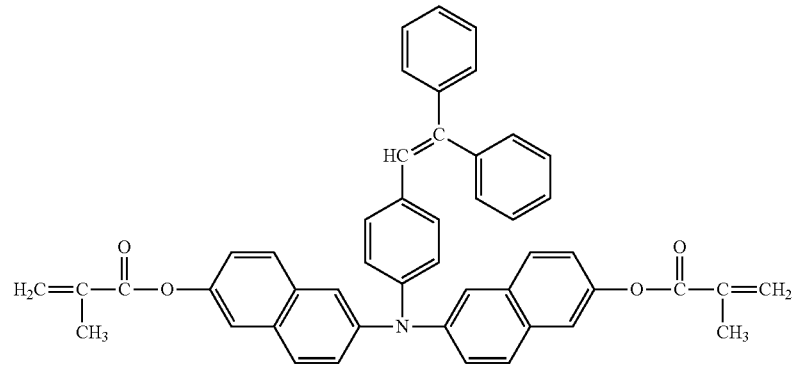
(F-15)
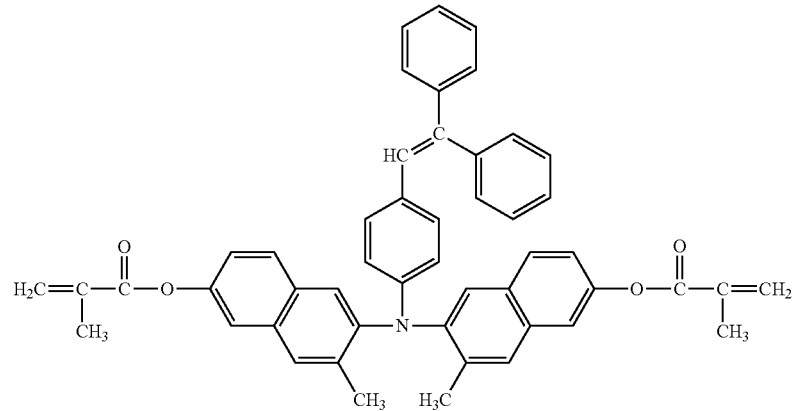
(F-16)

(F-17)
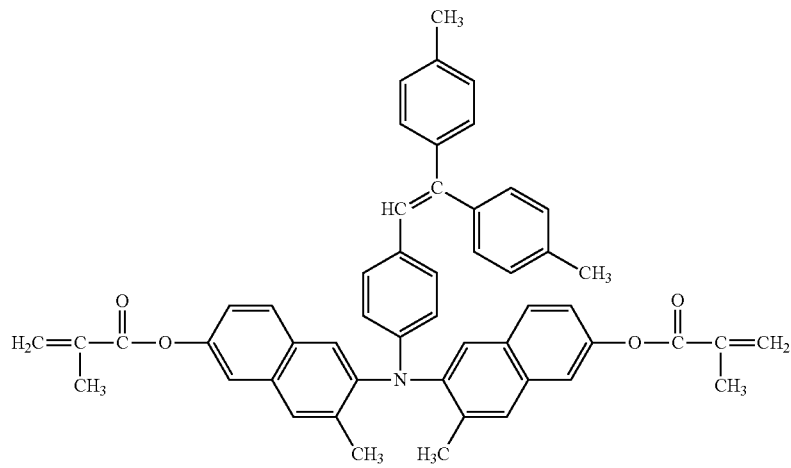
(F-18)
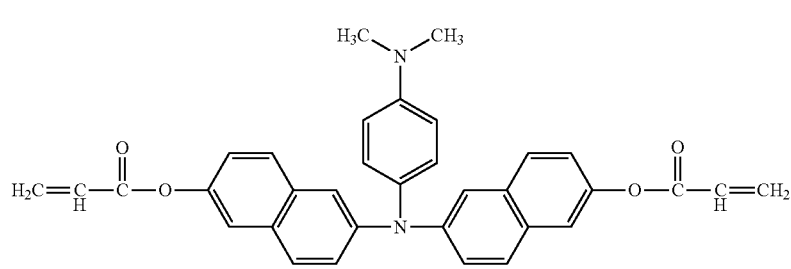
(F-19)
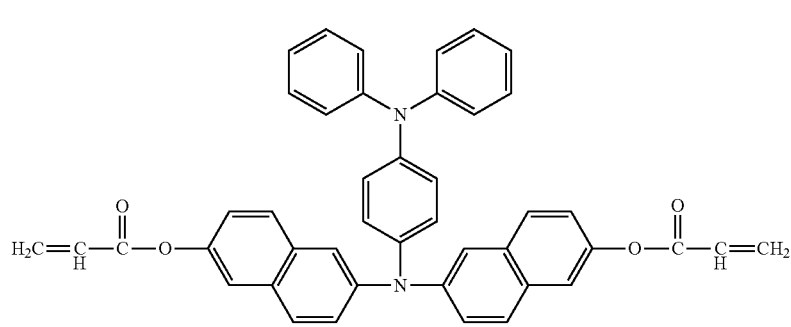
(F-20)
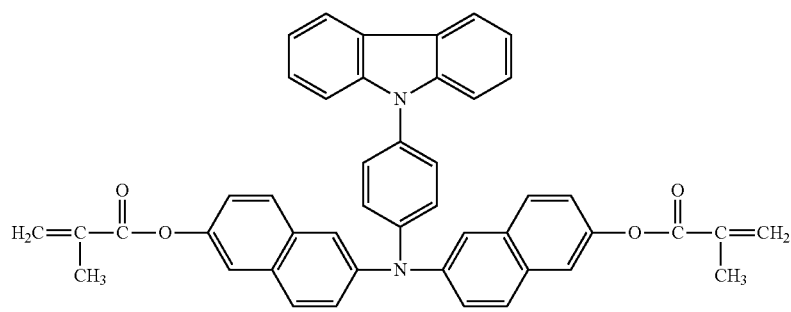

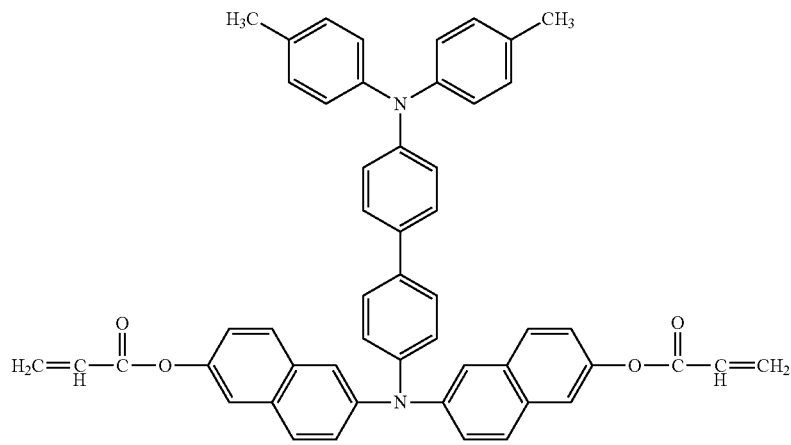
(F-21)
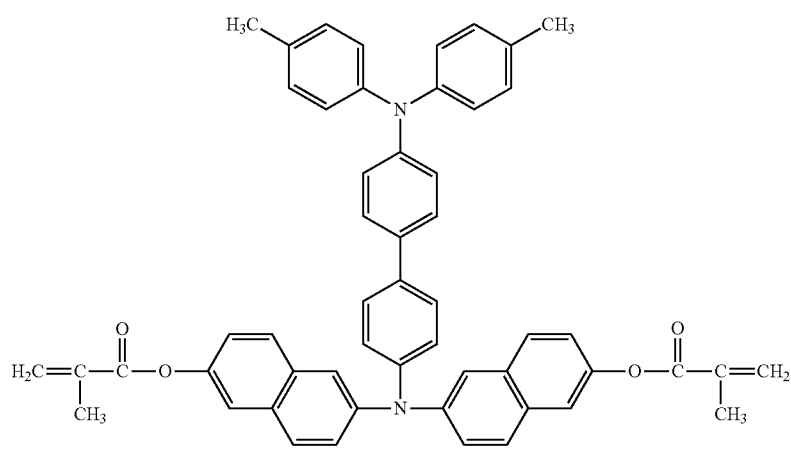
(F-22)
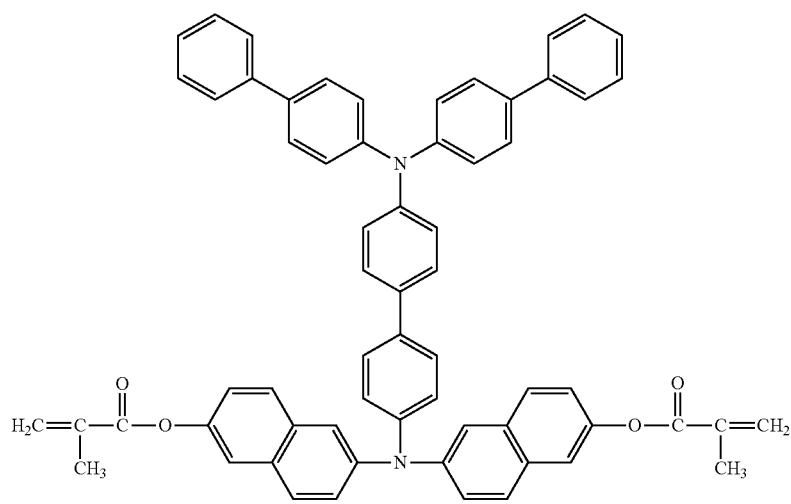
(F-23)

(F-24)
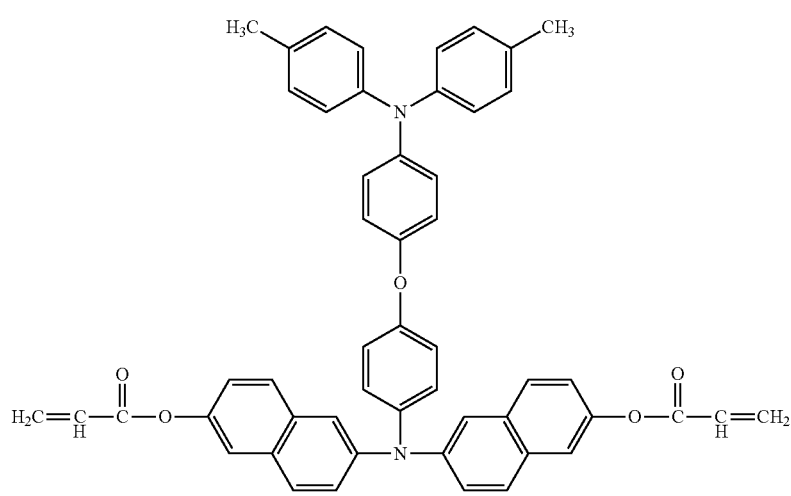
(F-25)
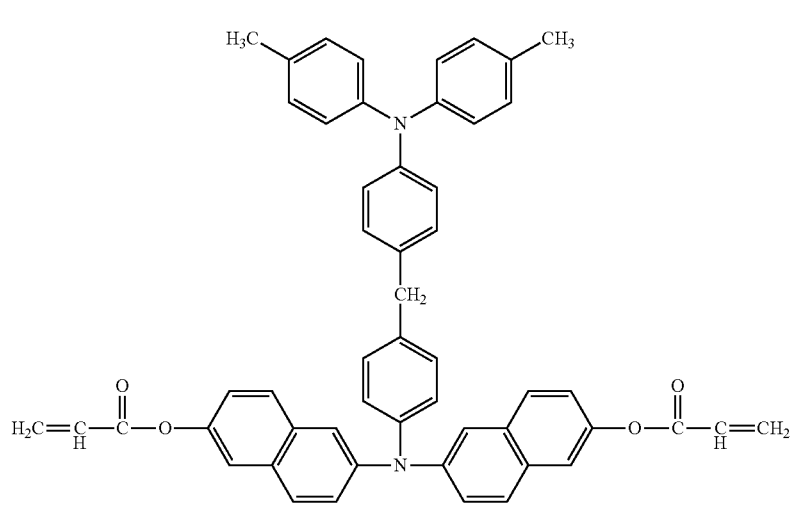
(F-26)
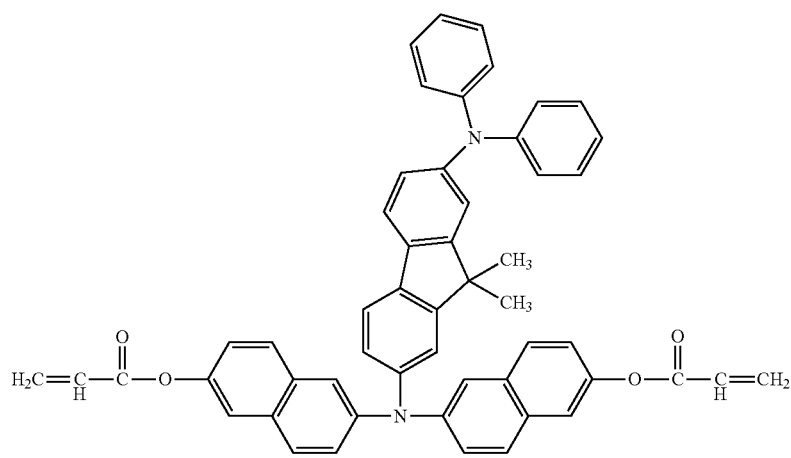

-continued
(F-27)
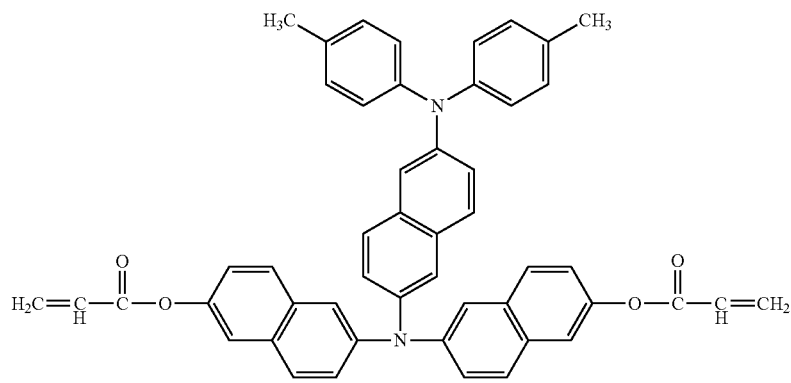
(F-28)
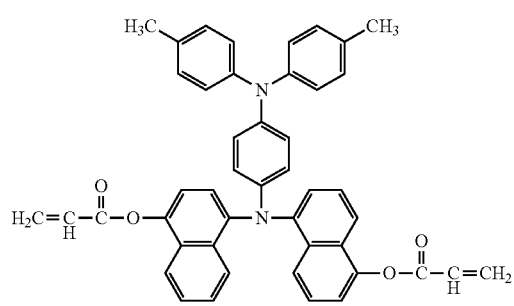
(F-29)
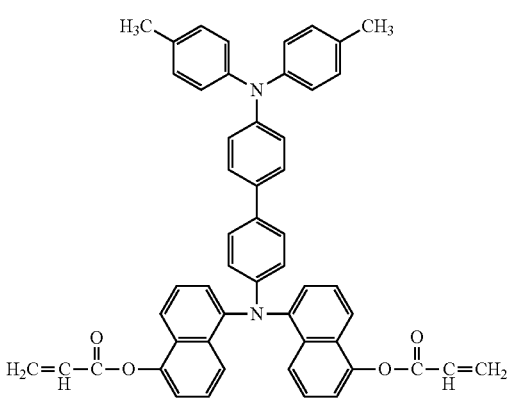
(F-30)
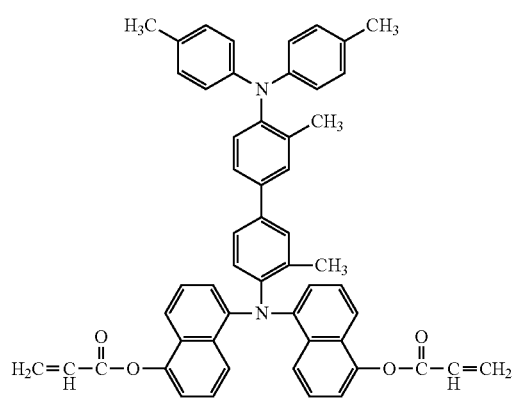
(F-31)
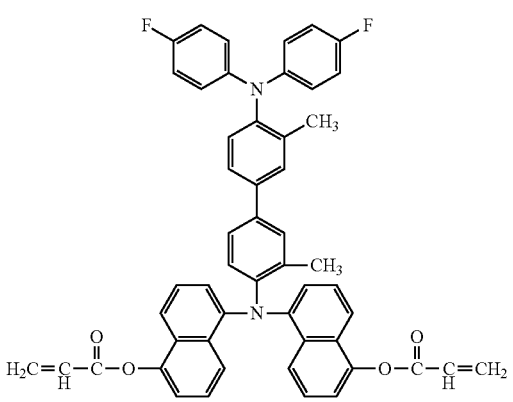
(F-32)
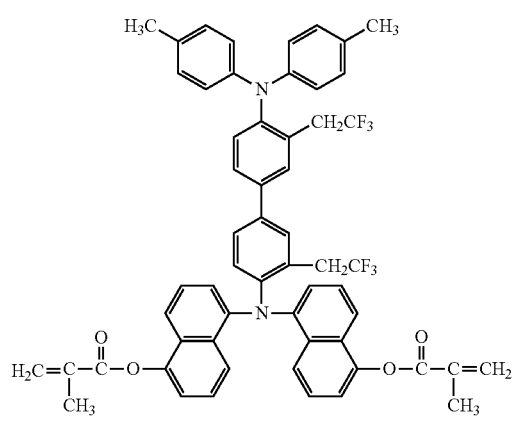
(F-33)
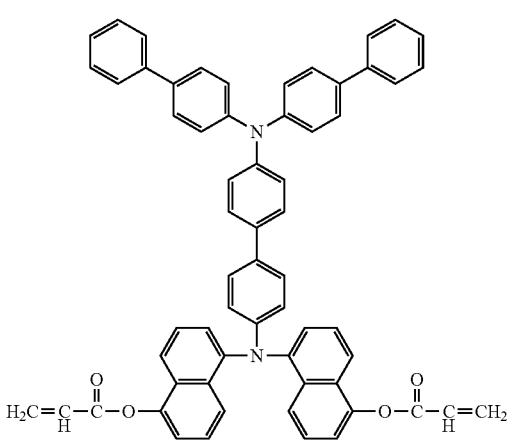

-continued
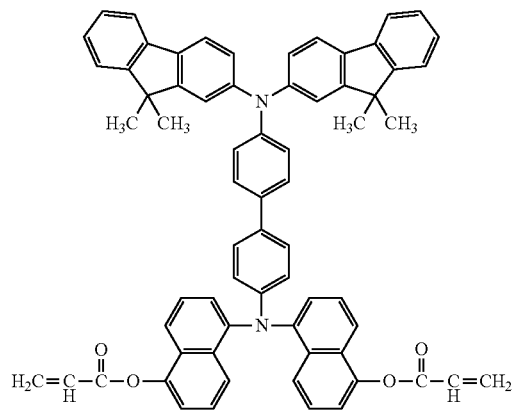
(F-34)
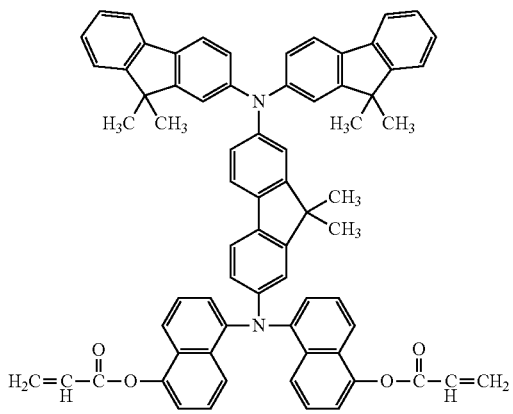
(F-35)
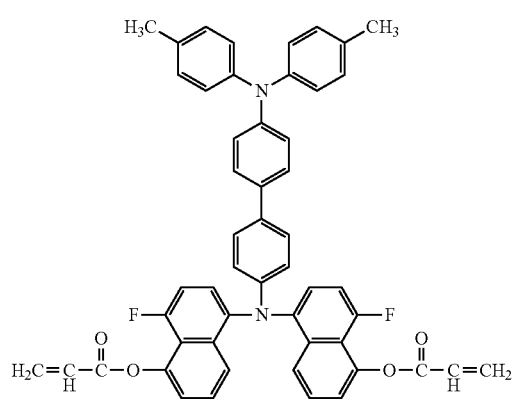
(F-36)
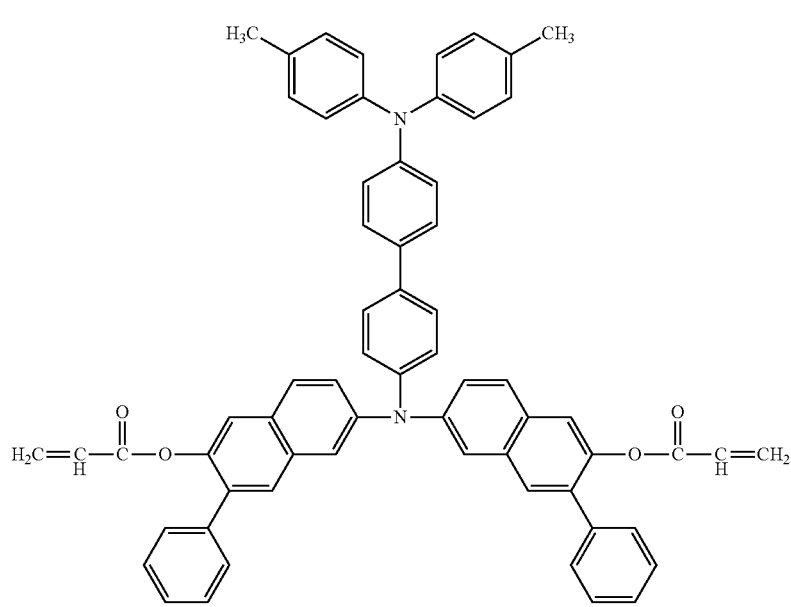
(F-37)

-continued
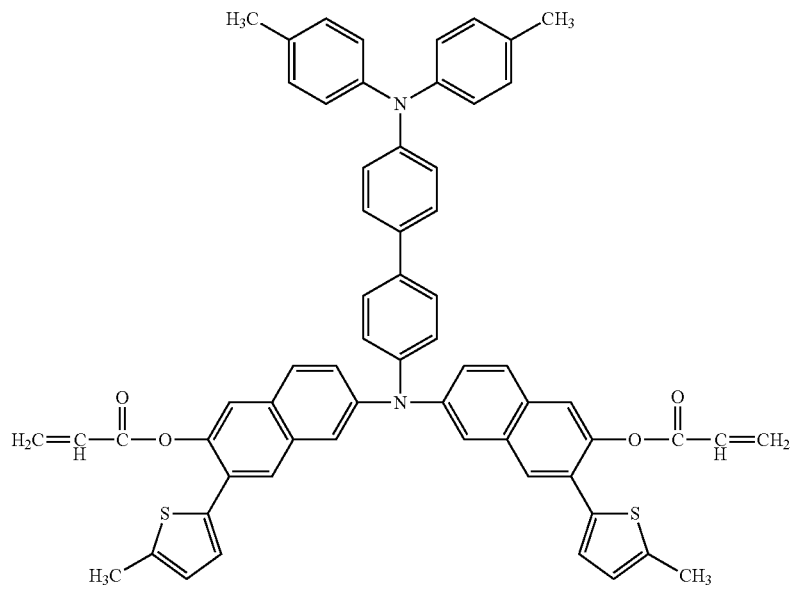
(F-38)
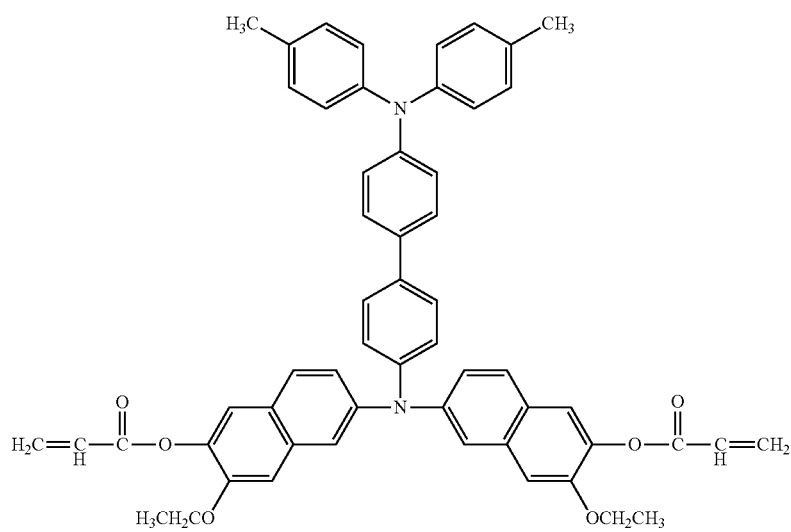
(F-39)
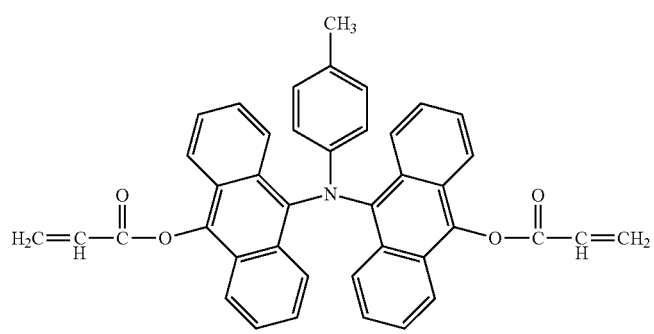
(F-40)
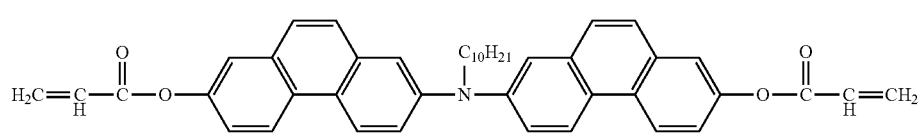
(F-41)

(F-42)
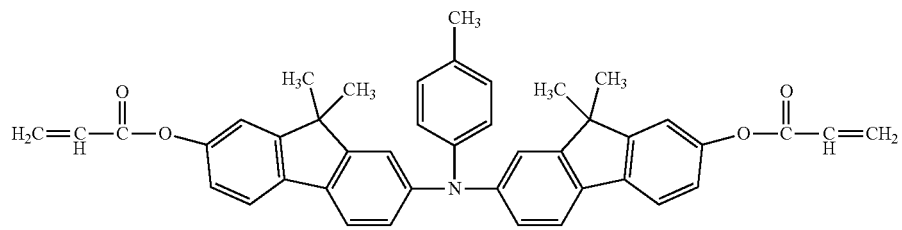
(F-43)
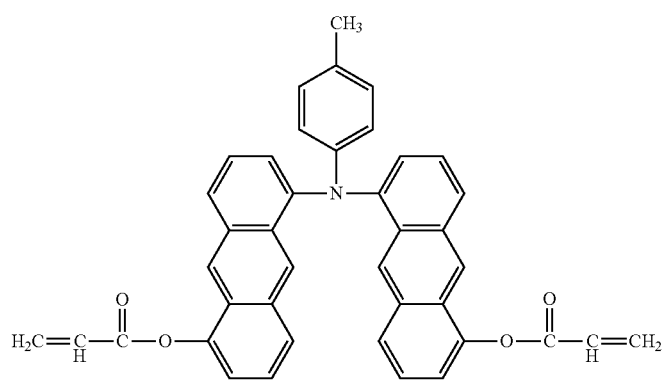
(F-44)
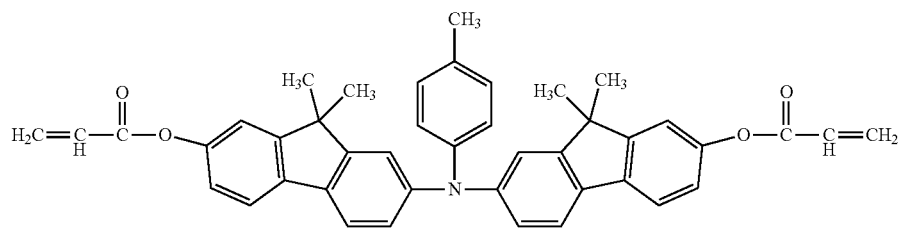
(F-45)
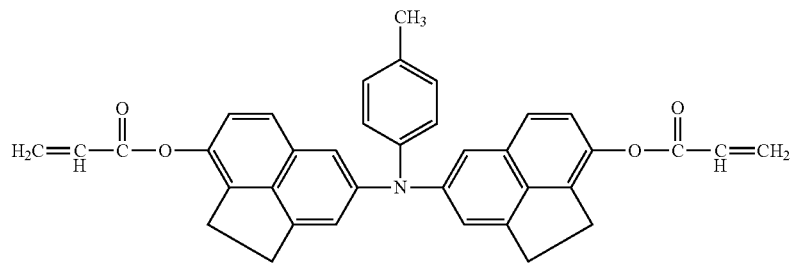
(F-46)
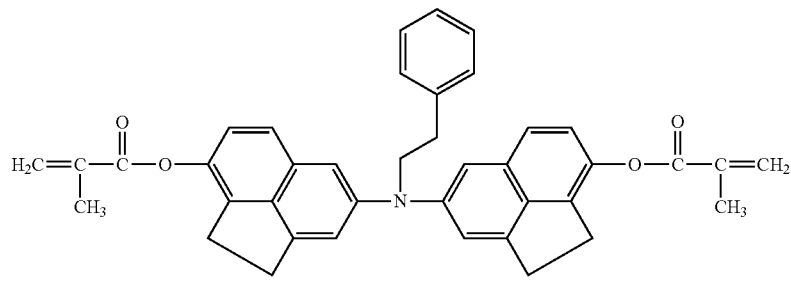
(F-47)
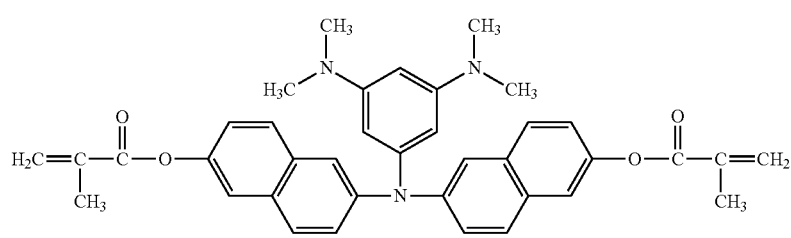

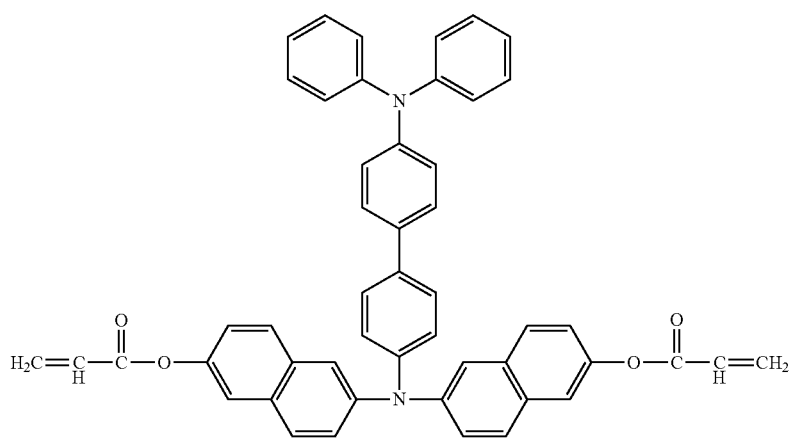
(F-48)
Next, acrylic ester compounds of the present invention represented by General Formulae (2-2) above are shown below as formulae (G-1) to (G-36).
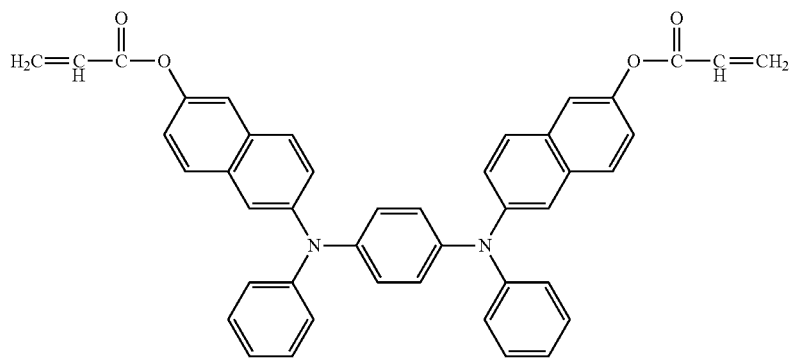
(G-1)
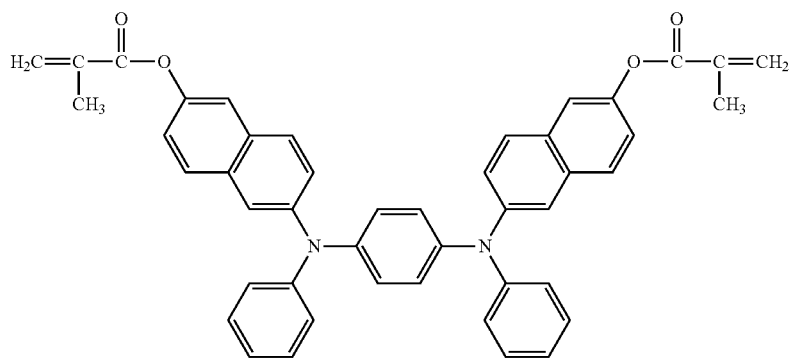
(G-2)
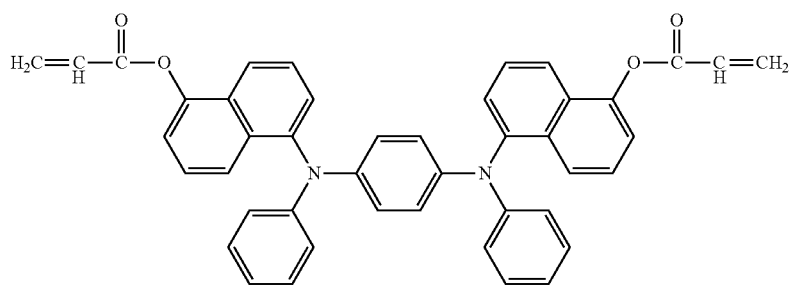
(G-3)

-continued
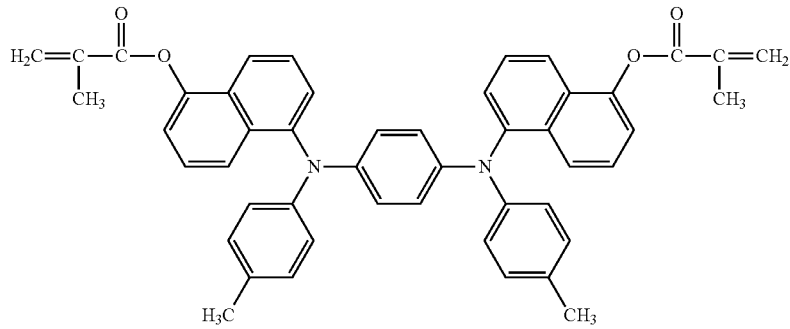
(G-4)
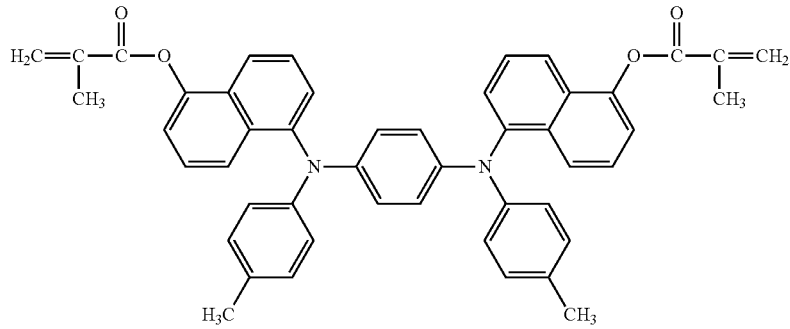
(G-5)
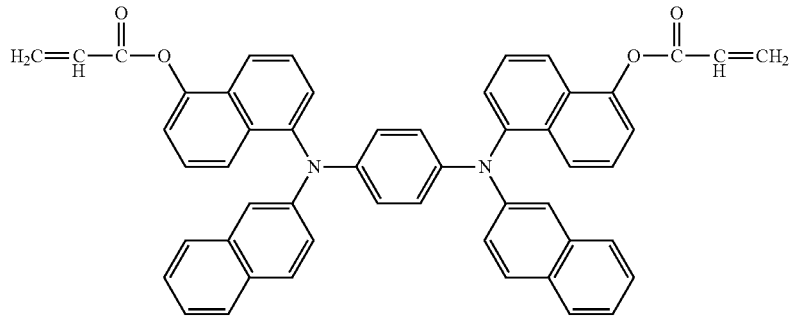
(G-6)
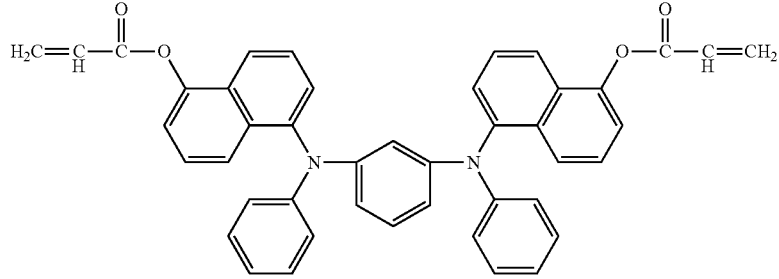
(G-7)
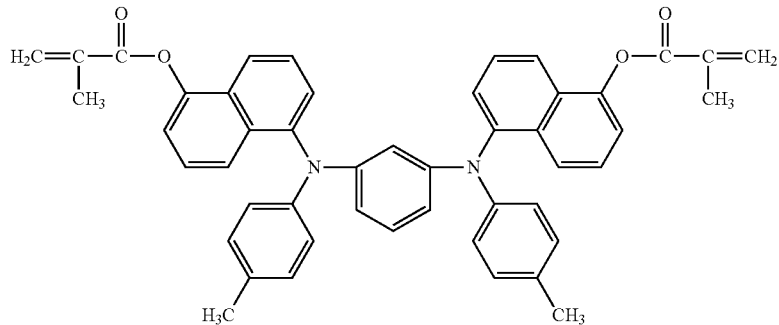
(G-8)

-continued
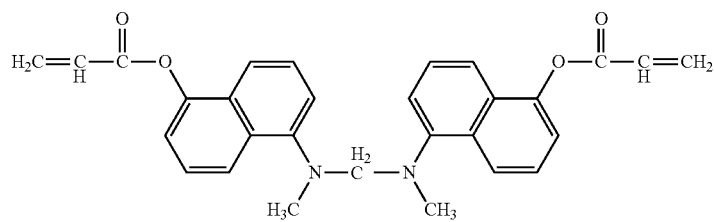
(G-9)
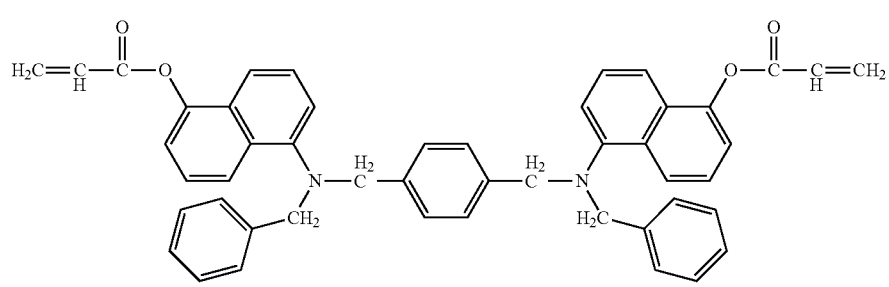
(G-10)
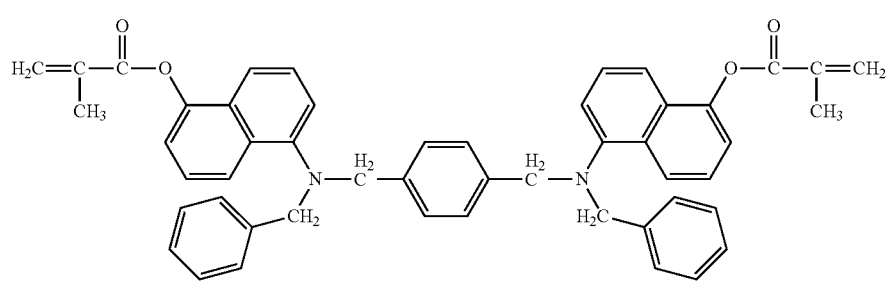
(G-11)
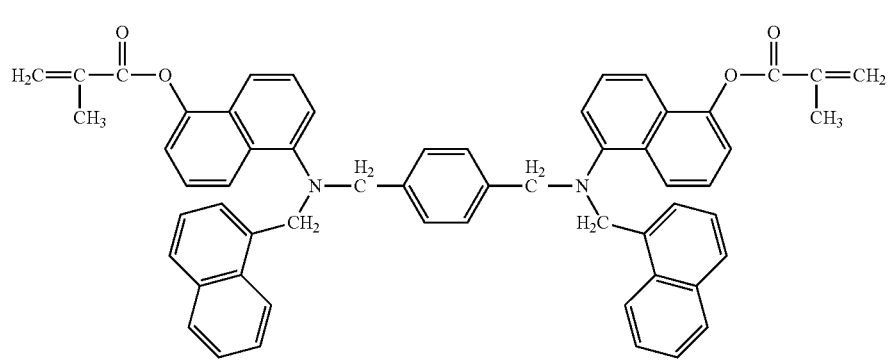
(G-12)
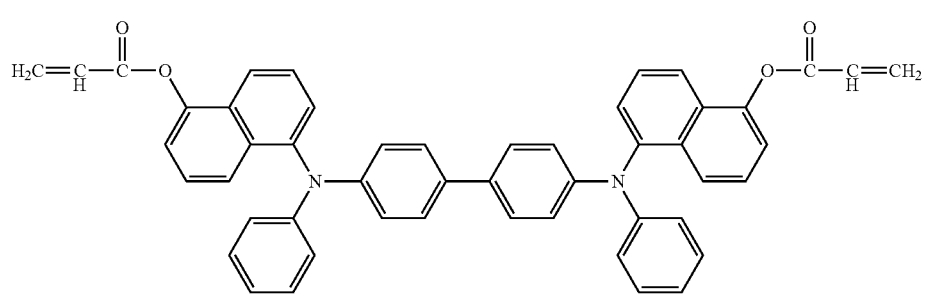
(G-13)

-continued
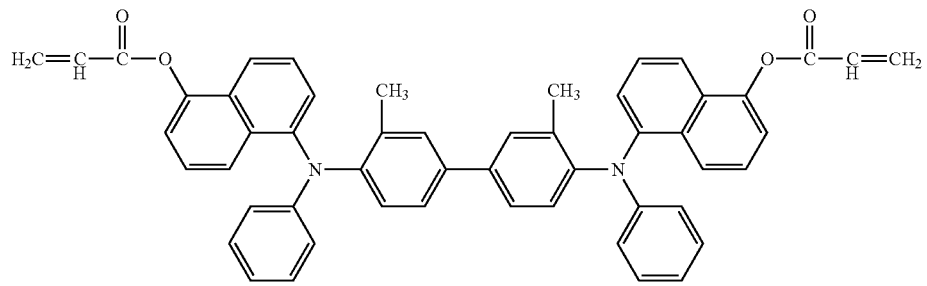
(G-14)
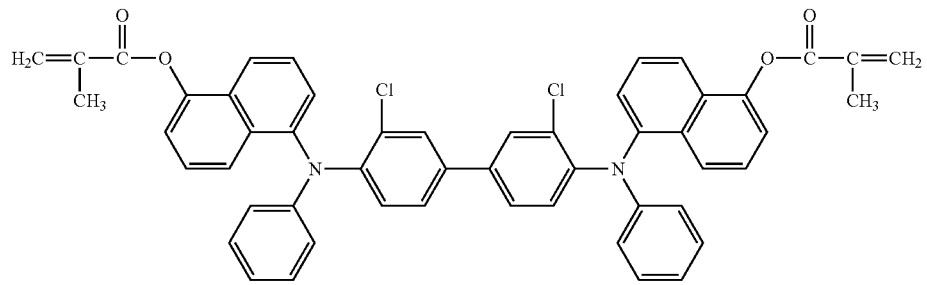
(G-15)
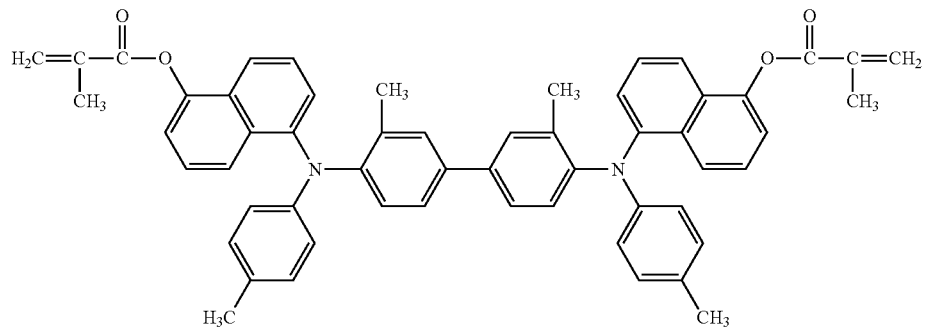
(G-16)
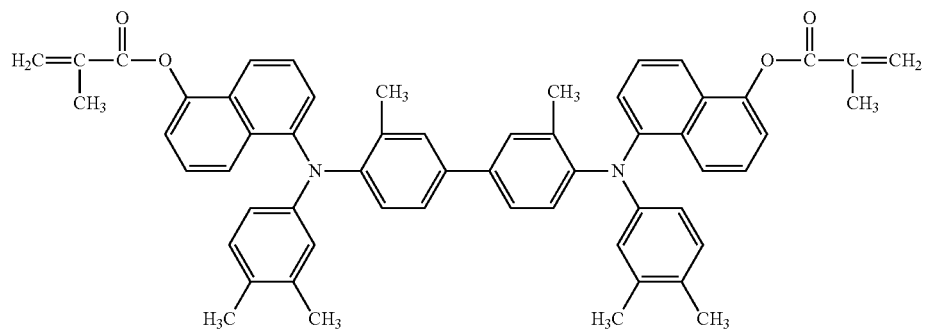
(G-17)
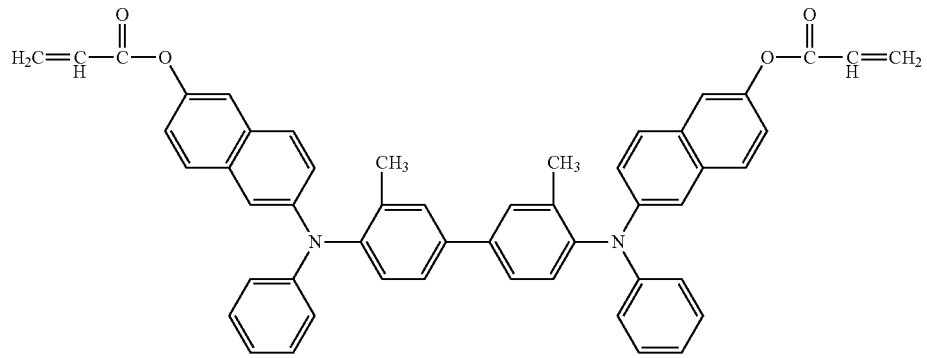
(G-18)

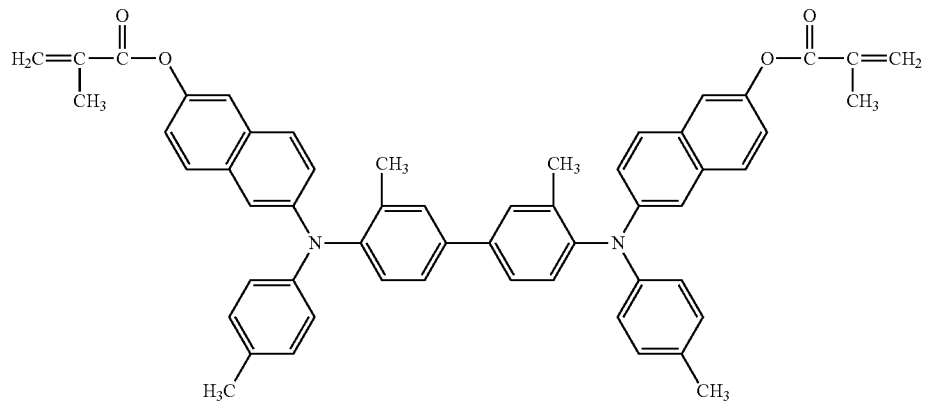
(G-19)
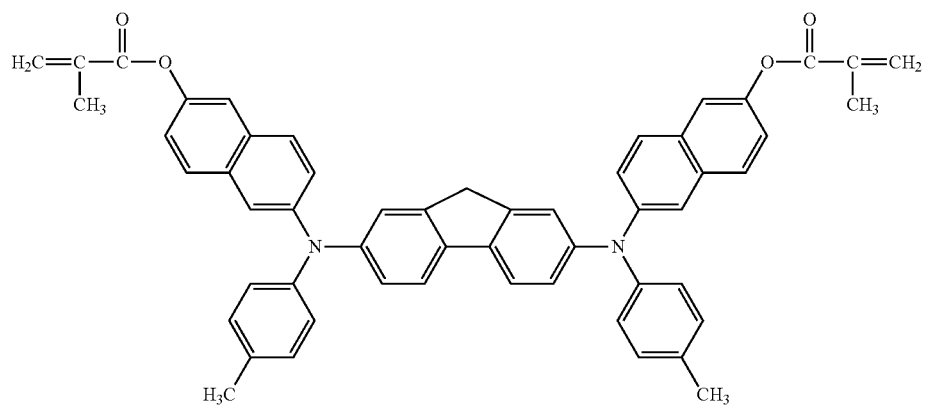
(G-20)
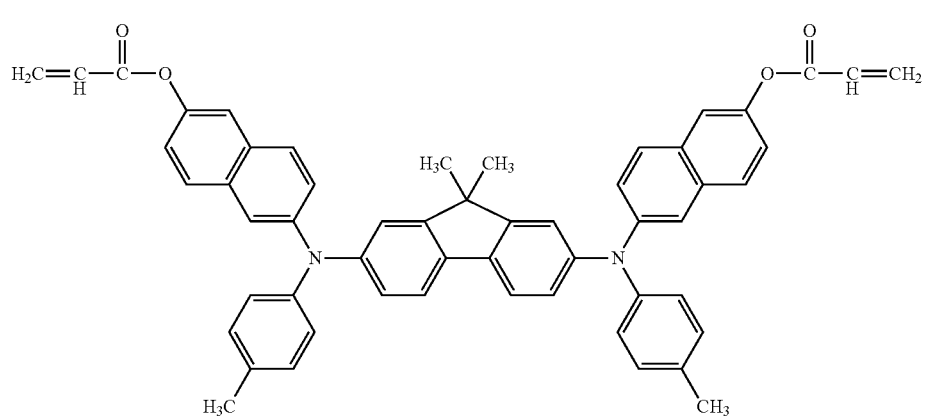
(G-22)

-continued
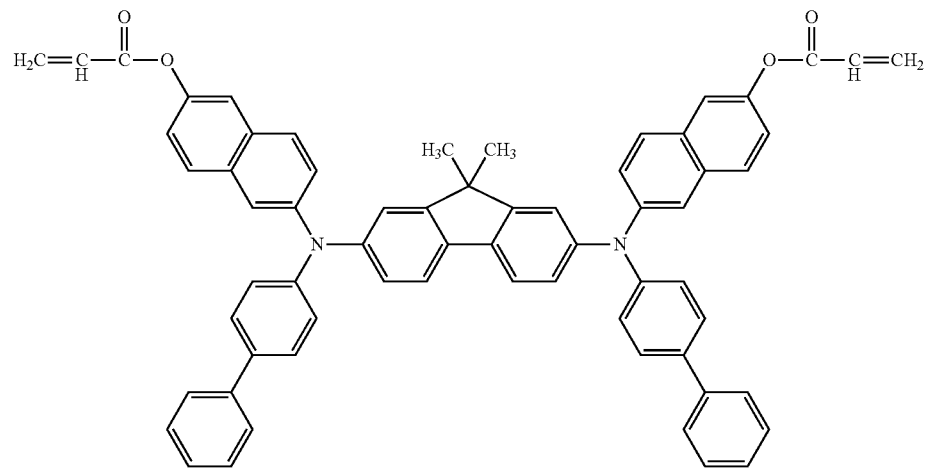
(G-23)
(C-23)
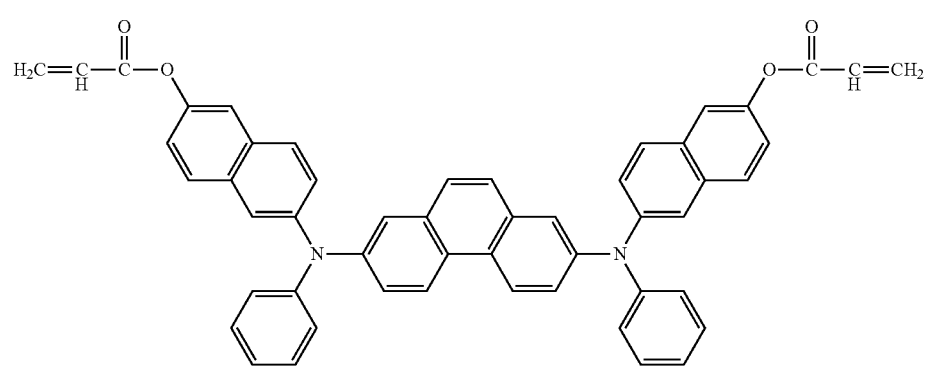
(G-24)
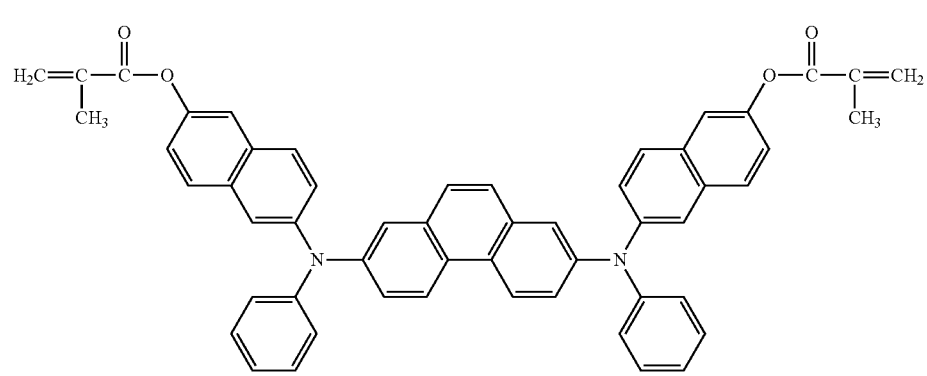
(G-25)
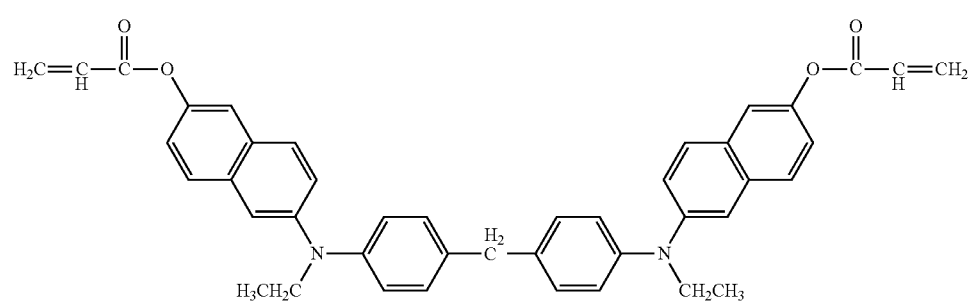
(G-26)

-continued
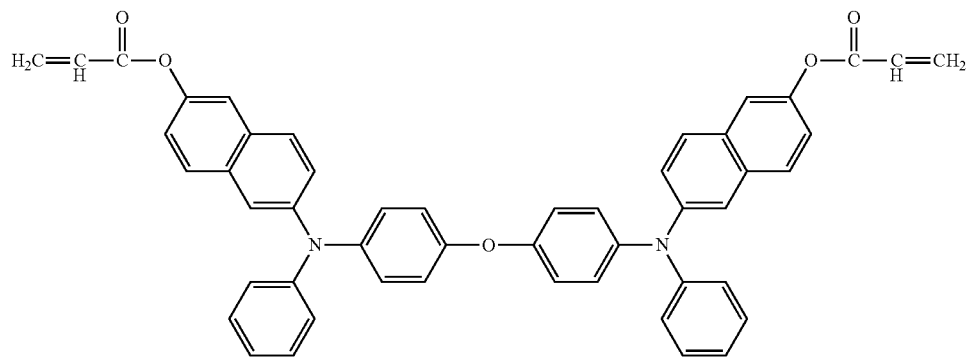
(G-27)
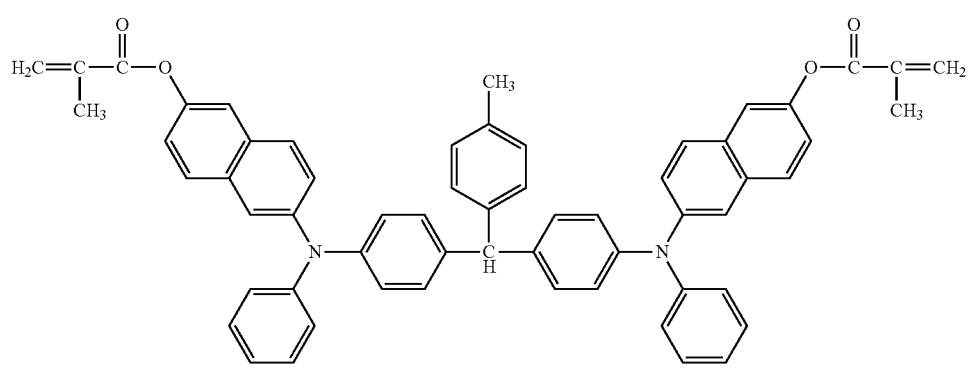
(G-28)
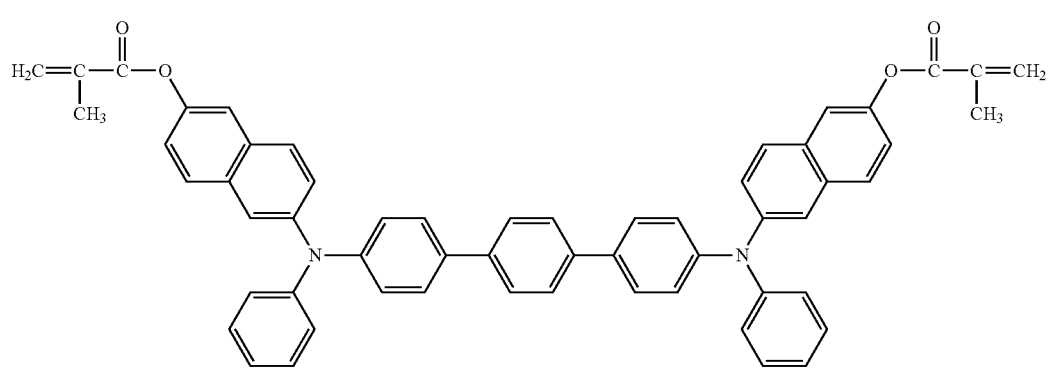
(G-29)
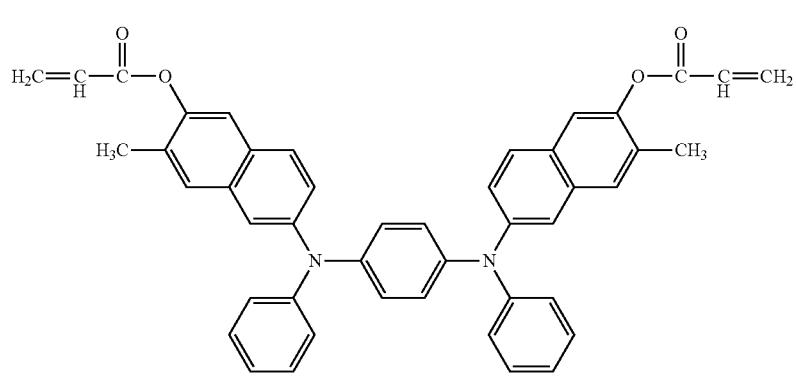
(G-30)

-continued
(G-31)
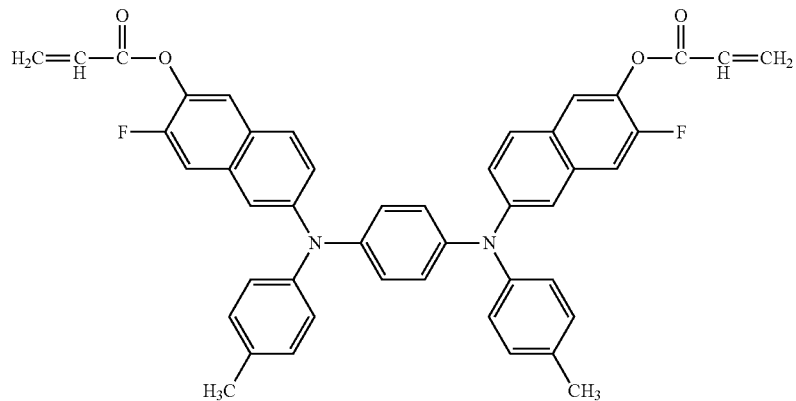
(G-32)
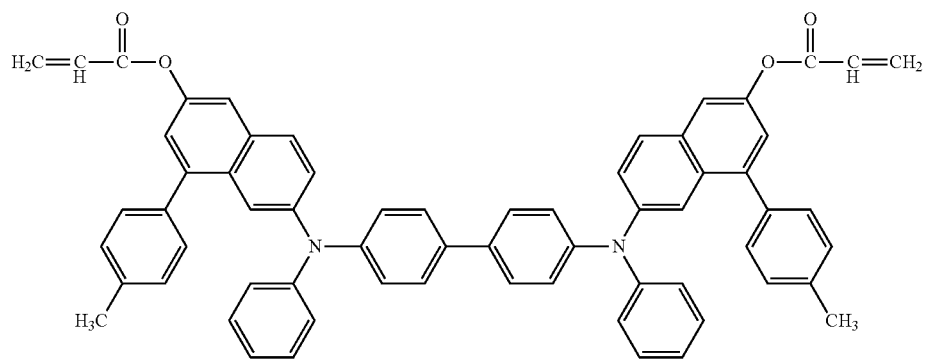
(G-33)
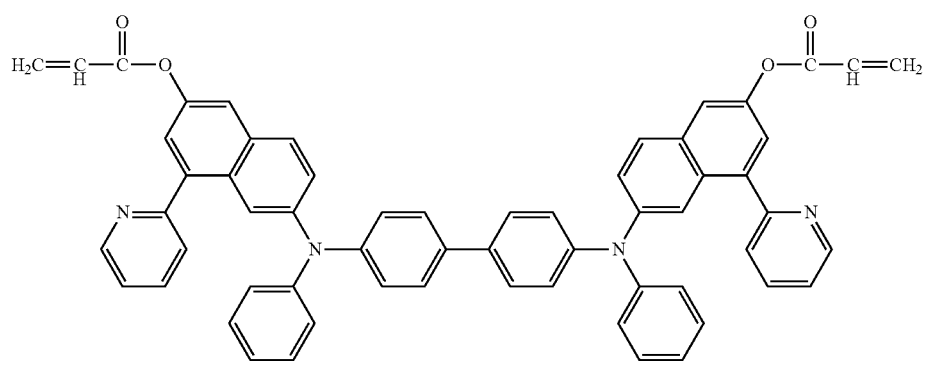
(G-34)
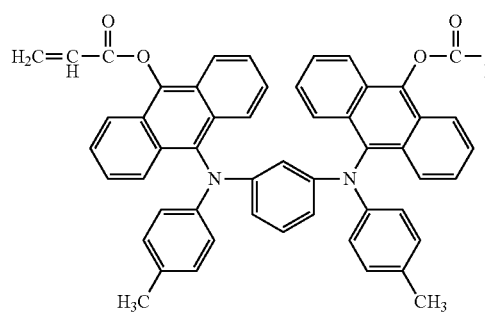
(G-35)
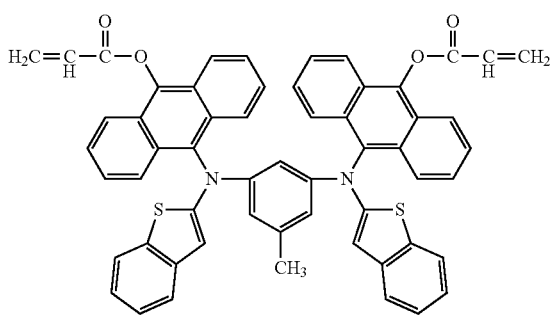

(G-36)

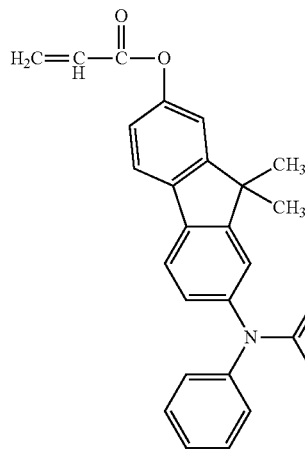
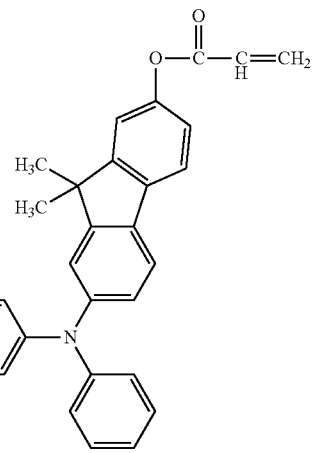

The acrylic ester compounds of the present invention represented by General Formulae (1-4) to (1-6) and (2-2) are novel substances, and they may be synthesized by using the hydroxy compound represented by General Formulae (1-4-1) to (1-6-1) and (2-2-1), respectively, as manufacturing intermediates, and by reacting these intermediates with acryloyl chloride or methacryloyl chloride.

<General Formula (1-4-1)>

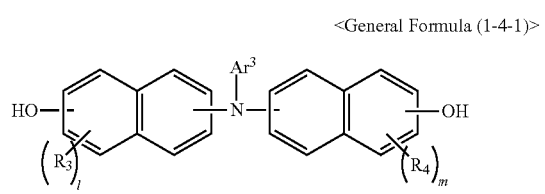

where, in General Formula (1-4-1), $R_3$ and $R_4$ represent an alkyl group which may have a substituent, an alkoxy group which may have a substituent, an aryl group which may have a substituent, a heterocyclic group which may have a substituent or a halogen atom; $Ar^3$ represents an alkyl group which may have a substituent, an aryl group which may have a substituent, a condensed polycyclic hydrocarbon group which may have a substituent or a heterocyclic group which may have a substituent, and each substituent may be bonded with the alkyl group, the aryl group, the condensed polycyclic hydrocarbon group or the heterocyclic group through a nitrogen atom; l and m are the same or different and represent an integer of zero to six.

<General Formula (1-5-1)>

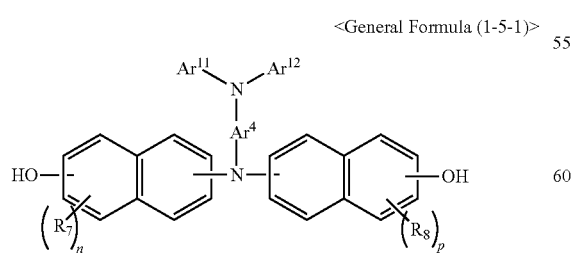

where, in General Formula (1-5-1), $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents an alkylene group which may have a substituent, an arylene group which may have a substituent, a bivalent condensed polycyclic hydrocarbon group which may have a substituent or a bivalent heterocyclic group which may have a substituent; $Ar^{11}$ and $Ar^{12}$ represent an alkyl group which may have a substituent, an aryl group which may have a substituent or a condensed polycyclic hydrocarbon group which may have a substituent, and $Ar^{11}$ and $Ar^{12}$ may be bonded together through adjacent carbon atoms to form a heterocycle; n and p are the same or different and represent an integer of zero to six.

<General Formula (1-6-1)>

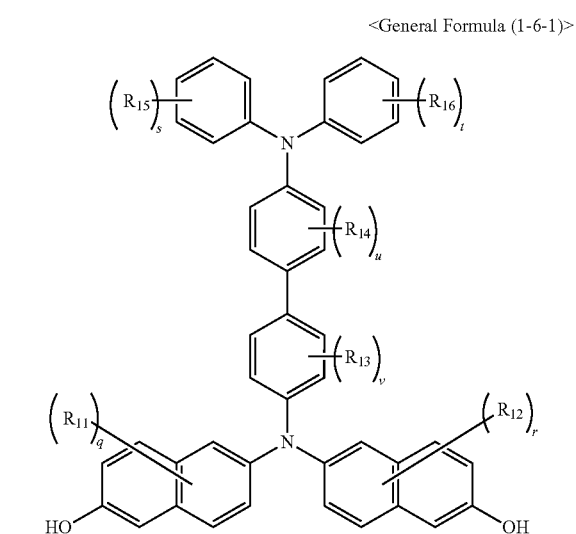

where, in General Formula (1-6), $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{16}$ represent an alkyl group which may have a substituent, an alkoxy group which may have a substituent, an aryl group which may have a substituent or a halogen atom; q and r are the same or different and represent an integer of zero to six, s and t are the same or different and represent an integer of zero to five, and u and v are the same or different and represent an integer of zero to four.

<General Formula (2-2-1)>

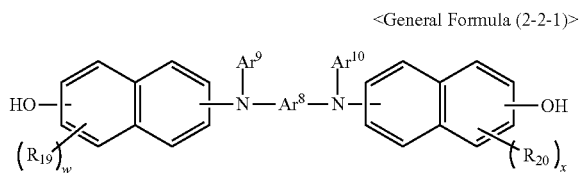

where, in General Formula (2-2-1), $R_{19}$ and $R_{20}$ represent an alkyl group which may have a substituent, an alkoxy group which may have a substituent, an aryl group which may have a substituent, a heterocyclic group which may have a substituent or a halogen atom; $Ar^9$ and $Ar^{10}$ represent an alkyl group which may have a substituent, an aryl group which may have a substituent or a heterocyclic group which may have a substituent; $Ar^8$ represents an alkylene group which may have a substituent, an arylene group which may have a substituent or a bivalent condensed polycyclic hydrocarbon group which may have a substituent; w and x are the same or different and represent an integer of zero to six.

For example, a hydroxy compound is synthesized with the following procedure, and the obtained hydroxy compound is reacted with acryloyl chloride or methacryloyl chloride. Thus, an acrylic compound or a methacrylic compound of the present invention may be easily synthesized.

<Synthesis of Hydroxy Compound>

As shown in Reaction Formula (a), a methoxy compound (E-1) as a raw material is demethylated by means of a heretofore known method to synthesize a hydroxy compound (E-2) (synthetic process of a hydroxy compound by demethylation').

Here, the structural formula of each compound in Reaction Formula (a) is abbreviated. (E-2) represents a compound whose structural formula corresponds to that of the hydroxy compounds represented by General Formulae (1-4-1) to (2-2-1).

<Reaction Formula (a)>

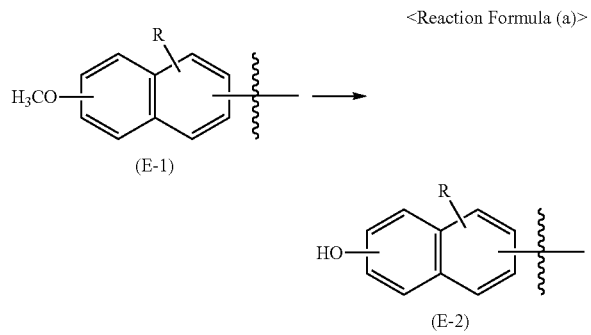

where, in Reaction Formula (a), R is synonymous to $R_3$, $R_4$, $R_7$, $R_8$, $R_{12}$, $R_{19}$ to $R_{20}$ in General Formulae (1-4-1) to (1-6-1) and (2-2-1).

Examples of the demethylation includes a method using acids such as concentrated hydrochloric acid, hydrobromic acid, hydriodic acid, trifluoroacetic acid, pyridine hydrochloride, magnesium iodide etherate, aluminum chloride, aluminum bromide, boron tribromide and boron tetrabromide; and a method using base or an organometallic reagents such as potassium hydroxide, Grignard reagent, sodium-butanol, lithium-biphenyl, lithium iodide-collidine, lithium diphenylphosphide-THF and sodium thiolate-DMF.

Among these, methods using boron tribromide and sodium thiolate-DMF are particularly effective, but the synthetic method for obtaining the intermediate of the present invention is not restricted to these. Specific synthetic examples are described hereinafter in Examples.

The hydroxy compound of the present invention obtained by the synthesis above is characterized by the expression of General Formulae (1-4-1) to (1-6-1) and (2-2-1). Examples of $R_3$, $R_4$, $R_7$, $R_8$, $R_{11}$, $R_{12}$, $R_{19}$ or $R_{20}$ are synonymous to those described in General Formulae (1-4) to (1-6) and (2-2).

<Synthesis of Acrylic Compound or Methacrylic Compound>

As shown in Reaction Formula (b), a hydroxy compound (E4) is used as a manufacturing intermediate, and an acrylic ester compound (E5) is synthesized similarly by means of a heretofore known esterification method ('acrylation or methacrylation process'). Here, the structural formula of each compound in Reaction Formula (b) is abbreviated and represents a compound whose structural formula corresponds to that of the hydroxy compounds represented by General Formulae (1-4-1) to (1-6-1) and (2-2-1). In Reaction Formula (b), R is synonymous to $R_3$, $R_4$, $R_7$, $R_8$, $R_{11}$, $R_{12}$, $R_{19}$ and $R_{20}$ in General Formulae (1-4-1) to (1-6-1) and (2-2-1).

<Reaction Formula (b)>

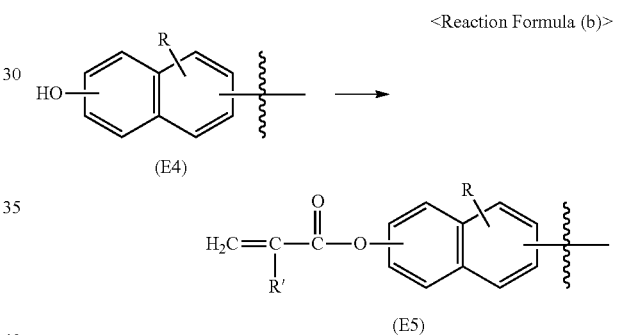

Examples of the methods for acrylation or methacrylation include a reaction of a hydroxy compound (E4) with acrylic acid or methacrylic acid, or an ester compound, acid halide or acid anhydride of these carboxylic acids.

For example, an acrylic ester compound may be synthesized by heating and stirring with dehydration a hydroxy compound (E4) and acrylic acid with an esterification catalyst in an organic solvent. It may also be synthesized simply by reacting a hydroxy compound and acryloyl chloride in an organic solvent under the presence of an alkali. Examples of the alkali used for this reaction includes alkalis such as sodium hydroxide and potassium hydroxide, aqueous solutions thereof, amine bases such as triethylamine and pyridine Examples of the organic solvent used for the reaction includes a hydrocarbon solvent such as toluene; an ether solvent such as tetrahydrofuran; an ester solvent such as ethyl acetate; a ketone solvent such as methyl ethyl ketone; and a halogen solvent such as chloroform. Specific synthetic examples are shown in Examples hereinafter.

The acrylic ester compounds represented by General Formulae (1-4), (1-5), (1-6) and (2-2) above of the present invention have a triamine structure with an expanded conjugated system having two naphthylene groups bonded in a molecule; therefore, a favorable charge transport function with high hole mobility is provided. Favorable chain polymerizability such as radical polymerizability may be provided as well since the acrylic ester or methacrylic ester group is introduced. Therefore, a cured resin film with high crosslink density may be easily formed with the irradiation of ultraviolet (UV) rays, electron rays and radioactive rays and with the use of radical initiator. The acrylic ester compounds have superior film formation properties, and they can meet the demand for mechanical resistance such as abrasion and heat resistance; moreover, they can provide favorable charge transport properties as well. Because of such superior properties, they are extremely useful as an organic functional material for various organic semiconductor devices such as organic electrophotographic photoconductor, organic EL, organic TFT and organic solar cell.

In addition, the acrylic ester compound of the present invention has a favorable compatibility with other monomers. Examples of the other monomers include trimethylolpropane triacrylate, trimethylolpropane trimethacrylate, trimethylolpropane alkylene-modified triacrylate, trimethylolpropane ethylene oxide-modified triacrylate (ethylene oxide-modified is hereinafter abbreviated as 'EO-modified'), trimethylolpropane propylene oxide-modified triacrylate ('propylene oxide-modified' is hereinafter abbreviated as 'PO-modified'), trimethylolpropane caprolactone-modified triacrylate, trimethylolpropane alkylene-modified trimethacrylate, pentaerythritol triacrylate, pentaerythritol tetraacrylate, glycerol triacrylate, glycerol epichlorohydrin-modified triacrylate, glycerol EO-modified triacrylate, glycerol PO-modified triacrylate, tris(acryloxyethyl)isocyanurate, dipentaerythritol hexaacrylate, dipentaerythritol caprolactone-modified hexaacrylate, dipentaerythritol hydroxypentaacrylate, alkylated dip entaerythritol pentaacrylate, alkylated dipentaerythritol tetraacrylate, alkylated dipentaerythritol triacrylate, dimethylolpropane tetraacrylate, pentaerythritol ethoxytetraacrylate, E0-modified triacrylate phosphate and 2,2,5,5-tetrahydroxymethylcyclopentanone tetraacrylate.

These monomers may be used alone, or they may be used in combination and mixed in an acrylic ester compound of the present invention, which may be selected according to the demand characteristics to be achieved. The mixed quantities of these monomers vary according to applications; for an application to the charge transport layer of an electrophotographic photoconductor, the mixing ratio of the monomer to an acrylic ester compound on a mass basis is usually around 0.01% to 1,500%, and preferably around 1% to 500%.

(Latent Electrostatic Image Bearing Member)

In the first aspect of a latent electrostatic image bearing member of the present invention, an outermost layer includes a cured material which may be obtained through radical polymerization of a radically polymerizable compound of component (A1), where the radically polymerizable compound of component (A1) includes two radically polymerizable groups and a substituted amino group which does not include a radically polymerizable group in a molecule; the radically polymerizable groups and the nearest substituted amino group do not include an unsaturated bond in between and are bonded with two or more aromatic hydrocarbon compounds. It further includes other components according to requirements.

Also, the outermost layer of the latent electrostatic image bearing member of the present invention related to the first aspect includes a cured material which may be obtained through radical polymerization of a radically polymerizable compound of component (A1), where the radically polymerizable compound of component (A1) includes two radically polymerizable groups and a substituted amino group which does not include a radically polymerizable group in a molecule; the radically polymerizable groups and the nearest substituted amino group do not include an unsaturated bond in between and are bonded with two or more aromatic hydrocarbon compounds. It further includes a radically polymerizable compound including three or more radically polymerizable groups in a molecule, a photo-polymerization initiator, and other compositions according to requirements.

In the second aspect of a latent electrostatic image bearing member of the present invention, an outermost layer includes a polymer including a condensed polycyclic aromatic hydrocarbon, and it further includes other components according to requirements.

The polymer including a condensed polycyclic aromatic hydrocarbon is not particularly restricted as long as it includes a condensed polycyclic aromatic hydrocarbon, and it can be appropriately selected according to applications. Examples thereof include a cured material (1) which is obtained by polymerization of a radically polymerizable compound including a condensed polycyclic aromatic hydrocarbon in which a radically polymerizable group and a non-radically-polymerizable substituted amino group are connected through a condensed polycyclic aromatic hydrocarbon group, and a cured material (2) which is obtained by polymerization of a radically polymerizable compound of (1) above including a condensed polycyclic aromatic hydrocarbon and a radically polymerizable compound including three or more radically polymerizable groups in a molecule.

Also, the latent electrostatic image bearing member of the present invention related to the second aspect includes an outermost layer which includes a cured material which may be obtained through radical polymerization of a radically polymerizable compound of component (A2), where the radically polymerizable compound of component (A2) includes a condensed polycyclic aromatic hydrocarbon connected with a radically polymerizable group and a substituted amino group which does not include a radically polymerizable group through a condensed polycyclic aromatic hydrocarbon group. It further includes a radically polymerizable compound including three or more radically polymerizable groups in a molecule, a photo-polymerization initiator, and other compositions according to requirements.

<Radically Polymerizable Compound of Component (A1)>

This relates to an electrophotographic photoconductor that a cured film obtained by radical polymerization of a specific radically polymerizable monomer is arranged on its surface, an image forming method which uses thereof, an image forming apparatus and a process cartridge for an image forming apparatus. The radically polymerizable monomer here preferably has a structure which develops a charge transport function as well as a structure of radical polymerizability. Many radically polymerizable monomers having the structure which develops a charge transport function as well as the structure of radical polymerizability have been proposed, and JP-A No. 2004-212959 discloses four hundred and several tens of compounds as examples.

However, these conventional radically polymerizable monomers cannot simultaneously satisfy the high abrasion resistance and the electrical property with little occurrence of rest potential at a high level. The reason thereof is presumably the following. It has become clear that the crosslink density should be sufficiently increased in order to achieve an advanced abrasion resistance such that hardly any scratches can be made. To increase the crosslink density, the content of the radically polymerizable group should be increased, and thus it is required that the radically polymerizable group is polyfunctionalized or that the molecular weight of the charge transport structure is reduced. However, the reduction in the molecular weight of the structure which develops favorable charge transport property is limited. On the other hand, the polyfunctionalization of the radically polymerizable group is effective in increasing the content but impairs the charge transport property after curing. The reason thereof remains unclear, but it is presumably because the heavy cross-linking constrains the molecular movement of the charge transport structural portion and reduces the range of free movement, which consequently decreases the hopping mobility of the charge.

The inventors of the present invention examined a novel radically polymerizable monomer which can simultaneously satisfy the high-density radical polymerizability and the charge transport property. As a result, they found an effective radically polymerizable monomer, where the radically polymerizable monomer includes two radically polymerizable groups and a substituted amino group which does not include a radically polymerizable group, and the radically polymerizable group and the nearest substituted amino group are connected with two or more aromatic hydrocarbon compounds without an unsaturated bond in between, and they found that a film produced by using and curing this monomer could simultaneously satisfy the high-density radical polymerizability and the charge transport property. In order to reduce the constraint of molecular movement despite high crosslink density, a favorable radically polymerizable monomer has a structure in which a charge transport group composed of an aromatic compound whose structure is bulky and hardly moves is connected to the crosslinking portion of an aliphatic structure in the form of a pendant that the group may easily rotate with only one bonding. Such structural refinement can balance the higher-density radical hardenability and favorable charge transport property.

A conventional polyfunctional charge transport monomer has problems such as the occurrence of cracks due to the growing deformation in curing and insufficient hardenability despite the polyfunctionality, but the specific radically polymerizable monomer of the present invention may be cured without the occurrences of cracks to provide a uniform and smooth film which is sufficiently cross-linked and cured and favorably functions as a surface layer of a photoconductor. Also, the formation of a high-density cured film with charge transfer property sufficiently increases the film strength, prevents an external additive in a toner with extremely high hardness such as silica particles from sticking in the photoconductor and therefore decreases image defects such as white spots.

The formation of a high-density cross-linking cured film may be achieved with the radically polymerizable monomer of the component (A1). More preferably, the component (A1) is mixed with a radically polymerizable monomer as a component B which includes three or more radically polymerizable groups in a molecule. Also, various heretofore known methods may be applied to the initiation of radical polymerization, and a latent electrostatic image bearing member with high crosslink density and superior mechanical strength may be obtained by adding a photo-polymerization initiator and irradiating a light for curing in a short period of time.

As a radically polymerizable group in the component (A1) of a radically polymerizable compound, any heretofore known group may be used. Examples thereof include a vinyl group, an allyl group, an acryloyloxy group, a methacryloyloxy group and an acrylamide group. Especially, an acryloyloxy group and a methacryloyloxy group are preferable in terms of polymerization property. The use of an acryloyloxy group, a methacryloyoxy group or a combination thereof enables the preparation of a sufficiently cured smooth film in a short period of time.

The substituted amino group which does not include a radically polymerizable group is a substituted amino group which does not include the vinyl group, allyl group, acryloyloxy group, methacryloyloxy group and acrylamide group, and it preferably has a structure which develops the charge transport property as described above. A secondary amino group is given as a precursor of the substituted amino group, and examples of the amino group include a dialkyl amine such as dimethylamine and diethylamine, an aralkyl amine such as dibenzyamine and bis(4-methylbenzyl)amine, a diarylamine such as diphenylamine and di-p-tolylamine, and diheterocyclic amine such as bis(2-thienyl)amine and bis(2-furyl)amine.

The charge transporting compound which includes the secondary amino group as a substituted group is a compound which has a property to transport the charge generated by the reception of a light by means of hopping conduction. The charge transport compound is categorized to a hole transport substance and an electron transport substance. Examples of the electron transport substance include electron accepting substances such as chloranil, bromanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-4H-indeno[1,2-b]thiophene-4-one, 1,3,7-trinitrodibenzothiophene-5,5-dioxide and diphenoquinone derivative. Examples of the hole transport substance include an oxazole derivative, an oxadiazole derivative, an imidazole derivative, a monoarylamine derivative, a diarylamine derivative, a triarylamine derivative, a stilbene derivative, an α-phenylstilbene derivative, a benzidine derivative, a diarylmethane derivative, a triarylmethane derivative, a 9-styrylanthracene derivative, a pyrazoline derivative, a divinylbenzene derivative, a hydrazone derivative, an indene derivative, a butadiene derivative, a pyrene derivative, a bisstilbene derivative, an enamine derivative and other heretofore known materials.

Among the radically polymerizable compounds of component (A1), a compound which may be represented by any one of General Formulae (1), (1-1), (1-2), (1-3) and (2-1) above is more preferable.

<Radically Polymerizable Compound Including a Condensed Polycyclic Aromatic Hydrocarbon of Component (A2)>

The component (A2) of the radically polymerizable compound including a condensed polycyclic aromatic hydrocarbon is a compound in which a radically polymerizable group is connected with a substituted amino group which does not include a radically polymerizable group through a condensed polycyclic aromatic hydrocarbon group.

The radically polymerizable group is not particularly restricted and can be appropriately selected according to applications. Examples thereof include a vinyl group, an allyl group, an acryloyloxy group, a methacryloyloxy group and an acrylamide group. Among these, the acryloyloxy group and the methacryloyloxy group are particularly preferably in terms of polymerization properties. The use of an acryloyloxy group, a methacryloyoxy group or a combination thereof enables the preparation of a sufficiently cured smooth film in a short period of time.

The substituted amino group which does not include a radically polymerizable group is not restricted as long as it is a secondary amino group which does not include a radically polymerizable group such as vinyl group, allyl group, acryloyloxy group, methacryloyloxy group and acrylamide group, and it can be appropriately selected according to applications. Examples thereof include a dialkyl amine such as dimethylamine and diethylamine, an aralkyl amine such as dibenzyamine and bis(4-methylbenzyl)amine, a diarylamine such as diphenylamine and di-p-tolylamine, and diheterocyclic amine such as bis(2-thienyl)amine and bis(2-furyl) amine.

The charge transporting compound which includes the secondary amino group which does not include a radically polymerizable group as a substituent is a compound which has a property to transport the charge generated by the reception of a light in the photosensitive layer by means of hopping conduction. The charge transport compound is categorized to a hole transport substance and an electron transport substance.

Examples of the electron transport substance include electron accepting substances such as chloranil, bromanil, tetracyanoethylene, tetracyanoquinodimethane, 2,4,7-trinitro-9-fluorenone, 2,4,5,7-tetransmitro-9-fluorenone, 2,4,5,7-tetranitroxanthone, 2,4,8-trinitrothioxanthone, 2,6,8-trinitro-4H-indeno[1,2-b]thiophene-4-one, 1,3,7-trinitrodibenzothiophene-5,5-dioxide and diphenoquinone derivative.

Examples of the hole transport substance include an oxazole derivative, an oxadiazole derivative, an imidazole derivative, a monoarylamine derivative, a diarylamine derivative, a triarylamine derivative, a stilbene derivative, an α-phenylstilbene derivative, a benzidine derivative, a diarylmethane derivative, a triarylmethane derivative, a 9-styrylanthracene derivative, a pyrazoline derivative, a divinylbenzene derivative, a hydrazone derivative, an indene derivative, a butadiene derivative, a pyrene derivative, a bis-stilbene derivative and an enamine derivative.

As a radically polymerizable compound which includes a condensed polycyclic aromatic hydrocarbon, a compound represented by any one of General Formulae (1), (1-4), (1-5), (1-6) and (2-2) above is more preferable.

<Radically Polymerizable Compound which Includes Three or More Radically Polymerizable Groups in a Molecule>

The radically polymerizable compound which includes three or more radically polymerizable groups in a molecule means a monomer which has neither a hole transport structure such as triarylamine, hydrazone, pyrazolene and carbazole nor an electron transport structure such as condensed polycyclic quinine, diphenoquinone and electron-absorbing aromatic ring having a cyano group or a nitro group, and has three or more radically polymerizable group. The radically polymerizable group is not restricted as long as it has a carbon-carbon double bond and is radically polymerizable. Examples of the radically polymerizable group include 1-substituted ethylene groups and 1,1-substituted ethylene groups. For example, 1-substituted ethylene groups may be represented by <Formula 1> below:

   <Formula 1> where, in Formula 1, $X_1$ represents an arylene group such as phenylene group and naphthylene group which may have a substituent; an alkenylene group which may have a substituent; a carboxylic group; a carbonyloxy group, —CON($R^{17}$)— group ($R^{17}$ represents a hydrogen atom, an alkyl group such as methyl group and ethyl group, an aralkyl group such as benzyl group, naphthylmethyl group and phenethyl group; and an aryl group such as phenyl group and naphthyl group) or a sulfide group.

Examples of the substituent thereof include a vinyl group, a styryl group, a 2-methyl-1,3-butadienyl group, a vinylcarbonyl group, an acryloyloxy group, an acryloylamide group and a vinylthioether group. Also, 1,1-substituted ethylene groups may be represented by <Formula 2> below:

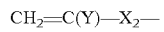   <Formula 2> where, in Formula 2, Y represents an alkyl group which may have a substituent; an aralkyl group which may have a substituent; an aryl group such as phenyl group and naphthyl group which may have a substituent; a halogen atom; a cyano group; a nitro group; an alkoxy group such as methoxy group and ethoxy group; a —COOR$^{18}$ group ($R^{18}$ represents a hydrogen atom; an alkyl group such as methyl group and ethyl group which may have a substituent; an aralkyl group such as benzyl group and phenethyl group which may have a substituent; and an aryl group such as phenyl group and naphthyl group which may have a substituent) or a —CONR$^{19}$R$^{20}$ ($R^{19}$ and $R^{20}$ represent a hydrogen atom; an alkyl group such as methyl group and ethyl group which may have a substituent; an aralkyl group such as benzyl group, naphthylmethyl group and phenethyl group which may have a substituent; and an aryl group such as phenyl group and naphthyl group which may have a substituent, and they are the same or different); $X_2$ represents a substituent and single bond which are equivalent to those of $X_1$ in Formula 1 and an alkylene group; at least any one of Y and $X_2$ is an oxycarbonyl group, a cyano group, an alkenylene group and an aromatic ring.

Specific examples of these substituents thereof include an α-acryloyloxy chloride group, a methacryloyloxy group, an α-cyanoethylene group, an α-cyanoacryloyloxy group, an α-cyanophenylene group and a methacryloylamino group. Examples of the substituents which $X_1$, $X_2$ and Y may have include: a halogen atom; a nitro group; a cyano group; an alkyl group such as methyl group and ethyl group; an alkoxy group such as methoxy group and ethoxy group; an aryloxy group such as phenoxy group; an aryl group such as phenyl group and naphthyl group; and an aralkyl group such as benzyl group and phenethyl group. Among these radically polymerizable groups, an acryloyloxy group and a methacryloyloxy group are especially useful, and a compound which has three or more acryloyloxy groups may be obtained through an esterification reaction or a transesterification reaction of a compound with three or more hydroxyl groups in a molecule with an acrylic acid (salt), an acrylic halide and an acrylic ester. Also, a compound which has three or more methacryloyloxy groups may be obtained in the same manner. Here, the radically polymerizable groups in a monomer which has three or more radically polymerizable groups are the same or different.

The radically polymerizable compound which has three or more radically polymerizable groups in a molecule is not particularly restricted and can be appropriately selected according to applications. Examples thereof include trimethylolpropane triacrylate (which is hereinafter referred to as TMPTA), trimethylolpropane trimethacrylate, trimethylolpropane alkylene-modified triacrylate, trimethylolpropane ethylene oxide-modified triacrylate ('ethylene oxide-modified' is hereinafter abbreviated as 'EO-modified'), trimethylolpropane propylene oxide-modified triacrylate ('propylene oxide-modified' is hereinafter abbreviated as 'PO-modified'), trimethylolpropane caprolactone-modified triacrylate, trimethylolpropane alkylene-modified trimethacrylate, pentaerythritol triacrylate, pentaerythritol tetraacrylate (which is hereinafter abbreviated as PETTA), glycerol triacrylate, glycerol epichlorohydrin-modified triacrylate ('epichlorohydrin-modified' is hereinafter abbreviated as 'ECH-modified'), glycerol EO-modified triacrylate, glycerol PO-modified triacrylate, tris(acryloxyethyl)isocyanurate, dipentaerythritol hexaacrylate (which is hereinafter abbreviated as DPHA), dipentaerythritol caprolactone-modified hexaacrylate, dipentaerythritol hydroxypentaacrylate, alkylated dipentaerythritol pentaacrylate, alkylated dipentaerythritol tetraacrylate, alkylated dipentaerythritol triacrylate, dimethylolpropane tetraacrylate (which is hereinafter abbreviated as DTMPTA), pentaerythritol ethoxytetraacrylate, EO-modified triacrylate phosphate and 2,2,5,5-tetrahydroxymethylcyclopentanone tetraacrylate.

These may be used alone or in combination of two or more types.

The ratio of the molecular weight of the radically polymerizable compound to the number of functional groups in the radically polymerizable compound, i.e. molecular weight/ number of polymerizable groups, is preferably 250 or less in order for the radically polymerizable compound having three or more radically polymerizable groups to form dense cross-linking in the cross-linked charge transport layer as the outermost layer. With the ratio exceeding 250, the cross-linked charge transport layer is soft, and the abrasion resistance decreases in some degree. Therefore, regarding the radically polymerizable compounds with modified groups such as EO, PO and caprolactone among the exemplary radically polymerizable compounds given above, it is not preferable to use a compound with an extremely long modified group by itself.

The content of the radically polymerizable compound which has three or more radically polymerizable groups in the outermost layer is preferably 20% by mass to 80% by mass, and more preferably 30% by mass to 70% by mass. It depends on the ratio of the radically polymerizable compound which has three or more radically polymerizable groups in a molecule in the solid content of the coating solution. When the content is less than 20% by mass, the three-dimensional crosslink density is low, and significant improvement in the abrasion resistance may not be achieved compared to a conventional thermoplastic binder resin. When it exceeds 80%, the content of a charge transport compound decreases, and electric properties may degrade.

<Photo-polymerization Initiator>

The photo-polymerization initiator is not particularly restricted and can be appropriately selected according to applications. Examples thereof include acetophenone photo-polymerization initiators, ketal photo-polymerization initiators, benzoin ether photo-polymerization initiators, benzophenone photo-polymerization initiators, thioxanthone photo-polymerization initiators and other photo-polymerization initiators.

Examples of the acetophenone photo-polymerization initiators and ketal photo-polymerization initiators include diethoxyacetophenone, 2,2-dimethoxy-1,2-diphenylethane-1-one, 1-hydroxy-cyclohexyl phenyl ketone, 4-(2-hydroxy-ethoxy)phenyl (2-hydroxy-2-propyl)ketone, 2-benzyl-2-dimethylamino-1-(4-morpholinophenyl)butanone-1,2-hydroxy-2-methyl-1-phenylpropane-1-one, 2-methyl-2-morpholino(4-methylthiophenyl)propane-1-one and 1-phenyl-1,2-propanedione-2-(o-ethoxycarbonyl)oxime.

Examples of the benzoin ether photo-polymerization initiators include benzoin, benzoin methyl ether, benzoin ethyl ether, benzoin isobutyl ether and benzoin isopropyl ether.

Examples of the benzophenone photo-polymerization initiators include benzophenone, 4-hydroxybenzophenon, o-methyl-benzoyl benzoate, 2-benzoylnaphthalene, 4-benzoylbiphenyl, 4-benzoyl phenyl ether, acrylated benzophenone and 1,4-benzoylbenzene.

Examples of the thioxanthone photo-polymerization initiators include 2-isopropylthioxanthone, 2-chlorothioxanthone, 2,4-dimethylthioxanthone and 2,4-diethylthioxanthone, 2,4-dichlorothioxanthone.

Examples of the other photo-polymerization initiators include ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-traimethylpentylphosphine oxide, methylphenyl glyoxy ester, 9,10-phenanthren, acridine compounds, triazine compounds and imidazole compounds.

A compound which promotes photo-polymerization may also be used independently or in combination with the above photo-polymerization initiators. Examples thereof include triethanolamine, methyldiethanolamine, ethyl 4-dimethylaminobenzoate, isoamyl 4-dimethylaminobenzoate, (2-dimethylamino)ethyl benzoate and 4,4'-dimethylaminobenzophenone.

These photo-polymerization initiators may be used alone or in combination of two or more.

The content of the photo-polymerization initiator in the outermost layer with respect to 100 parts of the total contents of the compound with radically polymerizable groups is preferably 0.5 parts by mass to 40 parts by mass, and more preferably one part by mass to 20 parts by mass. When the content is less than 0.5 parts by mass, photo-polymerization may not proceed sufficiently. When it exceeds 40 parts by mass, the electrical properties of the latent electrostatic image bearing member may be reduced.

Next, the method for forming the outermost layer is described.

The outermost layer is formed by preparing: (1) an outermost layer coating solution including a radically polymerizable compound of component (A1) or component (A2), and a radically polymerizable compound which includes three or more radically polymerizable groups in a molecule, or (2) an outermost layer coating solution including a radically polymerizable compound of component (A1) or component (A2), a radically polymerizable compound which includes three or more radically polymerizable groups in a molecule and a photo-polymerization initiator; and applying the coating solution to the surface of a photoconductor, which is then radically polymerized.

When the radically polymerizable compound is a liquid, other components are dissolved in the outermost layer coating solution for coating, and it may also be diluted by a solvent for coating. Examples of the solvent include: alcohols such as methanol, ethanol, 2-propanol and butanol; ketones such as acetone, methyl ethyl ketone, methyl isobutyl ketone and cyclohexanone; esters such as ethyl acetate and butyl acetate; ethers such as tetrahydrofuran, dioxane and propyl ether; halogens such as dichloromethane, dichloroethane, trichloroethane and chlorobenzene; aromatics such as benzene, toluene and xylene; cellosolves such as methyl cellosolve, ethyl cellosolve and cellosolve acetate. These solvents may be used alone or in combination of two or more. The dilution ratio varies depending on the solubility of the compositions, the coating method and the desired thickness, and it is discretionary. It may be coated with spray-coating, bead-coating and ring-coating methods.

The radically polymerizable compounds of component (A1) or component (A2) is important for providing the charge transport property to the outermost layer, and the content of the radically polymerizable compound in the outermost layer is preferably 20% by mass to 80% by mass, and more preferably 30% by mass to 70% by mass. When the content is less than 20% by mass, the charge transport property cannot be sufficiently maintained, and the degradation in the electrical properties under repeated use such as decrease in sensitivity and increase in rest potential. When it exceeds 80% by mass, the content of the radically polymerizable compound which includes three or more radically polymerizable groups in a molecule decreases. This reduces the crosslink density, and the desired property may not be fully exhibited.

Other than the radically polymerizable compound of component (A1) or component (A2), the radically polymerizable compound including three or more radically polymerizable groups in a molecule and the photo-polymerization initiator, a monofunctional or bifunctional radically polymerizable compound, a functional monomer and a radically polymerizable oligomer may be combined in the outermost layer coating solution according to requirements for the purpose of functionalization such as adjusting the viscosity in coating, easing the stress of the cross-linked charge transport layer, reducing the surface energy and reducing the friction factor. Heretofore known radically polymerizable compound, functional monomer and oligomer may be used.

Examples of the monofunctional radically polymerizable compound include 2-ethylhexyl acrylate, 2-hydroxyethyl acrylate, 2-hydroxypropyl acrylate, tetrahydrofurfuryl acrylate, 2-ethylhexylcarbitol acrylate, 3-methoxybutyl acrylate, benzyl acrylate, cyclohexyl acrylate, isoamyl acrylate, isobutyl acrylate, methoxy triethylene glycol acrylate, phenoxy tetraethylene glycol acrylate, cetyl acrylate, isostearyl acrylate, stearyl acrylate and styrene monomer.

Examples of the bifunctional radically polymerizable compound include 1,3-butanediol diacrylate, 1,4-butanediol diacrylate, 1,4-butanediol dimethacrylate, 1,6-hexanediol diacrylate, 1,6-hexane diol dimethacrylate, diethylene glycol diacrylate, neopentyl glycol diacrylate, bisphenol A-EO-modified diacrylate, bisphenol F-EO-modified diacrylate and neopentyl glycol diacrylate.

Examples of the functional monomer include a fluorinated monomer such as octafluoro pentyl acrylate, 2-perfluorooctyl ethyl acrylate, 2-perfluorooctyl ethyl methacrylate, a vinyl monomer, acrylate and methacrylate having a polysiloxane group such as acryloylpolydimethylsiloxaneethyl, methacryloylpolydimethylsiloxaneethyl, acryloylpolydimethylsiloxanepropyl, acryloylpolydimethylsiloxanebutyl and diacryloylpolydimethylsiloxanediethyl groups, which have 20 to 70 siloxane repeating units as described in JP-B Nos. 05-60503, JP-B 06-45770.

Examples of the radically polymerizable oligomer include epoxy acrylate, urethane acrylate and polyester acrylate oligomers. However, introduction of a large amount of a mono- and bi-functional radically polymerizable monomer or radically polymerizable oligomer may substantially decrease the three-dimensional cross-linkage density of the cross-linked surface layer, causing the reduction in abrasion resistance.

Therefore, the content of these monomers or oligomers is preferably 50 parts by mass or less, and more preferably 30 parts by mass or less, with respect to 100 parts by mass of the radically polymerizable compound which includes the condensed polycyclic aromatic hydrocarbon.

The outermost layer coating solution may further include additives such as various plasticizers (for the purpose of stress relaxation and adhesion improvement), leveling agents and low-molecular charge transport substances which do not have radical reactivity according to requirements. These additives are not particularly restricted, and any heretofore known substance may be used. As the plasticizer, substances used for a common resin such as dibutylphthalate and dioctylphthalate may be used, and the content is preferably 20% by mass or less, and more preferably 10% by mass or less with respect to the total solid content of the coating solution. Examples of the leveling agent include silicone oils such as dimethyl silicone oil and methylphenylsilicone oil and a polymer or an oligomer which includes perfluoroalkyl group in a side chain, and the content is preferably 3% by mass or less with respect to the total solid content of the coating solution.

After the outermost layer coating solution is applied, a drying process may take place in some situations, and then the coating is cured by light irradiation. Regarding the light irradiation, a UV light source such as high-pressure mercury-vapor lamp and metal halide lamp having an emission wavelength in an ultraviolet range may be used, and a visible light source may also be used to comply with the absorption wavelength of a radically polymerizable compound and a photo-polymerization initiator. The amount of the irradiated light is preferably 50 mW/cm$^2$ or greater, and more preferably 2,000 mW/cm$^2$ or less. When the amount of the irradiated light is less than 50 mW/cm$^2$, the curing reaction may require long time. When it exceeds 2,000 mW/cm$^2$, the reaction may proceed heterogeneously, resulting in local wrinkles as well as many non-reacted residues or halt ends on the surface of the outermost layer. Also, an abrupt cross-linking increases the inner stress, causing cracks or film exfoliation. In addition, nitrogen displacement may be performed during the light irradiation to prevent the oxygen from inhibiting the polymerization. The light irradiation may be performed continuously or intermittently with a few intervals. As an analogous means of the light irradiation, an electron beam irradiation may be used; however, it is preferable to use light energy by virtue of the ease of controlling the reaction speed and the simplicity of apparatus.

The increase in the quantity of the light irradiation increases the gel fraction, and the system becomes more insoluble and infusible. This gel fraction is preferably 95% or greater to achieve the purpose of the present invention. The gel fraction may be obtained by immersing the cured material in an organic solvent with high solubility such as tetrahydrofuran for five days and subsequently measuring the mass decrease. thickness of the charge transport layer is restricted to the hardening condition. The cross-linking charge transport layer is most preferably the outermost layer including the cured material. The cross-linking charge transport layer is preferably insoluble in an organic solvent.

The thickness of the cross-linking charge transport layer is preferably 1.0 μm to 11.5 μm, more preferably 1.5 μm to 11.5 μm, and even more preferably 3 μm to 10 μm. When the thickness exceeds 11.5 μm, cracks or film exfoliation tends to occur. Also, it becomes difficult to form a film with high crosslink density since the radical polymerization initiated by photo-fragmentation of a photo initiator does not occur easily in the deep portion. On the other hand, radical polymerization is easily inhibited by oxygen. That is, the cross-linking does not proceed or become non-uniform on the surface which is in contact with the atmosphere because of radical traps by oxygen. This effect is most prominent when the thickness of the cross-linking charge transport layer is 1.0 μm or less, and a cross-linking charge transport layer having a thickness of less than this value shows a decrease in the abrasion resistance and a non-uniform abrasion. In addition, the cross-linking charge transport layer is contaminated with the components of the lower charge transport layer during coating. When the coating thickness of the cross-linking charge transport layer is small, the contaminants spread in the whole layer, inhibiting the curing reaction and decreasing the crosslink density. In view of these reasons, the cross-linking charge transport layer can form a high-density cross-linking body with a thickness of 1.5 μm or greater, which can prevent white spots. The Gel fraction(%)=100×(mass of the cured coating composition after immersing and drying/initial mass of the cured coating composition)    <Mathematical Formula 1>

To form a cured covering composition having the gel fraction of 95% or greater, the cumulative energy of 10 J/cm$^2$ or greater is preferably irradiated. It is more preferable to harden to a gel fraction of 97% or greater. Raising the gel fraction can further prevent silica particles from sticking. In this case, the cumulative energy of 20 J/cm$^2$ or greater is preferably irradiated.

Having been cured by means of light irradiation, the material is annealed at 80° C. to 150° C. and then used as a latent electrostatic image bearing member. The time for annealing is preferably one minute to 60 minutes.

The latent electrostatic image bearing member of the present invention includes the cured material in its outermost layer. The composition is not restricted, but an organic photoconductor surface with negative-charge method is preferable since the radically polymerizable compound of component (A1) or component (A2) has a hole transport characteristic. A major example of a negatively charged organic photoconductor has a charge generating layer and a charge transport layer laminated in this order on a substrate, and the cured covering composition may be applied as the charge transport layer. However, the photoconductor is configured such that a cross-linking charge transport layer is further laminated on the charge transport layer since the cross-linking charge transport layer most preferably has a thickness of 3 μm or greater for a longer operational life since the decrease in the thickness due to abrasion in repeated use causes local variation in charge property and sensitivity.

<Multilayered Photosensitive Layer>

The multilayered photosensitive layer includes at least a charge generating layer, a charge transport layer and a cross-linking charge transport layer in this order, and it further includes an intermediate layer and other layers according to requirements.

The cross-linking charge transport layer is the outermost surface of the present invention.

Figure 6:
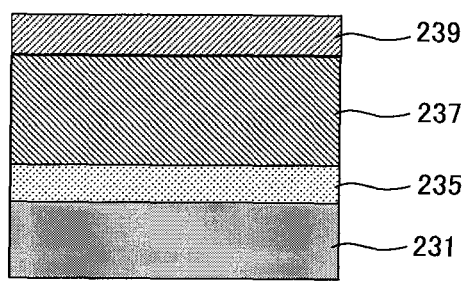
FIG. 6 is a schematic cross-sectional diagram showing an example of a latent electrostatic image bearing member of the present invention.

FIG. 6 is a schematic cross-sectional diagram showing an example of a latent electrostatic image bearing member of the present invention. It has a laminated structure that, on a substrate 231, a charge generating layer 235 which has a charge generating function, a charge transport layer 237 which has a charge transporting function and a cross-linking charge transport layer 239 are laminated.

-Charge Generating Layer-

The charge generating layer includes at least a charge generating material, and it further includes a binder resin and other components according to requirements.

The charge generating material includes inorganic materials and organic materials.

Examples of the inorganic materials include crystalline selenium, amorphous selenium, selenium-tellurium, selenium-tellurium-halogen, selenium-arsenic compound and amorphous silicon. The amorphous silicon may have a dangling bond terminated with a hydrogen atom or a halogen atom, or it may be doped with boron or phosphorus.

The organic materials are not particularly restricted and can be appropriately selected from heretofore known materials according to applications. Examples thereof include phthalocyanine pigments such as metal phthalocyanine and metal-free phthalocyanine, azulenium salt pigments, squaric acid squaric acid methine pigment, azo pigments having a carbazole moiety, azo pigments having a triphenylamine moiety, azo pigments having a diphenylamine moiety, azo pigments having a dibenzothiophene moiety, azo pigments having a fluorenone moiety, azo pigments having an oxadiazole moiety, azo pigments having a bisstilbene moiety, azo pigments having a distyryl oxadiazole moiety, azo pigments having a distyrylcarbazole moiety, perylene pigments, anthraquinone or polycyclic quinone pigments, quinone imine pigments, diphenylmethane or triphenylmethane pigments, benzoquinone or naphtoquinone pigments, cyanine or azomethine pigments, indigoido pigments and bisbenzimidazole pigments. These may be used alone or in combination of two or more.

The binder resin is not particularly restricted and can be appropriately selected according to applications. Examples thereof include a polyamide resin, a polyurethane resin, an epoxy resin, a polyketone resin, a polycarbonate resin, a silicone resin, an acrylic resin, a polyvinyl butyral resin, a polyvinyl formal resin, a polyvinyl ketone resin, a polystyrene resin, a poly-N-vinyl carbazole resin and a polyacrylamide resin. These may be used alone or in combination of two or more.

Other than the above-mentioned binder resins, a polymeric charge transfer material having a charge transferring function may be used as a binder resin in the charge generating layer. Examples thereof include (1) a polymeric material such as polycarbonate, polyester, polyurethane, polyether, polysiloxane and acrylic resin having an arylamine moiety, a benzidine moiety, a hydrazine moiety, a carbazole moiety, a stilbene moiety or a pyrazoline moiety; and (2) a polymeric material having a polysilane moiety.

Specific examples of (1) above include polymeric materials having a charge transport property described in JP-A Nos. 01-001728, 01-009964, 01-013061, 01-019049, 01-241559, 04-011627, 04-175337, 04-183719, 04-225014, 04-230767, 04-320420, 05-232727, 05-310904, 06-234836, 06-234837, 06-234838, 06-234839, 06-234840, 06-234841, 06-239049, 06-236050, 06-236051, 06-295077, 07-056374, 08-176293, 08-208820, 08-211640, 08-253568, 08-269183, 09-062019, 09-043883, 09-71642, 09-87376, 09-104746, 09-110974, 09-110976, 09-157378, 09-221544, 09-227669, 09-235367, 09-241369, 09-268226, 09-272735, 09-302084, 09-302085 and 09-328539.

Specific examples of (2) above include polysilylene polymers described in JP-A Nos. 63-285552, 05-19497, 05-70595 and 10-73944.

The charge generating layer may include a low-molecular charge transfer substance.

The low-molecular charge transfer substance is categorized to a hole transport substance and an electron transport substance.

Examples of the electron transfer substance include chloranil, bromanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro 4H-indeno[1,2-b]thiophene-4-one, 1,3,7-trinitrodibenzothiophene-5,5-dioxide and diphenoquinone derivative. These may be used alone or in combination of two or more.

Examples of the hole transport substance include an oxazole derivative, an oxadiazole derivative, an imidazole derivative, a monoarylamine derivative, a diarylamine derivative, a triarylamine derivative, a stilbene derivative, an α-phenylstilbene derivative, a benzidine derivative, a diarylmethane derivative, a triarylmethane derivative, a 9-styrylanthracene derivative, a pyrazoline derivative, a divinylbenzene derivative, a hydrazone derivative, an indene derivative, a butadiene derivative, a pyrene derivative, a bisstilbene derivative, an enamine derivative and other heretofore known materials. These may be used alone or in combination of two or more.

There are mainly two types of the methods for forming the charge generating layer, namely a vacuum thin-film preparation method and a casting method with solution dispersal.

Examples of the vacuum thin-film preparation method includes a vacuum deposition method, a glow discharge electrolysis method, an ion plating method, a sputtering method, a reactive sputtering method and a CVD method.

In the casting method, the inorganic or organic charge generating substance is dispersed, together with a binder resin if necessary, with a ball mill, an attritor, a sand mill or a bead mill, using a solvent such as tetrahydrofuran, dioxane, dioxolane, toluene, dichloromethane, monochlorobenzene, dichloroethane, cyclohexanone, cyclopentanone, anisole, xylene, methyl ethyl ketone, acetone, ethyl acetate and butyl acetate, the dispersion is appropriately diluted and coated, and thus a charge generating layer is formed. A leveling agent such as dimethyl silicone oil and methylphenyl silicone oil may be used according to requirements. The dispersion liquid may be applied by means of a dip-coating method, a spray-coating method, a bead-coating method and a ring-coating method.

The thickness of the charge generating layer is not particularly restricted and can be appropriately selected according to applications. The thickness is preferably 0.01 µm to 5 µm, and more preferably 0.05 µm to 2 µm.

-Charge Transport Layer-

The charge transport layer is installed for the purpose of maintaining the electrification charge, transporting the charge generated and separated in the charge generating layer by means of light exposure and combining the transported charge with the maintained charge. In order to maintain the electrification charge, the charge transport layer should have a high electric resistance. Also, in order to obtain a high surface potential with the maintained charge, a small dielectric constant and favorable charge mobility are required.

The charge transport layer includes at least a charge transport substance, and it further includes a binder resin and other components according to requirements.

Examples of the charge transport substance include a hole transport substance, an electron transport substance and a charge transport polymer.

Examples of the electron transport substance, i.e. electron-accepting substance, include chloranil, bromanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-4H-indeno[1,2-b]thiophene-4-one, 1,3,7-trinitrodibenzothiophene-5,5-dioxide and diphenoquinone derivative. These may be used alone or in combination of two or more.

Examples of the hole transport substance, i.e. electron donating substance, include an oxazole derivative, an oxadiazole derivative, an imidazole derivative, a triarylamine derivative, 9-(p-diethylaminostyrylanthracene), 1,1-bis-(4-dibenzylaminophenyl)propane, styrylanthracene, styrylpyrazoline, phenylhydrozone, an α-phenylstilbene derivative, a thiazole derivative, a triazole derivative, a phenazine derivative, an acridine derivative, a benzofuran derivative, a benzimidazole derivative and a thiophene derivative. These may be used alone or in combination of two or more.

The charge transport polymer has the following structure:

(a) A polymer having a carbazole ring such as poly-N-vinylcarbazole and compounds disclosed in JP-A Nos. 50-82056, 54-9632, 54-11737, 04-175337, 04-183719 and 06-234841.

(b) A polymer having a hydrozone structure such as compounds disclosed in JP-A Nos. 57-78402, 61-20953, 61-296358, 01-134456, 01-179164, 03-180851, 03-180852, 03-50555, 05-310904 and 06-234840.

(c) A polysilylene polymer such as compounds disclosed in JP-A Nos. 63-285552, 01-88461, 04-264130, 04-264131, 04-264132, 04-264133 and 04-289867.

(d) A polymer having a triarylamine moiety such as N,N-bis(4-methylphenyl)-4-aminopolystyrene and compounds disclosed in JP-A Nos. 01-134457, 02-282264, 02-304456, 04-133065, 04-133066, 05-40350 and 05-202135.

(e) Other polymers such as formaldehyde condensed polymer of nitropyrene and compounds disclosed in JP-A Nos. 51-73888, 56-150749, 06-234836 and 06-234837.

In addition, examples of the charge transport polymers include, other than those mentioned above, a polycarbonate resin having a triarylamine moiety, a polyurethane resin having a triarylamine moiety, a polyester resin having a triarylamine moiety and a polyether resin having a triarylamine moiety. The examples further include compounds disclosed in JP-A Nos. 64-1728, 64-13061, 64-19049, 04-11627, 04-225014, 04-230767, 04-320420, 05-232727, 07-56374, 09-127713, 09-222740, 09-265197, 09-211877 and 09-304956.

As a polymer having an electron donating group, a copolymer with a heretofore known monomer, a block polymer, a graft polymer, a star polymer and furthermore a cross-linking polymer having an electron donating group as disclosed in JP-A No. 03-109406 may also be used other than the polymers listed above.

Examples of the binder resin include a polycarbonate resin, a polyester resin, a methacrylic resin, an acrylic resin, a polyethylene resin, a polyvinyl chloride resin, polyvinyl acetate resin, a polystyrene resin, a phenol resin, an epoxy resin, a polyurethane resin, a polyvinylidene chloride resin, an alkyd resin, a silicone resin, a polyvinyl carbazole resin, a polyvinyl butyral resin, a polyvinyl formal resin, a polyacrylate resin, a polyacrylamide resin and a phenoxy resin. These may be used alone or in combination of two or more.

The charge transport layer may also include a copolymer of a cross-linkable binder resin and a cross-linkable charge transport substance.

The charge transport substance and a binder resin are dissolved or dispersed in an appropriate solvent, and the solution or dispersion is coated and dried to form the charge transport layer. Other than the charge transport substance and binder resin, the charge transport layer may further include additives such as plasticizer, antioxidant and leveling agent according to requirements.

The solvents used for coating a charge transport layer is the same as those for the charge generating layer, and a solvent which can favorably dissolve a charge transport substance and a binder resin is appropriate. These solvents may be used alone or in combination of two or more. The charge transport layer may be formed with the same methods as those for the charge generating layer 235.

A plasticizer and a leveling agent may be added according to requirements.

Regarding the plasticizer, a plasticizer which is generally used for a resin such as dibutylphthalate and dioctylphthalate may be used. The appropriate amount is zero parts by mass to 30 parts by mass with respect to 100 parts by mass of the binder resin.

Examples of the leveling agent include silicone oils such as dimethyl silicone oil and methylphenyl silicone oil as well as a polymer and an oligomer having a perfluoroalkyl group in their side chain. The appropriate amount is zero parts by mass to one part by mass with respect to 100 parts by mass of the binder resin.

The thickness of the charge transport layer is not particularly restricted and can be selected according to applications. It is preferably 5 μm to 40 μm, and more preferably 10 μm to 30 μm.

<Substrate>

The substrate is not particularly restricted and can be appropriately selected according to applications. A substrate having an electric conductivity with a volumetric resistance of $10^{10}$ Ω·cm or less is favorable.

The substrate is not particularly restricted in terms of materials, shape and size, and sheet-type, drum-type or belt-type substrate may be used. For example, a film-shaped or cylindrical plastic or paper covered with metals including aluminum, nickel, chromium, nichrome, copper, gold, silver, platinum and metal oxide such as tin oxide and indium oxide with a vapor deposition or sputtering method. The substrate may be a plate of aluminum, aluminum alloy, nickel or stainless steel, or the plate may be formed into a tube by extrusion or drawing, and a surface treatment such as cutting, finishing and polishing is given to the substrate. An endless nickel belt and an endless stainless steel belt such as those disclosed in JP-A No. 52-36016 may also be used as a substrate.

Other than the above, a conductive powder is dispersed in an appropriate binder resin, which is coated on the substrate to form a conductive layer.

Examples of the conductive powder include carbon black; acetylene black; a metal powder such as aluminum, nickel, iron, nichrome, copper, zinc and silver; and metal oxide powder such as of conductive tin oxide and ITO. Examples of the binder resin include a polystyrene resin, a styrene acrylonitrile copolymer, a styrene butadiene copolymer, a styrene maleic anhydride copolymer, a polyester resin, a polyvinyl chloride resin, a vinyl chloride-vinyl acetate copolymer, a polyvinyl acetate resin, a polyvinylidene chloride resin, a polyacrylate resin, a phenoxy resin, a polycarbonate resin, a cellulose acetate resin, an ethylcellulose resin, a polyvinyl butyral resin, a polyvinyl formal resin, a polyvinyl toluene resin, a poly-N-vinylcarbazole resin, a acrylate resin, a silicone resin, an epoxy resin, a melamine resin, a phenol resin and an alkyd resin.

The conductive powder and the binder resin are dissolved or dispersed in an appropriate solvent, and the solution or dispersion is coated and dried to form the conductive layer. Examples of the solvent include tetrahydrofuran, dichloromethane, methyl ethyl ketone and toluene.

Furthermore, a substrate having a conductive layer formed on a cylindrical body by means of a heat-shrinkable tube is also suitable, where the heat-shrinkable tube is prepared by mixing the conductive powder with a polyvinyl chloride resin, a polypropylene resin, a polyester resin, a polystyrene resin, a polyvinylidene chloride resin, a polyethylene resin, a chlorinated rubber resin or a polytetrafluoroethylene fluorine resin.

An undercoat layer may be installed between the substrate and the photosensitive layer according to necessity. The undercoat layer includes a resin as a main component, and it preferably has a high resistance to common organic solvent since a photosensitive layer is coated with a solvent over the resin.

Examples of the resin include a water-soluble resin such as polyvinyl alcohol, casein and sodium acrylate; an alcohol-soluble resin such as copolymer nylon and methoxymethylated nylon; and a curing resin which forms a three-dimensional network structure such as polyurethane resin, melamine resin, phenol resin, alkyd-melamine resin and epoxy resin.

Also, the undercoat layer may be added with a fine powder pigment of a metal oxide such as titanium oxide, silica, alumina, zirconium oxide, tin oxide and indium oxide for preventing Moire patterns and reducing the rest potential.

The undercoat layer may be formed with appropriate solvents and coating methods in the same manner as the photosensitive layer. Silane coupling agents, titanium coupling agents and chromium coupling agents can be used as the undercoat layer of the present invention. Also, the undercoat layer may be prepared with an anodic oxidation of $Al_2O_3$ or vacuum thin-film preparation process of organic materials such as polyparaxylylene (parylene) and inorganic materials such as $SiO_2$, $SnO_2$, $TiO_2$, ITO and $CeO_2$. Heretofore known materials may also be used.

The thickness of the undercoat layer is not particularly restricted and can be appropriately selected according to applications. It is preferably 0 μm to 5 μm.

An antioxidant may be added to each of the layers of the latent electrostatic image bearing member of the present invention, e.g. the charge generating layer, the charge transport layer and the undercoat layer, for the purpose of improving the environment resistance and especially preventing the decrease in sensitivity and increase in rest potential.

Examples of the antioxidants include phenol compounds, para-phenylenediamines, organosulfur compounds and organophosphorus compounds.

Examples of the phenol compounds include 2,6-di-t-butyl-p-cresol, butylhydroxyanisole, 2,6-di-t-butyl-4-ethylphenol, stearyl-β-(3,5-di-t-butyl-4-hydroxyphenyl)propionate, 2,2'-methylene-bis-(4-methyl-6-t-butylphenol), 2,2'-methylene-bis-(4-ethyl-6-t-butylphenol), 4,4'-thiobis-(3-methyl-6-t)-butylphenol, 4,4'-butylydenebis-(3-methyl-6-t-butylphenol), 1,1,3-tris-(2-methyl-4-hydroxy 5-t-butylphenyl)butane, 1,3, 5-trimethyl-2,4,6-tris-(3,5-di-t-butyl-4-hydroxybenzyl)benzene, tetrakis-[methylene-3-(3',5'-di-t-butyl-4'-hydroxyphenyl)propionate]methane, bis-[3,3'-bis-(4'-hydroxy-3'-t-butylphenyl)butylic acid]glycolester and tocopherols.

Examples of the para-phenylene diamine compounds include N-phenyl-N'-isopropyl-p-phenylene diamine, N,N'-di-sec-butyl-p-phenylene diamine, N-phenyl-N-sec-butyl-p-phenylene diamine, N,N'-di-isopropyl-p-phenylene diamine and N,N'-dimethyl-N,N'-di-t-butyl-p-phenylene diamine.

Examples of the hydroquinone compounds include 2,5-di-t-octylhydroquinone, 2,6-di-dodecylhydroquinone, 2-dodecylhydroquinone, 2-dodecyl-5-chlorohydroquinone, 2-t-octyl-5-methylhydroquinone and 2-(2-octadecenyl)-5-methylhydroquinone Examples of the organosulfur compounds include dilauril-3,3'-thio dipropionate, distearil-3,3'-thio dipropionate and ditetradecyl-3,3'-thio dipropionate.

Examples of the organophosphorus compounds include triphenylphosphine, tri(nonylphenyl)phosphine, tri(di-nonylphenyl)phosphine, tricresylphosphine and tri(2,4-dibutylphenoxy)phosphine These compounds are known as antioxidants of rubber, plastics and fats and may be easily obtained as commercial products.

The content of the antioxidant is preferably 0.01% by mass to 10% by mass with respect to the total mass of the layer to which the antioxidant is being added.

(Image Forming Method and Image Forming Apparatus)

An image forming apparatus of the present invention contains at least a latent electrostatic image bearing member, a latent electrostatic image forming means, a developing means, a transferring means and a fixing means, and it further contains other means appropriately selected according to requirements such as discharging means, cleaning means, recycling means and controlling means.

An image forming method of the present invention contains at least a latent electrostatic image forming process, a developing process, a transferring process and a fixing process, and it further contains other processes appropriately selected according to requirements such as discharging process, cleaning process, recycling process and controlling process.

The image forming method of the present invention may be favorably performed by means of the image forming apparatus of the present invention. The latent electrostatic image forming process may be performed by the latent electrostatic image forming means, the developing process may be performed by the developing means, the transferring process may be performed by the transferring means, the fixing process may be performed by the fixing means, and the other process may be performed by the other means.

-Latent Electrostatic Image Forming Process and Latent Electrostatic Image Forming Means- The latent electrostatic image forming process is a process to form a latent electrostatic image on the latent electrostatic image bearing member.

As the latent electrostatic image bearing member, the latent electrostatic image bearing member of the present invention is used.

The latent electrostatic image may be formed, for example, by charging uniformly the surface of the latent electrostatic image bearing member followed by imagewise exposure, which may be performed by the latent electrostatic image forming means.

The latent electrostatic image forming means houses at least a charging unit that uniformly charges the surface of the latent electrostatic image bearing member and an exposing unit that performs an imagewise exposure.

The charging may be performed, for example, by applying an electric potential on the surface of the latent electrostatic image bearing member with the charging unit.

The charging unit is not particularly restricted and can be appropriately selected according to applications. Examples thereof include a contact charging unit, which itself is heretofore known, having a conductive or semiconductive roll, a brush, a film or a rubber blade; and a noncontact charging unit utilizing corona discharge such as corotron and scorotron.

The configuration of the charging unit may be in the form of, other than a roller, a magnetic brush and a fur brush, and it may be selected according to the specification and the configuration of the electro photographic apparatus. The magnetic brush is configured with: various types of ferrite particles such as Zn—Cu ferrite used as a charging member; a nonmagnetic conductive sleeve for supporting the charging member; and a magnet roller included in the sleeve. Regarding the fur brush, a conduction-processed fur with carbon, copper sulfate, metal or metal oxide for conductivity is used as a material for the fur brush, and a charging unit is formed by wrapping or pasting the fur on a metal shaft or a conduction-processed shaft.

The charging unit is not restricted to the contact charging units above, but the use of a contact charging unit is preferable since an image forming apparatus may be obtained with which the generation of the ozone from the charging unit is suppressed.

It is preferable that the charging unit is placed in contact with or not in contact with the latent electrostatic image bearing member and that a direct and alternating voltages are superimposed and applied to the charge roller to electrify the surface of the latent electrostatic image bearing member.

It is preferable that the charging unit is a charge roller which is allocated near but without contacting the latent electrostatic image bearing member through a gap tape and that a direct and alternating voltages are superimposed and applied to the charge roller to electrify the surface of the latent electrostatic image bearing member.

The exposure may be performed, for example, by exposing imagewise the surface of the latent electrostatic image bearing member with the exposing unit.

The exposing unit is not particularly restricted as long as it can perform an imagewise exposure as intended on the surface of the latent electrostatic image bearing member charged by the charging unit, and it can be appropriately selected according to applications. Examples of the exposing unit include a copying optical system, a rod lens array system, a laser optical system and liquid crystal shutter optical system.

In the present invention, the back-exposure method may be adopted in which an exposure is performed imagewise from the back side of the latent electrostatic image bearing member.

-Developing Process and Developing Means-

The developing process is a process to develop the latent electrostatic image using a toner or a developer to form a visible image.

The formation of the visible image may be performed by developing the latent electrostatic image using the toner or the developer, and it may be performed by the developing means.

The developing means is not particularly restricted as long as it can perform a development using the toner or the developer, and it can be appropriately selected from heretofore known developing means. For example, a preferable developing means contains the toner or the developer and includes a developing unit which can impart the toner or the developer in a contact or noncontact manner to the latent electrostatic image.

The developing unit may be of a dry development or a wet development. It may also be a monochrome developing unit or a multi-color developing unit. For example, a developer having an agitator that frictions and agitates the toner or the developer for electrification and a rotatable magnet roller is preferable.

In the developing unit, for example, the toner and the carrier are mixed and agitated, which causes a friction to charge the toner and maintains the charged toner on the surface of the rotating magnet roller in a state of a chain of magnetic particles, and a magnetic brush is formed. The magnet roller is arranged near the latent electrostatic image bearing member, i.e. photoconductor; therefore, a part of the toner constituting the magnetic brush formed on the surface of the magnetic roller transfers to the surface of the latent electrostatic image bearing member, i.e. photoconductor, due to electric attraction. As a result, the latent electrostatic image is developed by the toner, and a visible image by the toner is formed on the surface of the latent electrostatic image bearing member, i.e. photoconductor.

The developer contained in the developing unit may be a one-component developer or a two-component developer.

-Transferring Process and Transferring Means-

The transferring process is a process to transfer the visible image to a recording medium. The transferring process preferably has an aspect that, with an intermediate recording medium, it performs a primary transfer to transfer the visible image to the intermediate recording medium followed by a secondary transfer to transfer the visible image to the recording medium. An aspect which includes a primary transferring process that transfers the visible image to the intermediate recording medium to form a complex transfer image and a secondary transferring process that transfers the complex transfer image to the recording medium using a toner having two or more colors or preferably a full-color toner is more preferable.

The transfer of the visible image may be performed by charging the latent electrostatic image bearing member, i.e. photoconductor, using a transfer charging unit, and it may be performed by the transferring means. The transferring means preferably has an aspect that includes a primary transferring means that transfers a visible image to an intermediate recording medium to form a complex transfer image and a secondary transferring means that transfers the complex transfer image to a recording medium.

The intermediate recording medium is not particularly restricted and can be appropriately selected according to applications from heretofore known recording media. Favorable examples include a transfer belt.

The transferring means, i.e. the primary transferring means and the secondary transferring means, preferably contain at least a transferring unit that strips and charges the visible image formed on the latent electrostatic image bearing member, i.e. photoconductor, to the side of the recording medium. There may be one transferring means, or there may be two or more.

Examples of the transferring unit include a corona transferring unit by corona discharge, a transfer belt, a transfer roller, a pressure transfer roller and an adhesive transferring unit.

Also, the typical recording medium is plain paper, but it is not particularly restricted as long as an unfixed image after developing can be transferred. It can be appropriately selected according to applications, and a PET base for OHP may be used.

-Fixing Process and Fixing Means-

The fixing process is a process to fix the visible image transferred to the recording medium by means of a fixing apparatus. It may be performed every time a toner of each color is transferred to the recording medium, or it may be performed at once when a toner of all colors is laminated.

The fixing apparatus is not particularly restricted and can be selected appropriately according to applications. A heretofore known hot-pressing means is favorable. Examples of the hot-pressing means include a combination of a heat roller and a pressure roller and a combination of a heat roller, a pressure roller and an endless belt.

In general, the heating in the hot-pressing means is preferably 80° C. to 200° C.

In the present invention, a heretofore known optical fixing unit, for example, may be used along with or in place of the fixing process and the fixing means according to applications.

-Discharging Process and Discharging Means-

The discharging process is a process to discharge the latent electrostatic image bearing member by applying a discharging bias, and it may be favorably performed by a discharging means.

The discharging means is not particularly restricted as long as the discharging bias is applied to the latent electrostatic image bearing member. It can be appropriately selected from heretofore known discharging units, and favorable examples include a discharge lamp.

-Cleaning Process and Cleaning Means-

The cleaning process is a process to remove the residual toner on the latent electrostatic image bearing member, and it may be favorably performed by a cleaning means.

The cleaning means is not particularly restricted as long as it can remove the electrophotographic toner remaining on the latent electrostatic image bearing member, and it can be appropriately selected from heretofore known cleaners. Favorable examples thereof include a magnetic brush cleaner, a static brush cleaner, a magnetic roller cleaner, a blade cleaner, a brush cleaner and a web cleaner.

-Recycling Process and Recycling Means-

The recycling process is a process to recycle the electrophotographic toner removed in the cleaning process to the developing means, and it may be favorably performed by a recycling means.

The recycling means is not particularly restricted, and a heretofore known transporting means may be used.

-Controlling Process and Controlling Means-

The controlling process is a process to control each of the above-mentioned processes, and it may be favorably performed by a controlling means.

The controlling means is not particularly restricted as long as it can control the behavior of each of the means. Examples thereof include equipment such as sequencer and computer.

Figure 7:
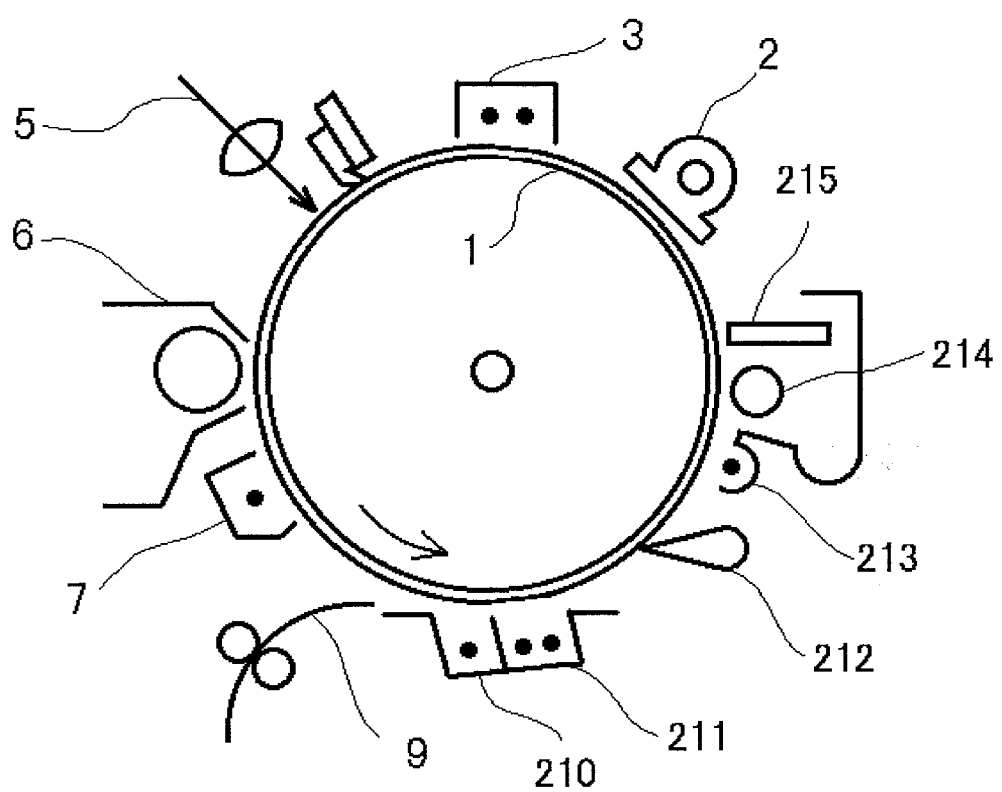
FIG. 7 is a schematic diagram showing an example of an image forming apparatus of the present invention.

An aspect that implements the image forming method of the present invention by the image forming apparatus of the present invention is illustrated with reference to FIG. 7. FIG. 7 is a schematic diagram showing an example of an image forming apparatus.

In this image forming apparatus, a charger 3 is used as a means to uniformly charge a latent electrostatic image bearing member, i.e. a photoconductor. As this charging means, a corotron device, scorotron device, a solid discharging element, a needle electrode device, a roller charging device and a conductive brush device may be used, and a heretofore known method may be used.

The configuration of the present invention is effective when a charging means decomposes a photosensitive composition by means of a close discharging from the discharging means such as contact charging method and noncontact, closely-spaced discharging method. The contact charging method is a charging method that a photoconductor directly contact with a charging roller, charging brush or charging blade. On the other hand, the closely-spaced discharging method is a charging method that a charging roller, for example, is allocated closely between a photoconductor and a charging means with a space of 200 μm or less in a noncontact state.

The size of the space is preferably 10 μm to 200 μm, and more preferably 10 μm to 100 μm. When the size of the space is too large, the charge may become unstable. When the size is too small, the surface of the charging member may be contaminated when there is a residual toner on the photoconductor.

An image exposing unit 5 is used to form a latent electrostatic image on a uniformly charged latent electrostatic image bearing member 1, i.e. photoconductor. A light source thereof may be light-emitting materials in general such as fluorescent lighting, tungsten lamp, halogen lamp, mercury lamp, sodium lamp, light-emitting diode (LED), laser diode (LD) and electroluminescence (EL). Various filters such as sharp-cut filter, band-pass filter, near-infrared-cut filter, dichroic filter, interference filter and color conversion filter may be used to irradiate only a light with a desired wavelength.

A developing unit 6 is used to visualize the latent electrostatic image formed on the photoconductor 1. Regarding the developing method, there are a one-component developing method with a dry toner and a two-component developing method with a wet toner. When an image exposure is performed with a positively (negatively) charged photoconductor, a positive (negative) latent electrostatic image is formed on the surface of the photoconductor. A positive image may be obtained by developing this with a negative (positive)

toner, i.e. detecting particles, and a negative image may be obtained by developing this with a positive (negative) toner.

Next, a toner image visualized on the photoconductor is transferred to a recording medium 9 by means of a transfer charger 210. A pre-transfer charger may also be used for a more favorable transfer. A transfer method thereof may be an electrostatic transfer method using a transfer charger or a bias roller, a mechanical transfer method such as adhesive transfer method and pressure transfer method and a magnetic transfer method. Regarding the electrostatic transfer method, the charging means may be used.

As a means to separate the recording medium 9 from the photoconductor 1, a separating charger 211 and a separating claw 212 are used. Other separating means include an inductive separation by electrostatic adsorption, side-to-end belt separation, tip-gripping transfer and separation by curvature. As the separation charger, the charging means may be used.

A fur brush 214 and a cleaning blade 215 are used to clean the toner remained on the photoconductor after transferring. A pre-cleaning charger 213 may also be used for efficient cleaning. Other cleaning means include a web method and a magnet brush method, and these may be used alone or in combination.

Next, a discharging means is used to remove the latent image on the photoconductor according to requirements. As the discharging means, a discharging lamp 2 and a neutralizing charger are used, for which the image exposure light source and the charging means may be used, respectively.

Moreover, heretofore known processes may be used for processes such as document scanning, paper feeding, fixing and paper delivery processes, which are not located near the photoconductor.

Figure 8:
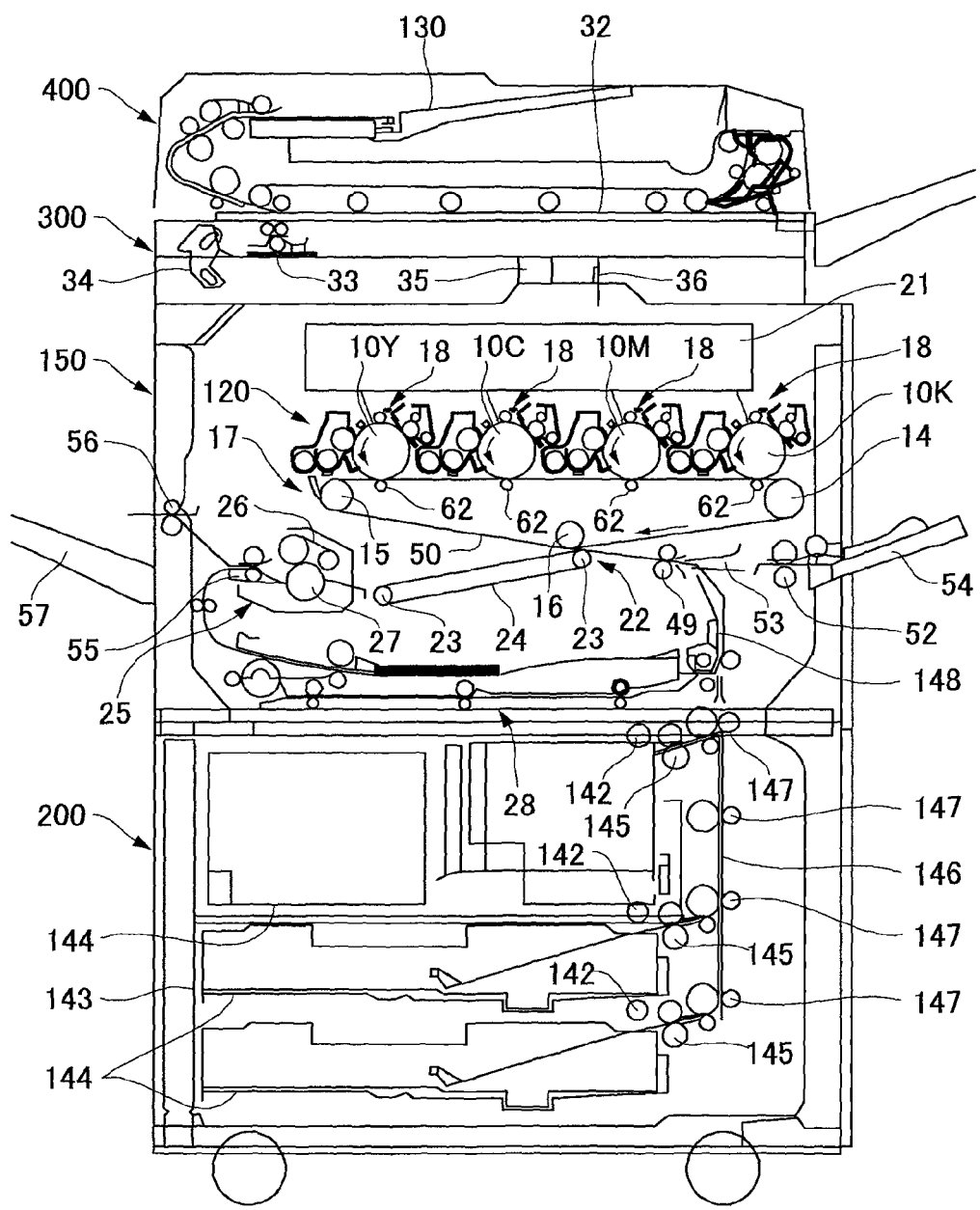
FIG. 8 is a schematic diagram showing an exemplary implementation of an image forming method of the present invention by means of an image forming apparatus of the present invention (tandem color image forming apparatus).
Figure 9:
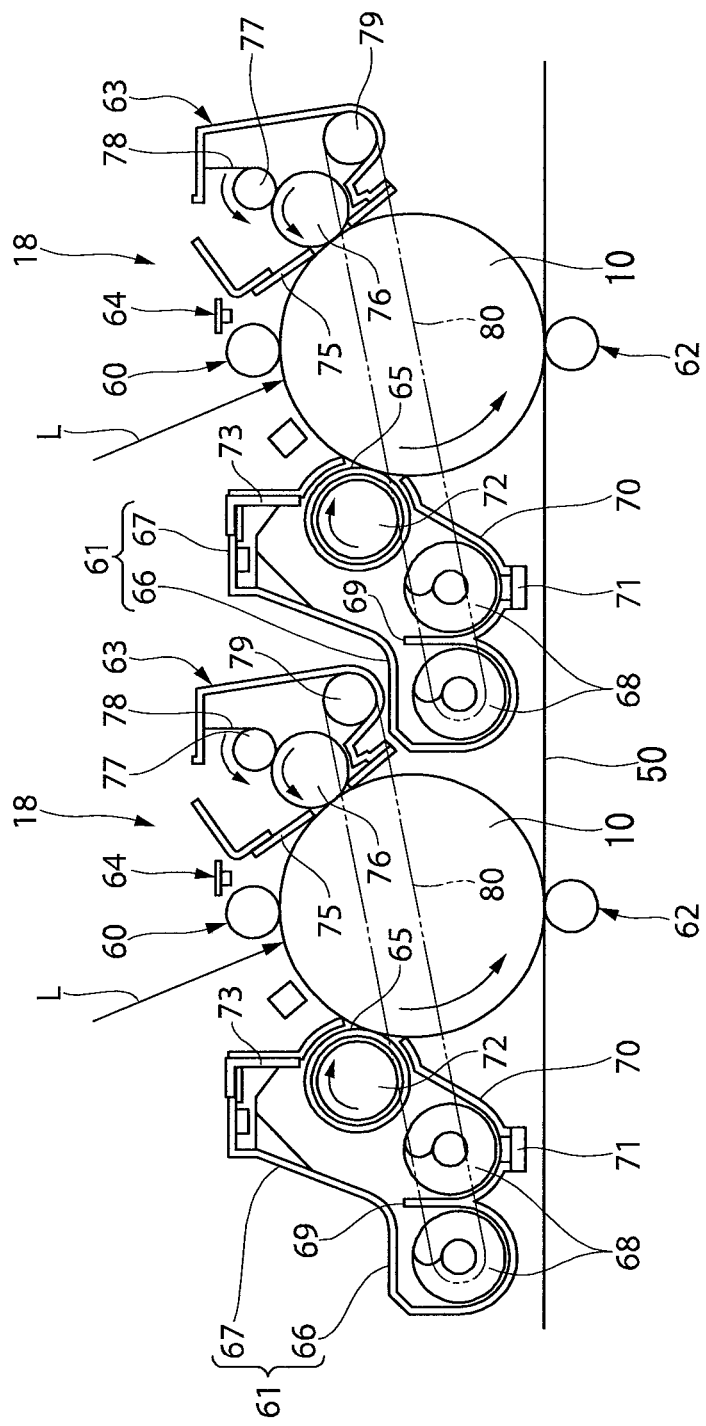
FIG. 9 is a partially-enlarged schematic diagram of the image forming apparatus shown in FIG. 8.

Another aspect to implement the image forming method of the present invention by means of the image forming apparatus of the present invention is illustrated with reference to FIGS. 8 and 9. A tandem image forming apparatus shown in FIG. 8 is a tandem color image forming apparatus. The tandem image forming apparatus has a copying apparatus body 150, a paper feed table 200, a scanner 300 and an automatic document feeder (ADF) 400.

In the copying apparatus body 150, an intermediate transferring member 50 is located as an endless belt at the center. The intermediate transfer member 50 is spanned over support rollers 14, 15 and 16 and rotatable clockwise in FIG. 9. Near the support roller 15, an intermediate transferring member cleaning apparatus 17 is placed to remove the residual toner on the intermediate transferring member 50. On the intermediate transferring member 50 spanned by the support roller 14 and the support roller 15, a tandem developing unit 120 is placed, opposite to which four image forming means 18 of yellow, cyan, magenta and black are arranged in parallel along the transporting direction. Near the tandem developing unit 120, an exposure apparatus 21 is placed. On the side of the intermediate transferring member 50 opposite to the side of the tandem developing unit 120, a secondary transferring apparatus 22 is placed. In the secondary transferring apparatus, a secondary transfer belt 24 as an endless belt is spanned over a pair of rollers 23, and transfer paper transported on the secondary transfer belt 24 and the intermediate transferring member 50 can contact with each other. Near the secondary transferring apparatus 22, a fixing apparatus 25 is placed. The fixing apparatus 25 has a fixing belt 26 as an endless belt and a pressure roller 27 arranged such that it is being pressed thereby.

Here, near the secondary transfer apparatus 22 and the fixing apparatus 25 of the tandem image forming apparatus, a sheet reversing apparatus 28 is placed to reverse transfer paper so that images are formed on both sides of the transfer paper.

Next, the formation of a full-color image, i.e. color copy, by means of the tandem image forming apparatus is illustrated. That is, first of all, an original document is placed on a document table 130 of the automatic document feeder (ADF) 400, or the original document is placed on a contact glass 32 of the scanner 300 by opening the automatic document feeder 400, which is then closed.

A start key (not shown) is pressed, and the scanner 300 is activated to drive a first carriage 33 and a second carriage 34 after the document is fed and transported onto the contact glass 32 when the original document has been placed on the automatic document feeder 400, or on the other hand immediately when the original copy is placed on the contact glass 300. At this time, the light from the light source is irradiated by the first carriage 33 as well as the light reflected from the document surface is reflected by a mirror in the second carriage 34, which is received by a reading sensor 36 through a lens 35. As a result, a color document (color image) is read as black, yellow, magenta and cyan image information.

Each of the black, yellow, magenta and cyan image information is transmitted to each image forming means 18 (black image forming means, yellow image forming means, magenta image forming means and cyan image forming means) in the tandem image forming apparatus, and black, yellow, magenta and cyan toner images are formed in the respective image forming means. That is, as illustrated in FIG. 9, each image forming means 18 (black image forming means, yellow image forming means, magenta image forming means and cyan image forming means) in the tandem image forming apparatus has: a photoconductor 10 (black photoconductor 10K, yellow photoconductor 10Y, magenta photoconductor 10M and cyan photoconductor 10C); a charging unit 60 that uniformly charges the respective photoconductor; an exposing unit that exposes imagewise the photoconductor (L in FIG. 9) corresponding to the respective color image based on the color image information and forms a latent electrostatic image of the respective color image on the photoconductor; a developing unit 61 that develops the latent electrostatic image using the respective color toner (black toner, yellow toner, magenta toner and cyan toner) and forms a toner image of the respective color toner; a transfer charging unit 62 for transferring the toner image on the image transferring member 50; a photoconductor cleaning apparatus 63; and a discharging unit 64. Therefore, based on the image information of the respective color, an image of a single color (black image, yellow image, magenta image and cyan image) may be formed. The black image formed on the black photoconductor 10K, the yellow image formed on the yellow photoconductor 10Y, the magenta image formed on the magenta photoconductor 10M and the cyan image formed on the cyan photoconductor 10C as above are sequentially transferred on the intermediate transferring member 50, which is rotationally shifted by means of the support rollers 14, 15 and 16 (primary transfer). Then, a composite color image (color transfer image) is formed by superimposing the black image, the yellow image, the magenta image and the cyan image on the intermediate transferring member 50.

On the other hand, on the paper feed table 200, one of the feed rollers 142 is selectively rotated to let out a sheet of recording paper from one of the multi-stage paper feeding cassettes 144 provided in a paper bank 143. The sheet is separated one by one and delivered to the paper feeding path 146 by separation rollers 145. It is then transported and guided by conveyance rollers 147 to a paper-feeding path 148 in the copying machine body 150 and finally stopped by striking to a paper stop roller 49. Here, the paper stop roller 49 is generally used grounded, but it may be used in the state a bias is applied for paper-powder removal.

Then, the paper stop roller 49 is rotated with precise timing with the composite color image (color transfer image) combined on the intermediate transferring member 50 to feed the sheet (recording paper) between the intermediate transferring member 50 and the secondary transferring apparatus 22, and by transferring the composite color image (color transfer image) on the sheet (recording paper) by means of the secondary transferring apparatus 22 (secondary transfer), a color image is transferred and formed on the sheet (recording paper). Here, the residual toner on the intermediate transferring member 50 after the image transfer is removed by means of the intermediate transferring member cleaning apparatus 17.

The sheet (recording paper) on which a color image is transferred and formed is transported and delivered by the secondary transferring apparatus 22 to the fixing apparatus 25, and in the fixing apparatus 25, the composite color image (color transfer image) is fixed on the sheet (recording paper) under heat and pressure. Then, the sheet (recording paper) is switched by a switching claw 55, discharged by a delivery roller 56 and stacked on a copy receiving tray 57. Alternatively, the sheet (recording paper) switched by the switching claw 55 is reversed by the sheet reversing apparatus 28 and guided again to the transferring position for recording an image on the back side. It is then discharged by the delivery roller 56 and stacked on the copy receiving tray 57.
(Process Cartridge)

A process cartridge of the present invention includes at least a latent electrostatic image bearing member of the present invention and at least any one means selected from the charging means, developing means, transferring means, cleaning means and discharging means, and it further includes other means according to requirements. It is detachably attached to the image forming apparatus body.

Figure 10:
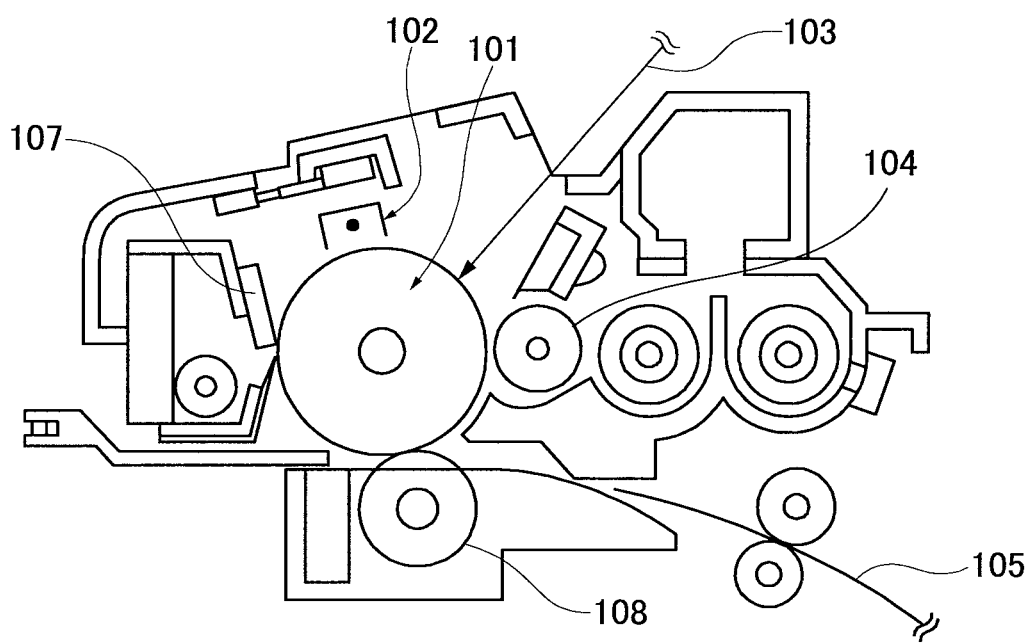
FIG. 10 is a schematic diagram showing an example of a process cartridge of the present invention.

The process cartridge, for example as shown in FIG. 10, houses a photoconductor 101. It also includes at least any one selected from a charging means 102, a developing means 104, a transferring means 108, a cleaning means 107 and a discharging means (not shown), and it is an apparatus (component) which can be detachably attached to the image forming apparatus body.

An image forming process by means of the process cartridge shown in FIG. 10 is illustrated. A latent electrostatic image corresponding to an exposure image is formed on the surface of the photoconductor 101, which is rotating in the direction of the arrow, by the charge from the charging means 102 and exposure 103 from an exposing means (not shown). This latent electrostatic image is toner developed in the developing means 104, and the toner development is transferred to the recording medium 105 by the transferring means 108. Next, the photoconductor surface after the image transfer is cleaned with the cleaning means 107 and further discharged by a discharging means (not shown) The above operations are repeated again.

Regarding the image forming apparatus of the present invention, components such as latent electrostatic image bearing member, developing unit and cleaning unit are integrated to form a process cartridge, and this unit may be detachably attached to the apparatus body. Also, at least any one of the charging unit, the image exposing unit, the developing unit, the transferring or separating unit and the cleaning unit is supported with the latent electrostatic image bearing member to form the process cartridge as a single unit which can be detachably attached to the apparatus body, and the unit may have a detachable configuration by a guiding means such as rail on the apparatus body.

The image forming apparatus, image forming method and process cartridge of the present invention have high abrasion resistance and scratch resistance, and they have a latent electrostatic image bearing member with a cross-linking charge transport layer on its surface, which is less subject to cracks and film exfoliation; therefore, an image degradation due to abrasion is prevented, and a high-definition and high-quality image may be formed over a long period of time.

The present invention can provide a latent electrostatic image bearing member which can resolve the conventional problems, has extremely high abrasion resistance, favorable electric properties such as charge property, sensitivity and rest potential accumulation property, is able to maintain high-quality image with reduced image defects, has high durability and high reliability, is resistant to image defects such as white spots and has a wide range of writing light source so that it is compatible with a blue-purple laser beam as a writing light source; a long-lasting and high-performance image forming method, a image forming apparatus and a process cartridge which use the latent electrostatic image bearing member.

The present invention is illustrated in detail with reference to examples given below, but these are not to be construed as limiting the present invention. In the examples below, a 'part' denotes a 'part by mass,' and '%' denotes '% by mass.'

SYNTHETIC EXAMPLE A-1

Synthesis of N,N-di-p-tolyl-N',N'-bis(4'-hydroxybiphenyl-4-yl)benzidine

In a reaction vessel equipped with an agitator, thermometer and a cooling pipe, 2.73 g of N,N-di-p-tolyl-N',N'-bis(4'-methoxybiphenyl-4-yl)benzidine and 100 mL of methylene chloride were placed. While the vessel was being cooled with ice, 10 mL of a 1M methylene chloride solution of boron tribromide was delivered by drops into the vessel, and furthermore the mixture was reacted at the same temperature for three hours. Then, the reacted solution was poured into ice water and extracted with methylene chloride. The organic layer was washed with water and separated, and it was then dried with magnesium sulfate and subjected to vacuum concentration. The residue was purified with a silica gel chromatography with a mixture of n-hexane and ethyl acetate as a solvent, where the ratio of n-hexane to ethyl acetate in the mixture was one to one. Thus, the objective product was obtained with the yield of 2.53 g.

SYNTHETIC EXAMPLE A-2

Synthesis of Illustrative Compound (D-35)

In a reaction vessel equipped with an agitator, thermometer, a cooling pipe and a dropping funnel, 2.44 g of N,N-di-p-tolyl-N',N'-bis(4'-methoxybiphenyl-4-yl)benzidine, 1.22 g of triethylamine and 50 mL of tetrahydrofuran were placed. Into the vessel, a mixture of 1.0 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with toluene as a solvent. Thus, the objective product was obtained with the yield of 1.92 g.

The data of the objective product were as follows:
Melting point=113.5° C. to 115.5° C.;
APCI-MS: m/z=737;
UV-absorption spectrum in methylene chloride: $\lambda_{max}$=357 nm and $\in$=66,600
HPCL purity (254 nm)=97.8%; and
IR measurement data: shown in the infrared absorption spectral diagram (IR data No. 1) in FIG. 1.

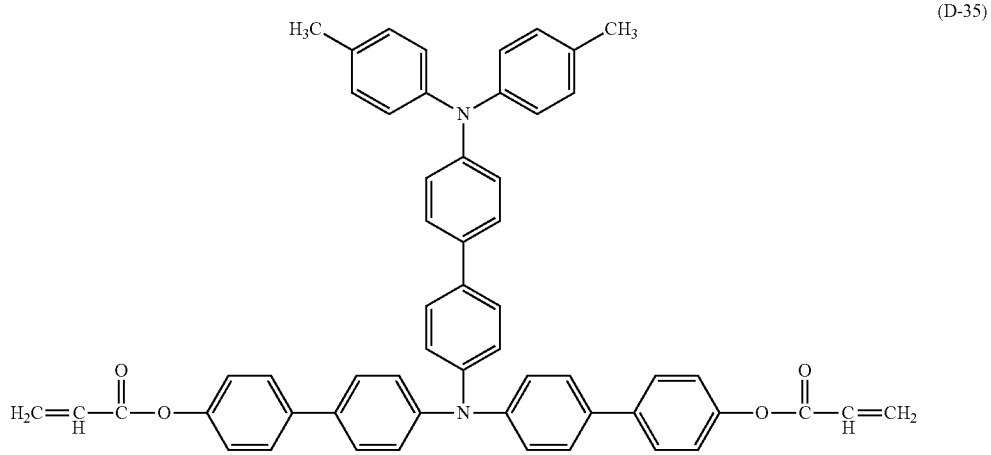 [SMILES: C=CC(=O)Oc1ccc(-c2ccc(N(c3ccc(-c4ccc(OC(=O)C=C)cc4)cc3)c3ccc(-c4ccc(N(c5ccc(C)cc5)c5ccc(C)cc5)cc4)cc3)cc2)cc1]

(D-35)

SYNTHETIC EXAMPLE A-3

Synthesis of N,N-diphenyl-N,N'-bis(4'-hydroxybiphenyl-4-yl)-3,3'-dimethylbenzidine In a reaction vessel equipped with an agitator, thermometer and a cooling pipe, 6.04 g of N,N'-diphenyl-N,N'-bis(4'-methoxybiphenyl-4-yl)-3,3'-dimethylbenzidine and 200 mL of methylene chloride were placed. While the vessel was being cooled with ice, 30 mL of a methylene chloride solution of boron tribromide was delivered by drops into the vessel, and furthermore the mixture was reacted at the same temperature for six hours. Then, the reacted solution was poured into ice water and extracted with chloroform. The organic layer was washed with water and separated, and it was then dried with magnesium sulfate and subjected to vacuum concentration. The residue was purified with a silica gel chromatography with a mixture of toluene and ethyl acetate as a solvent, where the ratio of toluene to ethyl acetate in the mixture was nine to one. Thus, the objective product was obtained with the yield of 5.47 g.

SYNTHETIC EXAMPLE A-4

Synthesis of Illustrative Compound (E-15)

In a reaction vessel equipped with an agitator, thermometer, a cooling pipe and a dropping funnel, 4.92 g of N,N-diphenyl-N,N'-bis(4'-methoxybiphenyl-4-yl)-3,3'-dimethyl-benzidine, 2.19 g of triethylamine and 50 mL of tetrahydrofuran were placed. Into the vessel, a mixture of 2.2 mL of acryloyl chloride and 3.0 mL of tetrahydrofuran was delivered by drops. The vessel was subjected to reaction for one hour at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of toluene and cyclohexane as a solvent, where the ratio of toluene to cyclohexane in the mixture was seven to three. Thus, the objective product was obtained with the yield of 4.32 g.

Figure 2:
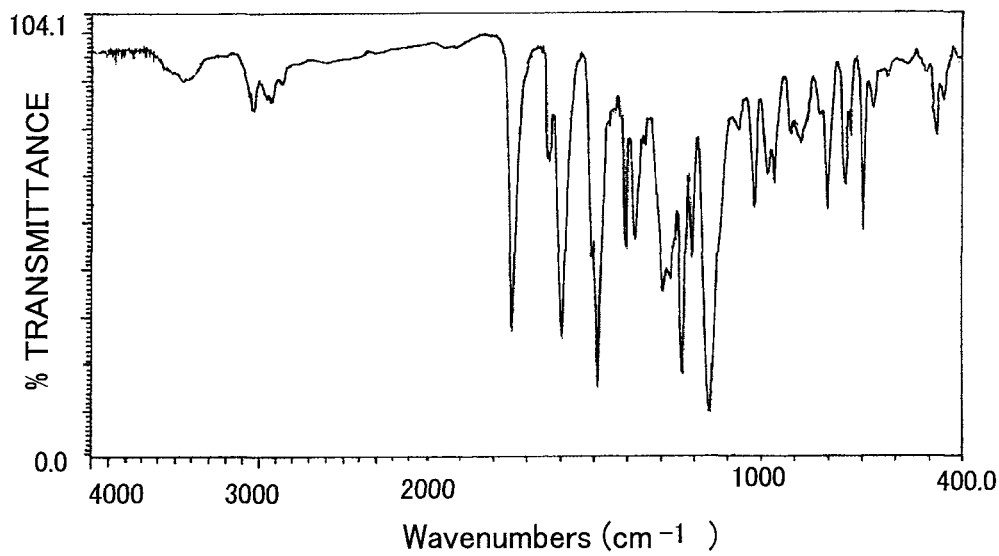
FIG. 2 is an infrared absorption spectral diagram of Illustrative Compound C-15 obtained in Synthetic Example A-4 (IR data No. 2).

The data of the objective product are as follows:
State: amorphous
APCI-MS: m/z=757;
UV-absorption spectrum in methylene chloride: $\lambda_{max}$=329.5 nm and $\in$=67,200 M$^{-1}$cm$^{-1}$;
HPCL purity (254 nm)=98.1%; and
IR measurement data: shown in the infrared absorption spectral diagram (IR data No. 2) in FIG. 2.

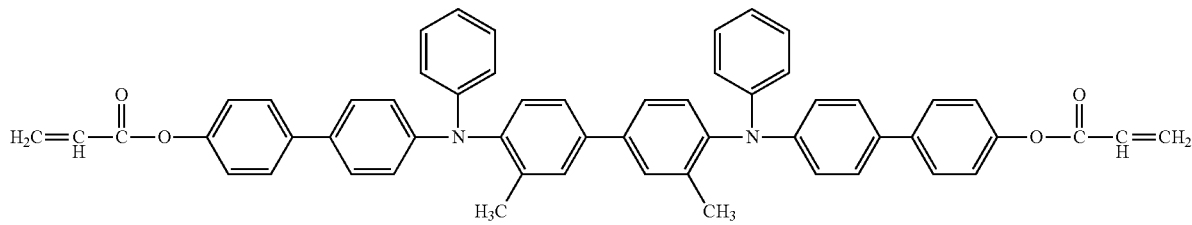

(E-15)

Using the hydroxy compounds synthesized with the demethylation reaction described above as manufacturing intermediates, the acrylic ester compound of the present invention expressed as General Formulae (1) to (4) above may be easily produced by reacting these with acrylic chloride.

Other Illustrative Compounds D-1 to D-57 and E-1 to E-33 may also be produced easily with the reactions above. Also, an acrylic ester compound may be produced easily when methacrylic chloride is used instead of acrylic chloride.

EVALUATION EXAMPLE 1

<Elution from Cured Film>

Coating Solutions (A) to (I) below were prepared with Illustrative Compound B-35, Illustrative Compound E-15 and compounds for reference (Ref-1 to Ref-7). These nine types of the coating solutions were blade-coated on an aluminum plate and dried to the touch, and ultraviolet light was irradiated under the conditions below. Thus, cured films with a thickness of 5 μm were prepared. The obtained cured films were immersed in tetrahydrofuran for seven days, and the amount of elution from each cured film was measured. The evaluation results are shown in Table 1 below.

| <Coating Solution A> | |
|---|---|
| Illustrative Compound B-35: | 10 parts |
| Trimethylolpropane triacrylate: | 10 parts |
| Polymerization initiator (1-hydroxycyclohexyl phenyl ketone): | 1 part |
| Tetrahydrofuran: | 84 parts |

<Coating Solution B>

Coating Solution B was prepared in the same manner as Coating Solution A except that Illustrative Compound C-15 was used instead of Illustrative Compound B-35 for Coating Solution A.

<Coating Solution C>

Coating Solution C was prepared in the same manner as Coating Solution A except that Compound (I) [Ref-1] below was used as a comparative compound instead of Illustrative Compound B-35 for Coating Solution A.

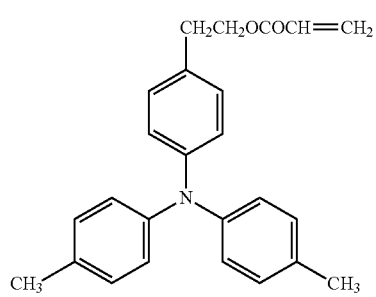

(I)

<Coating Solution D>

Coating Solution D was prepared in the same manner as Coating Solution A except that Compound (II) [Ref-2] below was used as a comparative compound instead of Illustrative Compound B-35 for Coating Solution A.

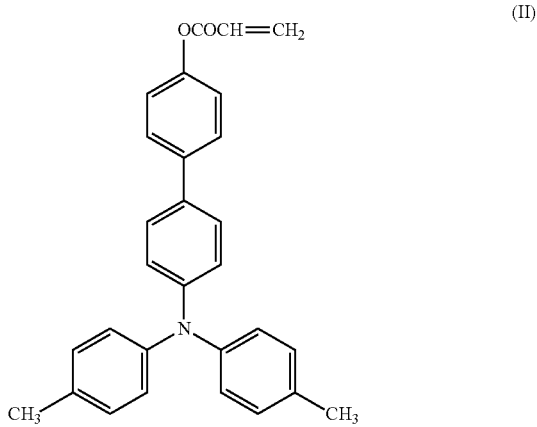

(II)

<Coating Solution E>

Coating Solution E was prepared in the same manner as Coating Solution A except that Compound (III) [Ref-3] below was used as a comparative compound instead of Illustrative Compound B-35 for Coating Solution A.

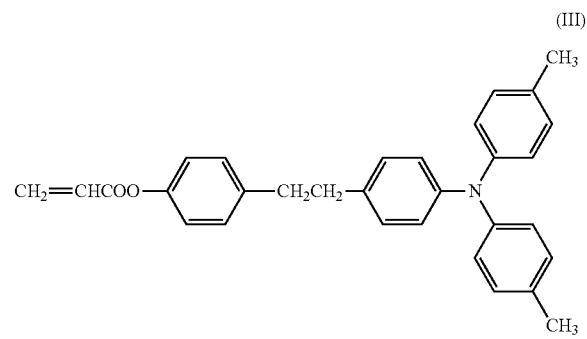

(III)

<Coating Solution F>

Coating Solution C was prepared in the same manner as Coating Solution A except that Compound (IV) [Ref-4] below was used as a comparative compound instead of Illustrative Compound B-35 for Coating Solution A.

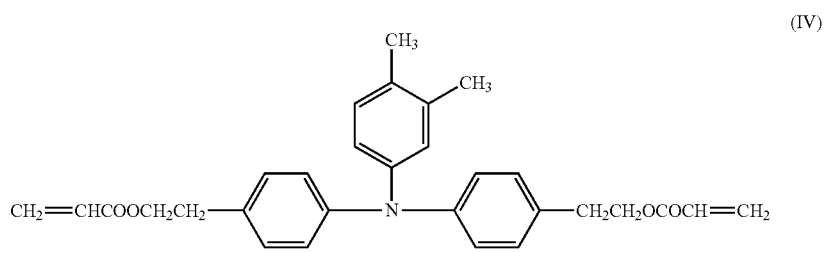

(IV)

<Coating Solution G>

Coating Solution G was prepared in the same manner as Coating Solution A except that Compound (V) [Ref-5] below was used as a comparative compound instead of Illustrative Compound B-35 for Coating Solution A.

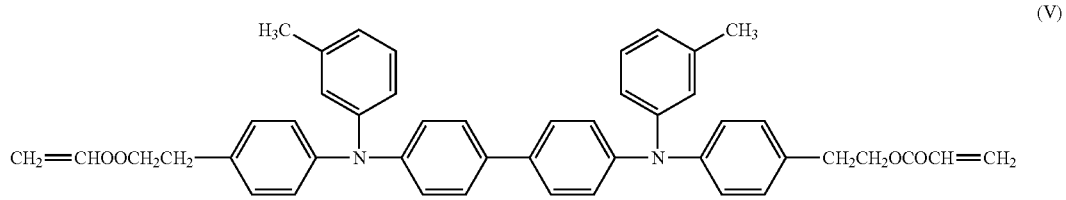

(V)

<Coating Solution H>

Coating Solution H was prepared in the same manner as Coating Solution A except that Compound (VI) [Ref-6] below was used as a comparative compound instead of Illustrative Compound B-35 for Coating Solution A.

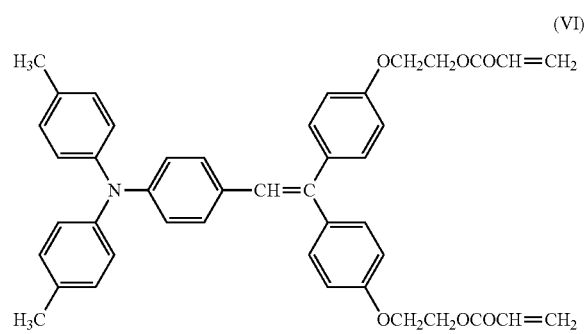

(VI)

<Coating Solution I>

Coating Solution I was prepared in the same manner as Coating Solution A except that Compound (VII) [Ref-7] below was used as a comparative compound instead of Illustrative Compound B-35 for Coating Solution A.

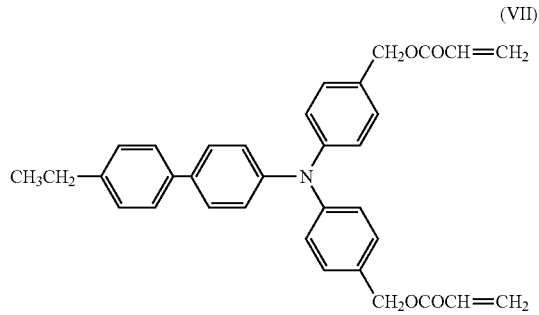

(VII)

<Ultraviolet-Light Irradiating Conditions for Cured Film Formation>

Lamp: metal halide lamp with 160 W/cm
Irradiation distance: 120 mm
Irradiation intensity: 500 mW/cm$^2$
Irradiation time: 60 seconds

TABLE 1

| Coating Solution | Amount of Elution (% by mass) |
|---|---|
| A | 1 |
| B | 1 |
| C | 4 |
| D | 5 |
| E | 7 |
| F | 1 |
| G | 4 |
| H | 5 |
| I | 3 |

The evaluation results indicate that the acrylic ester compounds of the present invention had smaller amount of elusion compared to heretofore known charge transport monomers shown in Comparative Examples and that they formed a cured film with higher crosslink density by chain polymerization. Owing to such high-density cross-linking structure, an acrylic ester compound of the present invention applied as an organic functional material for various organic semiconductor devices can meet the demand of the improvement in the mechanical durability and heat resistance against the abrasion and scratches.

EVALUATION EXAMPLE 2

<Evaluation of Charge Transport Property>

On an aluminum plate, a coating solution for an undercoat layer, a coating solution for a charge generating layer and a coating solution for a charge transport layer having the compositions below were applied and dried sequentially, and nine types of photoconductors (1) to (9) were prepared, each having an undercoat layer with a thickness of 0.3 μm, a charge generating layer with a thickness of 0.3 μm and a charge transport layer with a thickness of 20 μm. Regarding the coating solution for a charge transport layer, a cross-linking structure was formed by chain polymerization after coating and drying.

The nine types of photoconductors used the acrylic compounds of Illustrative Compounds B-35 and C-15 of the present invention synthesized in Synthetic Examples above and Ref-1 to Ref-7 used in the evaluation of hardenability above respectively as the compositions of the coating solutions of a charge transport layer.

| <Coating solution for undercoat layer> | |
|---|---|
| Polyamide resin (CM-8000: manufactured by Toray Industries, Inc.): | 2 parts |

<Coating solution for undercoat layer>

| | |
|---|---|
| Methanol: | 49 parts |
| Butanol: | 49 parts |

<Coating solution for charge generating layer>

| | |
|---|---|
| Bisazo pigment represented by Structural Formula (VIII) below: | 2.5 parts |
| Polyvinylbutyral (XYHL manufactured by UCC Inc.): | 0.5 parts |
| Cyclohexanone: | 200 parts |
| Methyl ethyl ketone: | 80 parts |

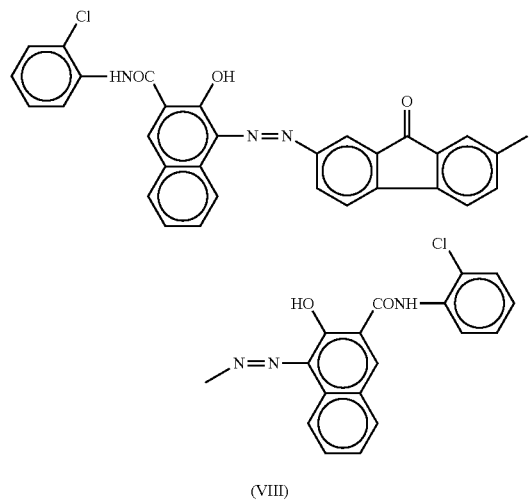

(VIII)

<Coating solutions for charge transport layer: (1) to (9)>

| | |
|---|---|
| Bisphenol Z polycarbonate (Panlite TS-2050 manufactured by Teijin Chemicals, Ltd.): | 10 parts |
| Charge transport monomer (acrylic ester compound shown in Table 2): | 10 parts |
| Tetrahydrofuran: | 80 parts |
| 1-% Tetrahydrofuran solution of silicone oil (KF-50-100CS manufactured by Shin-etsu Chemical Co., Ltd.): | 0.2 parts |

The obtained photoconductors (1) to (9) were evaluated for the charge transport property based on the half decay exposure and rest potential using a commercially available electrostatic paper analyzer (EPA8200 manufactured by Kawaguchi Electric Works Co., Ltd.).

That is, having electrified the photoconductors to −800 V with corona discharge of −6 kV in a dark room, a light of tungsten lamp was irradiated such that the illuminance at the surface of the photoconductor was 4.5 lux, and the time until the electric potential halved was measured in seconds to calculate the half decay exposure $E_{1/2}$ (lux·sec). Also, the rest potential (−V) was obtained after 30 seconds of exposure. Here, the smaller half decay exposure indicates the higher sensitivity, and the smaller rest potential indicates the smaller charge trapping.

The evaluation results are shown in Table 2 below.

TABLE 2

| Photoconductor No. | Acrylic Compound | Half Decay Exposure $E_{1/2}$ (lux·sec) | Residual Potential (−V) |
|---|---|---|---|
| Photoconductor (1) | Illustrative compound D-35 | 0.78 | 0 |
| Photoconductor (2) | Illustrative compound E-15 | 0.81 | 1 |
| Photoconductor (3) | Ref-1 Compound | 1.28 | 15 |
| Photoconductor (4) | Ref-2 Compound | 0.99 | 12 |
| Photoconductor (5) | Ref-3 Compound | 1.62 | 26 |
| Photoconductor (6) | Ref-4 Compound | 1.83 | 31 |
| Photoconductor (7) | Ref-5 Compound | 1.02 | 12 |
| Photoconductor (8) | Ref-6 Compound | 1.05 | 15 |
| Photoconductor (9) | Ref-7 Compound | 1.33 | 42 |

The evaluation results indicate that the photoconductors (1) and (2) with the acrylic ester compounds of the present invention had the favorable sensitivity and no charge trapping compared to the comparative photoconductors (3) to (9) with the conventional acrylic ester compounds since they had the small half decay exposure and no rest potential. Therefore, these photoconductors had the favorable charge transport property.

Evaluation Example 1 (elution from cured film) and Evaluation Example 2 (evaluation of charge transport property) indicate that the acrylic ester compounds of the present invention was able to satisfy simultaneously the formation of a high-density cross-linking structure by means of a chain reaction which could meet the mechanical durability and heat resistance and the development of the favorable charge transport property while the conventional charge transport monomers were not.

Therefore, the acrylic ester compounds of the present invention are highly effective as materials for providing the various organic semiconductor devices.

<Synthetic Example of Component (A1) Used in the Present Invention>

SYNTHETIC EXAMPLE A-5

Synthesis of N,N-di-p-tolyl-N',N'-bis(4'-hydroxybiphenyl-4-yl)benzidine

In a reaction vessel equipped with an agitator, thermometer and a cooling pipe, 2.73 g of N,N-di-p-tolyl-N',N'-bis(4'-methoxybiphenyl-4-yl)benzidine and 100 mL of methylene chloride were placed. While the vessel was being cooled with ice, 10 mL of a 1M methylene chloride solution of boron tribromide was delivered by drops into the vessel, and furthermore the mixture was reacted at the same temperature for three hours. Then, the reacted solution was poured into ice water and extracted with methylene chloride. The organic layer was washed with water and separated, and it was then dried with magnesium sulfate and subjected to vacuum concentration. The residue was purified with a silica gel chromatography with a mixture of n-hexane and ethyl acetate as a solvent, where the ratio of n-hexane to ethyl acetate in the mixture was one to one. Thus, the objective product was obtained with the yield of 2.53 g.

SYNTHETIC EXAMPLE A-6

Synthesis of Illustrative Compound D-35

In a reaction vessel equipped with an agitator, thermometer, a cooling pipe and a dropping funnel, 2.44 g of N,N-di-p-tolyl-N',N'-bis(4'-methoxybiphenyl-4-yl)benzidine, 1.22 g of triethylamine and 50 mL of tetrahydrofuran were placed.

Into the vessel, a mixture of 1.0 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with toluene as a solvent. Thus, the objective product was obtained with the yield of 1.92 g.

SYNTHETIC EXAMPLE A-8

Synthesis of Illustrative Compound E-15

In a reaction vessel equipped with an agitator, thermometer, a cooling pipe and a dropping funnel, 4.92 g of N,N'-diphenyl-N,N'-bis(4'-methoxybiphenyl-4-yl)-3,3'-dimethylbenzidine, 2.19 g of triethylamine and 50 mL of tetrahydrofuran were placed, which was agitated at a room

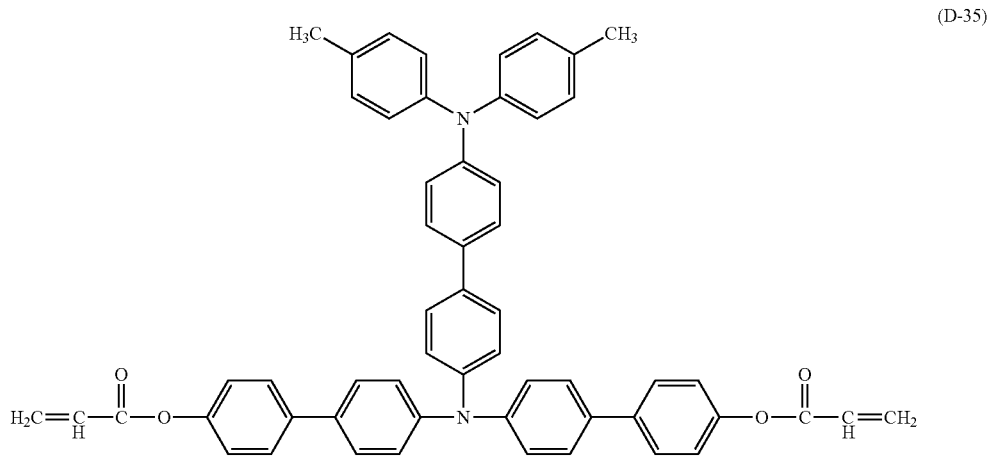 [SMILES: C=CC(=O)Oc1ccc(-c2ccc(N(c3ccc(-c4ccc(OC(=O)C=C)cc4)cc3)c3ccc(-c4ccc(N(c5ccc(C)cc5)c5ccc(C)cc5)cc4)cc3)cc2)cc1]

(D-35)

SYNTHETIC EXAMPLE A-7

Synthesis of N,N'-diphenyl-N,N'-bis(4'-hydroxybiphenyl-4-yl)-3,3'-dimethylbenzidine In a reaction vessel equipped with an agitator, thermometer and a cooling pipe, 6.04 g of N,N-diphenyl-N,N'-bis(4'-methoxybiphenyl-4-yl)-3,3'-dimethylbenzidine and 200 mL of methylene chloride were placed. While the vessel was being cooled with ice, 30 mL of a methylene chloride solution of boron tribromide was delivered by drops into the vessel, and furthermore the mixture was reacted at the same temperature for six hours. Then, the reacted solution was poured into ice water and extracted with chloroform. The organic layer was washed with water and separated, and it was then dried with magnesium sulfate and subjected to vacuum concentration. The residue was purified with a silica gel chromatography with a mixture of toluene and ethyl acetate as a solvent, where the ratio of toluene to ethyl acetate in the mixture was nine to one. Thus, the objective product was obtained with the yield of 5.47 g.

temperature. Into the vessel, a mixture of 2.2 mL of acryloyl chloride and 3.0 mL of tetrahydrofuran was delivered by drops. The vessel was subjected to reaction for one hour at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of toluene and cyclohexane as a solvent, where the ratio of toluene to cyclohexane in the mixture was seven to three. Thus, the objective product was obtained with the yield of 4.32 g.

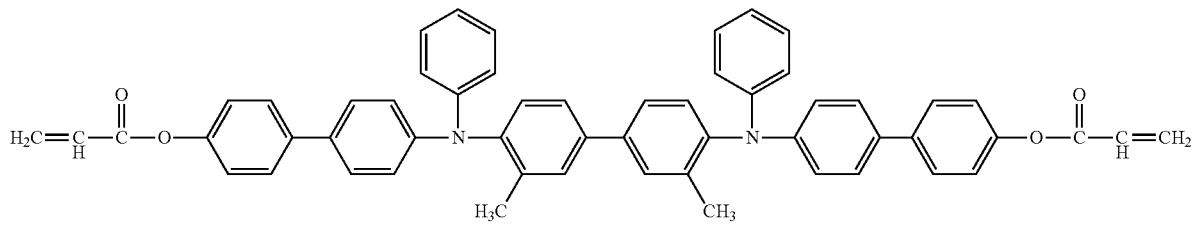

(E-15)

EXAMPLE A-1

An undercoat layer having a thickness of 3.5 μm, a charge generating layer having a thickness of 0.2 μm and a charge transport layer having a thickness of 18 μm were formed by sequentially applying and drying a coating solution for an undercoat layer, a coating solution for a charge generating layer and a coating solution for a charge transport layer having the following compositions respectively on an aluminum cylinder having a diameter of 30 mm. On this charge transport layer, a coating solution for a cross-linking charge transport layer having the following composition was spray-coated and let to dry for 20 minutes. Then, the coated layer was cured by irradiating a light under the conditions: a metal halide lamp with 160 W/cm, irradiation distance of 110 mm, irradiation intensity of 750 mW/cm² and irradiation time of 240 seconds. The sample was further dried at 130° C. for 20 minutes to form a cross-linking charge transport layer having a thickness of 5.0 μm. Thus, an electrophotographic photoconductor of the present invention was obtained.

| [Coating solution for undercoat layer] | |
|---|---|
| Alkyd resin (BECKOSOL 1307-60-EL manufactured by Dainippon Ink and Chemicals, Incorporated) | 6 parts |
| Melamine resin (SUPER BECKAMINE manufactured by Dainippon Ink and Chemicals, Incorporated) | 4 parts |
| Titanium oxide: | 40 parts |
| Methyl ethyl ketone: | 50 parts |

| [Coating solution for charge generating layer] | |
|---|---|
| Bisazo pigment represented by the following structural formula: | 2.5 parts |

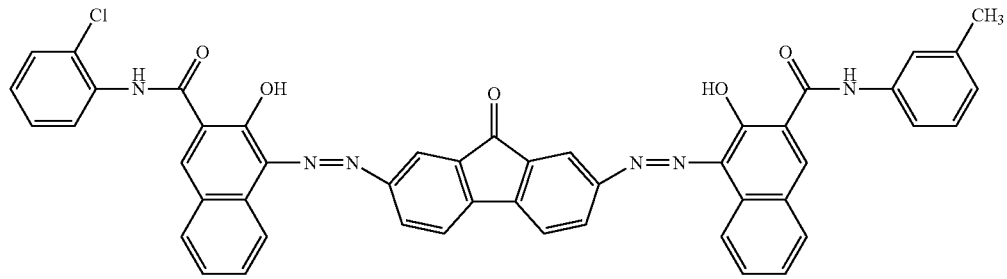 [SMILES: Cc1cccc(NC(=O)c2cc3ccccc3c(N=Nc3ccc4c(c3)C(=O)c3cc(N=Nc5c(O)c(C(=O)Nc6ccccc6Cl)cc6ccccc56)ccc3-4)c2O)c1]

| Polyvinylbutyral (XYHL manufactured by UCC Inc.): | 0.5 parts |
|---|---|
| Cyclohexanone: | 200 parts |
| Methyl ethyl ketone: | 80 parts |

| [Coating solution for charge transport layer] | |
|---|---|
| Bisphenol Z polycarbonate (Panlite TS-2050 manufactured by Teijin Chemicals, Ltd.): | 10 parts |
| Charge transport material represented by the following structural formula: | 7 parts |

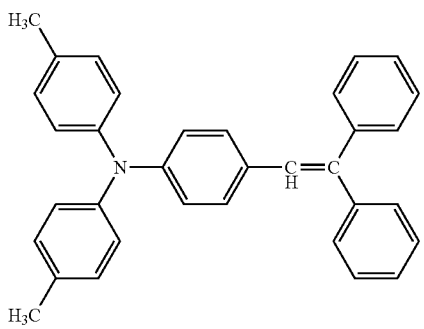 [SMILES: Cc1ccc(N(c2ccc(C)cc2)c2ccc(C=C(c3ccccc3)c3ccccc3)cc2)cc1]

| Tetrahydrofuran: | 100 parts |
|---|---|
| 1-% Tetrahydrofuran solution of silicone oil (KF-50-100CS manufactured by Shin-etsu Chemical Co., Ltd.): | 0.2 parts |

| [Coating solution for cross-linking charge transport layer] | |
|---|---|
| Component A (Illustrative Compound D-35): | 10 parts |
| Component B (trimethylolpropane triacrylate KAYARAD TMPTA manufactured by Nippon Kayaku Co., Ltd. having a molecular weight of 296, the number of functional groups of three and the ratio of the molecular weight to the number of functional groups of 99) | 10 parts |
| Component C | |
| 1-hydroxycyclohexyl phenyl ketone (IRGACURE 184 manufactured by Ciba Specialty Chemicals) | 1 part |
| Solvent (tetrahydrofuran) | 100 parts |

EXAMPLE A-2

An electrophotographic photoconductor was prepared in the same manner as Example A-1 except that Component A in Example A-1 was replaced by five parts of Illustrative Compound D-35 and five parts of Illustrative Compound E-15.

EXAMPLE A-3

An electrophotographic photoconductor of Example A-3 was prepared in the same manner as Example A-1 except that Component A in Example A-1 was replaced by Illustrative Compound E-15.

EXAMPLES A-4 TO A-8

Electrophotographic photoconductors of Examples A-4 to A-8 were prepared in the same manner as Example A-3 except that the thickness of the cross-linking charge transport layer in Example A-3 was changed to the film thicknesses shown in Table 1.

COMPARATIVE EXAMPLE A-1

An electrophotographic photoconductor of Comparative Example A-1 was prepared in the same manner as Example A-1 except that Component A in Example A-1 was replaced by the following compound.

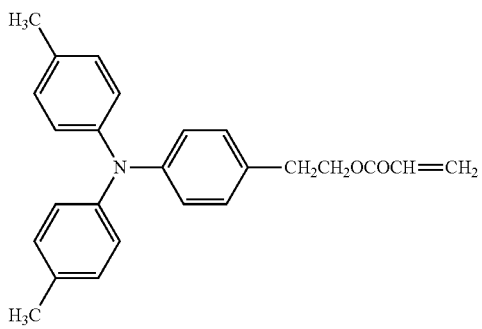

COMPARATIVE EXAMPLE A-2

An electrophotographic photoconductor of Comparative Example A-2 was prepared in the same manner as Example A-1 except that Component A in Example A-1 was replaced by the following compound.

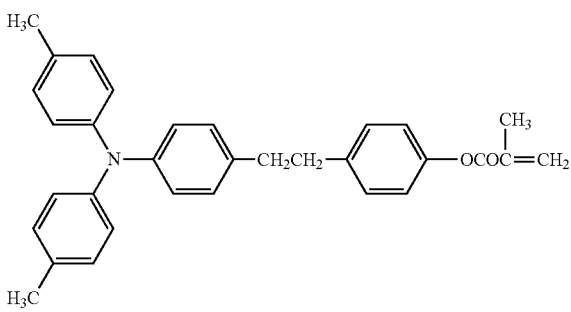

COMPARATIVE EXAMPLE A-3

An electrophotographic photoconductor of Comparative Example A-3 was prepared in the same manner as Example A-1 except that Component A in Example A-1 was replaced by the following compound.

COMPARATIVE EXAMPLE A-4

An electrophotographic photoconductor of Comparative Example A-4 was prepared in the same manner as Example A-1 except that Component A in Example A-1 was replaced by the following compound.

COMPARATIVE EXAMPLE A-5

An electrophotographic photoconductor of Comparative Example A-5 was prepared in the same manner as Example A-1 except that Component A in Example A-1 was replaced by the following compound.

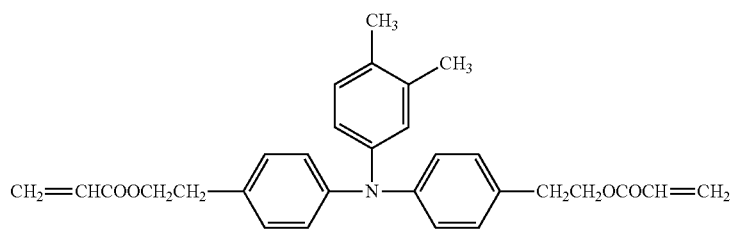

COMPARATIVE EXAMPLE A-6

An electrophotographic photoconductor of Comparative Example A-6 was prepared in the same manner as Example A-1 except that Component A in Example A-1 was replaced by the following compound.

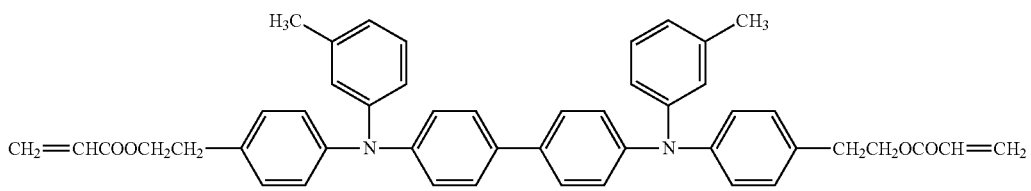

COMPARATIVE EXAMPLE A-7

An electrophotographic photoconductor of Comparative Example A-7 was prepared in the same manner as Example A-1 except that Component A in Example A-1 was replaced by the following compound.

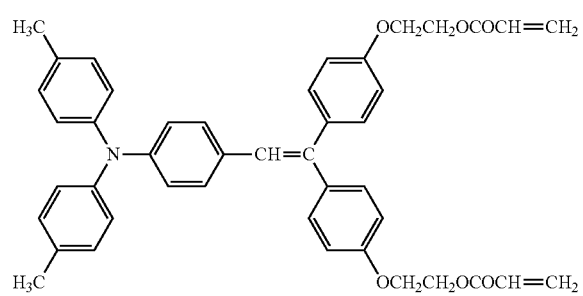

COMPARATIVE EXAMPLE A-8

An electrophotographic photoconductor of Comparative Example A-8 was prepared in the same manner as Example A-1 except that Component A in Example A-1 was replaced by the following compound.

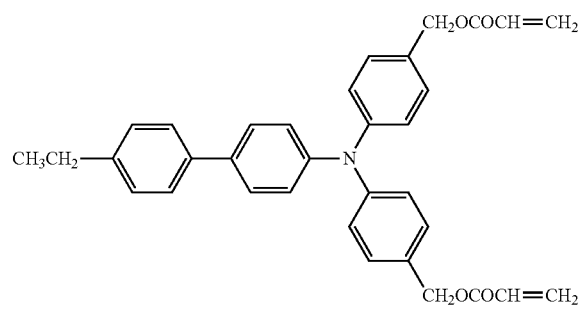

The prepared electrophotographic photoconductors of Examples A-1 to A-8 and Comparative Examples A-1 to A-8 were visually observed for the presence of cracks and film exfoliation. Also, the gel fraction of each cross-linking charge transport layer was obtained with the following procedure. That is, the coating solutions for a cross-linking charge transport layer was directly applied to an aluminum substrate in the same manner as respective Examples and Comparative Examples, and the samples were subjected to light irradiation and drying under the same conditions. The films were then immersed in a tetrahydrofuran solution at 25° C. for five days, and the gel fraction was obtained from the mass decrease. The results are shown in Table 3.

TABLE 3

| | Cross-linking Charge transport layer Film Thickness (μm) | Surface Observation | Gel fraction (%) |
|---|---|---|---|
| Example A-1 | 5.0 | Good | 99 |
| Example A-2 | 5.0 | Good | 99 |
| Example A-3 | 5.0 | Good | 99 |
| Example A-4 | 1.0 | Good | 99 |
| Example A-5 | 3.0 | Good | 99 |
| Example A-6 | 7.0 | Good | 99 |
| Example A-7 | 10.0 | Good | 97 |
| Example A-8 | 12.0 | Good | 92 |
| Comparative Example A-1 | 5.0 | Good | 95 |
| Comparative Example A-2 | 5.0 | Good | 93 |
| Comparative Example A-3 | 5.0 | Good | 95 |
| Comparative Example A-4 | 5.0 | Good | 90 |
| Comparative Example A-5 | 5.0 | Cracked | 97 |
| Comparative Example A-6 | 5.0 | Good | 96 |
| Comparative Example A-7 | 5.0 | Good | 94 |
| Comparative Example A-8 | 5.0 | Good | 96 |

Next, photoconductors were prepared in the same manner as Examples A-1 to A-8 and Comparative Examples A-1 to A-8 except for the photoconductor of Comparative Example A-5 which had cracks in the formation of the cross-linking charge transport layer. Using these photoconductors and a toner with silica additive, operating tests with 100,000 sheets of A4 paper were performed. The photoconductors were mounted on process cartridges for electrophotography, and an image exposure light source having 655 nm of laser diode of the remodeled imagio Neo 270, manufactured by Ricoh Company Ltd., was configured such that the initial unexposed electric potential was set at −700 V. Then, the film thicknesses of all the layers were measured prior to the operation and after 50,000 printings. Then, the wear amount was calculated from the difference thereof, and the number of white spots in a solid image area was counted per unit area. Also, the electric potential of the exposed area was measured prior to the operation and after 50,000 printings. The results are shown in Table 4.

TABLE 4

| | Image After 50,000 Copies | Wear (μm) | Number of White Spots | Initial VL (−V) | Final VL (−V) |
|---|---|---|---|---|---|
| Example A-1 | Good | 0.5 | 0 to 5 | 80 | 95 |
| Example A-2 | Good | 0.5 | 0 to 5 | 80 | 95 |
| Example A-3 | Good | 0.5 | 0 to 5 | 80 | 95 |
| Example A-4 | Slight background fog | 0.8 | 0 to 5 | 80 | 95 |
| Example A-5 | Good | 0.5 | 0 to 5 | 80 | 95 |
| Example A-6 | Good | 0.5 | 0 to 5 | 80 | 95 |
| Example A-7 | Good | 0.6 | 0 to 5 | 85 | 135 |
| Example A-8 | Slight decrease in image density | 0.6 | 0 to 5 | 95 | 150 |
| Comparative Example A-1 | Severe decrease in image density | 1.3 | 10 to 20 | 180 | 250 |
| Comparative Example A-2 | Severe decrease in image density | 2.1 | 10 to 20 | 180 | 230 |
| Comparative Example A-3 | Good | 1.2 | 10 to 20 | 85 | 120 |

TABLE 4-continued

| | Image After 50,000 Copies | Wear (μm) | Number of White Spots | Initial VL (−V) | Final VL (−V) |
|---|---|---|---|---|---|
| Comparative Example A-4 | Slight background fog | 2.7 | 10 to 20 | 85 | 115 |
| Comparative Example A-6 | Slight decrease in image density | 0.8 | 0 to 5 | 120 | 195 |
| Comparative Example A-7 | Severe decrease in image density | 1.0 | 0 to 5 | 120 | 200 |
| Comparative Example A-8 | Severe decrease in image density | 0.8 | 0 to 5 | 150 | 240 |

As indicated in Table 4, the electrophotographic photoconductors of the present invention on one hand had the more superior abrasion resistance and on the other hand enabled an image printing with fewer defects among the organic photoconductors with superior abrasion resistance. In particular, a white spot caused by silica stinging was less likely to occur, and they had the sufficient image stability for long-term use. It is evident from the comparison with Comparative Examples that these advantages are owing to Component A used in the present invention, and it shows that an electrophotographic photoconductor which contains on its surface a cured coating composition obtained from the radical polymerization of Component A of the present invention has superior properties. Also, as indicated by Examples, the combination of Component A and Component B of the present invention provides a highly durable photoconductor with the smooth surface, extremely superior abrasion resistance, low rest potential accumulation property and fewer image defects. Examples also show that the cured coating material of the composition which had been photo-cured under the presence of photo-polymerization initiator was effective. In addition, there was little allowance for wear after 50,000 printings when the thickness was less than 1 μm, and the residential potential accumulation property degraded with the decrease in gel fraction when the thickness exceeded 10 μm. Therefore, the favorable properties were maintained when the thickness of the cross-linking charge transport layer was 1 μm to 10 μm. The photoconductors cured under the curing conditions of Examples were determined practically insoluble with respect to an organic solvent based on the gel fraction data. This implies that the superior abrasion resistance and image stability may be achieved under such conditions.

EXAMPLES A-9 TO A-14

Electrophotographic photoconductors of Examples A-9 to A-14 were prepared in the same manner as Example A-1 except that Component A-1 in Example A-1 was replaced by Illustrative Compounds shown in Table 5. The film thickness of the cross-linking charge transport layer was 5.0 μm for all the photoconductors. The surface observation and determination of gel fraction were performed in the same manner as Example A-1. The results are shown in Table 5. In addition, operating tests were performed with these photoconductors and a toner with silica additive in the same manner as Example A-1. The results are shown in Table 6.

TABLE 5

| | Illustrative Compound No. | Surface Observation | Gel Fraction (%) |
|---|---|---|---|
| Example A-9 | C-32 | Good | 99 |
| Example A-10 | C-38 | Good | 99 |
| Example A-11 | C-39 | Good | 99 |
| Example A-12 | D-10 | Good | 99 |
| Example A-13 | D-14 | Good | 99 |
| Example A-14 | D-18 | Good | 99 |

TABLE 6

| | Image After 50,000 Copies | Wear (μm) | Number of White Spots | Initial VL (−V) | Final VL (−V) |
|---|---|---|---|---|---|
| Example A-9 | Good | 0.5 | 0 to 5 | 85 | 100 |
| Example A-10 | Good | 0.5 | 0 to 5 | 85 | 100 |
| Example A-11 | Good | 0.5 | 0 to 5 | 85 | 100 |
| Example A-12 | Good | 0.5 | 0 to 5 | 85 | 105 |
| Example A-13 | Good | 0.5 | 0 to 5 | 85 | 105 |
| Example A-14 | Good | 0.5 | 0 to 5 | 85 | 105 |

It is evident from the results in Table 5 and Table 6 that a photoconductor of the present invention has the superior properties, as in the case of Examples above.

According to the present invention, a long-lasting photoconductor having the favorable abrasion resistance as well as electric properties with fewer defects due to white spots may be provided by using a cured coating composition obtained from the radical polymerization of Component A1 on the surface of the photoconductor. Especially, a non-conventional electrophotographic photoconductor having the superior abrasion resistance as well as reduced rest potential may be obtained by disposing a cured coating composition obtained by the radical polymerization of Component A and Component B on the surface. An electrophotographic photoconductor having a cured coating composition obtained by the radical polymerization of Component A1, Component B and Component C on its surface may be provided commercially at a low cost since such photoconductor having the superior properties may be easily manufactured in a short period of time. Therefore, the use of this photoconductor can provide an image forming method, an image forming apparatus and a process cartridge for the image forming apparatus with high-quality image over a long period of time.

SYNTHETIC EXAMPLE B-1

Synthesis of p-tolyl-bis(6-hydroxy-2-naphthyl)amine

In a reaction vessel equipped with an agitator, thermometer and a cooling pipe, 2.1 g of p-tolyl-bis(4'-methoxy-2-naphthyl)amine and 50 mL of methylene chloride were placed. While the vessel was being cooled with ice, 120 mL of a methylene chloride solution of boron tribromide was delivered by drops into the vessel, and furthermore the mixture was reacted at the same temperature for one hour, and it was further reacted for one hour with the temperature increased to a room temperature. Then, the reacted solution was poured into ice water and extracted with ethyl acetate. The organic layer was washed with water and separated, and it was then dried with magnesium sulfate and subjected to vacuum concentration. Thus, the objective product was obtained with the yield of 2.38 g.

SYNTHETIC EXAMPLE B-2

Synthesis of Illustrative Compound F-9

In a reaction vessel equipped with an agitator, thermometer, a cooling pipe and a dropping funnel, 2.25 g of p-tolylbis(6-hydroxy-2-naphthylamine, 1.75 g of triethylamine and 25 mL of tetrahydrofuran were placed, which was agitated at a room temperature. Into the vessel, a mixture of 1.2 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of n-hexane and toluene as a solvent, where the ratio of n-hexane to toluene in the mixture was one to nine. Thus, the objective product was obtained with the yield of 1.42 g.

Figure 3:
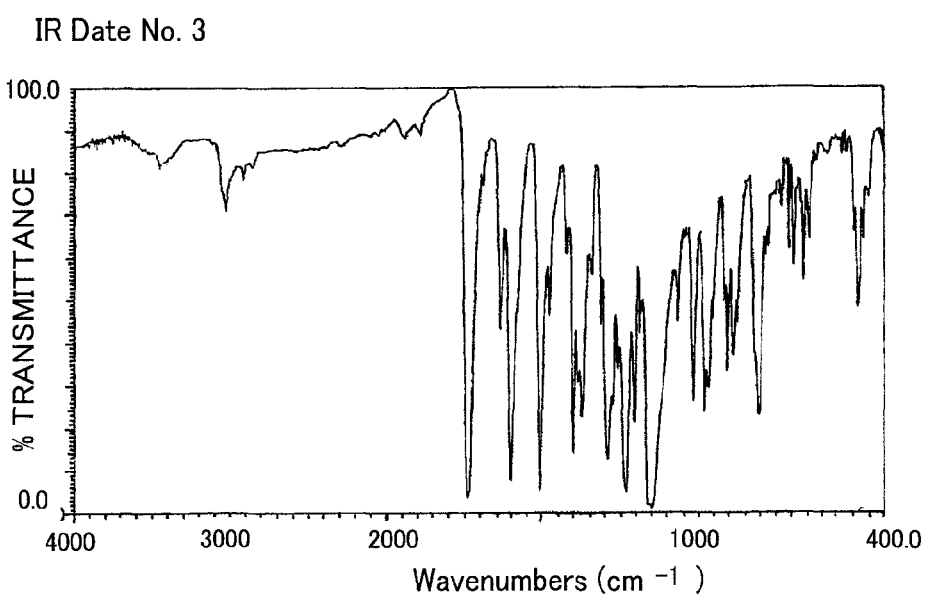
FIG. 3 is an infrared absorption spectral diagram of an Illustrative Compound B-9 obtained in Synthetic Example B-2 (IR data No. 3).

The data of the objective product are as follows:
Melting point=176.0° C. to 177.0° C.;
APCI-MS: m/z=500;
UV-absorption spectrum in methylene chloride: $\lambda_{max}$=319.5 nm and $\in$=29,100 M$^{-1}$cm$^{-1}$;
HPCL purity (254 nm)=99.2%; and
IR measurement data: shown in the infrared absorption spectral diagram (IR data No. 3) in FIG. 3 ethyl acetate. The organic layer was washed with water and separated, and it was then dried with magnesium sulfate and subjected to vacuum concentration. Thus, the objective product was obtained with the yield of 2.43 g.

SYNTHETIC EXAMPLE B-4

Synthesis of Illustrative Compound F-22

In a reaction vessel equipped with an agitator, thermometer, a cooling pipe and a dropping funnel, 2.31 g of 4-di-p-tolylamino-4'-bis(6-hydroxy-2-naphthyl)aminobiphenyl, 1.30 g of triethylamine and 25 mL of tetrahydrofuran were placed, which was agitated at a room temperature. Into the vessel, a mixture of 1.0 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of n-hexane

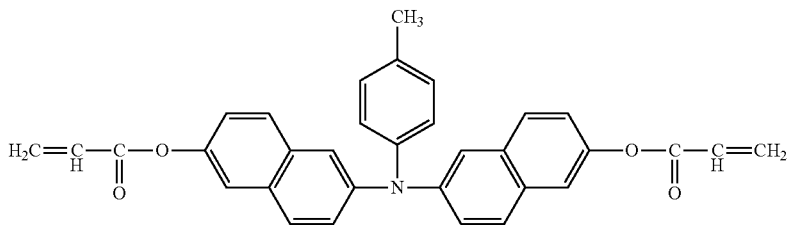

(F-9)

SYNTHETIC EXAMPLE B-3

Synthesis of 4-di-p-tolylamino-4'-bis(6-hydroxy-2-naphthyl)aminobiphenyl

Figure 4:
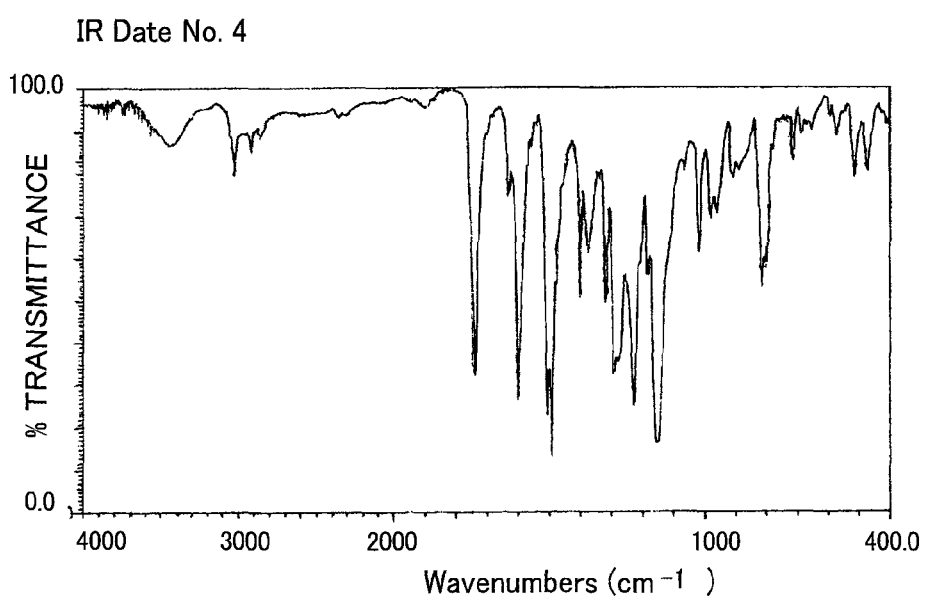
FIG. 4 is an infrared absorption spectral diagram of an Illustrative Compound B-22 obtained in Synthetic Example B-4 (IR data No. 4).

In a reaction vessel equipped with an agitator, thermometer and a cooling pipe, 2.79 g of p-tolylamino-4'-bis(4'-methoxy-2-naphtyl)aminobiphenyl and 50 mL of methylene chloride were placed. While the vessel was being cooled with ice, 10 mL of a 1M methylene chloride solution of boron tribromide was delivered by drops into the vessel, and the mixture was reacted at the same temperature for one hour. The mixture was further reacted at a room temperature for one hour. Then, the reacted solution was poured into ice water and extracted with and toluene as a solvent, where the ratio of n-hexane to toluene in the mixture was one to nine. Thus, the objective product was obtained with the yield of 1.99 g The data of the objective product are as follows:
State: amorphous
APCI-MS: m/z=757;
UV-absorption spectrum in methylene chloride: $\lambda_{max}$=357 nm and $\in$=56,200 M$^{-1}$cm$^{-1}$;
HPCL purity (254 nm)=99.7%; and
IR measurement data: shown in the infrared absorption spectral diagram (IR data No. 4) in FIG. 4.

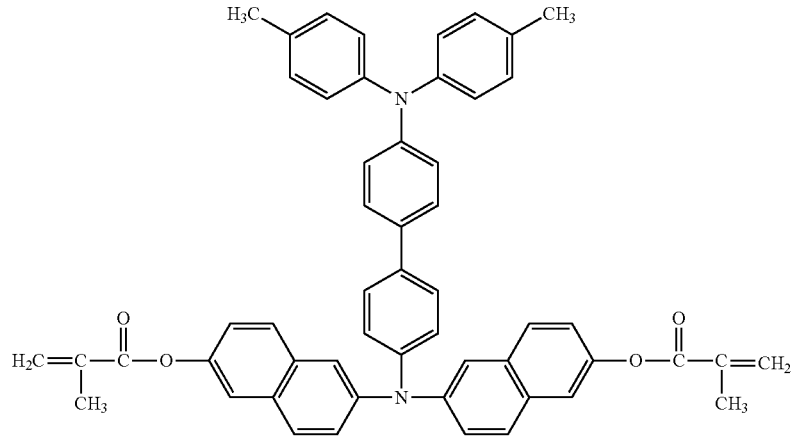

(F-22)

SYNTHETIC EXAMPLE B-5

Synthesis of N,N'-bis(6-hydroxy-2-naphthyl)-N,N'-diphenyl-3,3'-dimethylbenzidine In a reaction vessel equipped with an agitator, thermometer and a cooling pipe, 1.78 g of N,N'-bis(6-dimethoxy-2-naphthyl)-N,N'-diphenyl-3,3'-dimethylbenzidine and 20 mL of methylene chloride were placed. While the vessel was being cooled with ice, 6 mL of a 1M methylene chloride solution of boron tribromide was delivered by drops into the vessel, and the mixture was reacted at the same temperature for one hour. The mixture was further reacted at a room temperature for one hour. Then, the reacted solution was poured into ice water and extracted with ethyl acetate. The organic layer was washed with water and separated, and it was then dried with magnesium sulfate and subjected to vacuum concentration. Thus, the objective pro duct was obtained with the yield of 1.63 g.

SYNTHETIC EXAMPLE B-6

Synthesis of Illustrative Compound G-18

Figure 5:
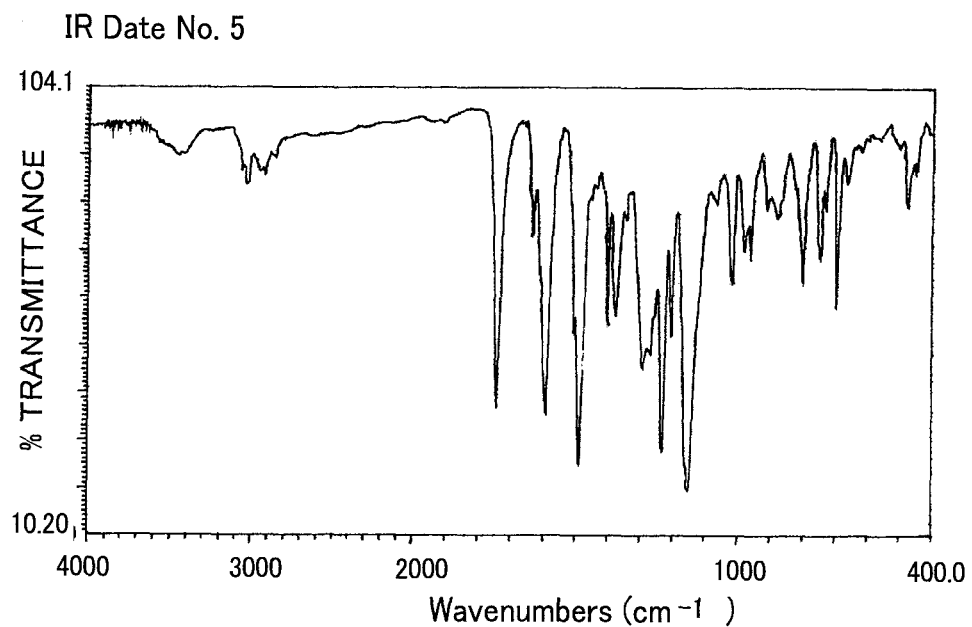
FIG. 5 is an infrared absorption spectral diagram of an Illustrative Compound C-18 obtained in Synthetic Example B-6 (IR data No. 5).

In a reaction vessel equipped with an agitator, thermometer, a cooling pipe and a dropping funnel, 1.51 g of N,N'-bis(6-hydroxy-2-naphthyl)-N,N'-diphenyl-3,3'-dimethylbenzidine, 0.71 g of triethylamine and 20 mL of tetrahydrofuran were placed, which was agitated at a room temperature. Into the vessel, a mixture of 0.5 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with toluene as a solvent. Thus, the objective product was obtained with the yield of 1.22 g The data of the objective product are as follows:
State: amorphous
APCI-MS: m/z=757;
UV-absorption spectrum in methylene chloride: $\lambda_{max}$=321.5 nm and $\in$=61,500 $M^{-1}cm^{-1}$;
HPCL purity (254 nm)=99.8%; and
IR measurement data: shown in the infrared absorption spectral diagram (IR data No. 5) in FIG. 5.

The hydroxy compounds synthesized with the demethylation reaction described above were used as manufacturing intermediates, and acrylic ester compound of the present invention expressed as General Formulae (1-4) to (1-6) and (2-2) above may be easily produced by reacting these with acrylic chloride.

Other Illustrative Compounds F-1 to F-48 and G-1 to G-36 may also be produced easily with the reactions above. Also, an acrylic ester compound may be produced easily when methacrylic chloride was used instead of acrylic chloride.

EVALUATION EXAMPLE 3

<Elution from Cured Film>

Coating Solutions (A) to (J) below were prepared with Illustrative Compounds F-9, F-22 and G-18 as well as compounds for reference (Ref-1 to Ref-7). These ten types of the coating solutions were blade-coated on an aluminum plate and dried to the touch, and ultraviolet light was irradiated under the conditions below. Thus, cured films with a thickness of 5 μm were prepared. The obtained cured films were immersed in tetrahydrofuran for seven days, and the amount of elution from each cured film was measured. The evaluation results are shown in Table 7 below.

| <Coating Solution A> | |
|---|---|
| Illustrative Compound F-9: | 10 parts |
| Trimethylolpropane triacrylate: | 10 parts |
| Polymerization initiator (1-hydroxycyclohexyl phenyl ketone): | 1 part |
| Tetrahydrofuran: | 84 parts |

<Coating Solution B>
Coating Solution B was prepared in the same manner as Coating Solution A except that Illustrative Compound F-22 was used instead of Illustrative Compound F-9 for Coating Solution A.

<Coating Solution C>
Coating Solution C was prepared in the same manner as Coating Solution A except that Illustrative Compound G-18 was used instead of Illustrative Compound F-9 for Coating Solution A.

<Coating Solution D>

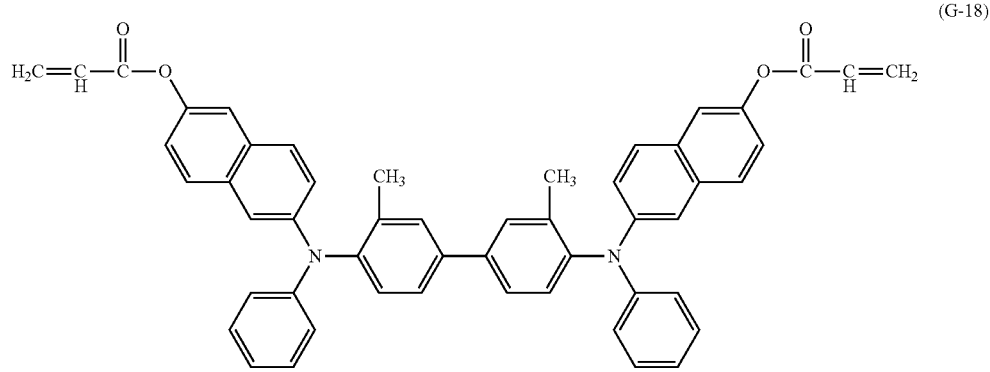 [SMILES: C=CC(=O)Oc1ccc2cc(N(c3ccccc3)c3ccc(-c4ccc(N(c5ccccc5)c5ccc6cc(OC(=O)C=C)ccc6c5)c(C)c4)cc3C)ccc2c1]

(G-18)

Coating Solution D was prepared in the same manner as Coating Solution A except that Compound (I) [Ref-1] below was used instead of Illustrative Compound F-9 for Coating Solution A.

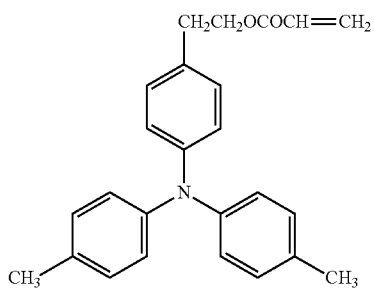

(I)

<Coating Solution E>

Coating Solution E was prepared in the same manner as Coating Solution A except that Compound (II) [Ref-2] below was used instead of Illustrative Compound F-9 for Coating Solution A.

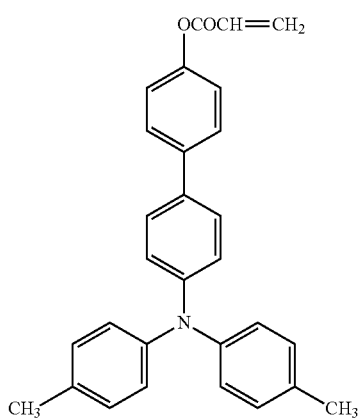

(II)

<Coating Solution F>

Coating Solution F was prepared in the same manner as Coating Solution A except that Compound (III) [Ref-3] below was used instead of Illustrative Compound F-9 for Coating Solution A.

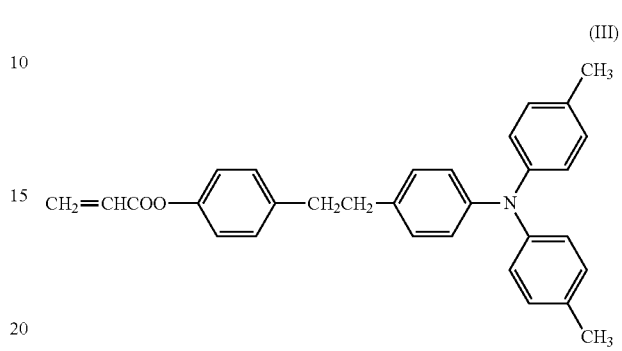

(III)

<Coating Solution G>

Coating Solution G was prepared in the same manner as Coating Solution A except that Compound (IV) [Ref-4] below was used instead of Illustrative Compound F-9 for Coating Solution A.

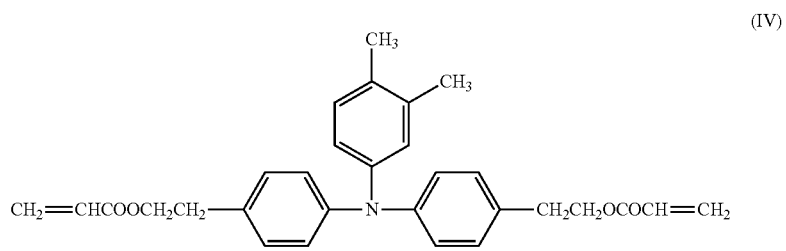

(IV)

<Coating Solution H>

Coating Solution H was prepared in the same manner as Coating Solution A except that Compound (V) [Ref-5] below was used instead of Illustrative Compound F-9 for Coating Solution A.

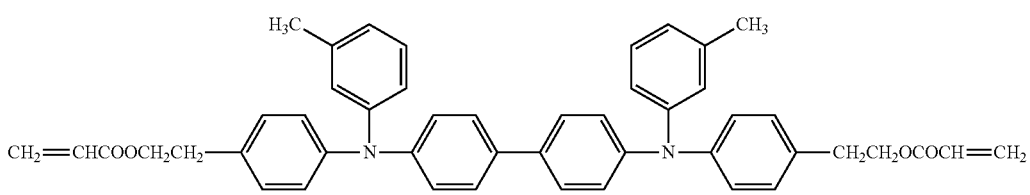

(V)

<Coating Solution I>

Coating Solution I was prepared in the same manner as Coating Solution A except that Compound (VI) [Ref-6] below was used instead of Illustrative Compound F-9 for Coating Solution A.

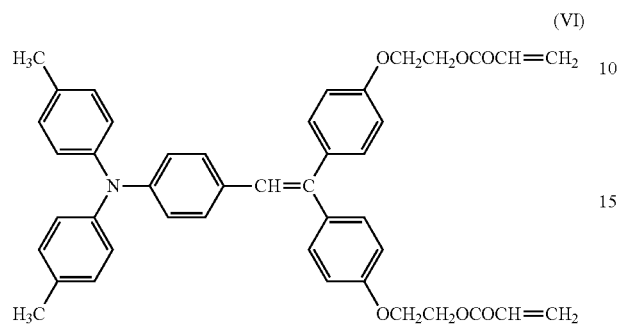

(VI)

<Coating Solution J>

Coating Solution J was prepared in the same manner as Coating Solution A except that Compound (VII) [Ref-7] below was used instead of Illustrative Compound F-9 for Coating Solution A.

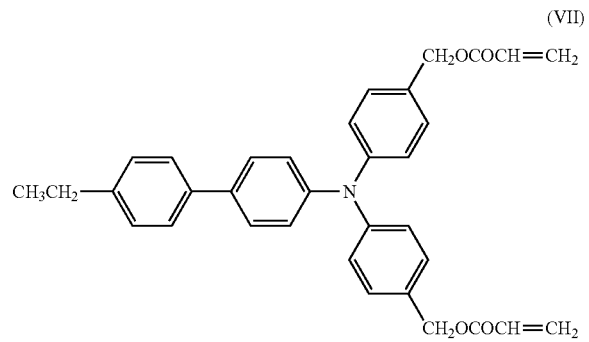

(VII)

<Ultraviolet-Light Irradiating Conditions for Cured Film Formation>

Lamp: metal halide lamp with 160 W/cm
Irradiation distance: 120 mm
Irradiation intensity: 500 mW/cm$^2$
Irradiation time: 60 seconds

TABLE 7

| Coating Solution | Elution (% by mass) |
|---|---|
| A | 1 |
| B | 1 |
| C | 1 |
| D | 4 |
| E | 5 |
| F | 7 |
| G | 1 |
| H | 4 |
| I | 5 |
| J | 3 |

The evaluation results indicate that the acrylic ester compounds of the present invention had smaller amount of elusion compared to heretofore known charge transport monomers shown in Comparative Examples and formed a cured film with higher crosslink density by chain polymerization. Owing to such high-density cross-linking structure, an acrylic ester compound of the present invention applied as an organic functional material for various organic semiconductor devices can meet the demand of the improvement in the mechanical durability and heat resistance against the abrasion and scratches.

EVALUATION EXAMPLE 4

<Evaluation of Charge Transport Property>

On an aluminum plate, a coating solution for an undercoat layer, a coating solution for a charge generating layer and a coating solution for a charge transport layer having the compositions below were applied and dried sequentially (including polymerization), and ten types of photoconductors (1) to (10) were prepared, each having an undercoat layer with a thickness of 0.3 μm, a charge generating layer with a thickness of 0.3 μm and a charge transport layer with a thickness of 20 μm.

The ten types of photoconductors used the acrylic compounds of Illustrative Compounds F-9, F-22 and G-18 of the present invention synthesized in Synthetic Examples above and Ref-1 to Ref-7 used in the evaluation of hardenability above respectively as the compositions of the coating solutions of a charge transport layer.

| <Coating solution for undercoat layer> | |
|---|---|
| Polyamide resin (CM-8000 manufactured by Toray Industries, Inc.): | 2 parts |
| Methanol: | 49 parts |
| Butanol: | 49 parts |

| <Coating solution for charge generating layer> | |
|---|---|
| Bisazo pigment represented by Structural Formula (VIII) below: | 2.5 parts |
| Polyvinylbutyral (XYHL manufactured by UCC Inc.): | 0.5 parts |
| Cyclohexanone: | 200 parts |
| Methyl ethyl ketone: | 80 parts |

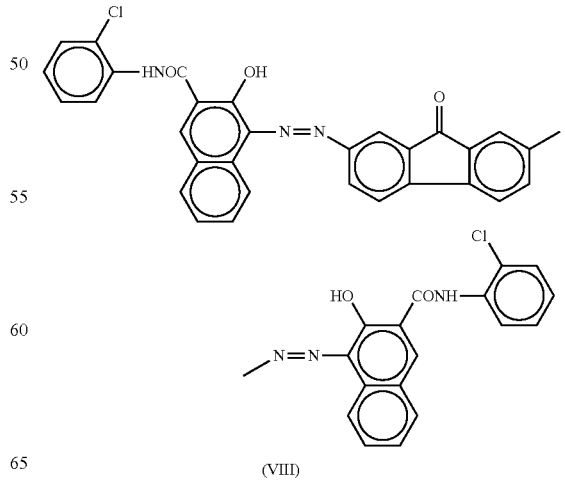

(VIII)

| <Coating solutions for charge generating layer: (1) to (10)> | |
|---|---|
| Bisphenol Z polycarbonate (Panlite TS-2050 manufactured by Teijin Chemicals, Ltd.): | 10 parts |
| Charge transport monomer (acrylic ester compound shown in Table 2): | 10 parts |
| Tetrahydrofuran: | 80 parts |
| 1-% Tetrahydrofuran solution of silicone oil (KF-50-100CS manufactured by Shin-etsu Chemical Co., Ltd.): | 0.2 parts |

The obtained photoconductors (1) to (10) were evaluated for the charge transport property based on the half decay exposure and rest potential using a commercially available electrostatic paper analyzer (EPA8200 manufactured by Kawaguchi Electric Works Co., Ltd.).

That is, having electrified the photoconductors to −800 V by means of corona discharge of −6 kV in a dark room, a light of tungsten lamp was irradiated such that the illuminance at the surface of the photoconductor was 4.5 lux, and the time until the electric potential halved was measured in seconds to calculate the half decay exposure $E_{1/2}$ (lux·sec). Also, the rest potential (−V) was obtained after 30 seconds of exposure. Here, the smaller half decay exposure indicates the higher sensitivity, and the smaller rest potential indicates the smaller charge trapping.

The evaluation results are shown in Table 8 below.

TABLE 8

| Photoconductor No. | Acrylic Compound | Half Decay Exposure $E_{1/2}$ (lux·sec) | Residual Potential (−V) |
|---|---|---|---|
| Photoconductor (1) | Illustrative compound F-9 | 0.81 | 0 |
| Photoconductor (2) | Illustrative compound F-22 | 0.80 | 0 |
| Photoconductor (3) | Illustrative compound G-18 | 0.75 | 0 |
| Photoconductor (4) | Ref-1 Compound | 1.28 | 15 |
| Photoconductor (5) | Ref-2 Compound | 0.99 | 12 |
| Photoconductor (6) | Ref-3 Compound | 1.62 | 26 |
| Photoconductor (7) | Ref-4 Compound | 1.83 | 31 |
| Photoconductor (8) | Ref-5 Compound | 1.02 | 12 |
| Photoconductor (9) | Ref-6 Compound | 1.05 | 15 |
| Photoconductor (10) | Ref-7 Compound | 1.33 | 42 |

The evaluation results indicate that the photoconductors (1) to (3) with the acrylic ester compounds of the present invention had the favorable sensitivity and no charge trapping compared to the comparative photoconductors (4) to (10) with the conventional acrylic ester compounds since they had the small half decay exposure and no rest potential. Therefore, these photoconductors had the favorable charge transport property.

Evaluation Example 1 (elution from cured film) and Evaluation Example 2 (evaluation of charge transport property) indicate that the acrylic ester compounds of the present invention was able to satisfy simultaneously the formation of a high-density cross-linking structure by means of a chain reaction which could meet the mechanical durability and heat resistance and the development of the favorable charge transport property while the conventional charge transport monomers were not.

Therefore, the acrylic ester compounds of the present invention are highly effective as materials for providing the various organic semiconductor devices.

SYNTHETIC EXAMPLE B-7

Synthesis of p-tolyl-bis(6-hydroxy-2-naphthyl)amine

In a reaction vessel equipped with an agitator, thermometer and a cooling pipe, 2.1 g of p-tolyl-bis(6-methoxy-2-naphthyl)amine and 50 mL of methylene chloride were placed. While the vessel was being cooled with ice, 12 mL of a 1M methylene chloride solution of boron tribromide was delivered by drops into the vessel, and the mixture was reacted at the same temperature for one hour. The temperature was raised to a room temperature and further reacted for one hour. Then, the reacted solution was poured into ice water and extracted with ethyl acetate. The organic layer was washed with water and separated, and it was then dried with magnesium sulfate and subjected to vacuum concentration. Thus, the objective product was obtained with the yield of 2.38 g.

Synthesis of Illustrative Compound F-9:
p-tolyl-bis(6-acryloxy-2-naphthyl)amine

In a reaction vessel equipped with an agitator, thermometer, a cooling pipe and a dropping funnel, 2.25 g of p-tolyl-bis(6-hydroxy-2-naphthylamine, 1.75 g of triethylamine and 25 mL of tetrahydrofuran were placed, which was agitated at a room temperature. Into the vessel, a mixture of 1.2 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of n-hexane and toluene as a solvent, where the ratio of n-hexane to toluene in the mixture was one to nine. Thus, the objective product was obtained as colorless crystal with the yield of 1.42 g.

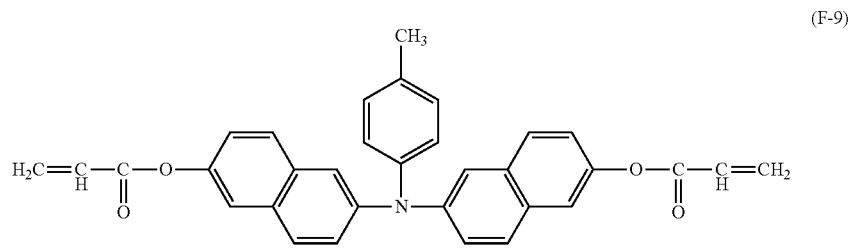 [SMILES: C=CC(=O)Oc1ccc2cc(N(c3ccc(C)cc3)c3ccc4cc(OC(=O)C=C)ccc4c3)ccc2c1]

(F-9)

SYNTHETIC EXAMPLE B-8

Synthesis of 4-di-p-tolylamino-4'-bis(6-hydroxy-2-naphthyl)aminobiphenyl

In a reaction vessel equipped with an agitator, thermometer and a cooling pipe, 2.79 g of p-tolylamino-4'-bis(4'-methoxy-2-naphtyl)aminobiphenyl and 50 mL of methylene chloride were placed. While the vessel was being cooled with ice, 10 mL of a 1M methylene chloride solution of boron tribromide was delivered by drops into the vessel, and the mixture was reacted at the same temperature for one hour. The mixture was further reacted at a room temperature for one hour. Then, the reacted solution was poured into ice water and extracted with ethyl acetate. The organic layer was washed with water and separated, and it was then dried with magnesium sulfate and subjected to vacuum concentration. Thus, the objective product was obtained with the yield of 2.43 g.

Synthesis of Illustrative Compound F-22

In a reaction vessel equipped with an agitator, thermometer, a cooling pipe and a dropping funnel, 2.31 g of 4-di-p-tolylamino-4'-bis(6-hydroxy-2-naphthyl)aminobiphenyl, 1.30 g of triethylamine and 25 mL of tetrahydrofuran were placed, which was agitated at a room temperature. Into the vessel, a mixture of 1.0 mL of acryloyl chloride and 2.0 mL of tetrahydrofuran was delivered by drops. The vessel was subjected to reaction for 30 minutes at a room temperature. When the reaction was completed, the reacted solution was poured into ice water and extracted with ethyl acetate. The extract was then dried with magnesium sulfate and subjected to vacuum concentration. The obtained residue was purified with a silica gel chromatography with a mixture of n-hexane and toluene as a solvent, where the ratio of n-hexane to toluene in the mixture was one to nine. Thus, the objective product was obtained as colorless crystal with the yield of 1.99 g

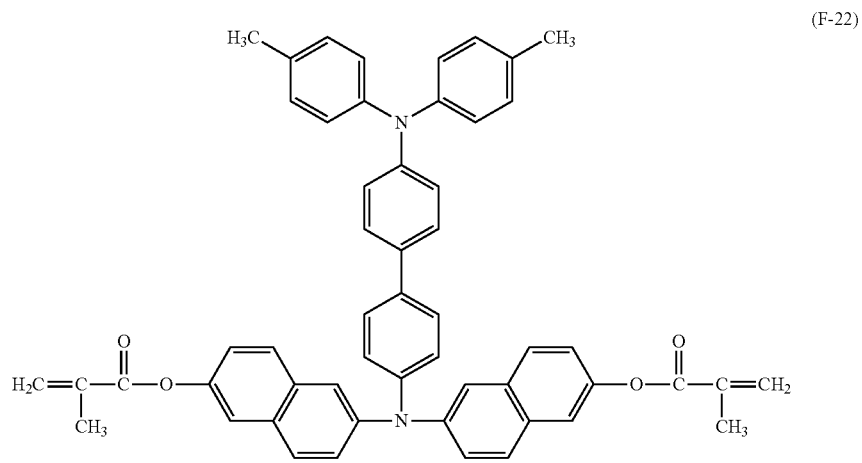 [SMILES: C=C(C)C(=O)Oc1ccc2cc(N(c3ccc(-c4ccc(N(c5ccc(C)cc5)c5ccc(C)cc5)cc4)cc3)c3ccc4cc(OC(=O)C(=C)C)ccc4c3)ccc2c1]

(F-22)

EXAMPLE B-1

-Preparation of Latent Electrostatic Image Bearing Member-

An undercoat layer having a thickness of 3.5 μm, a charge generating layer having a thickness of 0.2 μm and a charge transport layer having a thickness of 18 μm were formed by sequentially applying and drying a coating solution for an undercoat layer, a coating solution for a charge generating layer and a coating solution for a charge transport layer having the following compositions respectively on an aluminum cylinder having a diameter of 30 mm.

On this charge transport layer, a coating solution for a cross-linking charge transport layer having the following composition was spray-coated and let to dry for 20 minutes. Then, the coated layer was cured by irradiating a light under the conditions: a metal halide lamp with 160 W/cm, irradiation distance of 110 mm, irradiation intensity of 750 mW/cm² and irradiation time of 240 seconds.

The sample was further dried at 130° C. for 20 minutes to form a cross-linking charge transport layer having a thickness of 5.0 μm. Thus, an electrophotographic photoconductor of the present invention was obtained.

| [Coating solution for undercoat layer] | |
|---|---|
| Alkyd resin (BECKOSOL 1307-60-EL manufactured by Dainippon Ink and Chemicals, Incorporated) | 6 parts |
| Melamine resin (SUPER BECKAMINE manufactured by Dainippon Ink and Chemicals, Incorporated) | 4 parts |
| Titanium oxide: | 40 parts |
| Methyl ethyl ketone: | 50 parts |

| [Coating solution for cross-linking charge transport layer] | |
|---|---|
| groups of three and the ratio of the molecular weight to the number of functional groups of 99) | |
| 1-hydroxycyclohexyl phenyl ketone as a polymerization initiator (IRGACURE 184 manufactured by Ciba Specialty Chemicals) | 1 part |
| Tetrahydrofuran | 100 parts |

| [Coating solution for charge generating layer] | |
|---|---|
| Bisazo pigment represented by the following structural formula: | 2.5 parts |

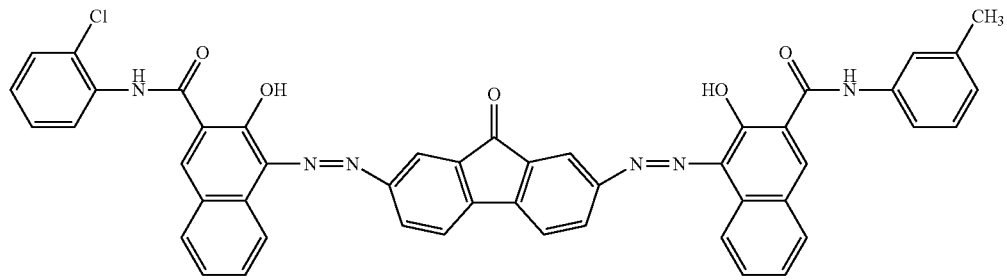 [SMILES: Cc1cccc(NC(=O)c2cc3ccccc3c(N=Nc3ccc4c(c3)C(=O)c3cc(N=Nc5c(O)c(C(=O)Nc6ccccc6Cl)cc6ccccc56)ccc3-4)c2O)c1]

| | |
|---|---|
| Polyvinylbutyral (XYHL manufactured by UCC Inc.): | 0.5 parts |
| Cyclohexanone: | 200 parts |
| Methyl ethyl ketone: | 80 parts |

| [Coating solution for charge transport layer] | |
|---|---|
| Bisphenol Z polycarbonate (Panlite TS-2050 manufactured by Teijin Chemicals, Ltd.): | 10 parts |
| Charge transport material represented by the following structural formula: | 7 parts |

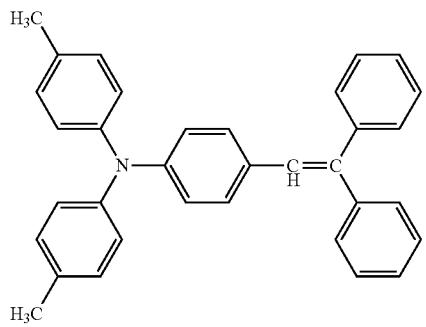

| | |
|---|---|
| Tetrahydrofuran: | 100 parts |
| 1-% Tetrahydrofuran solution of silicone oil (KF-50-100CS manufactured by Shin-etsu Chemical Co., Ltd.): | 0.2 parts |

| [Coating solution for cross-linking charge transport layer] | |
|---|---|
| Radically polymerizable compound including a condensed polycyclic aromatic hydrocarbon (Illustrative Compound F-9): | 10 parts |
| Trimethylolpropane triacrylate as a radically polymerizable compound having three or more radically polymerizable groups in a molecule (KAYARAD TMPTA manufactured by Nippon Kayaku Co., Ltd. having a molecular weight of 296, the number of functional | 10 parts |

EXAMPLE B-2

-Preparation of Latent Electrostatic Image Bearing Member-

A latent electrostatic image bearing member was prepared in the same manner as Example B-1 except that the radically polymerizable component having a condensed polycyclic aromatic hydrocarbon in Example B-1 was replaced by a mixture of Illustrative Components F-9 and F-22 above with the mixing ratio of 50 to 50 by mass.

EXAMPLE B-3

-Preparation of Latent Electrostatic Image Bearing Member-

A latent electrostatic image bearing member was prepared in the same manner as Example B-1 except that the radically polymerizable component having a condensed polycyclic aromatic hydrocarbon in Example B-1 was replaced by Illustrative Components F-22 above.

EXAMPLES B-4 to B-8

-Preparation of Latent Electrostatic Image Bearing Member-

Latent electrostatic image bearing members of Examples B-4 to B-8 were prepared in the same manner as Example B-3 except that the thicknesses of the cross-linking charge transport layer were changed to those indicated in Table 1.

COMPARATIVE EXAMPLE B-1

-Preparation of Latent Electrostatic Image Bearing Member-

A latent electrostatic image bearing member of Comparative Example B-1 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

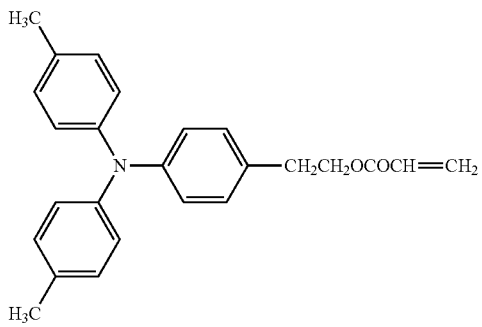

COMPARATIVE EXAMPLE B-2

-Preparation of Latent Electrostatic Image Bearing Member-

A latent electrostatic image bearing member of Comparative Example B-2 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

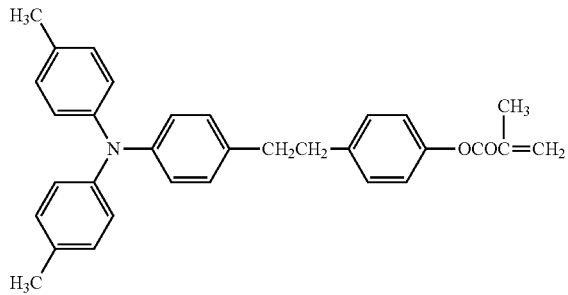

COMPARATIVE EXAMPLE B-3

-Preparation of Latent Electrostatic Image Bearing Member-

A latent electrostatic image bearing member of Comparative Example B-3 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

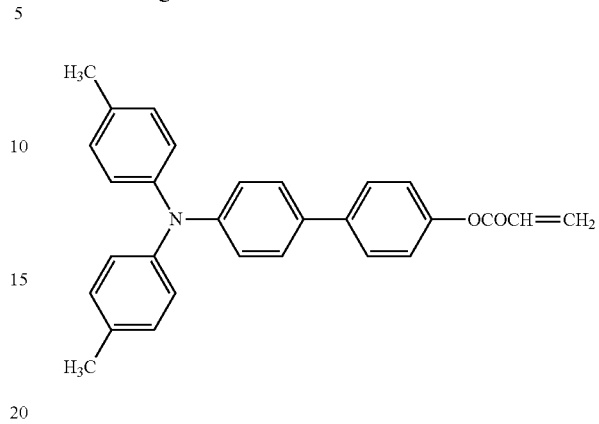

COMPARATIVE EXAMPLE B-4

-Preparation of Latent Electrostatic Image Bearing Member-

A latent electrostatic image bearing member of Comparative Example B-4 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

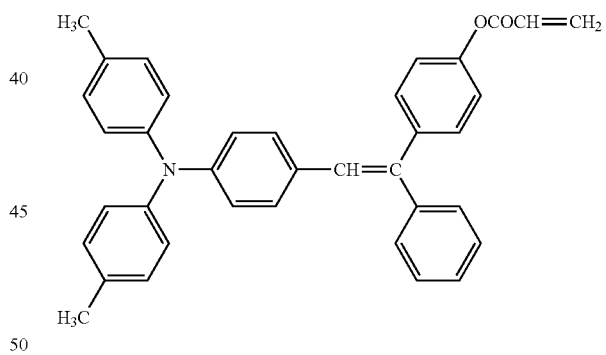

COMPARATIVE EXAMPLE B-5

-Preparation of Latent Electrostatic Image Bearing Member-

A latent electrostatic image bearing member of Comparative Example B-5 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

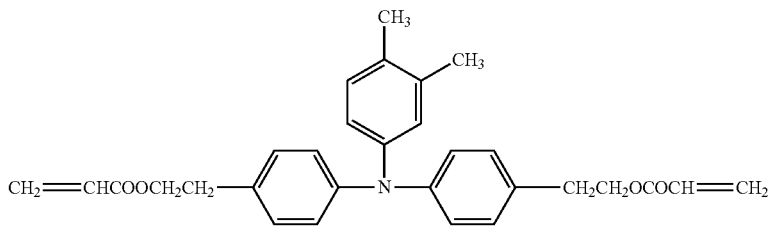

COMPARATIVE EXAMPLE B-6

-Preparation of Latent Electrostatic Image Bearing Member-
A latent electrostatic image bearing member of Comparative Example B-6 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

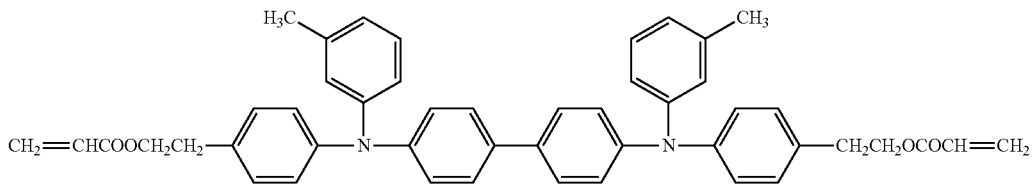

COMPARATIVE EXAMPLE B-7

-Preparation of Latent Electrostatic Image Bearing Member-
A latent electrostatic image bearing member of Comparative Example B-7 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

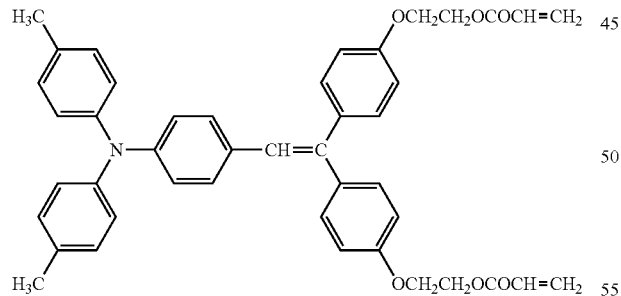

COMPARATIVE EXAMPLE B-8

-Preparation of Latent Electrostatic Image Bearing Member-
A latent electrostatic image bearing member of Comparative Example B-8 was prepared in the same manner as Example B-1 except that the radically polymerizable compound having a condensed polycyclic aromatic hydrocarbon in a coating solution for a cross-linking charge transport layer in Example B-1 was replaced by a compound represented by the following structural formula.

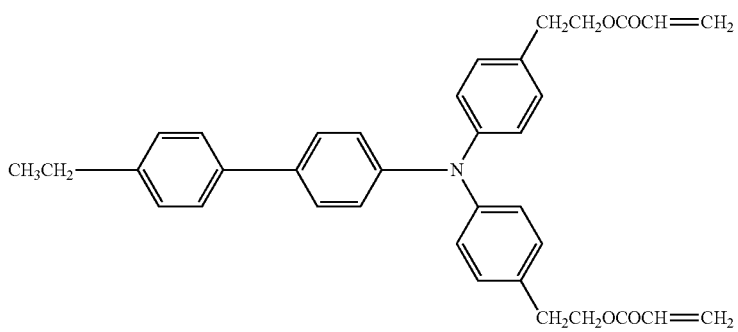

Next, the prepared latent electrostatic image bearing members of Examples B-1 to B-8 and Comparative Examples B-1 to B-8 were subjected to a surface observation, a gel fraction calculation and an operating test, respectively. The results are shown in Tables 9 to 10.

<Surface Observation>

Each latent electrostatic image bearing member was visually observed for the presence of cracks and film exfoliation.

<Gel Fraction>

The gel fraction of a cross-linking charge transport layer for each latent electrostatic image bearing member was obtained as follows. That is, the respective coating solution for a cross-linking charge transport layer was directly applied to an aluminum substrate in the same manner as respective Examples and Comparative Examples, and the film obtained by photo-irradiation and drying under the same conditions was immersed in tetrahydrofuran at 25° C. for five days, and the gel fraction was obtained from Mathematical Formula 1 below.

Gel fraction(%)=100×(mass of the cured coating composition after immersing and drying/initial mass of the cured coating composition)  <Mathematical Formula 1>

TABLE 9

| | Thickness of Cross-Linking Charge Transport Layer (μm) | Surface Observation | Gel Fraction (%) |
|---|---|---|---|
| Example B-1 | 5.0 | Good | 99 |
| Example B-2 | 5.0 | Good | 99 |
| Example B-3 | 5.0 | Good | 99 |
| Example B-4 | 1.0 | Good | 99 |
| Example B-5 | 3.0 | Good | 99 |
| Example B-6 | 7.0 | Good | 99 |
| Example B-7 | 10.0 | Good | 98 |
| Example B-8 | 12.0 | Good | 94 |
| Comparative Example B-1 | 5.0 | Good | 95 |
| Comparative Example B-2 | 5.0 | Good | 93 |
| Comparative Example B-3 | 5.0 | Good | 95 |
| Comparative Example B-4 | 5.0 | Good | 90 |
| Comparative Example B-5 | 5.0 | Cracked | 97 |
| Comparative Example B-6 | 5.0 | Good | 96 |
| Comparative Example B-7 | 5.0 | Good | 94 |
| Comparative Example B-8 | 5.0 | Good | 96 |

<Operating Test>

Photoconductors were prepared in the same manner as Examples B-1 to B-8 and Comparative Examples B-1 to B-8 except for the photoconductor of Comparative Example B-5 which had cracks in the formation of the cross-linking charge transport layer. Using these photoconductors and a toner with silica additive, operating tests with 50,000 sheets of A4 paper were performed.

The photoconductors were mounted on process cartridges for electrophotography, and an image exposure light source having 655 nm of laser diode of the remodeled imagio Neo 270, manufactured by Ricoh Company Ltd., was configured such that the initial unexposed electric potential was set at −700 V. Then, the film thicknesses of all the layers were measured prior to the operation and after 50,000 printings. Then, the wear amount was calculated from the difference thereof, and the number of white spots in a solid image area was counted per unit area.

Also, the electric potential of the exposed area (VL) was measured prior to the operation and after 50,000 printings for examining the rest potential accumulation property.

TABLE 10

| | Image After 50,000 Copies | Wear (μm) | Number of White Spots (count/ 100 cm²) | Initial VL (−V) | Final VL (−V) |
|---|---|---|---|---|---|
| Example B-1 | Good | 0.5 | 0 to 5 | 80 | 100 |
| Example B-2 | Good | 0.5 | 0 to 5 | 80 | 100 |
| Example B-3 | Good | 0.5 | 0 to 5 | 80 | 100 |
| Example B-4 | Slight background fog | 0.8 | 0 to 5 | 80 | 100 |
| Example B-5 | Good | 0.5 | 0 to 5 | 80 | 100 |
| Example B-6 | Good | 0.5 | 0 to 5 | 80 | 100 |
| Example B-7 | Good | 0.6 | 0 to 5 | 85 | 145 |
| Example B-8 | Slight decrease in image density | 0.6 | 0 to 5 | 95 | 160 |
| Comparative Example B-1 | Severe decrease in image density | 1.3 | 10 to 20 | 180 | 250 |
| Comparative Example B-2 | Severe decrease in image density | 2.1 | 10 to 20 | 180 | 230 |
| Comparative Example B-3 | Good | 1.2 | 10 to 20 | 85 | 120 |
| Comparative Example B-4 | Background fog | 2.7 | 10 to 20 | 85 | 115 |
| Comparative Example B-6 | Slight decrease in image density | 0.8 | 0 to 5 | 120 | 195 |
| Comparative Example B-7 | Severe decrease in image density | 1.0 | 0 to 5 | 120 | 200 |
| Comparative Example B-8 | Severe decrease in image density | 0.8 | 0 to 5 | 150 | 240 |

As indicated in Tables 9 to 10, the latent electrostatic image bearing members of Examples B-1 to B-8 on one hand had the more superior abrasion resistance and on the other hand enabled an image printing with fewer defects among the organic photoconductors with superior abrasion resistance. In particular, a white spot caused by silica stinging was less likely to occur, and they had the sufficient image stability for long-term use. It is evident from the comparison with Comparative Examples that these advantages are owing to a radically polymerizable compound having a specific condensed polycyclic aromatic hydrocarbon, and it shows that a latent electrostatic image bearing member which contains on its surface a cured material obtained from the radical polymerization of a radically polymerizable compound having a condensed polycyclic aromatic hydrocarbon of the present invention has superior properties. Also, as indicated by Examples, the combination of a radically polymerizable compound having a condensed polycyclic aromatic hydrocarbon and a radically polymerizable compound having three or more radically polymerizable groups in a molecule provides a highly durable latent electrostatic image bearing member with smooth surface, extremely superior abrasion resistance, low rest potential accumulation property and fewer image defects.

Examples B-1 to B-8 also show that the cured material of the composition which had been photo-cured under the presence of photo-polymerization initiator was effective.

In addition, there was little allowance for wear after 50,000 printings when the thickness was less than 1.5 μm, and the residential potential accumulation property degraded with the decrease in gel fraction when the thickness exceeded 11.50 μm. Therefore, the favorable properties were maintained when the thickness of the cross-linking charge transport layer was 1.5 μm to 11.5 μm. The photoconductors cured under the curing conditions of Examples were determined practically insoluble with respect to an organic solvent based on the gel fraction data. This implies that the superior abrasion resistance and image stability may be achieved under such conditions.

EXAMPLES B-9 to b-16

-Preparation of Latent Electrostatic Image Bearing Member-

Latent electrostatic image bearing members of Examples B-9 to B-16 were prepared in the same manner as Example B-1 except that the radically polymerizable component having a condensed polycyclic aromatic hydrocarbon in Example B-1 was replaced by a mixture of Illustrative Components shown in Table 11. The thickness of each cross-linking charge transport layer was 5.0 μm.

The obtained latent electrostatic image bearing members were evaluated for surface observation and gel fraction in the same manner as Example B-1. The results are shown in Table 11.

Using these prepared latent electrostatic image bearing member and a toner with silica additive, operating tests were performed in the same manner as Example B-1. The results are shown in Table 12.

TABLE 11

| Illustrative Compound No. | Surface Observation | Gel Fraction (%) |
|---|---|---|
| Example B-9 | F-3 | Good | 99 |
| Example B-10 | F-42 | Good | 99 |
| Example B-11 | F-29 | Good | 99 |
| Example B-12 | G-7 | Good | 99 |
| Example B-13 | G-14 | Good | 99 |
| Example B-14 | G-19 | Good | 99 |
| Example B-15 | F-40 | Good | 99 |
| Example B-16 | F-41 | Good | 99 |

TABLE 11-continued

| Illustrative Compound No. | Surface Observation | Gel Fraction (%) |
|---|---|---|

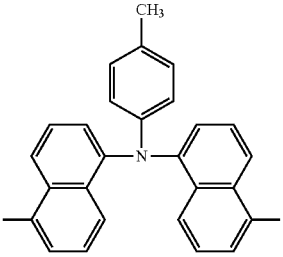

(F-3)

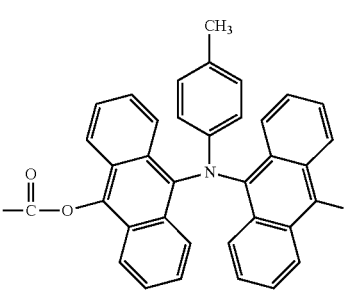

(F-40)

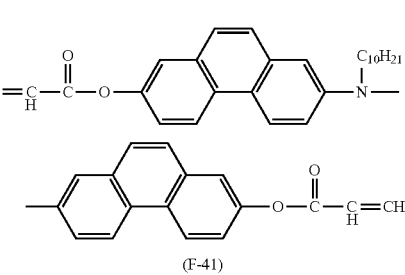

(F-41)

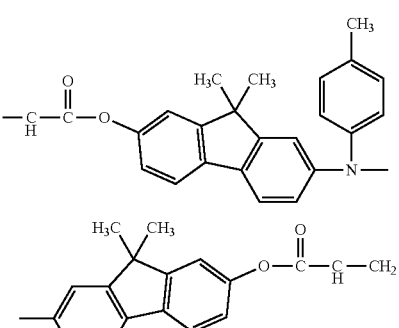

(F-42)

TABLE 11-continued

| Illustrative Compound No. | Surface Observation | Gel Fraction (%) |
|---|---|---|

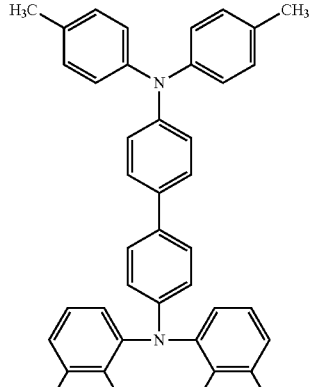
(F-29)

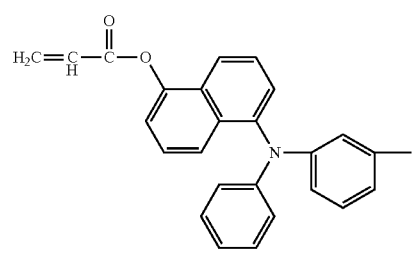
(G-7)

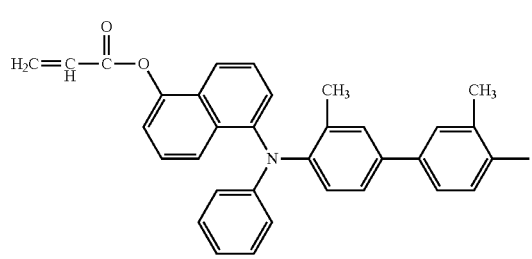
(G-14)

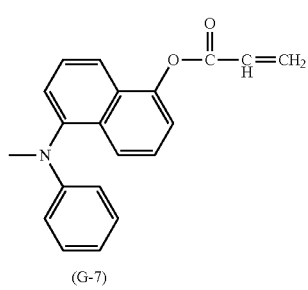
(G-19)

TABLE 12

| | Image After 50,000 Copies | Wear (μm) | Number of White Spots (count/ 100 cm$^2$) | Initial VL (−V) | Final VL (−V) |
|---|---|---|---|---|---|
| Example B-9 | Good | 0.5 | 0 to 5 | 80 | 100 |
| Example B-10 | Good | 0.5 | 0 to 5 | 85 | 105 |
| Example B-11 | Good | 0.5 | 0 to 5 | 80 | 100 |
| Example B-12 | Good | 0.5 | 0 to 5 | 85 | 105 |
| Example B-13 | Good | 0.5 | 0 to 5 | 85 | 105 |
| Example B-14 | Good | 0.5 | 0 to 5 | 90 | 110 |
| Example B-15 | Good | 0.5 | 0 to 5 | 90 | 110 |
| Example B-16 | Good | 0.5 | 0 to 5 | 90 | 110 |

The results in Tables 11 to 12 clearly indicate that the latent electrostatic image bearing members of Examples B-9 to B-16 show the superior properties similarly to those of Examples B-1 to B-8.

An acrylic ester compound of the present invention has a structural unit with a charge transporting function, i.e. hole transport property, as well as an acrylic ester or methacrylic ester group in a molecule, and it can form a polymer with high crosslink density by means of a chain reaction. Therefore, the acrylic ester compound is effective as an organic semiconductor material used for an organic electrophotographic photoconductor, an organic EL, an organic TFT and an organic solar cell.

An image forming method, image forming apparatus and process cartridge using the latent electrostatic image bearing member of the present invention may be widely used for a full-color copying machine which uses a direct or indirect electrophotographic multi-color image developing system, a full-color laser printer and a full-color plain paper facsimile.

What is claimed is:

1. A latent electrostatic image bearing member comprising one of:
   a cured material obtained through a radical polymerization of a radically polymerizable compound of component (A1); and
   a cured material obtained through a radical polymerization of a radically polymerizable compound of component (A2) in an outermost layer;
   wherein
   the radically polymerizable compound of component (A1) comprises two radically polymerizable groups and a substituted amino group which does not include a radically polymerizable group in a molecule;
   the radically polymerizable group and the nearest substituted amino group which do not comprise an unsaturated bond in between are connected with two or more aromatic hydrocarbon compounds;
   the radically polymerizable compound of component (A2) comprises a condensed polycyclic aromatic hydrocarbon formed by bonding a radically polymerizable group and a non-radically polymerizable substituted amine group through a condensed polycyclic aromatic hydrocarbon group;
   the radically polymerizable compound of component (A1) is at least one compound having a structure represented by formula (1-3); and
   the radically polymerizable compound of component (A2) is at least one compound selected from the group consisting of a compound having a structure represented by formula (1-5), and a compound having a structure represented by formula (1-6);

(1-3)

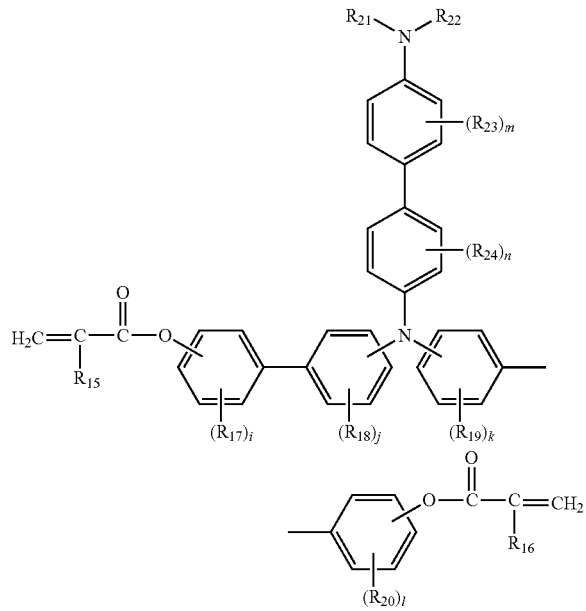

wherein $R_{15}$ and $R_{16}$ are the same or different and represent a hydrogen atom or a methyl group; $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; and i, j, k, l, m and n are the same or different and represent an integer of zero to four;

(1-5)

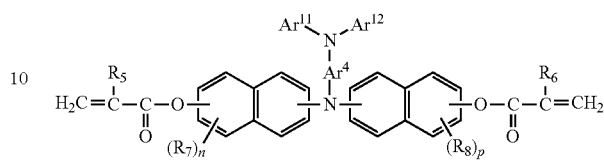

wherein $R_5$ and $R_6$ are the same or different and represent a hydrogen atom or a methyl group; $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents a 4,4'-biphenylene group; $Ar^{11}$ and $Ar^{12}$ represent an alkyl group which may have a substituent, an aryl group which may have a substituent or a condensed polycyclic hydrocarbon group which may have a substituent, and $Ar^{11}$ and $Ar^{12}$ may be bonded together through adjacent carbon atoms to form a heterocycle; and n and p are the same or different and represent an integer of zero to six;

(1-6)

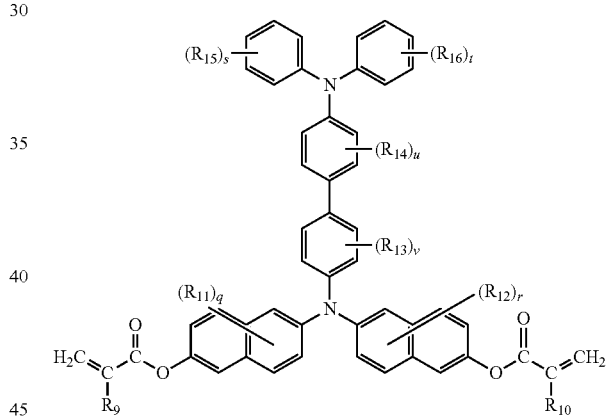

wherein $R_9$ and $R_{10}$ are the same or different and represent a hydrogen atom or a methyl group; $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{16}$ represent an alkyl group which may have a substituent, an alkoxy group which may have a substituent, an aryl group which may have a substituent or a halogen atom; and q and r are the same or different and represent an integer of zero to six, s and t are the same or different and represent an integer of zero to five, and u and v are the same or different and represent an integer of zero to four.

2. The latent electrostatic image bearing member according to claim 1, wherein the outermost layer comprises a radically polymerizable compound having three or more radically polymerizable groups in a molecule.

3. The latent electrostatic image bearing member according to claim 1, wherein the outermost layer comprises a photo-polymerization initiator.

4. The latent electrostatic image bearing member according to claim 1, wherein the radically polymerizable group is any one of an acryloyloxy group and an methacryloyloxy group.

5. The latent electrostatic image bearing member according to claim 1, wherein the latent electrostatic image bearing member comprises a substrate; a charge generation layer; a charge transport layer; and a cross-linked charge transport layer in this order on the substrate; and the cross-linked charge transport layer is the outermost layer.

6. The latent electrostatic image bearing member according to claim 5, wherein the cross-linked charge transport layer has a thickness of 1.0 μm to 11.5 μm.

7. The latent electrostatic image bearing member according to claim 5, wherein the cross-linked charge transport layer is insoluble with an organic solvent.

8. The latent electrostatic image bearing member according to claim 5, wherein
the outermost layer comprises a radically polymerizable compound having three or more radically polymerizable groups in a molecule; and
in the cross-linked charge transport layer the ratio of the number of functional groups in the radically polymerizable compound which comprises three or more radically polymerizable groups in a molecule to the molecular weight of the radically polymerizable compound (molecular weight/the number of functional groups), is 250 or less.

9. An image forming method comprising:
forming a latent electrostatic image on a latent electrostatic image bearing member;
developing the latent electrostatic image with a toner to form a toner image; and
transferring the toner image to a recording medium;
wherein the latent electrostatic image bearing member comprises one of:
a cured material obtained through a radical polymerization of a radically polymerizable compound (A1); and
a cured material obtained through a radical polymerization of a radically polymerizable compound (A2) in an outermost layer;
wherein
the radically polymerizable compound (A1) comprises two radically polymerizable groups and a substituted amino group which does not include a radically polymerizable group in a molecule;
the radically polymerizable group and the nearest substituted amino group which do not comprise an unsaturated bond in between are connected with two or more aromatic hydrocarbon compounds;
the radically polymerizable compound (A2) comprises a condensed polycyclic aromatic hydrocarbon formed by bonding a radically polymerizable group and a non-radically polymerizable substituted amine group through a condensed polycyclic aromatic hydrocarbon group;
the radically polymerizable compound of component (A1) is at least one compound having a structure represented by formula (1-3); and
the radically polymerizable compound of component (A2) is at least one compound selected from the group consisting of a compound having a structure represented by formula (1-5), and a compound having a structure represented by formula (1-6);

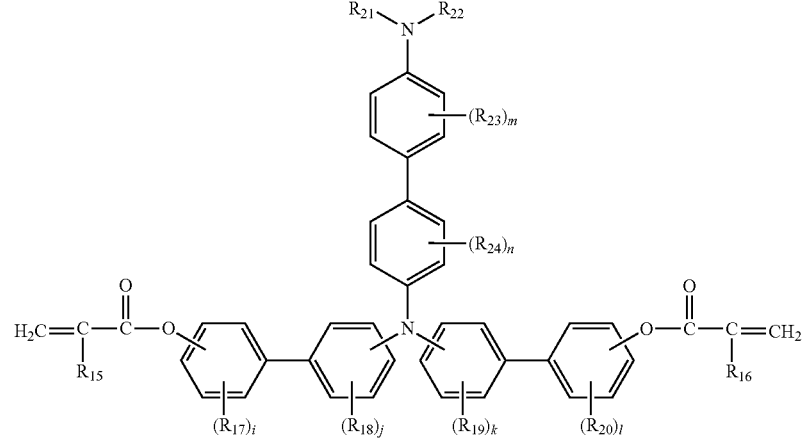

(1-3)

wherein $R_{15}$ and $R_{16}$ are the same or different and represent a hydrogen atom or a methyl group; $R_{17}$, $R_{18}$, $R_{19}$, $R_{20}$, $R_{23}$ and $R_{24}$ represent an alkyl group which may have a substituent, an alkoxy group which may have a substituent, an aryl group which may have a substituent, a heterocyclic group which may have a substituent or a halogen atom; $R_{21}$ and $R_{22}$ represent an alkyl group which may have a substituent, an aralkyl group which may have a substituent, an aryl group which may have a substituent, a heterocyclic group which may have a substituent or a condensed polycyclic hydrocarbon group which may have a substituent, and $R_{21}$ and $R_{22}$ may be bonded together to form a heterocycle; and i, j, k, l, m and n are the same or different and represent an integer of zero to four;

(1-5)

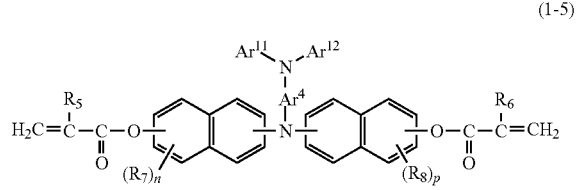

(1-6)

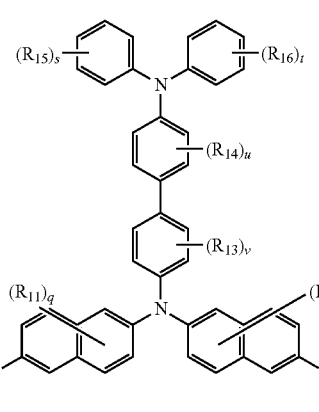

wherein $R_5$ and $R_6$ are the same or different and represent a hydrogen atom or a methyl group; $R_7$ and $R_8$ represent an alkyl group which may have a substituent, an alkoxy group which may have a substituent, an aryl group which may have a substituent, a heterocyclic group which may have a substituent or a halogen atom; $Ar^4$ represents a 4,4'-biphenylene group; $Ar^{11}$ and $Ar^{12}$ represent an alkyl group which may have a substituent, an aryl group which may have a substituent or a condensed polycyclic hydrocarbon group which may have a substituent, and $Ar^{11}$ and $Ar^{12}$ may be bonded together through adjacent carbon atoms to form a heterocycle; and n and p are the same or different and represent an integer of zero to six;

wherein $R_9$ and $R_{10}$ are the same or different and represent a hydrogen atom or a methyl group; $R_{11}$ and $R_{12}$ represent an alkyl group which may have a substituent, an alkoxy group which may have a substituent, an aryl group which may have a substituent, a heterocyclic group which may have a substituent or a halogen atom; $R_{13}$, $R_{14}$, $R_{15}$ and $R_{16}$ represent an alkyl group which may have a substituent, an alkoxy group which may have a substituent, an aryl group which may have a substituent or a halogen atom; and q and r are the same or different and represent an integer of zero to six, s and t are the same or different and represent an integer of zero to five, and u and v are the same or different and represent an integer of zero to four.

* * * * *